United States Patent
Thibonnier

(10) Patent No.: US 9,034,839 B2
(45) Date of Patent: May 19, 2015

(54) MIRNA MODULATORS OF THERMOGENESIS

(71) Applicant: Aptamir Therapeutics, Inc., Naples, FL (US)

(72) Inventor: Marc Thibonnier, Naples, FL (US)

(73) Assignee: Aptamir Therapeutics, Inc., Austin, TX (US)

( * ) Notice: Subject to any disclaimer, the term of this patent is extended or adjusted under 35 U.S.C. 154(b) by 0 days.

(21) Appl. No.: 13/826,775

(22) Filed: Mar. 14, 2013

(65) Prior Publication Data

US 2013/0331433 A1    Dec. 12, 2013

Related U.S. Application Data

(60) Provisional application No. 61/681,750, filed on Aug. 10, 2012, provisional application No. 61/636,059, filed on Apr. 20, 2012.

(51) Int. Cl.
*A61K 48/00* (2006.01)
*C12N 15/113* (2010.01)
*C12Q 1/68* (2006.01)

(52) U.S. Cl.
CPC .......... *C12N 15/113* (2013.01); *C12Q 1/68* (2013.01); *C12N 2310/141* (2013.01); *C12N 2310/16* (2013.01); *C12N 2310/3519* (2013.01); *C12N 2320/11* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 6,107,094 A | 8/2000 | Crooke | 435/455 |
| 2010/0255545 A1 | 10/2010 | Smolke et al. | 435/91.1 |
| 2011/0224286 A1 | 9/2011 | Yu et al. | 514/44 R |
| 2013/0331440 A1 | 12/2013 | Scheideler et al. | 514/44 |

FOREIGN PATENT DOCUMENTS

| | | |
|---|---|---|
| EP | 1 800 695 A1 | 6/2007 |
| WO | WO/2010/108126 | 9/2010 |
| WO | WO/2010/135714 | 11/2010 |
| WO | WO/2011/079263 | 6/2011 |
| WO | WO/2011/138457 | 11/2011 |
| WO | WO/2012/007725 | 1/2012 |

OTHER PUBLICATIONS

Alexander, et al., Exp Opin Therap Targets. 15(5):623-36, 2011.
Andersen, et al., Int J Obes. 37(2):175-81, 2013.
Bader, et al., Gene Ther. 18(12):1121-26, 2011.
Borgdorff, et al., Oncogene. 29(15):2262-71, 2010.
Broderick, et al., Gene Ther. 18(12):1104-1110, 2011.
Cerchia, et al., Pharmaceut. 4(12):1434-49, 2011.
Chen, et al., J Biol Chem. 284:5362-5369, 2009.
Czech, et al., Nat Rev Endocrinol. 7(8):473-84, 2011.
Davidson, et al., Nat Rev Genet. 12(5):329-40, 2011.
Dehwah, et al., J Genet Genom. 39(1):11-18, 2011.
Ebert, et al., Nature Methods. 4(9):721-26, 2007.
Elmen, et al., Nature. 452:896-99, 2008.
Esau, et al., Cell Metab. 3(2):87-98, 2006.
Esterbauer, et al., Nat Genet. 28(2):178-83, 2001.
Friedman, et al., BMC Bioinformatics. 26(15):1920-1, 2010.
Fujiki, et al., BMC Biol. 7:38, 2009.
Gallagher, et al., Genome Med. 2(2):9, 2010.
Hao, et al., Mol Biosyst. 8(11): 2828-38, 2012.
Hao, et al., Mol Biosyst. 8(2):663-70, 2012.
Hsu, et al., Nucleic Acids Res. 39(Database Issue):D163-9, 2011.
Kanasaki, et al., J Biomed Biotechnol. 2011:197636, 2011.
Kanwar, et al., Crit Rec Biochem Mol Biol. 46(6):459-77, 2011.
Kim, et al., Biomat. 33(1):20-17, 2011.
Krutzfeldt, et al., Nature. 438:685-9, 2005.
Lennox, et al., Gene Ther. 18(12):1111-1120, 2011.
Liu, et al., Cancer Invest. 30(8):577-82, 2012.
Liu, et al., Gene. 514(1):41-7, 2013.
Liu, et al., PLoS One. 7(5):e37789, 2012.
Lowell, et al., Nature. 404(6778):652-60, 2000.
McGregor, et al., Curr Mol Med. 11(4):304-16, 2011.
Okada, et al., J Androl. 31(1):75-8, 2010.
Petrovic, et al., J Biol Chem. 285(10):7153-64, 2010.
Rantalainen, et al., PLoS One. 6(11):1-12, 2011.
Rieger, et al., Frontiers in Genetics. 2:39, 2011.
Rosen & Spiegelman, Cell. 156:20-45, 2014.
Search Report and Written Opinion in International Application No. PCT/US2013/037579 mailed Oct. 25, 2013.
Search Report and Written Opinion in International Application No. PCT/US2013/053613 mailed Jan. 2, 2014.
Snead, et al., Nucleic Acid Ther. 22(3):139-46, 2012.
Speakman, et al., Obes Rev. 8(Suppl 1): 55-61, 2007.
Sun, et al., Mol Endocrinol. 23:925-31, 2009.
Sun, et al., Nature Cell Biol. 13(8):958-65, 2011.
Thorsen, et al., Cancer J. 18(3):275-84, 2012.
Tivnan, et al., PLoS One. 7(5):e38129, 2012.
Van Rooij, et al., Circ Res. 110(3):496-507, 2012.
Wang, et al., Am J Physiol. 286(1):E1-7, 2004.
Wang, et al., Meth Mol Biol. 821:421-433, 2012.
Wu, et al., Int J Nanomed. 6:1747-56, 2011.
Xiao, et al., J Cell Physiol. 212:285-92, 2007.
Yin, et al., Cell Metabl. 17(2):210-224, 2013.
Zaragosi, et al., Genoma Biol. 12:1-13, 2011.

*Primary Examiner* — Kimberly Chong
(74) *Attorney, Agent, or Firm* — Norton Rose Fulbright US LLP

(57) ABSTRACT

Provided are novel methods and compositions for the modulation of thermogenesis. Such methods are particularly advantageous in that they allow for the reduction of body fat in a subject without the subject having to adjust their caloric intake through dieting, modify their physical activity or undergo bariatric surgery. Accordingly, the methods of the invention are particularly useful for treating or preventing obesity. Also provided are methods of screening for novel agents that modulate the activity of thermogenic regulators.

12 Claims, 28 Drawing Sheets

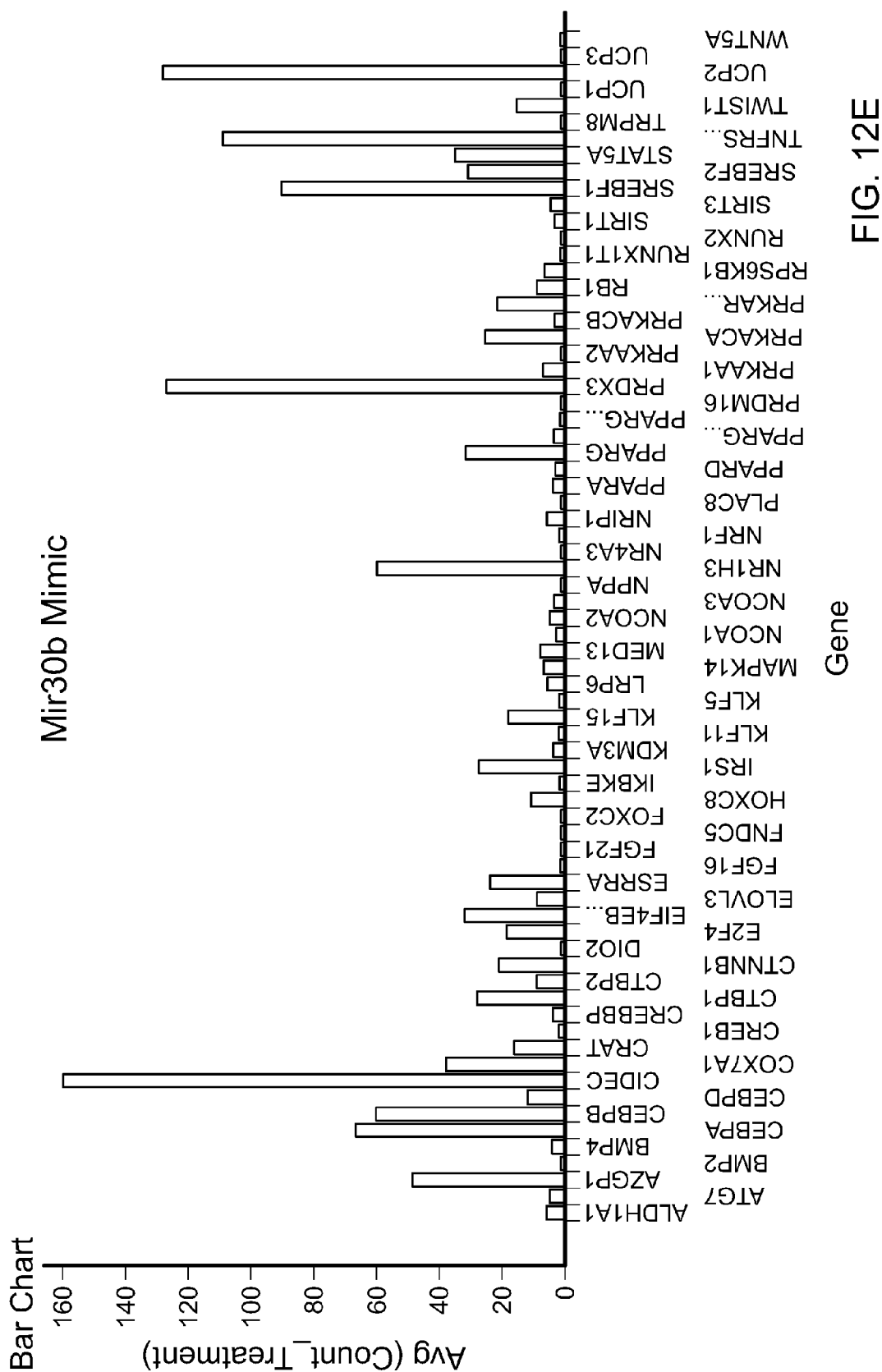

MIRNA MODULATORS OF THERMOGENESIS

BACKGROUND OF THE INVENTION

Obesity has reached pandemic proportions, affecting all ages and socioeconomic groups. The World Health Organization estimated that in 2008, 1.5 billion adults aged 20 years and older were overweight and over 200 million men and 300 million women were obese. These figures are estimated to increase to 2.16 billion overweight and 1.12 billion obese individuals by 2030. Obesity is the source of lost earnings, restricted activity days, absenteeism, lower productivity at work (presenteeism), reduced quality of life, permanent disability, significant morbidity and mortality, and shortened lifespan. Indeed, the total annual economic cost of overweight and obesity in the United States and Canada caused by medical costs, excess mortality and disability was estimated to be about $300 billion in 2009. International studies on the economic costs of obesity have shown that they account for between 2% and 10% of total health care costs.

Obesity is the result of a chronic imbalance between energy intake and expenditure. This leads to storage of excess energy into adipocytes, which typically exhibit both hypertrophy (increase in cell size) and hyperplasia (increase in cell number or adipogenesis). The recent worsening of obesity is due to the combination of excessive consumption of energy-dense foods high in saturated fats and sugars, and reduced physical activity.

The current symptomatic medical treatments of obesity fail to achieve their long-term therapeutic goals, largely due to limited drug efficacy and patients' poor adherence with lifestyle changes and therapies. Several obesity drugs have been removed from the market for safety reasons and small molecules currently in development are struggling to gain regulatory approval because of their modest short-term efficacy and unknown safety profile. Presently, only restrictive and malabsorptive bariatric surgery can achieve significant long-term reduction of weight excess with some favorable cardiovascular benefits.

Accordingly, there is a need in the art for novel treatments for obesity.

SUMMARY OF THE INVENTION

Obesity is the consequence of a chronic imbalance of energy intake over expenditure, leading to the storage of excess energy inside white adipocytes. This disclosure features a novel treatment for obesity targeting peripheral adipocytes, including energy-storing lipid-filled white adipocytes (WAT), and energy-expending mitochondria-rich brown adipocytes (BAT). In addition, the disclosure provides methods for the modulation of thermogenesis (the process of heat production in organisms) using microRNA (miRNAs) agents. The methods described herein generally involve the direct and/or indirect modulation of at least one thermogenic regulator (e.g., a mitochondrial uncoupler, such as Uncoupling Protein 1 (UCP1 also known as Thermogenin) or Uncoupling Protein 2 (UCP2)) in a cell, tissue and/or subject using an isolated miRNA agent. UCPs uncouple oxidative phosphorylation from ATP synthesis. In certain instances, this uncoupling results in energy dissipated as heat. Such methods are particularly advantageous in that they allow for the reduction of body fat in a subject without the subject having to adjust their caloric intake through dieting, modify their physical activity or undergo bariatric surgery. Accordingly, the methods of the invention are particularly useful for treating or preventing obesity.

The invention also provides novel miRNA agent compositions (e.g., miRNA, agomirs, and antagomirs) that can modulate the activity of thermogenic regulators. Yet further, the invention provides methods of screening for novel miRNA agents that modulate the activity of thermogenic regulators. Further still, the invention provides novel agent compositions (e.g. aptamer-miRNA complexes or "aptamirs") that provide cell/tissue-specific delivery of the miRNA agents.

Accordingly, in one aspect, the invention provides a method of modulating respiratory chain uncoupling in a cell, the method comprising contacting the cell with an isolated miRNA agent that modulates the expression level and/or activity of at least one mitochondrial uncoupler. In some embodiments, the method further comprises the step of selecting a subject in need of modulating respiratory chain uncoupling (e.g., an obese patient). In one embodiment, the miRNA agent increases the expression level and/or activity of the at least one mitochondrial uncoupler. In certain embodiments, the mitochondrial uncoupler is UCP1 or UCP2. In some embodiments, the method increases respiratory chain uncoupling in a cell in vivo. In other embodiments, the method increases respiratory chain uncoupling in a cell ex vivo. In certain embodiments, the method further comprises determining the level of expression (mRNA or protein) or activity of the mitochondrial uncoupler. In certain embodiments, the cell is a pre-adipocyte, adipocyte, adipose tissue derived mesenchymal stem cell, hepatocyte, myocyte, or a precursor thereof. Optionally, adipocytes can be white fat or brown fat adipocytes.

In another aspect, the invention provides a method of modulating thermogenesis in a tissue, the method comprising contacting the tissue with an isolated miRNA agent that modulates the expression level and/or activity of at least one mitochondrial uncoupler. In some embodiments, the method further comprises the step of selecting a subject in need of modulating thermogenesis (e.g., an obese patient). In one embodiment, the miRNA agent increases the expression level and/or activity of the at least one mitochondrial uncoupler. In certain embodiments, the mitochondrial uncoupler is UCP1 or UCP2. In certain embodiments, the method involves increasing thermogenesis. In certain embodiments, the method further comprises determining the level of expression (mRNA or protein) or activity of the mitochondrial uncoupler. In certain embodiments, the tissue is brown fat, white fat, subcutaneous adipose tissue, liver or muscle. In certain embodiments, the tissue is contacted with the miRNA agent ex vivo.

In another aspect, the invention provides a method of treating obesity in human subject in need of treatment thereof, the method generally comprising administering to the human subject an effective amount of a miRNA agent that modulates activity of at least one mitochondrial uncoupler. In certain embodiments, the human subject selected for treatment has a genetic or epigenetic predisposition to obesity. In certain embodiments, the mitochondrial uncoupler is UCP1 or UCP2.

In certain embodiments of all of the above aspects, the miRNA agent is an isolated miRNA selected from the group consisting of hsa-miR-1-1, hsa-miR-1-2, miR-19a-b, hsa-miR-105, hsa-miR-1283, hsa-mir-129, hsa-miR-133a-1, hsa-miR-133a-2, hsa-miR-143, hsa-mir-143-5p, hsa-mir-147, hsa-mir-149, hsa-mir-199a, hsa-mir-199b, hsa-mir-200c, hsa-mir-204, hsa-mir-205, hsa-miR-206, hsa-mir-21, hsa-mir-211, hsa-mir-218, hsa-mir-218-1, hsa-mir-218-2, hsamir-219-2, hsa-mir-219-2-3p, hsa-mir-22, hsa-mir-22-3p, hsa-mir-22-5p, hsa-mir-24-2, hsa-miR-30a-e, hsa-miR-3177-5p, hsa-mir-325, hsa-mir-331, hsa-mir-331-5p, hsa-miR-3613-3p, hsa-mir-362, hsa-mir-362-5p, hsa-miR-3658, hsa-mir-367, hsa-mir-371, hsa-mir-371-5p, hsa-mir-377, hsa-mir-378, hsa-mir-378a-5p, hsa-mir-382, hsa-mir-383, hsa-mir-422a, hsa-mir-425, hsa-miR-455-3p, hsa-miR-455-5p, hsa-miR-491, hsa-mir-508, hsa-mir-508-5p, hsa-mir-512-1, hsa-mir-512-2, hsa-miR-515-3p, hsa-mir-519e, hsa-miR-520a, hsa-mir-543, hsa-mir-545, hsa-mir-549, hsa-mir-556, and hsa-miR-568, hsa-mir-620, hsa-mir-643, hsa-mir-654-3p, hsa-miR-7a-g, hsa-mir-765, hsa-mir-871, hsa-mir-888, hsa-mir-888-3p, hsa-mir-92b, hsa-mir-93, hsa-mir-96, and hsa-mir-99a. In certain embodiments of all of the above aspects, the miRNA agent is an isolated miRNA that is 80%, 85%, 90%, 91%, 92%, 93%, 94%, 95%, 96%, 97%, 98%, or 99% identical to the sequence of a miRNA listed above. In certain embodiments of all of the above aspects, the miRNA agent is a seed sequence of a miRNA listed above.

In certain embodiments of all of the above aspects, the miRNA agent is an isolated miRNA selected from the group consisting of the 536 miRNAs set forth in Table A. In certain embodiments of all of the above aspects, the miRNA agent is an isolated miRNA that is 80%, 85%, 90%, 91%, 92%, 93%, 94%, 95%, 96%, 97%, 98%, or 99% identical to the sequence of a miRNA listed in Table A. In certain embodiments of all of the above aspects, the miRNA agent is a seed sequence of a miRNA listed in Table A.

TABLE A

Adipocyte miRNAs listed in ascending order (miRBase 19 nomenclature)

| | | | |
|---|---|---|---|
| hsa-let-7a-3p | hsa-miR-185-5p | hsa-miR-329 | hsa-miR-509-3p |
| hsa-let-7a-5p | hsa-miR-186-3p | hsa-miR-330-3p | hsa-miR-511 |
| hsa-let-7b-3p | hsa-miR-186-5p | hsa-miR-330-5p | hsa-miR-513a-3p |
| hsa-let-7b-5p | hsa-miR-187-3p | hsa-miR-331-3p | hsa-miR-513a-5p |
| hsa-let-7c | hsa-miR-188-5p | hsa-miR-331-5p | hsa-miR-513b |
| hsa-let-7d-3p | hsa-miR-18a-3p | hsa-miR-335-3p | hsa-miR-514a-3p |
| hsa-let-7d-5p | hsa-miR-18a-5p | hsa-miR-335-5p | hsa-miR-515-3p |
| hsa-let-7e-5p | hsa-miR-18b-5p | hsa-miR-337-3p | hsa-miR-516b-3p |
| hsa-let-7f-1-3p | hsa-miR-1909-3p | hsa-miR-337-5p | hsa-miR-516b-5p |
| hsa-let-7f-5p | hsa-miR-190a | hsa-miR-338-3p | hsa-miR-518b |
| hsa-let-7g-3p | hsa-miR-190b | hsa-miR-338-5p | hsa-miR-518e-3p |
| hsa-let-7g-5p | hsa-miR-191-3p | hsa-miR-339-3p | hsa-miR-518e-5p |
| hsa-let-7i-3p | hsa-miR-191-5p | hsa-miR-339-5p | hsa-miR-518f-3p |
| hsa-let-7i-5p | hsa-miR-192-5p | hsa-miR-33a-5p | hsa-miR-519a-5p |
| hsa-miR-1 | hsa-miR-193a-3p | hsa-miR-33b-5p | hsa-miR-519b-5p |
| hsa-miR-100-5p | hsa-miR-193a-5p | hsa-miR-340-3p | hsa-miR-519c-3p |
| hsa-miR-101-3p | hsa-miR-193b-3p | hsa-miR-340-5p | hsa-miR-519c-5p |
| hsa-miR-101-5p | hsa-miR-193b-5p | hsa-miR-342-3p | hsa-miR-519d |
| hsa-miR-103a-2-5p | hsa-miR-194-5p | hsa-miR-342-5p | hsa-miR-520c-3p |
| hsa-miR-103a-3p | hsa-miR-195-3p | hsa-miR-345-5p | hsa-miR-520e |
| hsa-miR-103b | hsa-miR-195-5p | hsa-miR-346 | hsa-miR-520f |
| hsa-miR-105-5p | hsa-miR-196a-5p | hsa-miR-34a-5p | hsa-miR-520g |
| hsa-miR-106a-5p | hsa-miR-196b-5p | hsa-miR-34b-3p | hsa-miR-520h |
| hsa-miR-106b-3p | hsa-miR-197-3p | hsa-miR-34b-5p | hsa-miR-521 |
| hsa-miR-106b-5p | hsa-miR-198 | hsa-miR-34c-5p | hsa-miR-522-5p |
| hsa-miR-107 | hsa-miR-199a-3p | hsa-miR-3545-5p | hsa-miR-523-5p |
| hsa-miR-10a-3p | hsa-miR-199a-5p | hsa-miR-3591-3p | hsa-miR-525-3p |
| hsa-miR-10a-5p | hsa-miR-199b-3p | hsa-miR-361-3p | hsa-miR-532-3p |
| hsa-miR-10b-3p | hsa-miR-199b-5p | hsa-miR-361-5p | hsa-miR-532-5p |
| hsa-miR-10b-5p | hsa-miR-19a-3p | hsa-miR-3613-5p | hsa-miR-539-5p |
| hsa-miR-1179 | hsa-miR-19b-3p | hsa-miR-3615 | hsa-miR-542-3p |
| hsa-miR-1185-5p | hsa-miR-200a-3p | hsa-miR-362-3p | hsa-miR-542-5p |
| hsa-miR-1208 | hsa-miR-200a-5p | hsa-miR-362-5p | hsa-miR-545-3p |
| hsa-miR-122-5p | hsa-miR-200b-5p | hsa-miR-363-3p | hsa-miR-545-5p |
| hsa-miR-1227-3p | hsa-miR-200c-3p | hsa-miR-363-5p | hsa-miR-548d-3p |
| hsa-miR-1228-5p | hsa-miR-202-3p | hsa-mir-365a-3p | hsa-miR-548e |
| hsa-miR-1229-3p | hsa-miR-203a | hsa-miR-3653 | hsa-miR-548i |

TABLE A-continued

Adipocyte miRNAs listed in ascending order (miRBase 19 nomenclature)

| | | | |
|---|---|---|---|
| hsa-miR-124-3p | hsa-miR-204-5p | hsa-miR-3656 | hsa-miR-548m |
| hsa-miR-125a-3p | hsa-miR-205-5p | hsa-miR-365a-3p | hsa-miR-550a-5p |
| hsa-miR-125a-5p | hsa-miR-206 | hsa-miR-365a-5p | hsa-miR-551b-3p |
| hsa-miR-125b-1-3p | hsa-miR-20a-3p | hsa-miR-367-3p | hsa-miR-552 |
| hsa-miR-125b-2-3p | hsa-miR-20a-5p | hsa-mir-3676-3p | hsa-miR-553 |
| hsa-miR-125b-5p | hsa-miR-20b-5p | hsa-miR-369-3p | hsa-miR-554 |
| hsa-miR-126-3p | hsa-miR-21-3p | hsa-miR-369-5p | hsa-miR-557 |
| hsa-miR-126-5p | hsa-miR-21-5p | hsa-miR-370 | hsa-miR-563 |
| hsa-miR-1260a | hsa-miR-210 | hsa-miR-371a-3p | hsa-miR-564 |
| hsa-miR-1260b | hsa-miR-211-5p | hsa-miR-373-3p | hsa-miR-567 |
| hsa-miR-1268a | hsa-miR-2110 | hsa-miR-373-5p | hsa-miR-569 |
| hsa-miR-127-3p | hsa-miR-212-3p | hsa-miR-374a-3p | hsa-miR-570-3p |
| hsa-miR-127-5p | hsa-miR-214-3p | hsa-miR-374a-5p | hsa-miR-572 |
| hsa-miR-1271-5p | hsa-miR-214-5p | hsa-miR-374b-3p | hsa-miR-574-3p |
| hsa-miR-1273a | hsa-miR-215 | hsa-miR-374b-5p | hsa-miR-574-5p |
| hsa-miR-1277-3p | hsa-miR-216a-5p | hsa-miR-375 | hsa-miR-575 |
| hsa-miR-128 | hsa-miR-217 | hsa-mir-376a-2-5p | hsa-miR-576-3p |
| hsa-miR-128-2 | hsa-miR-218-5p | hsa-miR-376a-3p | hsa-miR-576-5p |
| hsa-miR-1285-3p | hsa-miR-219-1-3p | hsa-miR-376a-5p | hsa-miR-582-3p |
| hsa-miR-1287 | hsa-miR-219-5p | hsa-miR-376b-3p | hsa-miR-582-5p |
| hsa-miR-1288 | hsa-miR-22-3p | hsa-miR-376c-3p | hsa-miR-583 |
| hsa-miR-129-5p | hsa-miR-22-5p | hsa-miR-377-3p | hsa-miR-584-5p |
| hsa-miR-1290 | hsa-miR-221-3p | hsa-miR-378a-3p | hsa-miR-585 |
| hsa-miR-1292-5p | hsa-miR-221-5p | hsa-miR-378a-5p | hsa-miR-586 |
| hsa-miR-1301 | hsa-miR-222-3p | hsa-miR-378c | hsa-miR-589-5p |
| hsa-miR-1305 | hsa-miR-222-5p | hsa-miR-378d | hsa-miR-590-3p |
| hsa-mir-1307-3p | hsa-miR-223-3p | hsa-miR-379-5p | hsa-miR-590-5p |
| hsa-miR-130a-3p | hsa-miR-223-5p | hsa-miR-380-3p | hsa-miR-595 |
| hsa-miR-130b-3p | hsa-miR-224-3p | hsa-miR-381-3p | hsa-miR-598 |
| hsa-miR-130b-5p | hsa-miR-224-5p | hsa-miR-382-5p | hsa-miR-601 |
| hsa-miR-132-3p | hsa-miR-2355-3p | hsa-miR-383 | hsa-miR-602 |
| hsa-miR-132-5p | hsa-miR-23a-3p | hsa-miR-384 | hsa-miR-603 |
| hsa-miR-1323 | hsa-miR-23b-3p | hsa-miR-3912 | hsa-miR-605 |
| hsa-miR-133a | hsa-miR-23b-5p | hsa-miR-3928 | hsa-miR-606 |
| hsa-miR-133b | hsa-miR-24-1-5p | hsa-miR-409-3p | hsa-miR-609 |
| hsa-miR-134 | hsa-miR-24-2-5p | hsa-miR-409-5p | hsa-miR-611 |
| hsa-miR-135a-5p | hsa-miR-24-3p | hsa-miR-410 | hsa-miR-615-3p |
| hsa-miR-135b-5p | hsa-miR-25-3p | hsa-miR-411-5p | hsa-miR-619 |
| hsa-miR-136-3p | hsa-miR-26a-2-3p | hsa-miR-421 | hsa-miR-625-5p |
| hsa-miR-136-5p | hsa-miR-26a-5p | hsa-miR-422a | hsa-miR-627 |
| hsa-miR-137 | hsa-miR-26b-3p | hsa-miR-422b | hsa-miR-628-3p |
| hsa-miR-138-1-3p | hsa-miR-26b-5p | hsa-miR-423-3p | hsa-miR-628-5p |
| hsa-miR-138-5p | hsa-miR-27a-3p | hsa-miR-423-5p | hsa-miR-629-3p |
| hsa-miR-139-3p | hsa-miR-27a-5p | hsa-miR-424-3p | hsa-miR-629-5p |
| hsa-miR-139-5p | hsa-miR-27b-3p | hsa-miR-424-5p | hsa-miR-630 |
| hsa-miR-140-3p | hsa-miR-27b-5p | hsa-miR-425-3p | hsa-miR-636 |
| hsa-miR-140-5p | hsa-miR-28-3p | hsa-miR-425-5p | hsa-miR-638 |
| hsa-miR-141-3p | hsa-miR-28-5p | hsa-miR-429 | hsa-miR-639 |
| hsa-miR-142-3p | hsa-miR-296-5p | hsa-miR-431-5p | hsa-miR-641 |
| hsa-miR-142-5p | hsa-miR-297 | hsa-miR-432-5p | hsa-miR-642a-3p |
| hsa-miR-143-3p | hsa-miR-298 | hsa-miR-433 | hsa-miR-642a-5p |
| hsa-miR-143-5p | hsa-miR-299-3p | hsa-miR-4421 | hsa-miR-646 |
| hsa-miR-144-3p | hsa-miR-299-5p | hsa-miR-449a | hsa-miR-649 |
| hsa-miR-144-5p | hsa-miR-29a-3p | hsa-miR-450a-5p | hsa-miR-651 |
| hsa-miR-145-3p | hsa-miR-29a-5p | hsa-miR-450b-3p | hsa-miR-652-3p |
| hsa-miR-145-5p | hsa-miR-29b-1-5p | hsa-miR-450b-5p | hsa-miR-653 |
| hsa-miR-1468 | hsa-miR-29b-2-5p | hsa-miR-4510 | hsa-miR-654-3p |
| hsa-miR-146a-5p | hsa-miR-29b-3p | hsa-miR-4516 | hsa-miR-659-3p |
| hsa-miR-146b-3p | hsa-miR-29c-3p | hsa-miR-451a | hsa-miR-660-5p |
| hsa-miR-146b-5p | hsa-miR-29c-5p | hsa-miR-452-3p | hsa-miR-663a |
| hsa-miR-147a | hsa-miR-301a-3p | hsa-miR-452-5p | hsa-miR-664a-3p |
| hsa-miR-148a-3p | hsa-miR-301b | hsa-miR-454-3p | hsa-miR-664a-5p |
| hsa-miR-148a-5p | hsa-miR-302a-5p | hsa-miR-454-5p | hsa-miR-668 |
| hsa-miR-148b-3p | hsa-miR-302b-5p | hsa-miR-455-3p | hsa-miR-671-3p |
| hsa-miR-148b-5p | hsa-miR-302c-5p | hsa-miR-455-5p | hsa-miR-675-3p |
| hsa-miR-149-5p | hsa-miR-302d-3p | hsa-miR-4634 | hsa-miR-675-5p |
| hsa-miR-150-3p | hsa-miR-3065-3p | hsa-miR-4732-5p | hsa-miR-7-2-3p |
| hsa-miR-150-5p | hsa-miR-3065-5p | hsa-miR-4792 | hsa-miR-7-5p |
| hsa-miR-151a-3p | hsa-miR-3074-3p | hsa-miR-483-3p | hsa-miR-708-3p |
| hsa-miR-151a-5p | hsa-miR-3074-5p | hsa-miR-483-5p | hsa-miR-708-5p |
| hsa-miR-151b | hsa-miR-30a-3p | hsa-miR-484 | hsa-miR-718 |
| hsa-miR-152 | hsa-miR-30a-5p | hsa-miR-485-5p | hsa-miR-744-5p |
| hsa-miR-153 | hsa-miR-30b-3p | hsa-miR-486-3p | hsa-miR-765 |

TABLE A-continued

Adipocyte miRNAs listed in ascending order (miRBase 19 nomenclature)

| | | | |
|---|---|---|---|
| hsa-miR-1539 | hsa-miR-30b-5p | hsa-miR-486-5p | hsa-miR-769-5p |
| hsa-miR-154-3p | hsa-miR-30c-1-3p | hsa-miR-487b | hsa-miR-770-5p |
| hsa-miR-154-5p | hsa-miR-30c-2-3p | hsa-miR-488-3p | hsa-miR-874 |
| hsa-miR-155-5p | hsa-miR-30c-5p | hsa-miR-489 | hsa-miR-885-3p |
| hsa-miR-15a-3p | hsa-miR-30d-3p | hsa-miR-491-3p | hsa-miR-887 |
| hsa-miR-15a-5p | hsa-miR-30d-5p | hsa-miR-491-5p | hsa-miR-889 |
| hsa-miR-15b-3p | hsa-miR-30e-3p | hsa-miR-492 | hsa-miR-890 |
| hsa-miR-15b-5p | hsa-miR-30e-5p | hsa-miR-493-3p | hsa-miR-891a |
| hsa-miR-16-1-3p | hsa-miR-31-3p | hsa-miR-493-5p | hsa-miR-891b |
| hsa-miR-16-2-3p | hsa-miR-31-5p | hsa-miR-494 | hsa-miR-9-5p |
| hsa-miR-16-5p | hsa-miR-3120-3p | hsa-miR-495-3p | hsa-miR-92a-3p |
| hsa-miR-17-3p | hsa-miR-3120-5p | hsa-miR-497-5p | hsa-miR-92b-3p |
| hsa-miR-17-5p | hsa-miR-3184-5p | hsa-miR-498 | hsa-miR-93-3p |
| hsa-miR-181a-2-3p | hsa-miR-32-3p | hsa-miR-499a-5p | hsa-miR-93-5p |
| hsa-miR-181a-3p | hsa-miR-32-5p | hsa-miR-500a-3p | hsa-miR-935 |
| hsa-miR-181a-5p | hsa-miR-320a | hsa-miR-501-3p | hsa-miR-942 |
| hsa-miR-181b-5p | hsa-miR-320b | hsa-miR-501-5p | hsa-miR-95 |
| hsa-miR-181c-3p | hsa-miR-320c | hsa-miR-502-3p | hsa-miR-96-3p |
| hsa-miR-181c-5p | hsa-miR-323a-3p | hsa-miR-502-5p | hsa-miR-96-5p |
| hsa-miR-181d | hsa-miR-324-3p | hsa-miR-503-5p | hsa-miR-98-5p |
| hsa-miR-182-5p | hsa-miR-324-5p | hsa-miR-504 | hsa-miR-99a-3p |
| hsa-miR-183-5p | hsa-miR-325 | hsa-miR-505-3p | hsa-miR-99a-5p |
| hsa-miR-184 | hsa-miR-326 | hsa-miR-505-5p | hsa-miR-99b-3p |
| hsa-miR-185-3p | hsa-miR-328 | hsa-miR-506-3p | hsa-miR-99b-5p |

In certain embodiments of all of the above aspects, the miRNA agent is a miRNA selected from the group consisting of the isolated miRNAs set forth in Table 7. In certain embodiments of all of the above aspects, the miRNA agent is an isolated miRNA that is 80%, 85%, 90%, 91%, 92%, 93%, 94%, 95%, 96%, 97%, 98%, or 99% identical to the sequence of a miRNA listed in Table 8. In certain embodiments of all of the above aspects, the miRNA agent is a seed sequence of a miRNA listed in Table 8.

In certain embodiments of all of the above aspects, the miRNA agent is an agomir or antagomir of a miRNA selected from the group consisting of the miRNAs set forth in Table A.

In certain embodiments of all of the above aspects, the miRNA agent is an agomir or antagomir of a miRNA selected from the group consisting of hsa-miR-1-1, hsa-miR-1-2, miR-19a-b, hsa-miR-105, hsa-miR-1283, hsa-mir-129, hsa-miR-133a-1, hsa-miR-133a-2, hsa-miR-143, hsa-mir-143-5p, hsa-mir-147, hsa-mir-149, hsa-mir-199a, hsa-mir-199b, hsa-mir-200c, hsa-mir-204, hsa-mir-205, hsa-miR-206, hsa-mir-21, hsa-mir-211, hsa-mir-218, hsa-mir-218-1, hsa-mir-218-2, hsa-mir-219-2, hsa-mir-219-2-3p, hsa-mir-22, hsa-mir-22-3p, hsa-mir-22-5p, hsa-mir-24-2, hsa-miR-30a-e, hsa-miR-3177-5p, hsa-mir-325, hsa-mir-331, hsa-mir-331-5p, hsa-miR-3613-3p, hsa-mir-362, hsa-mir-362-5p, hsa-miR-3658, hsa-mir-367, hsa-mir-371, hsa-mir-371-5p, hsa-mir-377, hsa-mir-378, hsa-mir-378a-5p, hsa-mir-382, hsa-mir-383, hsa-mir-422a, hsa-mir-425, hsa-miR-455-3p, hsa-miR-455-5p, hsa-miR-491, hsa-mir-508, hsa-mir-508-5p, hsa-mir-512-1, hsa-mir-512-2, hsa-miR-515-3p, hsa-mir-519e, hsa-miR-520a, hsa-mir-543, hsa-mir-545, hsa-mir-549, hsa-mir-556, and hsa-miR-568, hsa-mir-620, hsa-mir-643, hsa-mir-654-3p, hsa-miR-7a-g, hsa-mir-765, hsa-mir-871, hsa-mir-888, hsa-mir-888-3p, hsa-mir-92b, hsa-mir-93, hsa-mir-96, and hsa-mir-99a.

In certain embodiments of all of the above aspects, the miRNA agent is an agomir or antagomir of a miRNA selected from the group consisting of the miRNAs set forth in Table 7.

In certain embodiments of all of the above aspects, the miRNA agent is an antagomir of a miRNA selected from the group consisting of hsa-miR-19b-2-5p, hsa-miR-21-5p, hsa-miR-130b-5p, hsa-miR-211, hsa-miR-325, hsa-miR-382-3p/5p, hsa-miR-543, hsa-miR-515-3p, and hsa-miR-545.

In certain embodiments of all of the above aspects, the miRNA agent is an antagomir of a miRNA selected from the group consisting of hsa-miR-331-5p, hsa-miR-552, hsa-miR-620, and hsa-miR-1179.

In certain embodiments of all of the above aspects, the miRNA agent is linked to a targeting moiety (e.g., an aptamer). In one embodiment, the targeting moiety delivers the miRNA agent to a specific cell type or tissue.

In certain embodiments of all of the above aspects, the miRNA agent directly binds to the mRNA or promoter region of at least one mitochondrial uncoupler.

In certain embodiments of all of the above aspects, the miRNA agent directly binds to the 5'UTR or coding sequence of the mRNA of at least one mitochondrial uncoupler.

In certain embodiments of all of the above aspects, the miRNA agent directly binds to the 3'UTR of the mRNA of at least one mitochondrial uncoupler.

In certain embodiments of all of the above aspects, the miRNA agent modulates the activity of an activator or repressor of a mitochondrial uncoupling protein. In one embodiment, the miRNA agent directly binds to the mRNA or promoter region of the activator or repressor. In one embodiment, the miRNA agent directly binds to the 5'UTR or coding sequence of the mRNA of the activator or repressor. In one embodiment, the miRNA agent directly binds to the 3'UTR of the mRNA of the activator or repressor. In one embodiment, the activator or repressor is selected from the group listed in Table 1.

In certain embodiments of all of the above aspects, the mRNA or protein expression of the mitochondrial uncoupling protein is upregulated.

In certain embodiments of all of the above aspects, the mitochondrial uncoupling activity of the mitochondrial uncoupling protein is upregulated.

In another aspect, the invention provides a method of screening for a miRNA agent that modulates thermogenesis, the method generally comprising: providing an indicator cell; contacting the indicator cell with a test miRNA agent; and determining the cellular activity of at least one thermogenic regulator in the indicator cell in the presence and absence of the miRNA agent, wherein a change in the activity of the thermogenic regulator in the presence of the test miRNA agent identifies the test miRNA agent as a miRNA agent that modulates thermogenesis. The indicator cell can be a mammalian cell. In certain embodiments, the indicator cell is a human cell comprising at least a portion of a human genome.

In certain embodiments, the cell is a pre-adipocyte, adipocyte, adipose tissue derived mesenchymal stem cell, hepatocyte, myocyte, or a precursor thereof.

In certain embodiments, the cellular activity of the thermogenic regulator determined in the method is the mRNA expression level, protein expression level or mitochondrial uncoupling activity of the thermogenic regulator.

In certain embodiments, the test miRNA agent increases the activity of the thermogenic regulator compared to the level of activity of the thermogenic regulator in the absence of the test miRNA agent.

In certain embodiments, the thermogenic regulator is UCP1 or UCP2.

In another aspect, the invention provides an agomir or antagomir that modulates the activity of at least one thermogenic regulator in a cell.

In certain embodiments, the agomir or antagomir is an agomir or antagomir of a miRNA selected from the group consisting of the miRNAs set forth in Table 8.

In certain embodiments, the agomir or antagomir is an agomir or antagomir of a miRNA selected from the group consisting of the miRNAs set forth in Table A.

In certain embodiments, the agomir or antagomir is an agomir or antagomir of a miRNA selected from the group consisting of hsa-miR-1-1, hsa-miR-1-2, miR-19a-b, hsa-miR-105, hsa-miR-1283, hsa-mir-129, hsa-miR-133a-1, hsa-miR-133a-2, hsa-miR-143, hsa-mir-143-5p, hsa-mir-147, hsa-mir-149, hsa-mir-199a, hsa-mir-199b, hsa-mir-200c, hsa-mir-204, hsa-mir-205, hsa-miR-206, hsa-mir-21, hsa-mir-211, hsa-mir-218, hsa-mir-218-1, hsa-mir-218-2, hsa-mir-219-2, hsa-mir-219-2-3p, hsa-mir-22, hsa-mir-22-3p, hsa-mir-22-5p, hsa-mir-24-2, hsa-miR-30a-e, hsa-miR-3177-5p, hsa-mir-325, hsa-mir-331, hsa-mir-331-5p, hsa-miR-3613-3p, hsa-mir-362, hsa-mir-362-5p, hsa-miR-3658, hsa-mir-367, hsa-mir-371, hsa-mir-371-5p, hsa-mir-377, hsa-mir-378, hsa-mir-378a-5p, hsa-mir-382, hsa-mir-383, hsa-mir-422a, hsa-mir-425, hsa-miR-455-3p, hsa-miR-455-5p, hsa-miR-491, hsa-mir-508, hsa-mir-508-5p, hsa-mir-512-1, hsa-mir-512-2, hsa-miR-515-3p, hsa-mir-519e, hsa-miR-520a, hsa-mir-543, hsa-mir-545, hsa-mir-549, hsa-mir-556, and hsa-miR-568, hsa-mir-620, hsa-mir-643, hsa-mir-654-3p, hsa-miR-7a-g, hsa-mir-765, hsa-mir-871, hsa-mir-888, hsa-mir-888-3p, hsa-mir-92b, hsa-mir-93, hsa-mir-96, and hsa-mir-99a.

In certain embodiments, the agomir or antagomir is an antagomir of a miRNA selected from the group consisting of hsa-miR-19b-2-5p, ha-miR-21-5p, hsa-miR-130b-5p, hsa-miR-211, hsa-miR-325, hsa-miR-382-3p/5p, hsa-miR-543, hsa-miR-515-3p, and hsa-miR-545.

In certain embodiments, the agomir or antagomir is an antagomir of a miRNA selected from the group consisting of hsa-miR-331-5p, hsa-miR-552, hsa-miR-620, and hsa-miR-1179.

In certain embodiments, the agomir or antagomir is linked to a targeting moiety.

In certain embodiments, the targeting moiety is an aptamer.

In certain embodiments, the targeting moiety delivers the agomir or antagomir to a specific cell type or tissue.

In certain embodiments, the agomir or antagomir directly binds to the mRNA or promoter region of at least one mitochondrial uncoupler.

In certain embodiments, the agomir or antagomir directly binds to the 5'UTR or coding sequence of the mRNA of at least one mitochondrial uncoupler.

In certain embodiments, the agomir or antagomir directly binds to the 3'UTR of the mRNA of at least one mitochondrial uncoupler.

In certain embodiments, the agomir or antagomir modulates the activity of an activator or repressor of a mitochondrial uncoupling protein.

In certain embodiments, the activator or repressor is selected from the group listed in Table 1.

In certain embodiments, the agomir or antagomir directly binds to the mRNA or promoter region of the activator or repressor.

In certain embodiments, the agomir or antagomir directly binds to the 5'UTR or coding sequence of the mRNA of the activator or repressor. In other embodiments, the agomir or antagomir directly binds to the 3'UTR of the mRNA of the activator or repressor.

The disclosure also provides a pharmaceutical composition comprising two or more miRNAs selected from hsa-let-7a agomir, hsa-let-7a antagomir, hsa-miR-1 agomir, hsa-miR-1 antagomir, hsa-miR-19b agomir, hsa-miR-19b antagomir, hsa-miR-30b agomir and hsa-miR-30b antagomir. In certain embodiments the pharmaceutical composition also includes a pharmaceutically acceptable excipient. In certain embodiments, the two or more miRNAs are expressed from a recombinant vector. The recombinant vector can be selected from DNA plasmids, viral vectors and DNA minicircles.

The disclosure also provides a method of inducing pre-adipocytes to differentiate initially into white adipocytes and subsequently into brown adipocytes comprising administering to a population of pre-adipocytes one or more miRNAs selected from hsa-let-7a agomir, hsa-let-7a antagomir, hsa-miR-1 agomir, hsa-miR-1 antagomir, hsa-miR-19b agomir, hsa-miR-19b antagomir, hsa-miR-30b agomir and hsa-miR-30b antagomir. The one or more miRNAs can also be selected from hsa-let-7a agomir, hsa-let-7a antagomir, hsa-miR-1 agomir, hsa-miR-1 antagomir, hsa-miR-19b agomir, hsa-miR-19b antagomir, hsa-miR-30b agomir and hsa-miR-30b antagomir. In certain embodiments, the induction of pre-adipocytes to differentiate into adipocytes is greater than the differentiation of pre-adipocytes to adipocytes when pre-adipocytes are exposed to 100 mM rosiglitazone for two days followed by maintenance medium. In certain embodiments, the adipocytes are brown adipocytes. In other embodiments, the adipocytes are white adipocytes. Additional criteria for differentiation can be found in the Examples, below.

The disclosure also provides a method for decreasing the lipid content of adipocytes comprising administering to a population of adipocytes one or more miRNAs selected from the group consisting of hsa-let-7a agomir, hsa-let-7a antagomir, hsa-miR-1 agomir, hsa-miR-1 antagomir, hsa-miR-19b agomir, hsa-miR-19b antagomir, hsa-miR-30b agomir and hsa-miR-30b antagomir. In certain embodiments, the lipid content of the adipocytes is less than the lipid content of adipocytes exposed to 100 nM rosiglitazone for two days followed by maintenance medium or less than the fat content of adipocytes exposed to 100 nM rosiglitazone for the duration of culture. The duration of culture can be 8-16, 10-14 or 14 days. The duration of culture can also be 8, 9, 10, 11, 12, 13, 14, 15, 16, 17, 18, 19 or 20 days. Additional criteria for lipid content of adipocytes can be found in the Examples, below.

The disclosure also provides a method for increasing insulin sensitivity in a subject in need thereof comprising administering the subject one or more miRNAs selected from the group consisting of hsa-let-7a agomir, hsa-let-7a antagomir, hsa-miR-1 agomir, hsa-miR-1 antagomir, hsa-miR-19b agomir, hsa-miR-19b antagomir, hsa-miR-30b agomir and hsa-miR-30b antagomir.

In certain embodiments, the subject is a mammal.

The disclosure also provides a method of increasing expression or activity of one or more uncoupling proteins in a cell comprising administering to the cell one or more, two or more, or three or more miRNAs selected from the group consisting of hsa-let-7a antagomir, hsa-miR-1 agomir, hsa-miR-19b agomir and hsa-miR-30b agomir. In certain embodiments, the cell is selected from the group consisting of a brown adipocyte, a white adipocyte, a subcutaneous adipocyte, a liver cell or a muscle cell. In other embodiments, the one or more uncoupling proteins include UCP1 or UCP2. In certain embodiments, the method is an ex vivo method. In other embodiments, the method is an in vivo method. In certain embodiments, the method involves selecting a subject (e.g., a human) in need of increasing the level of expression or activity of one or more uncoupling proteins (e.g., UCP1, UCP2). In some embodiments, the subject has, or is at risk of developing, obesity. In certain embodiments, the subject has, or is at risk of developing, diabetes. In certain embodiments, the method further comprises determining the expression level (mRNA or protein) or activity of the one or more uncoupling proteins.

The disclosure also provides a method of causing fat loss in a subject in need thereof comprising administering the subject one or more miRNAs selected from the group consisting of hsa-let-7a antagomir, hsa-miR-1 agomir, hsa-miR-19b agomir and hsa-miR-30b agomir. In certain embodiments, the subject is a mammal. In other embodiments, the mammal is a human.

BRIEF DESCRIPTION OF THE DRAWINGS

FIG. 12E is a bar graph showing mRNA expression of thermogenesis targets in the presence of and hsa-miR-30b mimic.

DETAILED DESCRIPTION OF THE INVENTION

I. Definitions

Figure 1A:
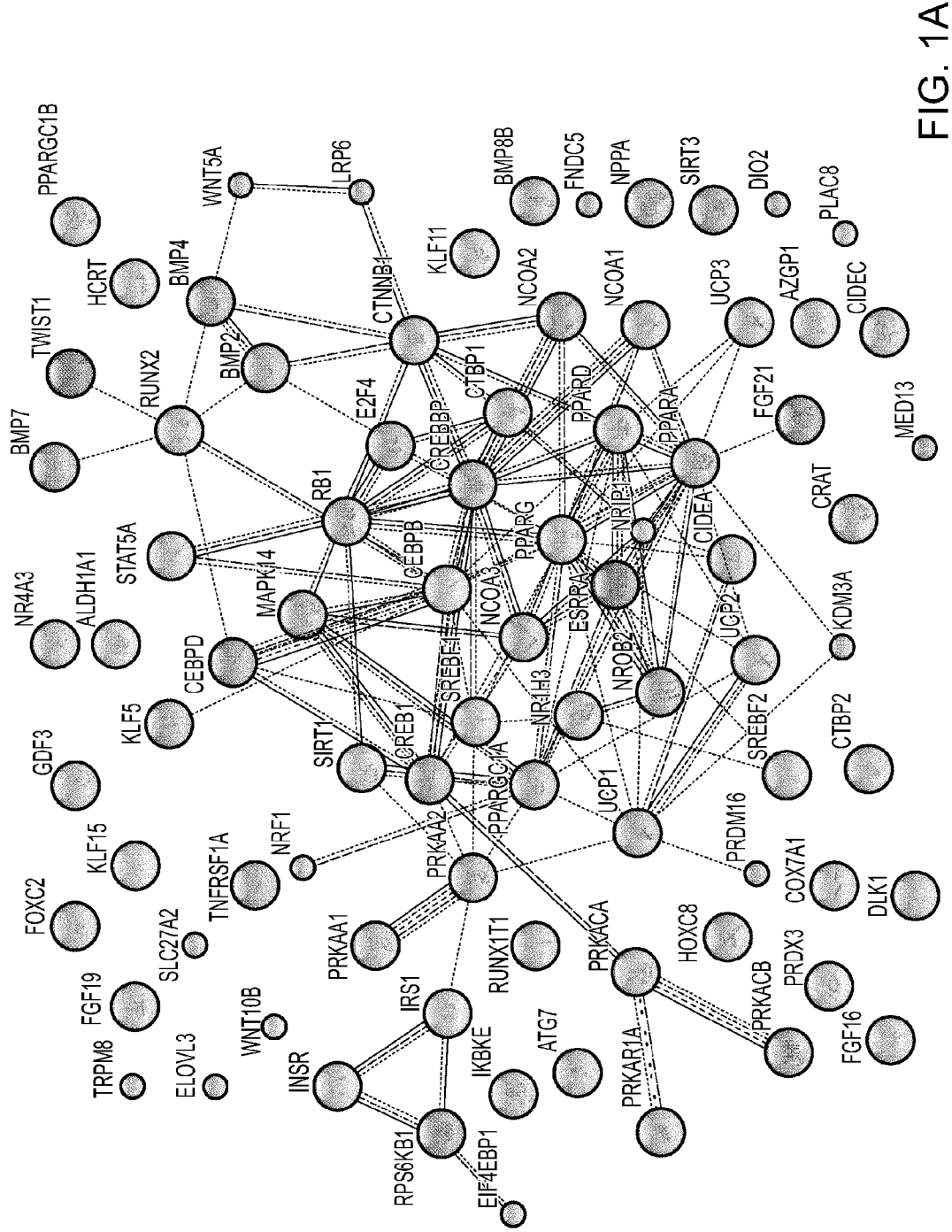
FIGS. 1A and 1B are schematic representations of the interactions of 83 thermogenic regulators determined using the STRING 9.0 database.

Unless otherwise defined, all technical and scientific terms used herein have the same meaning as commonly understood by one of ordinary skill in the art to which this invention belongs. In case of conflict, the present application, including definitions, will control.

As used herein, the term "miRNA agent" refers to an oligonucleotide or oligonucleotide mimetic that directly or indirectly modulates the activity of a thermogenic regulator (e.g., a mitochondrial uncoupler or an activator or repressor thereof). miRNA agents can act on a target gene or on a target miRNA.

As used herein, the term "miRNA" refers to a single-stranded RNA molecule (or a synthetic derivative thereof), which is capable of binding to a target gene (either the mRNA or the DNA) and regulating expression of that gene. In certain embodiments, the miRNA is naturally expressed in an organism.

As used herein, the term "seed sequence" refers to a 6-8 nucleotide (nt) long substring within the first 8 nt at the 5'-end of the miRNA (i.e., seed sequence) that is an important determinant of target specificity.

As used herein, the term "agomir" refers to a synthetic oligonucleotide or oligonucleotide mimetic that functionally mimics a miRNA. An agomir can be an oligonucleotide with the same or similar nucleic acid sequence to a miRNA or a portion of a miRNA. In certain embodiments, the agomir has 1, 2, 3, 4, 5, 6, 7, 8, 9 or 10 nucleotide differences from the miRNA that it mimics. Further, agomirs can have the same length, a longer length or a shorter length than the miRNA that it mimics. In certain embodiments, the agomir has the same sequence as 6-8 nucleotides at the 5' end of the miRNA it mimics. In other embodiments, an agomir can be 5, 6, 7, 8, 9, 10, 11, 12, 13, 14, 15, 16, 17, 18, 19, 20, 21, 22, 23, 24, 25, 27, 28, 29, 30, 31, 32, 33, 34, 35, 36, 37, 38, 39, 40, 41, 42, 43, 44, 45, 46, 47, 48, 49 or 50 nucleotides in length. In other embodiments, an agomir can be 5-10, 6-8, 10-20, 10-15 or 5-500 nucleotides in length. In certain embodiments, agomirs include any of the sequences shown in Table A. These chemically modified synthetic RNA duplexes include a guide strand that is identical or substantially identical to the miRNA of interest to allow efficient loading into the miRISC complex, whereas the passenger strand is chemically modified to prevent its loading to the Argonaute protein in the miRISC complex (Thorsen S B et al., Cancer J., 18(3):275-284 (2012); Broderick J A et al., Gene Ther., 18(12):1104-1110 (2011)).

As used herein, the term "antagomir" refers to a synthetic oligonucleotide or oligonucleotide mimetic having complementarity to a specific microRNA, and which inhibits the activity of that miRNA. In certain embodiments, the antagomir has 1, 2, 3, 4, 5, 6, 7, 8, 9 or 10 nucleotide differences from the miRNA that it inhibits. Further, antagomirs can have the same length, a longer length or a shorter length than the miRNA that it inhibits. In certain embodiments, the antagomir hybridizes to 6-8 nucleotides at the 5' end of the miRNA it inhibits. In other embodiments, an antagomir can be 5, 6, 7, 8, 9, 10, 11, 12, 13, 14, 15, 16, 17, 18, 19, 20, 21, 22, 23, 24, 25, 27, 28, 29, 30, 31, 32, 33, 34, 35, 36, 37, 38, 39, 40, 41, 42, 43, 44, 45, 46, 47, 48, 49 or 50 nucleotides in length. In other embodiments, an antagomir can be 5-10, 6-8, 10-20, 10-15 or 5-500 nucleotides in length. In certain embodiments, antagomirs include nucleotides that are complementary to any of the sequences shown in Table A. The antagomirs are synthetic reverse complements that tightly bind to and inactivate a specific miRNA. Various chemical modifications are used to improve nuclease resistance and binding affinity. The most commonly used modifications to increase potency include various 2' sugar modifications, such as 2'-O-Me, 2'-O-methoxyethyl (2'-MOE), or 2'-fluoro(2'-F). The nucleic acid structure of the miRNA can also be modified into a locked nucleic acid (LNA) with a methylene bridge between the 2' oxygen and the 4' carbon to lock the ribose in the 3'-endo (North) conformation in the A-type conformation of nucleic acids (Lennox K A et al. Gene Ther. December 2011; 18(12):1111-1120; Bader A G et al. Gene Ther. December 2011; 18(12): 1121-1126). This modification significantly increases both target specificity and hybridization properties of the molecules.

As used herein, the term "aptamir" refers to the combination of an aptamer (oligonucleic acid or peptide molecule that bind to a specific target molecule) and an agomir or antagomir as defined above, which allows cell or tissue-specific delivery of the miRNA agents.

As used herein, the term "interfering RNA" refers to any double stranded or single stranded RNA sequence capable of inhibiting or down-regulating gene expression by mediating RNA interference. Interfering RNAs include, but are not limited to, small interfering RNA ("siRNA") and small hairpin RNA ("shRNA"). "RNA interference" refers to the selective degradation of a sequence-compatible messenger RNA transcript.

As used herein, the term "small interfering RNA" or "siRNA" refers to any small RNA molecule capable of inhibiting or down regulating gene expression by mediating RNA interference in a sequence specific manner. The small RNA can be, for example, about 16 to 21 nucleotides long.

As used herein, the term "shRNA" (small hairpin RNA) refers to an RNA molecule comprising an antisense region, a loop portion and a sense region, wherein the sense region has complementary nucleotides that base pair with the antisense region to form a duplex stem. Following post-transcriptional processing, the small hairpin RNA is converted into a small interfering RNA (siRNA) by a cleavage event mediated by the enzyme Dicer, which is a member of the RNase III family.

As used herein, the term "antisense oligonucleotide" refers to a synthetic oligonucleotide or oligonucleotide mimetic that is complementary to a DNA or mRNA sequence (e.g., a miRNA).

As used herein, the term "miR-mask" refers to a single stranded antisense oligonucleotide that is complementary to a miRNA binding site in a target mRNA, and that serves to inhibit the binding of miRNA to the mRNA binding site. See, e.g., Xiao, et al. "Novel approaches for gene-specific interference via manipulating actions of microRNAs: examination on the pacemaker channel genes HCN2 and HCN4," Journal of Cellular Physiology, vol. 212, no. 2, pp. 285-292, 2007, which is incorporated herein in its entirety.

As used herein, the term "miRNA sponge" refers to a synthetic nucleic acid (e.g. a mRNA transcript) that contains multiple tandem-binding sites for a miRNA of interest, and that serves to titrate out the endogenous miRNA of interest, thus inhibiting the binding of the miRNA of interest to its endogenous targets. See, e.g., Ebert et al., "MicroRNA sponges: competitive inhibitors of small RNAs in mammalian cells," Nature Methods, vol. 4, no. 9, pp. 721-726, 2007, which is incorporated herein in its entirety.

As used herein, the term "respiratory chain uncoupling" refers to the dissipation of the mitochondrial inner membrane proton gradient, thereby preventing the synthesis of ATP in the mitochondrion by oxidative phosphorylation.

As used herein, the term "mitochondrial uncoupler" refers to a protein (or the encoding nucleic acid) that can dissipate of the mitochondrial inner membrane proton gradient, thereby preventing the synthesis of ATP in the mitochondrion by oxidative phosphorylation. Exemplary mitochondrial uncouplers include UCP1 and UCP2.

As used herein, the terms "activator" or "repressor" of a mitochondrial uncoupler refers to a protein that serves to upregulate or downregulate, respectively, an activity of a mitochondrial uncoupler.

As used herein, the term "thermogenic regulator" refers to a protein (or the encoding nucleic acid) that regulates thermogenesis either directly or indirectly. The term encompasses mitochondrial uncouplers, and also activators and repressors of mitochondrial uncouplers. Exemplary thermogenic regulators are set forth in Table 1 herein.

As used herein, the term "modulate" refers to increasing or decreasing a parameter. For example, to modulate the activity of a protein that protein's activity could be increased or decreased.

As used herein, the term "activity" of mitochondrial uncoupler or thermogenic regulator refers to any measurable biological activity including, without limitation, mRNA expression, protein expression, or respiratory chain uncoupling.

The "effective amount" of the miRNA agent composition is an amount sufficient to be effective in treating or preventing a disorder or to regulate a physiological condition in humans. In certain embodiments, this physiological condition is obesity.

A "subject" is a vertebrate, including any member of the class Mammalia, including humans, domestic and farm animals, zoo, sports or pet animals, such as mouse, rabbit, pig, sheep, goat, cattle and higher primates.

The term "mammal" refers to any species that is a member of the class mammalia, including rodents, primates, dogs, cats, camelids and ungulates. The term "rodent" refers to any species that is a member of the order rodentia including mice, rats, hamsters, gerbils and rabbits. The term "primate" refers to any species that is a member of the order primates, including monkeys, apes and humans. The term "camelids" refers to any species that is a member of the family camelidae including camels and llamas. The term "ungulates" refers to any species that is a member of the superorder ungulata including cattle, horses and camelids. According to some embodiments, the mammal is a human.

"Treatment", or "treating" as used herein, is defined as the application or administration of a therapeutic agent (e.g., a miRNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

"Pharmacogenomics", as used herein, refers to the application of genomics technologies such as gene sequencing, statistical genetics, and gene expression analysis to drugs in clinical development and on the market. More specifically, the term refers to the study of how a patient's genes determine his or her response to a drug (e.g., a patient's "drug response phenotype", or "drug response genotype").

The "effective amount" of the miRNA agent composition is an amount sufficient to be effective in treating or preventing a disorder or to regulate a physiological condition in humans.

II. Thermogenesis and Obesity

In certain embodiments, the invention provides methods for modulating thermogenesis. These methods generally involve contacting cells or tissue with a miRNA agent that modulates activity of at least one mitochondrial uncoupler (e.g., UCP1 and/or UCP2). Such methods and compositions are particularly useful for treating obesity.

Mammalian adipocytes can be categorized into two major categories based on their functional profiles: 1) energy-storing and releasing, lipid-filled white adipocytes (WAT) and; 2) energy-expending and heat producing, mitochondria-rich brown adipocytes (BAT). Until recently, it was believed that BAT underwent rapid involution in early childhood, leaving only vestigial amounts in adults. However, positron-emission tomography (PET) studies performed in humans with the tracer 18F-fluorodeoxyglucose (18F-FDG) demonstrated that: 1) multiple depots of BAT are still present in the cervical, supraclavicular, axillary and paravertebral regions in adult subjects; 2) BAT in adult humans can be rapidly activated by exposure to cold temperatures; 3) there is an inverse correlation between the activity of BAT and age, body-mass index (BMI), the percentage of body fat, fasting plasma glucose level, beta-blocker use and outdoor temperature; and 4) BAT expansion may drive the weight loss associated with catecholamine-producing phaeochromocytomas, whereas beta3-adrenoreceptor polymorphisms leading to a reduction in receptor function have been linked to weight gain and early onset type 2 diabetes mellitus.

Although WAT and BAT are derived from mesenchymal stem cells, they have distinct lineages, with Myf5 (Myogenic Regulatory Factor 5) (shared with skeletal myocyte progenitors), PGC-1alpha and PRDM16 (PR-domain-containing 16) expression distinguishing the brown from white adipocyte precursors. In addition to the classic brown adipocytes, a different type of brown fat cells can be induced in tissues where WAT predominates. The termed "brite" (brown-in-white) adipocyte has been coined and the appearance of brown-like adipocytes within WAT depots is associated with improved metabolic phenotypes. Increasing BAT mass and/or activity offers a degree of protection from obesity. Heat production by BAT is 300 W/g compared to 1 W/g in all other tissues. Relatively limited amounts of BAT would be required to make significant impact on energy balance, since as little as 50 g of BAT would account for 20% of daily energy expenditure. It has been speculated that the estimated 63 g of BAT found in the supraclavicular/paracervical depot of one subject could combust the energy equivalent of 4.1 kg of WAT over 1 year.

Mitochondrial uncoupling proteins (UCP) are members of the family of mitochondrial anion carrier proteins (MACP). UCPs separate oxidative phosphorylation from ATP synthesis with energy dissipated as heat (also referred to as the "mitochondrial proton leak"). UCPs facilitate the transfer of anions from the inner to the outer mitochondrial membrane and the return transfer of protons from the outer to the inner mitochondrial membrane generating heat in the process. UCPs are the primary proteins responsible for thermogenesis and heat dissipation. Uncoupling Protein 1 (UCP1), also named thermogenin, is a BAT specific protein responsible for thermogenesis and heat dissipation. UCP2 is another Uncoupling Protein also expressed in adipocytes. UCPs are part of network of thermogenic regulator proteins (see FIG. 1). Exemplary thermogenic regulators are set forth in Table 1.

Modulation of thermogenic regulators to induce BAT differentiation and/or mitochondrial uncoupling proteins provides a method to induce thermogenesis in a subject and, hence, to treat obesity. However, chemical pharmacologic approaches cannot target these molecules, as they do not belong to the classic 'target classes' (kinases, ion channels, G-protein coupled receptors, etc.) that dominate the 'druggable space' of traditional drug discovery. Accordingly, the invention provides novel methods and compositions for modulating these thermogenic regulators using miRNA agents.

In certain embodiments, miRNA agents are employed to upregulate the activity of a mitochondrial uncoupler (e.g., the mRNA expression level, protein expression level, or mitochondrial uncoupling activity). Upregulation of a mitochondrial uncoupler can be achieved in several ways. In one embodiment, the miRNA agent directly inhibits the activity of a naturally occurring miRNA that is responsible for downregulation of the activity (e.g., the mRNA expression level, protein expression level) of the mitochondrial uncoupler. In another embodiment, the miRNA agent upregulates the activity (e.g., the mRNA expression level or the protein expression level) of an activator of the mitochondrial uncoupler. This upregulation can be achieved, for example, by directly inhibiting the activity of a naturally occurring miRNA that is responsible for downregulation of the expression of the activator. In yet another embodiment, the miRNA agent downregulates the activity (e.g., the mRNA expression level or the protein expression level) of a repressor of the mitochondrial uncoupler. This downregulation can be achieved, for example, by directly inhibiting the expression of a repressor of a mitochondrial uncoupler using a miRNA agent.

In certain embodiments, miRNA agents are employed that are capable of modulating the activity of multiple thermogenic regulators simultaneously (Pathway-specific miRNA agents as opposed to universal miRNA agents). For example, a single miRNA, agomir or antagomir that binds to multiple thermogenic regulators can be used. This approach is particularly advantageous in that it allows for the modulation of multiple members of an entire signaling pathway using a single miRNA agent.

In certain embodiments, multiple inhibitory miRNA agents (e.g., antagomirs or miR-masks) are employed. These inhibitory miRNA agents can have the same or different miRNA targets.

III. miRNA Agents

In certain embodiments, the invention employs miRNA agents for the modulation of thermogenic regulators (e.g., mitochondrial uncouplers, such as UCP1 and/or UCP2). miRNA agents, suitable for use in the methods disclosed herein, included, without limitation, miRNA, agomirs, antagomirs, miR-masks, miRNA-sponges, siRNA (single- or double-stranded), shRNA, antisense oligonucleotides, ribozymes, or other oligonucleotide mimetics which hybridize to at least a portion of a target nucleic acid and modulate its function.

In certain embodiments, the miRNA agents are miRNA molecules or synthetic derivatives thereof (e.g., agomirs). In one particular embodiment, the miRNA agent is a miRNA. miRNAs are a class of small (e.g., 18-24 nucleotides) noncoding RNAs that exist in a variety of organisms, including mammals, and are conserved in evolution. miRNAs are processed from hairpin precursors of about 70 nucleotides which are derived from primary transcripts through sequential cleavage by the RNAse III enzymes drosha and dicer. Many miRNAs can be encoded in intergenic regions, hosted within introns of pre-mRNAs or within ncRNA genes. Many miRNAs also tend to be clustered and transcribed as polycistrons and often have similar spatial temporal expression patterns. In general, miRNAs are post-transcriptional regulators that bind to complementary sequences on a target gene (mRNA or DNA), resulting in gene silencing by, e.g., translational repression or target degradation. One miRNA can target many different genes simultaneously. Exemplary miRNA molecules for use in the disclosed methods include without limitation: hsa-miR-1-1, hsa-miR-1-2, hsa-miR-7a-g, hsa-miR-105, hsa-miR-1283, hsa-mir-129, hsa-miR-133a-1, hsa-miR-133a-2, hsa-miR-143, hsa-mir-143-5p, hsa-mir-147, hsa-mir-149, hsa-miR-19a-b, hsa-mir-199a, hsa-mir-199b, hsa-mir-200c, hsa-mir-204, hsa-mir-205, hsa-miR-206, hsa-mir-21, hsa-mir-211, hsa-mir-218, hsa-mir-218-1, hsa-mir-218-2, hsa-mir-219-2, hsa-mir-219-2-3p, hsa-mir-22, hsa-mir-22-3p, hsa-mir-22-5p, hsa-mir-24-2, hsa-miR-30a-e, hsa-miR-3177-5p, hsa-mir-325, hsa-mir-331, hsa-mir-331-5p, hsa-miR-3613-3p, hsa-mir-362, hsa-mir-362-5p, hsa-mir-367, hsa-mir-371, hsa-mir-371-5p, hsa-mir-377, hsa-mir-378, hsa-mir-378a-5p, hsa-mir-382, hsa-mir-383, hsa-miR-3658, hsa-mir-422a, hsa-mir-425, hsa-miR-455-3p, hsa-miR-455-5p, hsa-miR-491, hsa-mir-508, hsa-mir-508-5p, hsa-mir-512-1, hsa-mir-512-2, hsa-miR-515-3p, hsa-mir-519e, hsa-miR-520a, hsa-mir-543, hsa-mir-545, hsa-mir-549, hsa-mir-556, hsa-miR-568, hsa-mir-620, hsa-mir-643, hsa-mir-654-3p, hsa-mir-765, hsa-mir-871, hsa-mir-888, hsa-mir-888-3p, hsa-mir-92b, hsa-mir-93, hsa-mir-96, hsa-mir-99a. In other embodiments, exemplary miRNA molecules for use in the disclosed methods miRNA disclosed in Table A and/or Table 8, herein. In one particular embodiment, the miRNA agent is human miR-22, or a functional derivative thereof.

In another particular embodiment, the miRNA agent is an agomir. Agomirs of a particular miRNA can be identified using the screening methods disclosed herein. In one particular embodiment, the agomir is a functional mimetic of human miR-22 (Davidson B L et al., Nat Rev Genet., 12(5):329-340 (2011).

In certain embodiments, the miRNA agents are oligonucleotide or oligonucleotide mimetics that inhibit the activity of one or more miRNA. Examples of such molecules include, without limitation, antagomirs, interfering RNA, antisense oligonucleotides, ribozymes, miRNA sponges and miR-masks. In one particular embodiment, the miRNA agent is an antagomir. In general, antagomirs are chemically modified antisense oligonucleotides that bind to a target miRNA and inhibit miRNA function by preventing binding of the miRNA to its cognate gene target. Antagomirs can include any base modification known in the art. In one particular embodiment, the antagomir inhibits the activity of human miR-22 (van Rooij E et al., Circ Res., 110(3):496-507 (2012); Snead N M et al., Nucleic Acid Ther., 22(3):139-146 (2012); Czech M P et al., Nat Rev Endocrinol., 7(8):473-484 (2011).

In certain embodiments, the miRNA agents are 10 to 50 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin.

In certain embodiments, the miRNA agents are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5, 220,007; 5,256,775; 5,366,878; 5,403,711; 5,491,133; 5,565,350; 5,623,065; 5,652,355; 5,652,356; and 5,700,922, each of which is herein incorporated by reference in its entirety.

In certain embodiments, the miRNA agents comprise at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, a basic residue or an inverted base at the 3' end of the RNA. Such modifications are routinely incorporated into oligonucleotides and these oligonucleotides have been shown to have a higher Tm (i.e., higher target binding affinity) than 2'-deoxyoligonucleotides against a given target.

A number of nucleotide and nucleoside modifications have been shown to make an oligonucleotide more resistant to nuclease digestion, thereby prolonging in vivo half-life. Specific examples of modified oligonucleotides include those comprising backbones comprising, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, ~N($CH_3$)~O~$CH_2$ (known as a methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—$CH_1$); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497), each of which is herein incorporated by reference in its entirety. Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3' alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321, 131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050, each of which is herein incorporated by reference in its entirety. Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol, 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991, each of which is herein incorporated by reference in its entirety. Cyclohexenyl nucleic acid oligonucleotide mimetics are described in Wang et al., J. Am. Chem. Soc., 2000, 122, 8595-8602, the contents of which is incorporated herein in its entirety.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference in its entirety.

In certain embodiments, miRNA agents comprise one or more substituted sugar moieties, e.g., one of the following at the 2' position: OH, SH, $SCH_3$, F, OCN, $OCH_3OCH_3$, $OCH_3O(CH_2)nCH_3$, $O(CH_2)nNH_2$ or $O(CH_2)nCH_3$ where n is from 1 to about 10; Ci to ClO lower alkyl, alkoxyalkoxy, substituted lower alkyl, alkaryl or aralkyl; Cl; Br; CN; CF3; OCF3; O-, S-, or N-alkyl; O-, S-, or N-alkenyl; $SOCH_3$; $SO_2$ $CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacokinetic/pharmacodynamic properties of an oligonucleotide and other substituents having similar properties. A preferred modification includes 2'-methoxyethoxy [2'-O—$CH_2CH_2OCH_3$, also known as 2'-O-(2-methoxyethyl)] (Martin et al., Helv. Chim. Acta, 1995, 78, 486). Other preferred modifications include 2'-methoxy (2'-O—$CH_3$), 2'-propoxy (2'-$OCH_2$ $CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

In certain embodiments, miRNA agents comprise one or more base modifications and/or substitutions. As used herein, "unmodified" or "natural" bases include adenine (A), guanine (G), thymine (T), cytosine (C) and uracil (U). Modified bases include, without limitation, bases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic bases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco 1980, pp 75-77; Gebeyehu, G., et al. Nucl. Acids Res. 1987, 15:4513). A "universal" base known in the art, e.g., inosine, can also be included. 5-Me-C substitutions can also be included. These have been shown to increase nucleic acid duplex stability by 0.6-1.2OC. (Sanghvi, Y. S., in Crooke, S. T. and Lebleu, B., eds., Antisense Research and Applications, CRC Press, Boca Raton, 1993, pp. 276-278). Further suitable modified bases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

It is not necessary for all positions in a given oligonucleotide to be uniformly modified, and in fact more than one of the aforementioned modifications may be incorporated in a single oligonucleotide or even at a single nucleoside within an oligonucleotide.

In certain embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

In certain embodiments, the miRNA agent is linked (covalently or non-covalently) to one or more moieties or conjugates that enhance the activity, cellular distribution, or cellular uptake of the oligonucleotide. Such moieties include, without limitation, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937), each of which is herein incorporated by reference in its entirety. See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference in its entirety.

In one particular embodiment, the miRNA agent is linked to (covalently or non-covalently) to a nucleic acid aptamer. Aptamers are synthetic oligonucleotides or peptide molecules that bind to a specific target molecule. Aptamers appropriate for use with the miRNA agents provided herein are described in U.S. Provisional Patent Application No. 61/695,477 filed Aug. 31, 2012 and incorporated by reference herein in its entirety.

Accordingly, in a first aspect, the invention provides an adipocyte-specific miRNA modulator composition comprising i) a targeting moiety that selectively binds to a cellular surface marker on an adipose target cell in a human and ii) a thermogenic miRNA modulator moiety, wherein the targeting moiety facilitates uptake of the miRNA modulatory moiety by the target cell such that the miRNA is capable of targeting a thermogenic pathway and upregulating thermogenesis in the target cell.

In one embodiment, the composition comprises an aptamir comprising an aptamer as the targeting moiety.

In certain embodiments, the aptamers used with the miRNAs disclosed herein specifically bind to cell surface marker proteins on an adipose tissue mesenchymal stem cell (AT-MSC), white adipose tissue (WAT) adipocytes and brown adipose tissue (BAT) adipocytes. Cell surface markers for ATMSCs include CD9, CD10, CD13, CD29, CD36, CD44, CD49d, CD54, CD55, CD59, CD73, CD90, CD91, CD105, CD137, CD146, CD166, and HLA-ABC. Cell surface markers for WAT adipocytes include Adiponectin, Caveolin-1, Caveolin-2, CD36 (FAT), CLH-22 (Clathrin Heavy Chain Chr 22), FABP4 (Adipocyte protein 2, aP2), SLC27A1 (FATP1), SLC27A2 (FATP2), GLUT4 (Glucose Transporter 4), Perilipin 2 or Resistin. Cell surface markers for all adipocytes include Neprilysin (CD10), FAT (CD36), Thy-1 (CD90), Low density lipoprotein receptor-related protein 1 (LRP1 or CD91), Caveolin-1, Caveolin-2, Fatty acid binding protein 4 (FABP4), Cell surface glycoprotein MUC18 (CD146), Activated leukocyte cell adhesion molecule (CD166) and Natriuretic peptide receptor A (NPR1). According to other embodiments, the aptamers for use with the miRNAs disclosed herein can also specifically bind to markers of adipose tissue including adiponectin, leptin, resistin, FGF 17, FGF 19, BMP7, PYY, MetAP2, RBP4, endostatin, and angiostatin.

In certain embodiments, the aptamers are selected by the Cell-SELEX technology, which uses whole living cells as the target, whereby aptamers that recognize specific molecules in their native conformation in their natural environment on the surface of intact cells are selected by repeated amplification and binding to living cells. In this cell-based selection, specific cell surface molecules or even unknown membrane receptors can be directly targeted within their native environment, allowing a straightforward enrichment of cell-specific aptamers.

In certain exemplary embodiments, the miRNA modulator is combined with an aptamer to create an "AptamiR" composition. There are many different ways to combine an aptamer and miRNA analog(s) to create an aptamir. They include, for example, aptamer-miRNA analog chimeras, aptamer-splice-switching oligonucleotide chimeras, and aptamer conjugated to nanoparticles or liposomes containing the miRNA analog(s). "Escort Aptamers" may be inserted at the surface of functional polymers, liposomes, and nanoparticles, each of which can carry many miRNA analogs. For instance, the size of thioaptamer-conjugated liposomes is about 120 nm. Nanoparticle approaches have several functional advantages, including, for example, cellular uptake, the ability to cross membranes, and triggered nanoparticle disassembly.

In one embodiment, an aptamiR composition comprises an aptamer that is directly linked or fused to a miRNA modulator. Such aptamiR5 are entirely chemically synthesized, which provides more control over the composition of the conjugate. For instance, the stoichiometry (ratio of miRNA analog per aptamer) and site of attachment can be precisely defined. The linkage portion of the conjugate presents a plurality (2 or more) of nucleophilic and/or electrophilic moieties that serve as the reactive attachment point for the aptamers and miRNA analogs. In addition, the aptamir may further comprise a linker between the aptamer and the miRNA analog. In some embodiments, the linker is a polyalkylene glycol, particularly a polyethylene glycol. In other embodiments, the linker is a liposome, exosome, dendrimer, or comb polymer. Other linkers can mediate the conjugation between the aptamer and the miRNA analog, including a biotinstreptavidin bridge, or a ribonucleic acid. Exemplary non-covalent linkers include linkers formed by base pairing a single stranded portion or overhang of the miRNA moiety and a complementary single-stranded portion or overhang of the aptamer moiety.

In another particular embodiment, an aptamer is combined with a miRNA analog in the form of a liposome-based aptamiR. Liposomes are spherical nanostructures made of a lipid bilayer that can be loaded with pharmaceuticals, such as miRNAs. Furthermore, the liposome surface can be loaded with different substances, such as polyethylene glycol (extending their systemic half life) or molecular recognition moieties like aptamers for specific binding to targeted cells. For example, aptamer-modified liposomes have been developed, with each liposome displaying approximately 250 aptamers tethered to its surface to facilitate target binding. In a preferred embodiment, liposomes are created to encapsulate miRNA analog(s) and display at their surface aptamers that specifically bind with high affinity and specificity to molecules (e.g. lipid transporters) highly expressed at the surface of adipocytes and ATMSCs. The fusion of the liposomes with the targeted cells causes the release of the miRNA analog(s) into the cell cytoplasm, which then alter a specific intra-cellular pathway. Alternatively, stable thioaptamers may be inserted at the surface of liposomes to guide delivery of the liposome miRNA analog(s) load to targeted ATMSCs and adipocytes.

In a further particular embodiment, an aptamer is combined with a miRNA analog in the form of a carrier-based aptamiR. Exemplary carriers include nanoparticles, lipsomes or exosomes. Such carrier-based aptamiR compositions have the capability of delivering a cargo of multiple miRNA modulators to the target cell in a single carrier. To accomplish targeting and accumulation, the carriers are formulated to present the targeting moiety on their external surface so they can react/bind with selected cell surface antigens or receptors on the adipose target cell. As an example, carriers may be created to encapsulate miRNA modulators while displaying at their surface aptamers that specifically bind with high affinity and specificity to molecules (e.g. lipid transporters) highly expressed at the surface of adipocytes and ATMSCs. The internalized exosomes release inside the cell cytoplasm their miRNA analog(s) load, which alters a specific intracellular pathway.

In one embodiment, the carrier is an exosome. Exosomes, which originate from late endosomes, are naturally occurring nanoparticles that are specifically loaded with proteins, mRNAs, or miRNAs, and are secreted endogenously by cells. Exosomes are released from host cells, are not cytotoxic, and can transfer information to specific cells based on their composition and the substance in/on the exosome. Because exosomes are particles of approximately 20-100 nm in diameter, the exosomes evade clearance by the mononuclear phagocyte system (which clears circulating particles >100 nm in size), and are very efficiently delivered to target tissues.

Moreover, synthetic exosomes may offer several advantages over other carriers. For example, they may deliver their cargo directly into the cytosol, while their inertness avoids attack and clearance in the extracellular environment. The structural constituents of exosomes may include small molecules responsible for processes like signal transduction, membrane transport, antigen presentation, targeting/adhesion, among many others.

The miRNA agents must be sufficiently complementary to the target mRNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of a miRNA agent is capable of hydrogen bonding with a base at the corresponding position of a target nucleic acid sequence, then the bases are considered to be complementary to each other at that position. In certain embodiments, 100% complementarity is not required. In other embodiments, 100% complementarity is required.

miRNA agents for use in the methods disclosed herein can be designed using routine methods. While the specific sequences of certain exemplary target nucleic acid sequences and miRNA agents are set forth herein, one of skill in the art will recognize that these serve to illustrate and describe particular embodiments within the scope of the present invention. Additional target segments are readily identifiable by one having ordinary skill in the art in view of this disclosure. Target segments of 5, 6, 7, 8, 9, 10 or more nucleotides in length comprising a stretch of at least five (5) consecutive nucleotides within the seed sequence, or immediately adjacent thereto, are considered to be suitable for targeting a gene. In some embodiments, target segments can include sequences that comprise at least the 5 consecutive nucleotides from the 5'-terminus of one of the seed sequence (the remaining nucleotides being a consecutive stretch of the same RNA beginning immediately upstream of the 5'-terminus of the seed sequence and continuing until the miRNA agent contains about 5 to about 30 nucleotides). In some embodiments, target segments are represented by RNA sequences that comprise at least the 5 consecutive nucleotides from the 3'-terminus of one of the seed sequence (the remaining nucleotides being a consecutive stretch of the same miRNA beginning immediately downstream of the 3'-terminus of the target segment and continuing until the miRNA agent contains about 5 to about 30 nucleotides). One having skill in the art armed with the sequences provided herein will be able, without undue experimentation, to identify further preferred regions to target using miRNA agents. Once one or more target regions, segments or sites have been identified, inhibitory nucleic acid compounds are chosen that are sufficiently complementary to the target, i.e., that hybridize sufficiently well and with sufficient specificity (i.e., do not substantially bind to other non-target nucleic acid sequences), to give the desired effect.

In certain embodiments, miRNA agents used to practice this invention are expressed from a recombinant vector. Suitable recombinant vectors include, without limitation, DNA plasmids, viral vectors or DNA minicircles. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989), Coffin et al. (Retroviruses. (1997) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors can be delivered as described herein, and persist in target cells (e.g., stable transformants).

In certain embodiments, miRNA agents used to practice this invention are synthesized in vitro using chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68: 109; Beaucage (1981) Tetra. Lett. 22: 1859; U.S. Pat. No. 4,458,066, each of which is herein incorporated by reference in its entirety.

IV. Methods of Treatment

In one aspect, the invention provides a method of treating obesity in human subject. The method generally comprises administering to the human subject an effective amount of a miRNA agent that modulates activity of at least one thermogenic regulator, (e.g., a mitochondrial uncoupler, such as UCP1 and/or UCP2).

Such methods of treatment may be specifically tailored or modified, based on knowledge obtained from the field of pharmacogenomics. Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

miRNA agents can be tested in an appropriate animal model e.g., an obesity model including ob/ob mice (Lindstrom P., ScientificWorld Journal, 7:666-685 (2007) and db/db mice (Sharma K et al., Am J Physiol Renal Physiol., 284(6):F1138-1144 (2003)). For example, a miRNA agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, a miRNA agent can be used in an animal model to determine the efficacy, toxicity, or side effects of treatment with such an agent. Alternatively, an agent can be used in an animal model to determine the mechanism of action of such an agent.

The disclosure also provides a method of inducing pre-adipocytes to differentiate into white adipocytes and white adipocytes into brown adipocytes, comprising administering to a population of pre-adipocytes one or more miRNAs selected from hsa-let-7a agomir, hsa-let-7a antagomir, hsa-miR-1 agomir, hsa-miR-1 antagomir, hsa-miR-19 agomir, hsa-miR-19b agomir, hsa-miR-19b antagomir, hsa-miR-30b agomir and hsa-miR-30b antagomir. In certain embodiments, the induction of pre-adipocytes to differentiate into adipocytes is greater than the differentiation of pre-adipocytes to adipocytes than when pre-adipocytes are exposed to 100 mM rosiglitazone for two days followed by maintenance medium. In certain embodiments, the adipocytes are brown adipocytes. In other embodiments, the adipocytes are white adipocytes.

The disclosure also provides a method for increasing insulin sensitivity in a subject in need thereof comprising administering the subject one or more miRNAs selected from the group consisting of hsa-let-7a agomir, hsa-let-7a antagomir, hsa-miR-1 agomir, hsa-miR-1 antagomir, hsa-miR-19 agomir, hsa-miR-19b agomir, hsa-miR-19b antagomir, hsa-miR-30b agomir and hsa-miR-30b antagomir. In certain embodiments, the subject is a mammal.

The disclosure also provides a method of causing fat loss in a subject in need thereof comprising administering the subject one or more miRNAs selected from the group consisting of hsa-let-7a antagomir, hsa-miR-1 agomir, hsa-miR-19b agomir and hsa-miR-30b agomir. In certain embodiments, the subject is a mammal. In other embodiments, the mammal is a human.

A miRNA agent modified for enhancing uptake into cells (e.g., adipose cells) can be administered at a unit dose less than about 15 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of miRNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA silencing agent per kg of bodyweight. The unit dose, for example, can be administered by injection (e.g., intravenous or intramuscular), an inhaled dose, or a topical application. Particularly preferred dosages are less than 2, 1, or 0.1 mg/kg of body weight.

Delivery of a miRNA agent directly to an organ or tissue (e.g., directly to adipose tissue) can be at a dosage on the order of about 0.00001 mg to about 3 mg per organ/tissue, or preferably about 0.0001-0.001 mg per organ/tissue, about 0.03-3.0 mg per organ/tissue, about 0.1-3.0 mg per organ/tissue or about 0.3-3.0 mg per organ/tissue. The dosage can be an amount effective to treat or prevent obesity or to increase insulin sensitivity. In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. In one embodiment, the effective dose is administered with other traditional therapeutic modalities.

In certain embodiment, a subject is administered an initial dose, and one or more maintenance doses of a miRNA agent. The maintenance dose or doses are generally lower than the initial dose, e.g., one-half less of the initial dose. A maintenance regimen can include treating the subject with a dose or doses ranging from 0.01 mg/kg to 1.4 mg/kg of body weight per day, e.g., 10, 1, 0.1, 0.01, 0.001, or 0.00001 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in condition, e.g., changes in percentage body fat. The dosage of the compound may either be increased in the event the patient does not respond significantly to current dosage levels, or the dose may be decreased if a decrease in body fat is observed, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., sub-cutaneous, intravenous, intraperitoneal, intracisternal or intracapsular), or reservoir may be advisable. In one embodiment, a pharmaceutical composition includes a plurality of miRNA agent species. In another embodiment, the miRNA agent species has sequences that are non-overlapping and non-adjacent to another species with respect to a naturally occurring target sequence. In another embodiment, the plurality of miRNA agent species is specific for different naturally occurring target genes. In another embodiment, the miRNA agent is allele specific. In another embodiment, the plurality of miRNA agent species target two or more SNP alleles (e.g., two, three, four, five, six, or more SNP alleles).

Following successful treatment, it may be desirable to have the patient undergo maintenance therapy to prevent the recurrence of the disease state, wherein the compound of the invention is administered in maintenance doses, ranging from 0.01 mg per kg to 100 mg per kg of body weight (see U.S. Pat. No. 6,107,094).

The concentration or amount of miRNA agent administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a miRNA agent can include a single treatment or, preferably, can include a series of treatments. It will also be appreciated that the effective dosage of a miRNA agent for treatment may increase or decrease over the course of a particular treatment. Changes in dosage may result and become apparent from the results of diagnostic assays as described herein. For example, the subject can be monitored after administering a miRNA agent composition. Based on information from the monitoring, an additional amount of the miRNA agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human gene, e.g., a gene that produces a target mRNA (e.g., a thermogenic regulator). The transgenic animal can be deficient for the corresponding endogenous mRNA. In another embodiment, the composition for testing includes a miRNA agent that is complementary, at least in an internal region, to a sequence that is conserved between a nucleic acid sequence in the animal model and the target nucleic acid sequence in a human.

Several studies have reported successful mammalian dosing using miRNA agents. For example, Esau C, et al., Cell Metabolism, 3(2): 87-98 (2006) reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, nontoxic dose. Another study by Krutzfeldt J., et al., Nature, 438, 685-689 (2005), injected antagomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) Nature 452, 896-899, report that efficient silencing of miR-122 was achieved in primates by three doses of 10 mg per kg LNA-antimiR, leading to a long-lasting and reversible decrease in total plasma cholesterol without any evidence for LNA-associated toxicities or histopathological changes in the study animals.

In certain embodiments, miRNA agents used to practice this invention are administered through expression from a recombinant vector. Suitable recombinant vectors include, without limitation, DNA plasmids, viral vectors or DNA minicircles. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors can be delivered as described herein, and persist in target cells (e.g., stable transformants).

miRNA agents may be directly introduced into a cell (e.g., an adipocyte); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The miRNA agents of the invention can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The miRNA agents may be introduced along with other components e.g., compounds that enhance miRNA agent uptake by a cell.

In certain embodiments, the methods described herein include co-administration of miRNA agents with other drugs or pharmaceuticals, e.g., compositions for modulating thermogenesis, compositions for treating diabetes, compositions for treating obesity. Compositions for modulating thermogenesis include beta-3 adrenergic agonists, thyroid hormones, PPARG agonists, leptin, adiponectin, and orexin.

V. Screening Methods

In another aspect, the invention provides a method of screening for a miRNA agent that modulates thermogenesis, decreases obesity, or improves insulin sensitivity. The method generally comprises the steps of: providing an indicator cell; contacting the indicator cell with a test miRNA agent; and determining the expression level and/or cellular activity of at least one thermogenic regulator in the indicator cell in the presence and absence of the miRNA agent, wherein a change in the activity of the thermogenic regulator in the presence of the test miRNA agent identifies the test miRNA agent as a miRNA agent that modulates thermogenesis, decreases obesity, or improves insulin sensitivity. In certain embodiments, the method involves determining an increase the expression level and/or activity of the thermogenic regulator (e.g., UCP1, UCP2). The indicator cell can be a mammalian cell. In certain embodiments, the mammalian cell is a human cell, which comprises at least a portion of a human genome.

Any thermogenic regulator can be assayed in the methods disclosed herein. Exemplary thermogenic regulators are set forth in Table 1. In a preferred embodiment, the thermogenic regulator is a mitochondrial uncoupling protein e.g., UCP1 and/or UCP2.

Any cell in which the activity of a thermogenic regulator can be measured is suitable for use in the methods disclosed herein. Exemplary cells include pre-adipocytes, adipocytes, adipose tissue derived mesenchymal stem cells, hepatocytes, myocytes, or precursors thereof.

Any activity of a thermogenic regulator can be assayed, including, without limitation, mRNA expression level, protein expression level or mitochondrial uncoupling activity of the thermogenic regulator. Methods for determining such activities are well known in the art.

Any miRNA agent can be screened, including, without limitation, miRNA, agomirs, antagomirs, aptamirs, miR-masks, miRNA sponges, siRNA (single- or double-stranded), shRNA, antisense oligonucleotides, ribozymes, or other oligonucleotide mimetics which hybridize to at least a portion of a target nucleic acid and modulate its function.

VI. Pharmaceutical Compositions

In one aspect, the methods disclosed herein can include the administration of pharmaceutical compositions and formulations comprising miRNA agents capable of modulating the activity of at least one thermogenic modulator.

In certain embodiments, the compositions are formulated with a pharmaceutically acceptable carrier. The pharmaceutical compositions and formulations can be administered parenterally, topically, by direct administration into the gastrointestinal tract (e.g., orally or rectally), or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., Remington: The Science and Practice of Pharmacy, 21st ed., 2005.

The miRNA agents can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations of the invention can be prepared according to any method known to the art for the manufacture of pharmaceuticals. Such drugs can contain sweetening agents, flavoring agents, coloring agents and preserving agents. A formulation can be admixtured with non-toxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragées, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragée cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In certain embodiments, oil-based pharmaceuticals are used for administration of the miRNA agents. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

In certain embodiments, the pharmaceutical compositions and formulations are in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

In certain embodiments, the pharmaceutical compositions and formulations are administered by in intranasal, intraocular and intravaginal routes including suppositories, insufflation, powders and aerosol formulations (for examples of steroid inhalants, see e.g., Rohatagi (1995) J. Clin. Pharmacol. 35: 1187-1193; Tjwa (1995) Ann. Allergy Asthma Immunol. 75: 107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In certain embodiments, the pharmaceutical compositions and formulations are delivered transdermally, by a topical route, formulated as applicator sticks, solutions, suspensions, emulsions, gels, creams, ointments, pastes, jellies, paints, powders, and aerosols.

In certain embodiments, the pharmaceutical compositions and formulations are delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In certain embodiments, the pharmaceutical compositions and formulations are parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In certain embodiments, the pharmaceutical compounds and formulations are lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL nucleic acid, about 15 mg/mL sucrose, about 19 mg/mL NaCl, and a sodium citrate buffer having a pH greater than 5.5 but less than 6.5. See, e.g., U.S. 20040028670.

In certain embodiments, the pharmaceutical compositions and formulations are delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46: 1576-1587.

The formulations of the invention can be administered for prophylactic and/or therapeutic treatments. In certain embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications; this can be called a therapeutically effective amount. For example, in certain embodiments, pharmaceutical compositions of the invention are administered in an amount sufficient to treat obesity in a subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84: 1144-1146; Rohatagi (1995) Pharmazie 50:610-613; Brophy (1983) Eur. J. Clin. Pharmacol. 24: 103-108; Remington: The Science and Practice of Pharmacy, 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate. Single or multiple administrations of formulations can be given depending on for example: the dosage and frequency as required and tolerated by the patient, the degree and amount of cholesterol homeostasis generated after each administration, and the like. The formulations should provide a sufficient quantity of active agent to effectively treat, prevent or ameliorate conditions, diseases or symptoms, e.g., treat obesity.

In certain embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington: The Science and Practice of Pharmacy, 21st ed., 2005.

VII. Exemplification

The present invention is further illustrated by the following examples which should not be construed as further limiting. The contents of Sequence Listing, figures and all references, patents and published patent applications cited throughout this application are expressly incorporated herein by reference.

Furthermore, in accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Example 1

In-Silico Analysis of Thermogenic Regulators

Eighty three proteins that are involved in regulation of thermogenesis were selected based upon a critical assessment and review of the available scientific information and our own experimental data. These proteins were categorized as activators or repressors of thermogenesis based upon their functions. These thermogenic regulator proteins are set forth in Table 1.

TABLE 1

Thermogenic regulator proteins.

| | Name | Entrez Gene ID | Ensembl Gene ID |
|---|---|---|---|
| | Activators | | |
| 1 | ALDH1A1 | 216 | ENSG00000165092 |
| 2 | ANP (NPPA) | 4878 | ENSG00000175206 |
| 3 | AZGP1 | 563 | ENSG00000160862 |
| 4 | BMP7 | 655 | ENSG00000101144 |
| 5 | BMP8b | 656 | ENSG00000116985 |
| 6 | CEBPA | 1050 | ENSG00000245848 |
| 7 | CEBPB | 1051 | ENSG00000172216 |

TABLE 1-continued

Thermogenic regulator proteins.

| | Name | Entrez Gene ID | Ensembl Gene ID |
|---|---|---|---|
| 8 | CEBPD | 1052 | ENSG00000221869 |
| 9 | CIDEA | 1149 | ENSG00000176194 |
| 10 | COX7A1 | 1346 | ENSG00000161281 |
| 11 | CRAT | 1384 | ENSG00000095321 |
| 12 | CREB1 | 1385 | ENSG00000118260 |
| 13 | CREBBP | 1387 | ENSG00000005339 |
| 14 | CTBP1 | 1487 | ENSG00000159692 |
| 15 | CTBP2 | 1488 | ENSG00000175029 |
| 16 | DIO2 | 1734 | ENSG00000211448 |
| 17 | ELOVL3 | 83401 | ENSG00000119915 |
| 18 | FGF16 | 8823 | ENSG00000196468 |
| 19 | FGF19 | 9965 | ENSG00000162344 |
| 20 | FGF21 | 26291 | ENSG00000105550 |
| 21 | FNDC5 | 252995 | ENSG00000160097 |
| 22 | FOXC2 | 2303 | ENSG00000176692 |
| 23 | GDF3 | 9573 | ENSG00000184344 |
| 24 | HCRT (OREXIN) | 3060 | ENSG00000161610 |
| 25 | HOXC8 | 3224 | ENSG00000037965 |
| 26 | INSR | 3643 | ENSG00000171105 |
| 27 | IRS1 | 3667 | ENSG00000169047 |
| 28 | KDM3A (JMJD1A) | 55818 | ENSG00000115548 |
| 29 | KLF5 | 688 | ENSG00000102554 |
| 30 | KLF11 | 8462 | ENSG00000172059 |
| 31 | KLF15 | 28999 | ENSG00000163884 |
| 32 | LRP6 | 4040 | ENSG00000070018 |
| 33 | MAPK14 | 1432 | ENSG00000112062 |
| 34 | MED13 | 9969 | ENSG00000108510 |
| 35 | NCOA1 | 8648 | ENSG00000084676 |
| 36 | NCOA2 | 10499 | ENSG00000140396 |
| 37 | NCOA3 | 8202 | ENSG00000124151 |
| 38 | NR4A3 | 8013 | ENSG00000119508 |
| 39 | NRF1 | 4899 | ENSG00000106459 |
| 40 | PLAC8 | 51316 | ENSG00000145287 |
| 41 | PPARA | 5465 | ENSG00000186951 |
| 42 | PPARD | 5467 | ENSG00000112033 |
| 43 | PPARG | 5468 | ENSG00000132170 |
| 44 | PPARGC1A | 10891 | ENSG00000109819 |
| 45 | PPARGC1B | 133522 | ENSG00000155846 |
| 46 | PRDM16 | 63976 | ENSG00000142611 |
| 47 | PRDX3 | 10935 | ENSG00000165672 |
| 48 | PRKAA1 (AMPKA1) | 5562 | ENSG00000132356 |
| 49 | PRKAA2 (AMPKA2) | 5563 | ENSG00000162409 |
| 50 | PRKACA | 5566 | ENSG00000072062 |
| 51 | PRKACB | 5567 | ENSG00000142875 |
| 52 | PRKAR1A | 5573 | ENSG00000108946 |
| 53 | SIRT1 | 23411 | ENSG00000096717 |
| 54 | SIRT3 | 23410 | ENSG00000142082 |
| 55 | SLC27A2 (FATP2) | 11001 | ENSG00000140284 |
| 56 | SREBF1 | 6720 | ENSG00000072310 |
| 58 | SREBF2 | 6721 | ENSG00000198911 |
| 58 | STAT5A | 6776 | ENSG00000126561 |
| 59 | TRPM8 | 79054 | ENSG00000144481 |
| 60 | UCP1 (SLC25A7) | 7350 | ENSG00000109424 |
| 61 | UCP2 (SLC25A8) | 7351 | ENSG00000175567 |
| 62 | UCP3 (SLC25A9) | 7352 | ENSG00000175564 |

Repressors

| | Name | Entrez Gene ID | Ensembl Gene ID |
|---|---|---|---|
| 1 | ATG7 | 10533 | ENSG00000197548 |
| 2 | BMP2 | 650 | ENSG00000125845 |
| 3 | BMP4 | 652 | ENSG00000125378 |
| 4 | CIDEC | 63924 | ENSG00000187288 |
| 5 | CTNNB1 | 1499 | ENSG00000168036 |
| 6 | DLK1 (Pref-1) | 8788 | ENSG00000185559 |
| 7 | E2F4 (p107) | 1874 | ENSG00000205250 |
| 8 | EIF4EBP1 | 1978 | ENSG00000187840 |
| 9 | ESRRA (NR3B1) | 2101 | ENSG00000173153 |
| 10 | IKBKE | 9641 | ENSG00000143466 |
| 11 | NR1H3 (LXRA) | 10062 | ENSG00000025434 |
| 12 | NRIP1 (RIP140) | 8204 | ENSG00000180530 |
| 13 | RB1 (pRb) | 5925 | ENSG00000139687 |
| 14 | NR0B2 (SHP) | 8431 | ENSG00000131910 |
| 15 | RPS6KB1 | 6198 | ENSG00000108443 |
| 16 | RUNX1T1 | 862 | ENSG00000079102 |
| 17 | RUNX2 | 860 | ENSG00000124813 |

TABLE 1-continued

Thermogenic regulator proteins.

| | Name | Entrez Gene ID | Ensembl Gene ID |
|---|---|---|---|
| 18 | TNFRSF1A | 7132 | ENSG00000067182 |
| 19 | TWIST1 | 7291 | ENSG00000122691 |
| 20 | WNT5A | 7474 | ENSG00000114251 |
| 21 | WNT10B | 7480 | ENSG00000169884 |

The STRING 9.0 database of known and predicted protein interactions (string-db.org/) was used to test these 83 candidate molecules. The interactions include direct (physical) and indirect (functional) associations; they are derived from four sources: genomic context; high-throughput experiments; co-expression; and previous knowledge. STRING quantitatively integrates interaction data from these sources for a large number of organisms, and transfers information between these organisms where applicable. The database currently covers 5,214,234 proteins from 1,133 organisms. As an example, the relationships between the 83 thermogenic regulator molecules were centered around UCP1, and molecules having direct and indirect connections with UCP1 could be distinguished using the highest confidence score of 0.90. This relationship is set forth in schematic form in FIG. 1A. From this analysis, it was discovered that nine molecules (CEBPB, CIDEA, KDM3A, NRIP1, PRDM16, PPARG, PPARGC1A, PPKAA2, and UCP2) are directly linked to UCP1, whereas many more molecules are connected to UCP1 on a second or higher degree order.

Figure 1B:
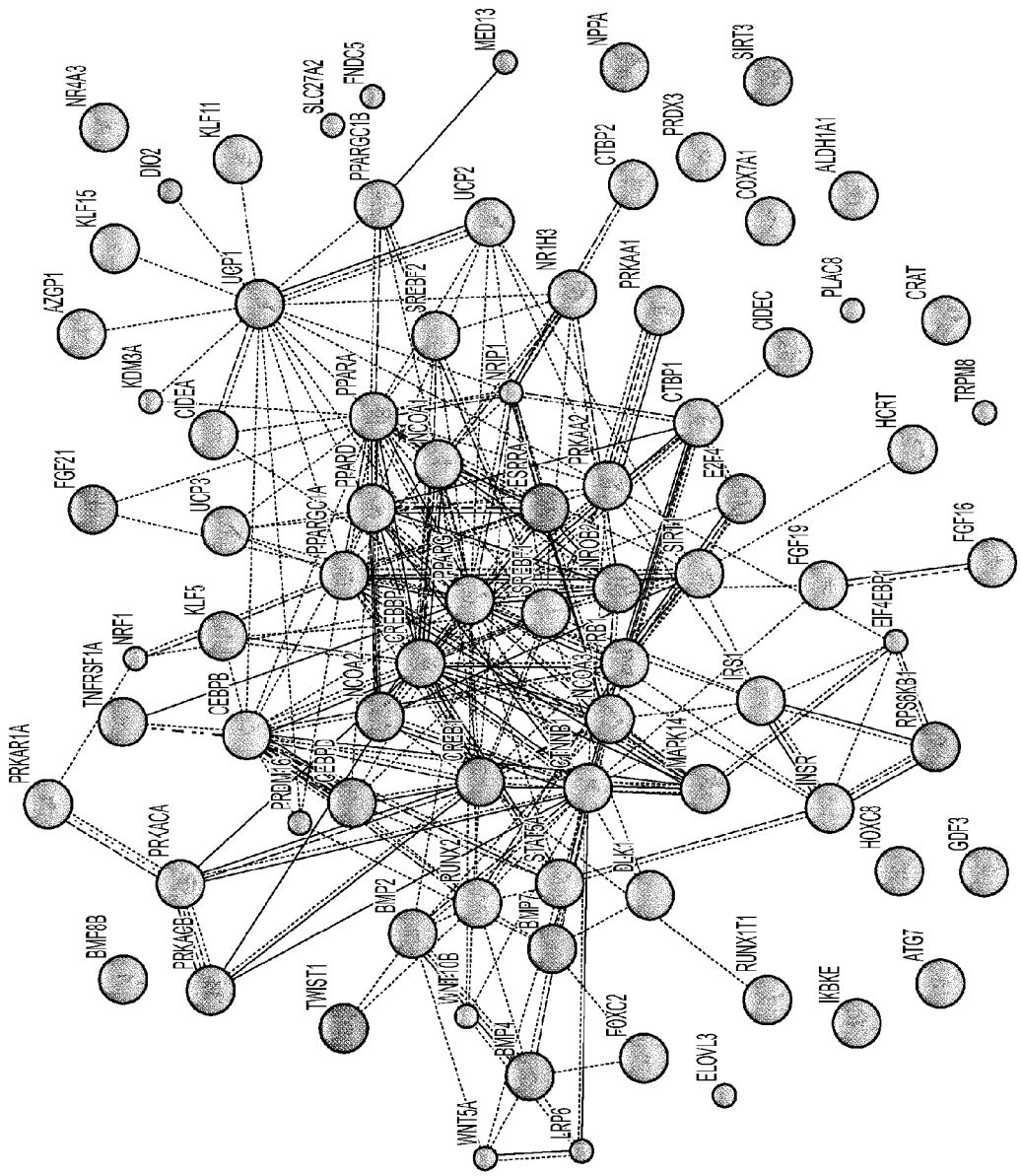

When the degree of confidence was set to high with a score of 0.70, eight additional proteins were found to be directly linked to UCP1 (AZGP1, DIO2, KLF11, KLF15, NR1H3, PPARA, PPARD, and PPARGC1B), FIG. 1B.

Figure 2A:
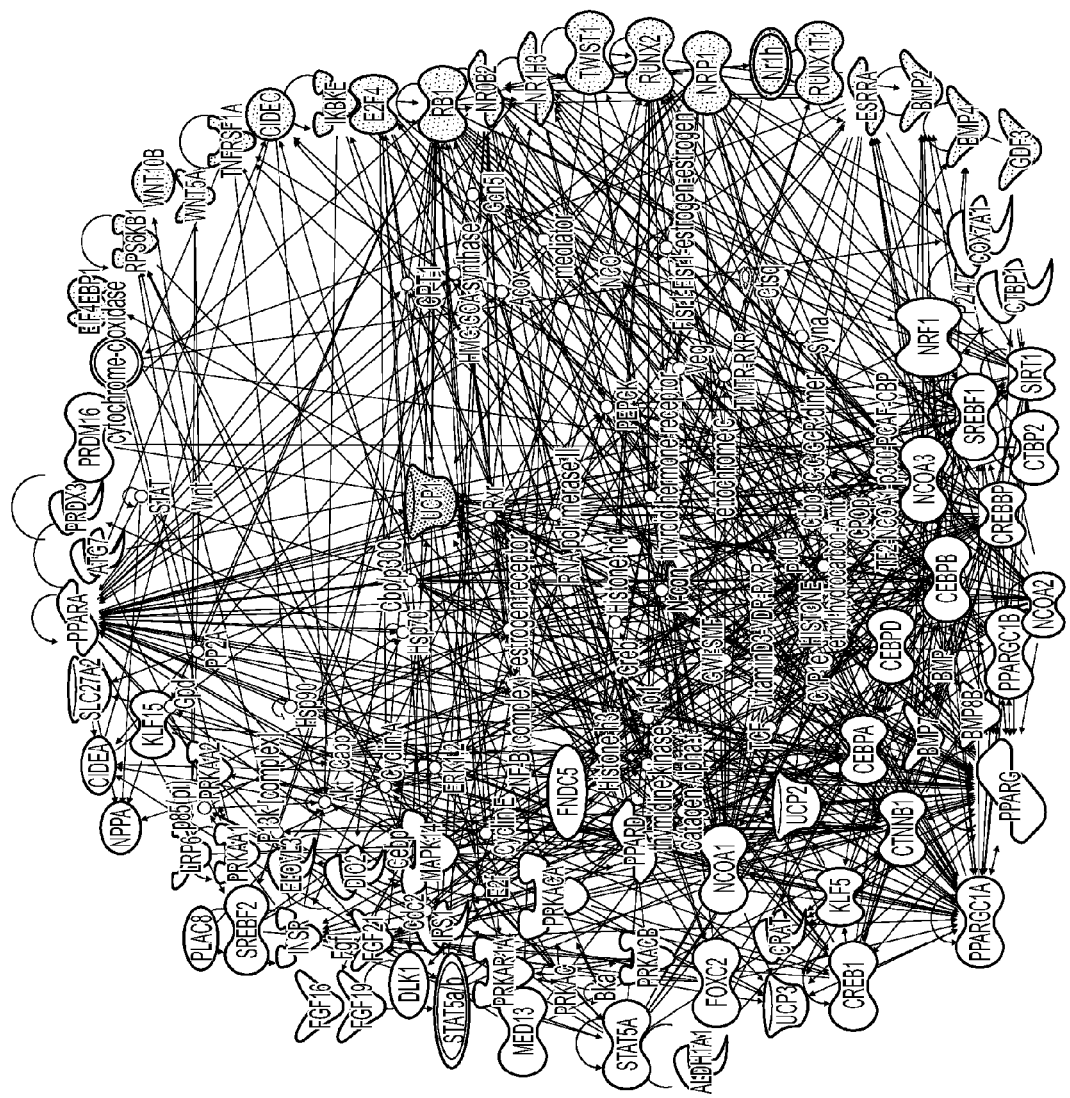
FIG. 2A is a schematic representation of the interaction of 83 thermogenic regulators determined using the Ingenuity Pathway Analysis Software program.
Figure 2B:
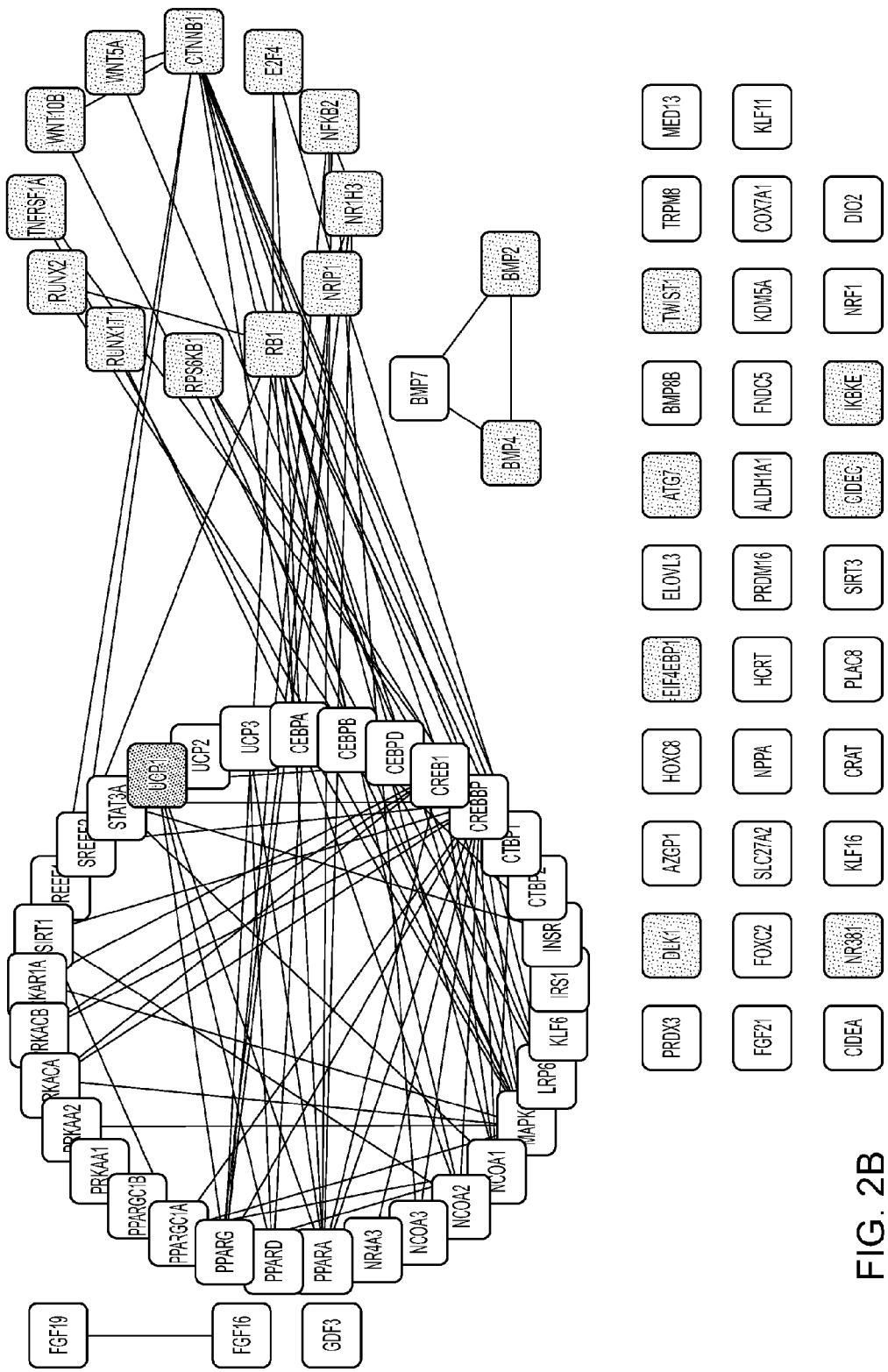
FIG. 2B is a schematic representation of the interaction of 83 thermogenic regulators determined using the Reactome Functional Interaction Network program.

Similarly, the interactions among these 83 thermogenic regulator molecules were independently assessed using other software programs. The interactions predicted by the Ingenuity Pathway Analysis (IPA) Software program (www.ingenuity.com) are shown in FIG. 2A (UCP1 in yellow, activators in green and repressors in purple). The interactions predicted by the Reactome Functional Interaction (Reactome IF) Software program (http://wiki.reactome.org) are shown in FIG. 2B (UCP1 in yellow, activators in green and repressors in purple). The IPA and Reactome IF networks differ from the one set forth in FIG. 1, obtained with the STRING program. It is not surprising that the results of these algorithms are different because they rely on different predefined parameters, sources of information and selection criteria.

Example 2

In-Silico Selection of Relevant miRNA Targets

To select thermogenic regulators suitable as targets for miRNA agents, several internet-based resources were employed to match miRNAs and their targets (the "micronome"). Exemplary tools are set forth in Table 2A.

TABLE 2A

Exemplary bioinformatics tools used to select miRNAs and their targets.

| Field & Name | Function | Web Address |
|---|---|---|
| Integrated Data Mining (8) | | |
| BioCarta | Catalogs and summarizes important resources providing information for over 120,000 genes from multiple species. Find both classical pathways as well as current suggestions for new pathways | biocarta.com |
| Database for Annotation, Visualization and Integrated Discovery (DAVID) | Integrated biological knowledgebase and analytic tools aimed at systematically extracting biological meaning from large gene/protein lists | david.abcc.ncifcrf.gov/home.jsp |
| GeneOntology | Standardizing the representation of gene and gene product attributes across species and databases | geneontology.org/ |
| Gene Set Enrichment Analysis (GSEA) | Computational method that determines whether an a priori defined set of genes shows statistically significant, concordant differences between two biological states (e.g. phenotypes). | broadinstitute.org/gsea/index.jsp |
| KEGG | Kyoto Encyclopedia of Genes and Genomes | genome.jp/kegg/ |
| PubGene | Connecting up-to-date information on genes and related terms | pubgene.org/ |
| Reactome | An open-source, open access, manually curated and peer-reviewed pathway database. | reactome.org/ReactomeGWT/entrypoint.html |
| STRING | Database of known and predicted protein interactions; direct (physical) and indirect (functional) associations | string-db.org/ |
| miRNA Mining & Mapping (8) | | |
| deepBase | Platform for annotating and discovering small and long ncRNAs (microRNAs, siRNAs, piRNAs . . .) | deepbase.sysu.edu.cn/ |
| Human microRNA disease database (HMDD) | Contains miRNA names, disease names, dysfunction evidences, and the literature PubMed ID | 202.38.126.151/hmdd/mirna/md/ |
| miRBase V19 | Searchable database of published miRNA sequences and annotation | mirbase.org/ |
| miRGen 2.0 | Database of microRNA genomic information and regulation | diana.cslab.ece.ntua.gr/mirgen/ |
| miRNAMap | Experimentally verified microRNAs Shows tissue expression profile | mirnamap.mbc.nctu.edu.tw/ |
| miRSel | Automated extraction of associations between microRNAs and genes from the biomedical literature | services.bio.ifi.lmu.de/mirsel/ |
| miRStart | Database of human microRNA TSSs (transcription start sites) | mirstart.mbc.nctu.edu.tw/home.php |
| miR2Disease | A manually curated database providing a comprehensive resource of miRNA deregulation in various human diseases | mir2disease.org |
| miRNA Targets & Expression (21) | | |
| DIANA-microT 3.0 | Algorithm based on several parameters calculated individually for each microRNA and it combines conserved and non-conserved microRNA recognition elements into a final prediction score. | diana.cslab.ece.ntua.gr/microT/ |
| DIANA-mirExTra | Algorithm that can identify microRNA effects to the Expression levels of protein-coding transcripts, based on the frequency of six nucleotide long motifs in the 3'UTR sequences of genes. | diana.cslab.ece.ntua.gr/hexamers/ |

TABLE 2A-continued

Exemplary bioinformatics tools used to select miRNAs and their targets.

| Field & Name | Function | Web Address |
|---|---|---|
| GSEA Molecular Signatures Database v3.0 | Gene sets that contain genes sharing a 3'-UTR microRNA binding motif (n = 221) | broadinstitute.org/gsea/index.jsp |
| MicroCosm Targets | Computationally predicted targets for microRNAs across many species. The miRNA sequences are obtained from the miRBase Sequence database and most genomic sequence from EnsEMBL | ebi.ac.uk/enright-srv/microcosm/cgi-bin/targets/v5/download.pl |
| MicroInspector | A scanning software for detection of miRNA binding sites using hybridization temperature and free energy cut-off value | bioinfo.uni-plovdiv.bg/microinspector/ |
| microRNA.org (ex. miRanda) | Predicted microRNA targets & target downregulation scores. Experimentally observed expression patterns. | microrna.org/microrna/home.do |
| miRDB | Online database for miRNA target prediction and functional annotations in animals by a new bioinformatics tool analyzing thousands of genes impacted by miRNAs with an SVM learning machine. | mirdb.org/miRDB/ |
| miRTarBase | Has accumulated more than three thousand miRNA-target interactions (MTIs), which are collected by manually surveying pertinent literature | mirtarbase.mbc.nctu.edu.tw/index.html |
| miRTar.Human | An integrated web server for identifying miRNA-target interactions. Identifies the biological functions and regulatory relationships between a group of known/putative miRNAs and protein coding genes. It also provides perspective of information on the miRNA targets on alternatively spliced transcripts in human | mirtar.mbc.nctu.edu.tw/human/download.php |
| miRvestigator | Takes as input a list of co-expressed genes and will return the most likely miRNA regulating these genes. It does this by searching for an over-represented sequence motif in the 3'UTRs of the genes using Weeder and then comparing this to the miRNA seed sequences in miRBase using our custom built miRvestigator hidden Markov model (HMM) | mirvestigator.systemsbiology.net/ |
| mirZ | A server that provides statistical analysis and data mining tools operating on up-to-date databases of sequencing-based miRNA expression profiles and of predicted miRNA target sites | mirz.unibas.ch/E1MMo2/ |
| MultiMiTar | A Support Vector Machine (SVM) based classifier integrated with a multiobjective metaheuristic based feature selection technique. | isical.ac.in/~bioinfo_miu/multimitar.htm |
| PhenomiR | Provides information about differentially regulated miRNA expression in diseases and other biological processes. The content of PhenomiR is completely generated by manual curation of experienced annotators. Data was extracted from more than 365 scientific articles and resulted in more than 632 database entries as of February 2011 | mips.helmholtz-muenchen.de/phenomir/index.gsp |
| PicTar | Algorithm for the identification of microRNA targets. This searchable website provides details (3' UTR alignments with predicted sites, | pictar.mdc-berlin.de/ |

TABLE 2A-continued

Exemplary bioinformatics tools used to select miRNAs and their targets.

| Field & Name | Function | Web Address |
|---|---|---|
| | links to various public databases, etc.) | |
| PITA | Incorporates the role of target-site accessibility, as determined by base-pairing interactions within the mRNA, in microRNA target recognition. | genie.weizmann.ac.il/pubs/mir07/mir07_data.html |
| RepTar | Database of miRNA target predictions, based on an algorithm that is independent of evolutionary conservation considerations and is not limited to seed pairing sites. | bioinformatics.ekmd.huji.ac.il/reptar/ |
| RNAhybrid | A tool for finding the minimum free energy hybridisation of a long and a short RNA. The hybridisation is performed in a kind of domain mode, ie. the short sequence is hybridised to the best fitting part of the long one. | bibiserv.techfak.uni-bielefeld.de/rnahybrid/ |
| RNA22 | First finds putative microRNA binding sites in the sequence of interest, then identifies the targeted microRNA (IBM). | cbcsrv.watson.ibm.com/rna22.html |
| Sylamer | A system for finding significantly over or under-represented words in sequences according to a sorted gene list. It is used to find significant enrichment or depletion of microRNA or siRNA seed sequences from microarray expression data. | ebi.ac.uk/enright/sylamer/ |
| TarBase 6.0 | Database of experimentally supported microRNA targets. | diana.cslab.ece.ntua.gr/DianaToolsNew/index.php?r=tarbase/index |
| TargetScanHuman 6.2 | Predicts biological targets of miRNAs by searching for the presence of conserved 8mer and 7mer sites that match the seed region of each miRNA, using 6 features: site-type contribution, 3' pairing contribution, local AU contribution, position contribution, TA (target site abundance) contribution, SPS (seed-pairing stability) contribution. | targetscan.org/ |
| Integrated miRNA Targets & Expression Tools (13) | | |
| GOmir | Integrates the predicted target genes from TargetScan, miRanda, RNAhybrid and PicTar computational tools and also providing a full gene description and functional analysis for each target gene. | bioacademy.gr/bioinformatics/projects/GOmir/ |
| MAMI (MetaMiR: Target Inference) | Compiles predictions from five different miRNA target prediction algorithms (TargetScanS, miRanda, microT, miRtarget, and picTar). | mami.med.harvard.edu/ |
| mimiRNA | Allows the visualization of miRNA expression levels in 188 different tissue or cell types, provides a robust statistical method for discovering functional interactions between miRNAs and mRNA genes. Uses a novel sample classification algorithm, ExParser, that allows mimiRNA to automatically classify imported experiments with minimal curation | mimirna.centenary.org.au/mep/formulaire.html |
| MMIA (microRNA and mRNA Integrated Analysis) | Integrates the predicted target genes from TargetScan, PicTar, PITA | 147.46.15.115/MMIA/index.html |

TABLE 2A-continued

Exemplary bioinformatics tools used to select miRNAs and their targets.

| Field & Name | Function | Web Address |
|---|---|---|
| mirDIP | Integrates twelve microRNA prediction datasets from six microRNA prediction databases, allowing users to customize their microRNA target searches. Combining microRNA predictions allows users to obtain more robust target predictions, giving you more confidence in your microRNA targets. | ophid.utoronto.ca/mirDIP/ |
| miRGator V3.0 | Integrated database of miRNA-associated gene expression, target prediction, disease association and genomic annotation, using mirBridge, miRanda, PITA and TargetScan. Now includes 73 deep sequencing datasets on human samples from GEO, SRA, and TCGA archives | mirgator.kobic.re.kr |
| miRecords | Integrates the predictions form DIANA-microT, MicroInspector, miRanda, mirTarget2, miTarget, NBmiRTar, PicTar, PITA, rna22, RNAhybrid, TargetScan/TargetScanS | mirecords.biolead.org/ |
| MIRNA-DISTILLER | Automatically extracts miRNAs predicted to interact with a given set of target genes from several selectable public databases. | ikp-stuttgart.de/content/language1/html/10415.asp |
| MiRonTop | Online java web tool that integrates DNA microarrays or high-throughput sequencing data to identify the potential implication of miRNAs on a specific biological system. It allows a rapid characterization of the most pertinent mRNA targets according to several existing miRNA target prediction approaches (Mirbase, miRanda, exact seed, TargetScan or PicTar) | microarray.fr:8080/miRonTop/index |
| miRror | Integrates predictions from a dozen of miRNA resources that are based on complementary algorithms into a unified statistical framework. | proto.cs.huji.ac.il/mirror |
| miRSystem | Database which integrates 7 miRNA target gene prediction programs: DIANA, miRanda, miRBridge, PicTar, PITA, rna22, and TargetScan. | mirsystem.cgm.ntu.edu.tw/ |
| miRWalk | Comprehensive database that provides information on miRNA on their predicted as well as validated binding sites on their target genes. | ma.uni-heidelberg.de/apps/zmf/mirwalk/index.html |
| StarBase | Public platform for decoding microRNA-target and protein-RNA interaction maps from CLIP-Seq (HITS-CLIP, PAR-CLIP) and degradome sequencing (Degradome-Seq, PARE) data. | starbase.sysu.edu.cn/index.php |
| miRNA Secondary Structure (5) | | |
| OligoWalk | An online server calculating thermodynamic features of sense-antisense hybridization. It predicts the free energy changes of oligonucleotides binding to a target RNA. It can be used to design efficient siRNA targeting a given mRNA sequence. | rna.urmc.rochester.edu/cgi-bin/server_exe/oligowalk/oligowalk_form.cgi |
| PicTar RNA Studio | The BiBiServ Tool section offers bioinformatics tools for a large variety of tasks, including RNA studio | www.pictar.org/ |

TABLE 2A-continued

Exemplary bioinformatics tools used to select miRNAs and their targets.

| Field & Name | Function | Web Address |
|---|---|---|
| RNA2D | Suite of programs for discovering structural features in RNAs. | protein3d.ncifcrf.gov/shuyun/rna2d.html |
| Vienna RNA Package | RNA Secondary Structure Prediction and Comparison. | tbi.univie.ac.at/ivo/RNA/ |
| Whitehead siRNA algorithm | Helps select siRNAs to knock down your gene of interest | jura.wi.mit.edu/bioc/siRNAext/ |
| Network Searches & Analyses (8) | | |
| ARIADNE Pathway Studio | Pathway analysis software helping to: Interpret gene expression and other high throughput data Build, expand and analyze pathways Find relationships among genes, proteins, cell processes and diseases Draw publication-quality diagrams | ariadnegenomics.com/products/pathway-studio/ |
| Cytoscape | Open source bioinformatics software platform for visualizing molecular interaction networks and biological pathways and integrating these networks with annotations, gene expression profiles and other state data. | cytoscape.org/ |
| Database for Annotation, Visualization and Integrated Discovery (DAVID) | Integrated biological knowledgebase and analytic tools aimed at systematically extracting biological meaning from large gene/protein lists | david.abcc.ncifcrf.gov/home.jsp |
| Genego MetaCore | An integrated knowledge database and software suite for pathway analysis of experimental data and gene lists based on a proprietary manually curated database of human protein-protein, protein-DNA and protein compound interactions, metabolic and signaling pathways. | genego.com/metacore.php |
| Ingenuity Systems IPA (Ingenuity Pathway Analysis) | To understand biology at multiple levels by integrating data from a variety of experimental platforms and providing insight into the molecular and chemical interactions, cellular phenotypes, and disease processes. | ingenuity.com/products/IPA/microRNA.html |
| MATISSE (Module Analysis via Topology of Interactions and Similarity SEts) | A program for detection of functional modules using interaction networks and expression data | acgt.cs.tau.ac.il/matisse/ |
| MIR@NT@N | a framework integrating transcription factors, microRNAs and their targets to identify sub-network motifs in a meta-regulation network model | mironton.uni.lu |
| NAViGaTOR | Network Analysis, Visualization, & Graphing TORonto is a software package for visualizing and analyzing protein-protein interaction networks. | ophid.utoronto.ca/navigator/index.html |
| Molecular Visualization (4) | | |
| Foldit | Multiplayer online game that enlists players worldwide to solve difficult protein-structure prediction problems. | fold.it/portal/info/science |
| PyMOL | A user-sponsored molecular visualization system on an open-source foundation. | .pymol.org/ |

TABLE 2A-continued

Exemplary bioinformatics tools used to select miRNAs and their targets.

| Field & Name | Function | Web Address |
|---|---|---|
| Qlucore Omics Explorer | To examine and analyze data from miRNA experiments. | qlucore.com/ProdOverviewmiRNA.aspx |
| WebMol | Displays and analyzes structural information contained in the Brookhaven Protein Data Bank (PDB). It can be run as an applet or as a stand-alone application. | cmpharm.ucsf.edu/cgi-bin/webmol.pl |
| Information Integration (1) | | |
| TIBCO Spotfire | Comprehensive software platform that allows customers to analyze data, using predictive and complex statistics in the analysis | |

Specifically, these tools were used to perform: 1) Integrated Data Mining (8 tools); 2) miRNA Mining and Mapping (6 tools); 3) miRNA Target Targets and Expression (21 tools); 4) Integrated miRNA Targets and Expression (13 tools); 5) miRNA Secondary Structure Prediction and Comparison (5 tools); 6) Network Searches and Analyses (8 tools); 7) Molecular Visualization (4 tools); and 8) Information Integration and Exploitation (1 tool).

A single gene target can be controlled by several miRNAs whereas a single miRNA can control several gene targets. Sophisticated bioinformatics resources have been developed to select the most relevant miRNAs to target diseases (Gallagher I J, et al. *Genome medicine.* 2010; Fujiki K, et al. *BMC Biol.* 2009; Okada Y, et al., *J Androl.* 2010; Hao T, et al., *Mol. Biosyst.* 2012; Hao T, et al., *Mol. Biosyst.* 2012). However, the results of these algorithms are acutely dependent on predefined parameters and the degree of convergence between these algorithms is rather limited. Therefore, there is a need to develop better performing bioinformatics tools with improved sensitivity, specificity and selectivity for the identification of miRNA/target relationships.

The interactions between miRNAs and their targets go beyond the original description of miRNAs as post-transcriptional regulators whose seed region of the driver strand (5' bases 2-7) bind to complementary sequences in the 3' UTR region of target mRNAs, usually resulting in translational repression or target degradation and gene silencing. The interactions can also involve various regions of the driver or passenger strands of the miRNAs as well as the 5'UTR, promoter, and coding regions of the mRNAs.

Upon analysis of the available data, it was decided to favor pathway-specific miRNAs which target multiple genes within one discrete signaling pathway, rather than universal miRNAs which are involved in many signaling pathways, functions or processes. Using 34 publicly available Internet tools predicting miRNA targets, specific huma miRNAs were searched for that could potentially modulate several targets among the 83 thermogenic regulator molecules (which include 36 Transcription Factors) selected in Example 1.

Several paradigms were considered:
a) A One microRNA-Multiple mRNAs Pathway-Specific Paradigm.

A. The methylation state of histones can be dynamically regulated by histone methyltransferases and demethylases. The human lysine (K)-specific demethylase 3A (KDM3A) is critically important in regulating the expression of metabolic genes. Its loss of function results in obesity and hyperlipidemia in mice. Beta-adrenergic stimulation of KDM3A binding to the PPAR responsive element (PPRE) of the UCP1 gene not only decreases levels of H3K9me2 (dimethylation of lysine 9 of histone H3) at the PPRE, but also facilitates the recruitment of PPARG and RXRA and their co-activators PPARGC1A, CREBBP and NCOA1 to the PPRE. The interrogation of the TargetScan Human database (release 6.0) revealed that the human KDM3A 3' UTR 29-35 region is a conserved target for hsa-miR-22. Several other miRNA Targets Databases also confirmed this match between hsa-miR-22 and KDM3A. Therefore, increased production of the demethylase KDM3A by an hsa-miR-22 antagomir should lead to demethylation of the UCP1 gene promoter region, thus facilitating binding of several regulatory elements and increased UCP1 production.

In addition, we used the 34 miRNA Targets and Expression tools (Table 2B) to identify the mRNA targets of a given miRNA.

TABLE 2B

Bioinformatics tools used to select miRNAs and their targets.

| | | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|---|
| *DIANA-microT 3.0* | 1 | X | | | | | | | ✓ | | | | | | | | | | |
| DIANA-mirExTra | 2 | | X | | | | | | | | | | | | | | | | |
| GOmir | 3 | | | X | | | | | ✓ | | | | | | | | | | |
| GSEA MSD v3.0 | 4 | | | | X | | | | | | | | | | | | | | |
| MAMI | 5 | ✓ | | | | X | ✓ | | ✓ | | | | | | | | | | |
| *MicroCosm Targets* | 6 | | | | | | X | | | | | | | | | | | | |
| *MicroInspector* | 7 | | | | | | | X | | | | | | | | | | | |
| *microRNA.org* | 8 | | | | | | | | X | | | | | | | | | | |

TABLE 2B-continued

Bioinformatics tools used to select miRNAs and their targets.

| Tool | # | | | | | | | | | | | | | |
|---|---|---|---|---|---|---|---|---|---|---|---|---|---|---|
| mimiRNA | 9 | | | | ✓ | X | | | | | | | | |
| MMIA | 10 | | | | | | X | | | | | | | |
| *miRDB* | 11 | | | | | | | X | | | | | | |
| mirDIP | 12 | ✓ | | | ✓ | ✓ | | | X | | | | | |
| miRGator v3.0 | 13 | | | | ✓ | ✓ | | ✓ | | X | ✓ | | | |
| miRecords | 14 | ✓ | | | ✓ | ✓ | | | | | X | | | |
| MiRNA Distiller | 15 | | | | ✓ | | | ✓ | | | | X | | |
| MiRonTop | 16 | | | | ✓ | ✓ | | | | | | | X | |
| miRror | 17 | ✓ | | | ✓ | ✓ | | ✓ | | | | | | X |
| miRSystem | 18 | ✓ | | | | ✓ | | | | | | | | | X |
| miRTarBase | 19 | | | | | | | | | | | | | |
| miRTar · Human | 20 | | | | | | | | | | | | | |
| miRvestigator | 21 | | | | | | | | | | | | | |
| miRWalk | 22 | ✓ | | | | ✓ | | ✓ | | | | | | |
| *mirZ* | 23 | | | | | | | | | | | | | |
| MultiMiTar | 24 | | | | | | | | | | | | | |
| PhenomiR | 25 | | | | | | | | | | | | | |
| *PicTar* | 26 | | | | | | | | | | | | | |
| *PITA* | 27 | | | | | | | | | | | | | |
| RepTar | 28 | | | | | | | | | | | | | |
| *RNA22* | 29 | | | | | | | | | | | | | |
| *RNAhybrid* | 30 | | | | | | | | | | | | | |
| StarBase | 31 | | | | | ✓ | | | | | | | | |
| Sylamer | 32 | | | | | | | | | | | | | |
| TarBase 6.0 | 33 | | | | | | | | | | | | | |
| *TargetScanHuman* | 34 | | | | | | | | | | | | | |
| | | 5 | | | 4 | 1 | 10 | | | 3 | | | | |

| Tool | # | 19 | 20 | 21 | 22 | 23 | 24 | 25 | 26 | 27 | 28 | 29 | 30 | 31 | 32 | 33 | 34 | |
|---|---|---|---|---|---|---|---|---|---|---|---|---|---|---|---|---|---|---|
| *DIANA-microT 3.0* | 1 | | | | | | | | | | | | | | | | | |
| DIANA-mirExTra | 2 | | | | | | | | | | | | | | | | | |
| GOmir | 3 | | | | | | | | ✓ | | | ✓ | | | | | ✓ | 4 |
| GSEA MSD v3.0 | 4 | | | | | | | | | | | | | | | | | |
| MAMI | 5 | | | | | | | | ✓ | | | | | | | | ✓ | 5 |
| *MicroCosm Targets* | 6 | | | | | | | | | | | | | | | | | |
| *MicroInspector* | 7 | | | | | | | | | | | | | | | | | |
| *microRNA.org* | 8 | | | | | | | | | | | | | | | | | |
| mimiRNA | 9 | | | | | | | | ✓ | | | ✓ | | | | | ✓ | 4 |
| MMIA | 10 | | | | | | | | ✓ | ✓ | | | | | | | ✓ | 3 |
| *miRDB* | 11 | | | | | | | | | | | | | | | | | |
| mirDIP | 12 | | | | | | | | ✓ | ✓ | | ✓ | | | | | ✓ | 7 |
| miRGator v3.0 | 13 | ✓ | | | | | | | ✓ | ✓ | | | | | ✓ | | ✓ | 9 |
| miRecords | 14 | | | | | | | | ✓ | ✓ | | ✓ | ✓ | | | | ✓ | 8 |
| MiRNA Distiller | 15 | | | | | | | | | | | | | | | | ✓ | 3 |
| MiRonTop | 16 | | | | | | | | ✓ | | | | | | | | ✓ | 4 |
| miRror | 17 | | | | ✓ | | | | ✓ | ✓ | | ✓ | | | | | ✓ | 9 |
| miRSystem | 18 | | | | | | | | ✓ | ✓ | | ✓ | | | | | ✓ | 7 |
| miRTarBase | 19 | X | | | | | | | | | | | | | | | | |
| miRTar · Human | 20 | | X | | | | | | | | | | | | | | | |
| miRvestigator | 21 | | | X | | | | | | | | | | | | | | |
| miRWalk | 22 | | | | X | | | | ✓ | ✓ | | ✓ | ✓ | | | | ✓ | 8 |
| *mirZ* | 23 | | | | | X | | | | | | | | | | | | |
| MultiMiTar | 24 | | | | | | X | | | | | | | | | | | |
| PhenomiR | 25 | | | | | | | X | | | | | | | | | | |
| *PicTar* | 26 | | | | | | | | X | | | | | | | | | |
| *PITA* | 27 | | | | | | | | | X | | | | | | | | |
| RepTar | 28 | | | | | | | | | | X | | | | | | | |
| *RNA22* | 29 | | | | | | | | | | | X | | | | | | |
| *RNAhybrid* | 30 | | | | | | | | | | | | X | | | | | |
| StarBase | 31 | | | | | | | | ✓ | ✓ | | ✓ | | X | | | ✓ | 5 |
| Sylamer | 32 | | | | | | | | | | | | | | X | | | |
| TarBase 6.0 | 33 | | | | | | | | | | | | | | | X | | |
| *TargetScanHuman* | 34 | | | | | | | | | | | | | | | | X | |
| | | | | | 1 | | | | 10 | 8 | | 7 | 3 | | | | 12 | |

Meta Tools in bold (13)
Engines called by Meta Tools in *Italics* (11)

Applying the above in silico strategy, it was discovered that hsa-miR-22-3p and hsa-miR-22-5p interact respectively with a total of 42 and 8 of the chosen 83 thermogenic targets. This data is set forth in Table 3.

TABLE 3

Thermogenic regulators identified as predicted and/or validated targets for hsa-miR-22-3p.

| | | | | |
|---|---|---|---|---|
| ALDH1A1 | DIO2 | NCOA1 | PRKAA1 | STAT5A |
| BMP4 | FGF19 | NPPA | PRKACA | TNFRSF1A |
| BMP7 | FGF21 | NRF1 | PRKACB | TRPM8 |
| CEBPA | FOXC2 | NRIP1 | PRKAR1A | UCP2 |
| CEBPD | INSR | PPARA | RUNX1T1 | WNT10B |
| CIDEC | KDM3A | PPARGC1A | RUNX2 | WNT5A |
| CREB1 | KLF11 | PPARGC1B | SIRT1 | |
| CREBBP | LRP6 | PRDM16 | SREBF1 | |
| CTNNB1 | MAPK14 | PRDX3 | SREBF2 | |

Thermogenic regulators identified as predicted and/or validated targets for hsa-miR-22-5p

| | | | | | | | |
|---|---|---|---|---|---|---|---|
| BMP7 | DIO2 | FNDC5 | IKBKE | INSR | MAPK14 | NR1H3 | PPARA |

B. We also utilized the 34 miRNA Targets and Expression tools (Table 2B) to look for potential relations between any of the adipocyte 536 miRNAs (Table A) and the 83 thermogenic targets (Table 1).

It appears that many adipocyte miRNAs interact (prediction and/or validation) with at least one of the 83 thermogenic targets. For example, miR-17-3p and hsa-miR-17-5p interact respectively with a total of 23 and 65 of the chosen thermogenic 83 targets. This data is set forth in Table 4.

TABLE 4

Thermogenic regulators identified as predicted and/or validated targets for hsa-miR-17-3p.

| | | | | |
|---|---|---|---|---|
| ATG7 | CTBP2 | KLF11 | PPARD | TNFRSF1A |
| BMP2 | E2F4 | MAPK14 | PRDM16 | TWIST1 |
| BMP4 | FGF19 | NCOA3 | RB1 | WNT10B |
| CEBPB | IKBKE | PLAC8 | RUNX1T1 | |
| CREB1 | IRS1 | PPARA | STAT5A | |

Thermogenic regulators identified as predicted and/or validated targets for hsa-miR-17-5p

| | | | | |
|---|---|---|---|---|
| ALDH1A1 | CREB2 | IKBKE | NRIP1 | RB1 |
| ATG7 | CTNNB1 | INSR | PLAC8 | RPS6KB1 |
| BMP2 | CTBP1 | IRS1 | PPARA | RUNX1T1 |
| BMP4 | CTBP2 | KLF11 | PPARD | RUNX2 |
| BMP7 | DIO2 | MAPK14 | PPARG | SIRT1 |
| BMP8b | ELOVL3 | MED13 | PPARGC1A | SIRT3 |
| CEBPA | FGF19 | NCOA1 | PPARGC1B | SREBF1 |
| CEBPB | FGF21 | NCOA2 | PRDX3 | STAT5A |
| CEBPD | FNDC5 | NCOA3 | PRKAA1 | TNFRSF1A |
| CIDEC | FOXC2 | NPPA | PRKAA2 | TWIST1 |
| COX7A1 | GDF3 | NR1H3 | PRKACA | UCP1 |
| CRAT | HCRT | NR4A3 | PRKACB | UCP3 |
| CREB1 | HOXC8 | NRF1 | PRKAR1A | WNT5A |

Once the lists of miRNAs of interest and their mRNA targets were produced, the following filters were applied to refine the results:

Parameters

1 Expression of miRNAs in tissue/cell of interest
2 Number of algorithms predicting one miRNA for a given gene or set of genes
3 Score/percent from algorithms
4 Number of preferred genes targeted by one miRNA
5 Number of binding sites in a target gene for one miRNA
6 Number of binding sites in a target gene for several miRNAs
7 Over-representation of one miRNA seed complementary sequence among target genes (miRvestigator)
8 Validated miRNA-mRNA target couples
9 Genomic location of miRNA binding site (5'UTR-Promoter-CDS-3'UTR)
10 Intronic location of miRNA
11 Clustering of miRNAs
12 Abundance of miRNA in specific tissue/cell of interest Applying the above parameters, it was discovered that 229 miRNAs met at least two of these criteria. This data is set forth in Table 5.

TABLE 5

Ranking of miRNAs according to selection critria.

| | | |
|---|---|---|
| hsa-miR-20b-5p | hsa-let-7c | hsa-miR-30d-5p |
| hsa-miR-27b-3p | hsa-let-7d-5p | hsa-miR-424-5p |
| hsa-miR-103a-3p | hsa-miR-141-3p | hsa-miR-454-3p |
| hsa-miR-22-3p | hsa-miR-183-5p | hsa-miR-545-3p |
| hsa-miR-34a-5p | hsa-miR-19a-3p | hsa-miR-485-5p |
| hsa-miR-130b-3p | hsa-miR-196a-5p | hsa-miR-335-5p |
| hsa-miR-132-3p | hsa-miR-30b-5p | hsa-miR-133a |
| hsa-miR-181b-5p | hsa-miR-378a-3p | hsa-miR-222-3p |
| hsa-miR-211-5p | hsa-miR-302c-5p | hsa-miR-494 |
| hsa-miR-148b-3p | hsa-miR-30e-5p | hsa-miR-498 |
| hsa-miR-17-5p | hsa-miR-130a-3p | hsa-miR-513a-5p |
| hsa-miR-182-5p | hsa-let-7e-5p | hsa-miR-92a-3p |
| hsa-miR-20a-5p | hsa-miR-216a-5p | hsa-miR-495-3p |
| hsa-miR-27a-3p | hsa-miR-450a-5p | hsa-miR-503-5p |
| hsa-miR-301a-3p | hsa-let-7d-3p | hsa-miR-539-5p |
| hsa-miR-204-5p | hsa-miR-26b-5p | hsa-miR-16-2-3p |
| hsa-miR-143-3p | hsa-miR-181c-5p | hsa-miR-302b-5p |
| hsa-miR-1 | hsa-miR-186-5p | hsa-miR-425-3p |
| hsa-miR-9-5p | hsa-miR-519c-3p | hsa-miR-99a-3p |
| hsa-miR-30a-5p | hsa-let-7b-5p | hsa-let-7a-3p |
| hsa-miR-138-5p | hsa-miR-10b-5p | hsa-miR-126-3p |
| hsa-miR-217 | hsa-miR-125b-5p | hsa-miR-20a-3p |
| hsa-miR-19b-3p | hsa-miR-134 | hsa-miR-499a-5p |
| hsa-miR-382-5p | hsa-miR-137 | hsa-let-7g-5p |
| hsa-miR-106a-5p | hsa-miR-150-5p | hsa-miR-152 |
| hsa-miR-107 | hsa-miR-153 | hsa-miR-26a-5p |
| hsa-miR-135a-5p | hsa-miR-15b-5p | hsa-miR-124-3p |
| hsa-miR-93-5p | hsa-miR-16-5p | hsa-miR-203a |
| hsa-miR-21-5p | hsa-miR-195-5p | hsa-miR-24-3p |
| hsa-miR-515-3p | hsa-miR-196b-5p | hsa-miR-301b |
| hsa-miR-106b-3p | hsa-miR-23a-3p | hsa-miR-590-3p |
| hsa-miR-125a-5p | hsa-miR-29c-3p | hsa-miR-1179 |
| hsa-miR-148a-3p | hsa-miR-373-3p | hsa-miR-325 |
| hsa-miR-155-5p | hsa-miR-7-5p | hsa-miR-552 |
| hsa-miR-181a-5p | hsa-miR-214-3p | hsa-miR-185-5p |
| hsa-miR-519d | hsa-miR-421 | hsa-miR-455-3p |
| hsa-miR-96-5p | hsa-miR-15a-5p | hsa-miR-583 |
| hsa-miR-212-3p | hsa-miR-193b-3p | hsa-miR-122-5p |
| hsa-miR-29a-3p | hsa-miR-194-5p | hsa-miR-1305 |
| hsa-miR-98-5p | hsa-miR-223-3p | hsa-miR-139-5p |
| hsa-miR-146a-5p | hsa-miR-30c-5p | hsa-miR-224-3p |
| hsa-miR-18a-5p | hsa-miR-335-3p | hsa-miR-24-1-5p |
| hsa-miR-18b-5p | hsa-miR-374a-5p | hsa-miR-24-2-5p |
| hsa-miR-199b-5p | hsa-miR-410 | hsa-miR-27a-5p |
| hsa-miR-340-5p | hsa-miR-429 | hsa-miR-27b-5p |
| hsa-miR-34c-5p | hsa-miR-497-5p | hsa-miR-29b-1-5p |
| hsa-miR-423-3p | hsa-miR-513a-3p | hsa-miR-302a-5p |

TABLE 5-continued

Ranking of miRNAs according to selection critria.

| | | |
|---|---|---|
| hsa-miR-489 | hsa-miR-542-3p | hsa-miR-3065-5p |
| hsa-miR-520f | hsa-miR-653 | hsa-miR-30d-3p |
| hsa-miR-520g | hsa-miR-122-3p | hsa-miR-34a-3p |
| hsa-miR-605 | hsa-miR-101-5p | hsa-miR-371a-3p |
| hsa-miR-668 | hsa-miR-1178-3p | hsa-miR-373-5p |
| hsa-let-7a-5p | hsa-miR-191-5p | hsa-miR-374a-3p |
| hsa-let-7f-5p | hsa-miR-214-5p | hsa-miR-376a-5p |
| hsa-miR-10a-3p | hsa-miR-302d-5p | hsa-miR-378a-5p |
| hsa-miR-135b-5p | hsa-miR-572 | hsa-miR-424-3p |
| hsa-miR-144-3p | hsa-miR-574-3p | hsa-miR-451a |
| hsa-miR-181d | hsa-miR-26a-2-3p | hsa-miR-452-3p |
| hsa-miR-200b-3p | hsa-miR-611 | hsa-miR-487b |
| hsa-miR-200c-3p | hsa-let-7f-1-3p | hsa-miR-493-5p |
| hsa-miR-218-5p | hsa-let-7i-3p | hsa-miR-500a-3p |
| hsa-miR-23b-3p | hsa-miR-100-5p | hsa-miR-502-3p |
| hsa-miR-25-3p | hsa-miR-106b-5p | hsa-miR-516b-3p |
| hsa-miR-29b-3p | hsa-miR-132-5p | hsa-miR-518e-3p |
| hsa-miR-383 | hsa-miR-135b-3p | hsa-miR-518f-3p |
| hsa-miR-202-3p | hsa-miR-136-3p | hsa-miR-519a-5p |
| hsa-miR-381-3p | hsa-miR-150-3p | hsa-miR-519b-5p |
| hsa-miR-377-3p | hsa-miR-154-3p | hsa-miR-521 |
| hsa-miR-452-5p | hsa-miR-15a-3p | hsa-miR-523-5p |
| hsa-miR-501-3p | hsa-miR-15b-3p | hsa-miR-545-5p |
| hsa-miR-514a-3p | hsa-miR-16-1-3p | hsa-miR-585 |
| hsa-miR-654-3p | hsa-miR-181a-2-3p | hsa-miR-7-2-3p |
| hsa-let-7b-3p | hsa-miR-181c-3p | hsa-miR-93-3p |
| hsa-miR-125a-3p | hsa-miR-186-3p | hsa-miR-96-3p |
| hsa-miR-133b | hsa-miR-195-3p | hsa-miR-99b-3p |
| hsa-miR-192-5p | hsa-miR-20b-3p | |
| hsa-miR-199a-3p | hsa-miR-223-5p | | c) A Multiple microRNAs-One mRNA Paradigm.

Figure 5:
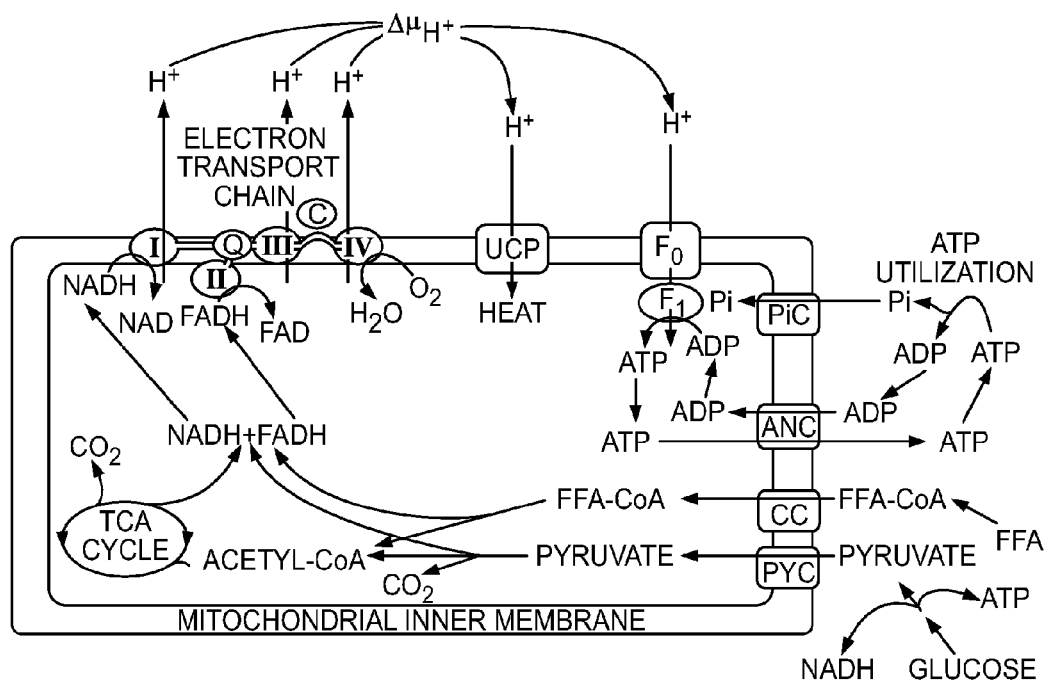
FIG. 5 is a schematic representation of oxidative phosphorylation in mitochondria, illustrating the uncoupling of oxidative phosphorylation from ATP synthesis by UCP1 to generate heat.

A. One exemplary multiple miRNAs-one mRNA paradigm involves UCP1. In adipocytes the key thermogenic regulator ultimately is UCP1 (also named thermogenin) and, thus, all thermogenic regulators must ultimately impact UCP1 activity. UCP1 is a mitochondrial transporter protein that creates proton leaks across the inner mitochondrial membrane, thus uncoupling oxidative phosphorylation from ATP synthesis. As a result, energy is dissipated in the form of heat (adaptive thermogenesis) (see FIG. 5) Lowell et al., Nature (2000); Friedman et al., Bioinformatics (2010); Hsu et al., Nucleic acids research (2011); Rieger et al., Frontiers in Genetics (2011)).

Figure 6:
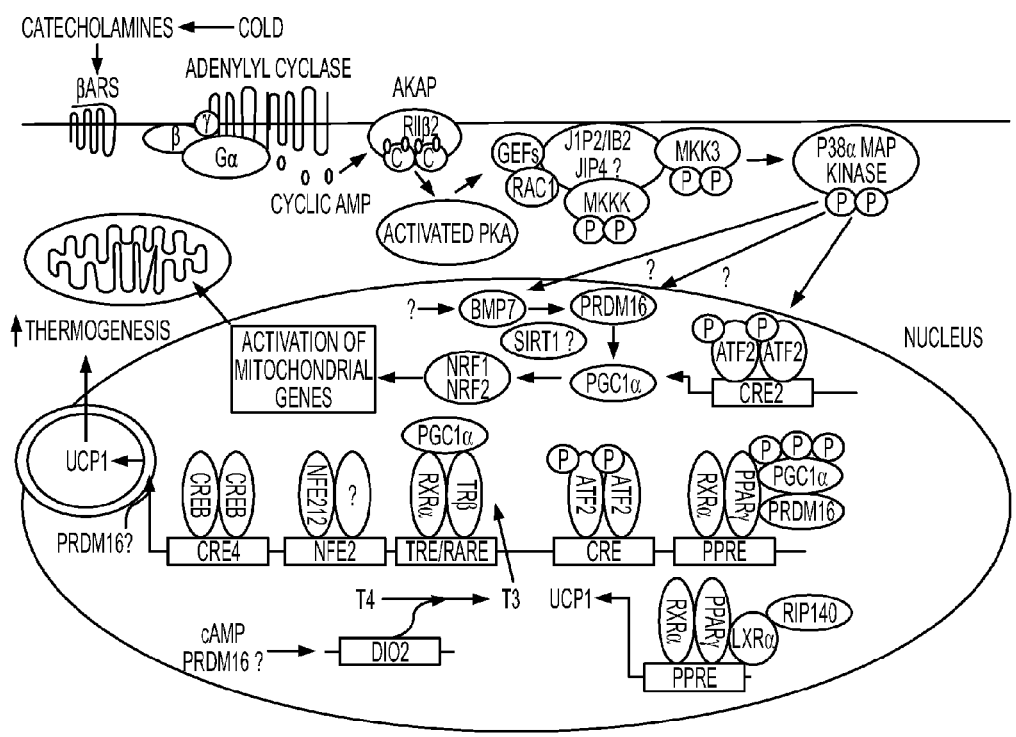
FIG. 6 depicts the transcriptional control of UCP1 by other exemplary thermogenic regulators.
Figure 7:
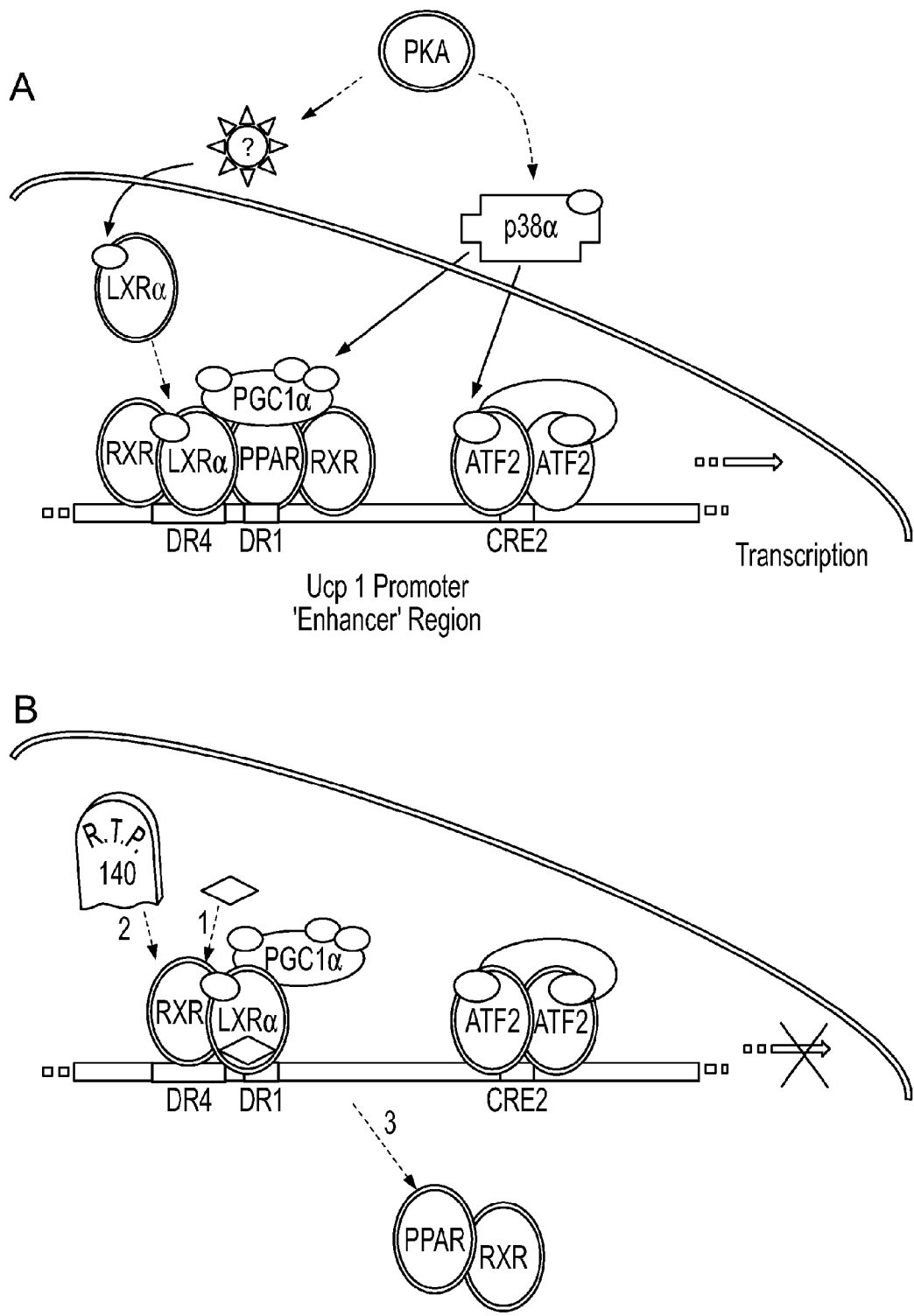
FIG. 7 depicts exemplary positive (A) and negative (B) transcriptional regulators of the UCP1 gene.

UCP1 biosynthesis is mainly controlled at the transcription level. FIG. 6 depicts the transcriptional control of UCP1 by other exemplary thermogenic regulators. The promoter's region of the UCP1 gene contains many distinct regulatory sites, allowing a wide range of proteins to influence its transcription, both positively (see FIG. 7A) and negatively (see FIG. 7B).

Mendelian randomization is a method of using measured variation in genes of known function to examine the causal effect of a modifiable exposure on disease in non-experimental studies. Mendelian randomization can be thought of as a "natural" Randomized Clinical Trial. Genetic polymorphism of the UCP1 gene, such as the −3826 A/G single nucleotide polymorphism in the promoter in exon 2 of UCP1, has been reported to be associated with reduced mRNA expression and obesity. Healthy children with the G/G genotype had a lower capacity for thermogenesis in response to a high-fat meal and acute cold exposure. The same −3826 A/G UCP1 genetic polymorphism diminishes resting energy expenditure and thermoregulatory sympathetic nervous system activity in young females. In a study of 367 Korean women, the G allele of −3826A>G and the C allele of −412A>C were significantly associated with larger areas of abdominal subcutaneous fat in a dominant model ($p<0.001$ and $p<0.0004$, respectively); combining them together (ht2[GC]) enhanced this significance ($p<0.00005$). A study of 100 severe obese adults (BMI>40 kg/m2) and 100 normal-weight control subjects (BMI range=19-24.9 kg/m2) identified 7 variations in the promoter region, 4 in the intronic region and 4 in the exonic region of the UCP1 gene. These variations could contribute to the development of obesity, particularly, g.−451C>T, g.940G>A, and g.IVS4-208T>G could represent "thrifty" factors that promote energy storage. Finally, two polymorphisms (A-3826G and C-3740A), located in the upstream promoter region of the UCP1 gene affect gene expression and are correlated with human longevity.

All aforementioned information supports targeting UCP1 expression and activity as a meaningful way to alter adaptive thermogenesis and consequently treat human obesity. Many strategies could be implemented to achieve this goal, however, the one employed in the methods of the invention uses miRNA agents to modulate simultaneously several elements within the thermogenic pathways to increase UCP1 synthesis and activity. Both direct and indirect interactions between miRNAs and the UCP1 gene are considered. Direct interaction means the direct binding of miRNAs to the various regions of the UCP1 gene, resulting in alterations of the transcription, translation, stability and/or degradation of the UCP1 mRNA. Indirect interaction means that miRNAs alter the transcription, translation, stability and/or degradation of thermogenic mRNAs, whose expressed proteins alter the transcription of the UCP1 gene. Furthermore, indirect interaction means that miRNAs alter the transcription, translation, stability and/or degradation of other miRNAs that modify the transcription of the UCP1 gene.

The promoter region of the human UCP1 gene (gi|237858805|ref|NG_012139.1| *Homo sapiens* uncoupling protein 1 (mitochondrial, proton carrier) (UCP1), RefSeqGene on chromosome 4) is particularly rich is regulatory element motifs:

```
UCP1 Gene Regulatory Elements:
1. Brown Fat Response Element 1 (BRE1) Motif:
                                                                [SEQ ID NO: 1]
CCTCTCTGCTTCTTCT
One
Length: 16, Interval: 1,129 -> 1,144, Mismatches: 0.

2. Brown Fat Response Element 2 (BRE2) Motif:
                                                                [SEQ ID NO: 2]
CTCCTTGGAA
One
Length: 10, Interval: 1,269 -> 1,278, Mismatches: 0.

3. CRE2 Motif:
ATTCTTTA
Four
```

-continued

Length: 8, Intervals: 1,121 -> 1,128, 3,631 -> 3,638, 10,982 -> 10,989, 15,881 -> 15,888, Mismatches: 0.

4. CREB Motif:
ACGTCA
Five
Length: 6, Intervals: 1,082 -> 1,087, 1,345 -> 1,350, 1,348 -> 1,343, 11,439 -> 11,434, 13,831 -> 13,836, Mismatches: 0.

5. DR1 Motif:
[SEQ ID NO: 3]
TTGCCCTTGCTCA
One
Length: 13, Interval: 1,099 -> 1,111, Mismatches: 0.

6. DR4 Motif:
[SEQ ID NO: 4]
ACGTCATAAAGGGTCA
One
Length: 16, Interval: 1,082 -> 1,097, Mismatches: 0.

7. DR4 Type RARE Motif:
[SEQ ID NO: 5]
RGKTCANNNNRGKTCA
One
Length: 16, Interval: 1,316 -> 1,301, Mismatches: 0.

8. ERE Motif:
[SEQ ID NO: 6]
GCTCATACTGACCT
One
Length: 14, Interval: 1,107 -> 1,120, Mismatches: 0.

9. PRE Motif:
[SEQ ID NO: 7]
GTTAATGTGTTCT
One
Length: 13, Interval: 1,009 -> 1,021, Mismatches: 0.

10. RARE Motif:
[SEQ ID NO: 8]
TGACCACAGTTTGATCA
One
Length: 17, Interval: 983 -> 999, Mismatches: 0.

11. RXR Motif:
AGGTCA
Twelve
Length: 6, Interval: 1,120 -> 1,115, 1,316 -> 1,311, 3,517 -> 3,522, 3,560 -> 3,555, 3,813 -> 3,808, 5,318 -> 5,313, 6,233 -> 6,238, 6,831 -> 6,836, 8,122 -> 8,127, 9,966 -> 9,971, 11,339 -> 11,334, 11,412 -> 11,407, Mismatches: 0.

12. GC Box 1 Motif:
CGCCC
Seven
Length: 5, Interval: 4,593 -> 4,589, 4,615 -> 4,619, 4,615 -> 4,619, 4,747 -> 4,751, 4,765 -> 4,769, 5,914 -> 5,910, 13,715 -> 13,711, Mismatches: 0.

13. GC Box 2 Motif:
GCGGG
Nine
Length: 5, Interval: 4,463 -> 4,459, 4,585 -> 4,589, 4,593 -> 4,597, 4,639 -> 4,643, 4,883 -> 4,887, 5,176 -> 5,172, 5,929 -> 5,933, 5,940 -> 5,944, 14,994 -> 14,990, Mismatches: 0.

14. GT Box 1 Motif:
CACCC
Twenty Five
Length: 5, Interval: 194 -> 190, 452 -> 448, 1,184 -> 1,188, 1,803 -> 1,807, 2,428 -> 2,424, 3,037 -> 3,041, 3,330 -> 3,334, 4,137 -> 4,141, 4,566 -> 4,562, 4,599 -> 4,595, 4,869 -> 4,865, 5,104 -> 5,108, 5,461 -> 5,457, 6,237 -> 6,241, 6,293 -> 6,289, 8,096 -> 8,092, 8,198 -> 8,194, 9,649 -> 9,645, 9,912 -> 9,908, 12,962 -> 12,958, 13,136 -> 13,132, 13,723 -> 13,719, 14,404 -> 14,400, 14,960 -> 14,964, 15,576 -> 15,572, Mismatches: 0.

15. GT Box 2 Motif:
GTGGG
Twenty
Length: 5, Interval: 25 -> 21, 1,805 -> 1,801, 1,809 -> 1,805, 2,119 -> 2,123, 3,854 -> 3,850, 4,310 -> 4,314, 4,339 -> 4,343, 4,765 -> 4,761, 4,867 -> 4,871, 6,291 -> 6,295, 7,554 -> 7,558, 8,280 -> 8,284, 8,681 -> 8,685, 9,615 -> 9,619, 9,689 -> 9,693, 9,906 -> 9,910, 10,363 -> 10,359, 13,074 -> 13,070, 13,640 -> 13,644, 13,941 -> 13,945, Mismatches: 0.

-continued

16. CpG Methylation Island Motif: CG
Three Hundred and Sixty Six, including many between positions 4,519 to 5,258 and 5,639 to 6,694.

Figure 8A:
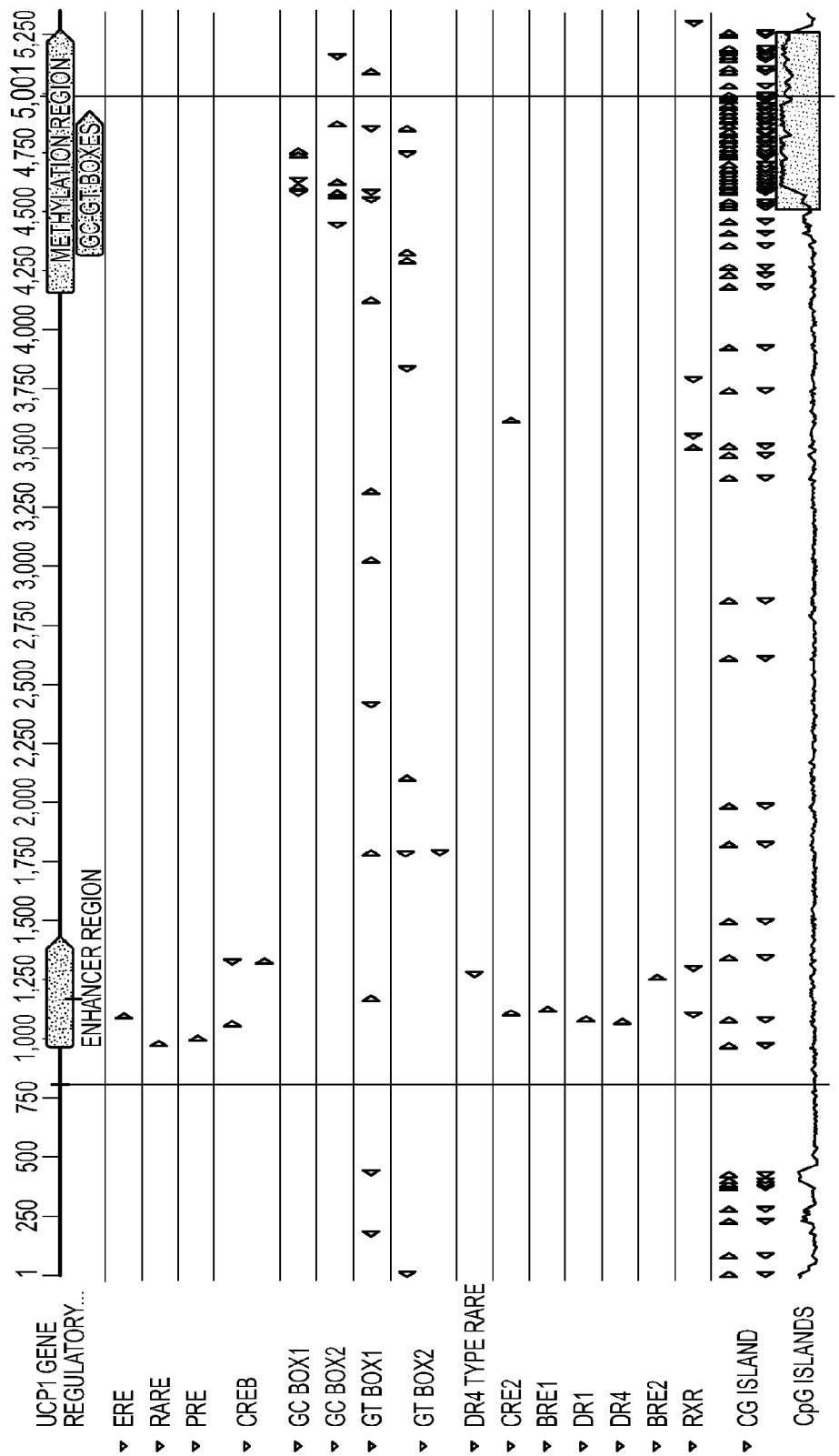
FIG. 8A depicts the location of various regulatory elements in reference to the transcription start site in the 15,910 base pair (bp) human UCP1 gene sequence (NCBI Reference Sequence: gi|237858805|ref|NG_012139.1| *Homo sapiens* uncoupling protein 1 (mitochondrial, proton carrier) (UCP1), RefSeqGene on chromosome 4).

FIG. 8A depicts the location of these various regulatory elements in reference to the UCP1 transcription start site at nucleotide position 5,001 of the 15,910 base pair human UCP-1 gene (FASTA accession number: >gi|237858805|ref|NG_012139.1| Homo sapiens uncoupling protein 1 (mitochondrial, proton carrier) (UCP1), RefSeqGene on chromosome 4; NCBI Reference Sequence: NG_012139.1).

Direct or indirect activation or repression of these regulatory elements by miRNAs will result in alterations of UCP1 gene expression and activity. Under normal conditions, the UCP1 gene expression and activity are repressed by a rich network of regulatory elements, in order to avoid energy wasting. Under stress, such as exposure to a cold environment, the expression of the UCP1 gene is upregulated, via various activators and repressors which are under the control of several miRNAs.

An initial survey of miRNAs targeting the human UCP1 3'UTR with several programs, including microRNA.org, was negative. However, other programs, including MicroCosm Targets, using the UCP1 Ensembl 1,462 base pair transcript ENST00000262999 as a target revealed binding sites for 27 miRNAs at 28 locations in UCP1 3'UTR as shown in Table 6.

TABLE 6

Binding sites for miRNAs in the 3'UTR of UCP1 (NCBI Reference Sequence. NG_012139.1) determined using microCosm Targets.

| Name | Sequence | SEQ ID NO | Minimum | Maximum | Length |
|---|---|---|---|---|---|
| hsa-miR-21 | AATGTAATGCAGATAAGCTA | 9 | 14143 | 14162 | 20 |
| hsa-miR-219-2-3p | ACATGTTTTAATTACAATTC | 10 | 14217 | 14236 | 20 |
| hsa-miR-22 | GATTGGCAGCTT | 11 | 14857 | 14868 | 12 |
| hsa-miR-222a | GATTTTTAATGTTTAGAGTCCAG | 12 | 14500 | 14522 | 23 |
| hsa-miR-290-3p | TTTAGAGCTGGAGGGTACTT | 13 | 14621 | 14640 | 20 |
| hsa-miR-292-3p | TTTAGAGCTGGAGGGTACTT | 14 | 14621 | 14640 | 20 |
| hsa-miR-292-5p | GACAGAGGAACAGTTTGAG | 15 | 14648 | 14666 | 19 |
| hsa-miR-325 | ATTTTGGCAGGATTGCTACTAG | 16 | 14568 | 14589 | 22 |
| hsa-miR-331-5p | TTTTGAGATCTATACCTGG | 17 | 14383 | 14401 | 19 |
| hsa-miR-362-5p | ATTTTAAGCTAAATCCAAGGATT | 18 | 14838 | 14860 | 23 |
| hsa-miR-367 | TGACCATTTCTGGAGTGCAATT | 19 | 14170 | 14191 | 22 |
| hsa-miR-371-5p | ACAGTTTGAT | 20 | 988 | 997 | 10 |
| hsa-miR-371-5p | ACAGTTTGAG | 21 | 14657 | 14666 | 10 |
| hsa-miR-377 | CTGGAGTGCAATTGTGTGA | 22 | 14179 | 14197 | 19 |
| hsa-miR-378 | TTTTAATGTTTAGAGTCCAG | 23 | 14503 | 14522 | 20 |
| hsa-miR-382 | TGATGACATCTCTAACAACTTC | 24 | 14526 | 14547 | 22 |
| hsa-miR-460 | AGAAACTGAGTGAAATGCAG | 25 | 14250 | 14269 | 20 |
| hsa-miR-508-5p | TGACCATTTCTGGAGTG | 26 | 14170 | 14186 | 17 |
| hsa-miR-543 | TACTCTGAATGTT | 27 | 14478 | 14490 | 13 |
| hsa-miR-549 | TTAACCACAGTTGTCA | 28 | 14321 | 14336 | 16 |
| hsa-miR-643 | CAAGTTCACTAGAATACAAG | 29 | 14412 | 14431 | 20 |
| hsa-miR-654-3p | AAGGTTACAGGCTGCCAGACAT | 30 | 14880 | 14901 | 22 |
| hsa-miR-664 | GTGTGAATGAATG | 31 | 14192 | 14204 | 13 |
| hsa-miR-871 | TAGGCATGAACCTACTCTGAATG | 32 | 14466 | 14488 | 23 |
| hsa-miR-883a-3p | AAACTGAGTGAAATGCAGTT | 33 | 14252 | 14271 | 20 |
| hsa-miR-883b-3p | AAACTGAGTGAAATGCAGTT | 34 | 14252 | 14271 | 20 |

TABLE 6-continued

Binding sites for miRNAs in the 3'UTR of UCP1 (NCBI Reference Sequence.
NG_012139.1) determined using microCosm Targets.

| Name | Sequence | SEQ ID NO | Minimum | Maximum | Length |
|---|---|---|---|---|---|
| hsa-miR-888-3p | TTTATTAACCACAGTTGTCAGTT | 35 | 14317 | 14339 | 23 |
| hsa-miR-92b | GAGTGCAAT | | 14182 | 14190 | 9 |

Other programs, such as miRWalk, miRGen, miRGator-miRanda, and DIANA microT, using the UCP1 Ensembl 1,462 base pair transcript (ENST00000262999), the UCP1 Ensembl 9,371 base pair gene sequence (ENSG00000109424) or the 15,910 base pair UCP1 sequence (NCBI Reference Sequence: NG_012139.1) as targets, revealed binding sites for a total of 50 miRNAs at 69 locations in UCP1 3'UTR as shown in Table 7.

TABLE 7

Binding sites for miRNAs in the 3'UTR of UCP1 (NCBI Reference Sequence.
NG_012139.1) according to several programs.

| | Name | Sequence | SEQ ID NO | Minimum | Maximum | Length |
|---|---|---|---|---|---|---|
| 1 | hsa-miR-1179 | AAGTATCCTTT | 36 | 15346 | 15356 | 11 |
| 2 | hsa-miR-1302 | ATGGGACACA | 37 | 15021 | 15030 | 10 |
| 3 | hsa-miR-130b | TTATTTTCCCT | 38 | 15161 | 15171 | 11 |
| 4 | hsa-miR-146a | TGACAACTGT | 39 | 14327 | 14336 | 10 |
| | hsa-miR-146a | AGGGAACTGA | 40 | 15231 | 15240 | 10 |
| | hsa-miR-146a | TGTGAACTGG | 41 | 15679 | 15688 | 10 |
| 5 | hsa-miR-181c | AACCATAGT | | 15304 | 15312 | 9 |
| 6 | hsa-miR-19b-2 | ACTTTTGCGG | 42 | 14991 | 15000 | 10 |
| 7 | hsa-miR-203 | TTAAATGTT | | 15584 | 15592 | 9 |
| 8 | hsa-miR-204-5p | TTCCTTTATC | 43 | 14006 | 14015 | 10 |
| | hsa-miR-204-5p | TTCCTCTGTC | 44 | 14648 | 14657 | 10 |
| 9 | hsa-miR-21-5p | TAGCTTATCT | 45 | 14153 | 14162 | 10 |
| 10 | hsa-miR-211-5p | TTCCCTATCTC | 46 | 14779 | 14789 | 11 |
| 11 | hsa-miR-214 | CAGCAAGCA | 47 | 15052 | 15060 | 9 |
| 12 | hsa-miR-22-3p | AAGCTGCCAA | 48 | 14859 | 14868 | 10 |
| | hsa-miR-22-5p | AGTTCTTCACA | 49 | 14203 | 14213 | 11 |
| 13 | hsa-miR-26a-2-3p | CATTTTCTTG | 50 | 13918 | 13927 | 10 |
| | hsa-miR-26a-2-3p | CCAATCCTTG | 51 | 14853 | 14862 | 10 |
| | hsa-miR-26a-2-3p | CCTTTTCATG | 52 | 15616 | 15625 | 10 |
| 14 | hsa-miR-30b | GTAACCTTCC | 53 | 14878 | 14887 | 10 |
| 15 | hsa-miR-325 | CAGAGTAGGT | 54 | 14475 | 14484 | 10 |
| | hsa-miR-325 | CCTTGTAGGC | 55 | 15378 | 15387 | 10 |
| 16 | hsa-miR-328 | CTGTTCCTCT | 56 | 14651 | 14660 | 10 |
| 17 | hsa-miR-362-5p | ATCCTTGGAT | 57 | 14850 | 14859 | 10 |
| 18 | hsa-miR-367-3p | AATTGCACTC | 58 | 14182 | 14191 | 10 |
| 19 | hsa-miR-371a-3p | AAGTGCCTGC | 59 | 15435 | 15444 | 10 |
| | hsa-miR-371a-5p | TCTCAAACTG | 60 | 14658 | 14667 | 10 |

TABLE 7-continued

Binding sites for miRNAs in the 3'UTR of UCP1 (NCBI Reference Sequence. NG_012139.1) according to several programs.

| Name | Sequence | SEQ ID NO | Minimum | Maximum | Length |
|---|---|---|---|---|---|
| 20 hsa-miR-378a-3p | ACTGGCCTTG | 61 | 15816 | 15825 | 10 |
| 21 hsa-miR-382-3p | ATTCATTCAC | 62 | 14194 | 14203 | 10 |
| 22 hsa-miR-382-5p | GAAGTTGTTAGAGAT | 63 | 14533 | 14547 | 15 |
| 23 hsa-miR-383 | AGATTAGAA | 64 | 14545 | 14553 | 9 |
| 24 hsa-miR-421 | ATTAACTGAC | 65 | 14333 | 14342 | 10 |
| hsa-miR-421 | CTCAAAAGAC | 66 | 14380 | 14389 | 10 |
| 25 hsa-miR-422a | ACTGGCCTT | | 15817 | 15825 | 9 |
| 26 hsa-miR-431 | TGTCTGGCA | | 14892 | 14900 | 9 |
| 27 hsa-miR-452 | TTATCTGC | | 14151 | 14158 | 8 |
| hsa-miR-452 | TCTTCTGC | | 14773 | 14780 | 8 |
| hsa-miR-452 | ACATCTGC | | 15009 | 15016 | 8 |
| 28 hsa-miR-455-3p | CAGTCCAT | | 13893 | 13900 | 8 |
| hsa-miR-455-5p | TGTGTGCCTT | 67 | 15641 | 15650 | 10 |
| 29 hsa-miR-491-5p | AATGGGGAAG | 68 | 14975 | 14984 | 10 |
| 30 hsa-miR-501-3p | ATGCATCAGG | 69 | 15547 | 15556 | 10 |
| 31 hsa-miR-504 | AGACCCTGT | | 15325 | 15333 | 9 |
| | TATTCTAGTGAACTTG | 70 | | | |
| 32 hsa-miR-508-5p | ACTCTTA | | 14405 | 14427 | 23 |
| 33 hsa-miR-512-5p | CACTCAG | | 14255 | 14261 | 7 |
| 34 hsa-miR-514a-3p | TTGACTCTT | | 14406 | 14414 | 9 |
| 35 hsa-miR-515-3p | GACTGCCTT | | 15539 | 15547 | 9 |
| hsa-miR-515-3p | GTGTGCCTT | | 15641 | 15649 | 9 |
| 36 hsa-miR-517a-3p | ATGGTGCATT | 71 | 15650 | 15659 | 10 |
| 37 hsa-miR-545 | CAGCAAGCACT | 72 | 15050 | 15060 | 11 |
| 38 hsa-miR-549 | TGACAACTGT | 73 | 14327 | 14336 | 10 |
| 39 hsa-miR-552 | CACAGGTGA | | 15130 | 15138 | 9 |
| 40 hsa-miR-616-5p | ACTCTAAAC | | 14510 | 14518 | 9 |
| 41 hsa-miR-620 | ATGAATATAG | 74 | 14560 | 14569 | 10 |
| 42 hsa-miR-643 | ACTGGTATGT | 75 | 13933 | 13942 | 10 |
| hsa-miR-643 | TCTTGTATTC | 76 | 14423 | 14432 | 10 |
| hsa-miR-643 | CCTTGTAGGC | 77 | 15378 | 15387 | 10 |
| hsa-miR-643 | ACATGCATGC | 78 | 15553 | 15562 | 10 |
| 43 hsa-miR-651 | TTAAAATAAG | 79 | 13988 | 13997 | 10 |
| hsa-miR-651 | TTAGGTTAAA | 80 | 13993 | 14002 | 10 |
| hsa-miR-651 | TCATGATAAG | 81 | 15700 | 15709 | 10 |
| 44 hsa-miR-654-3p | TATCTCTTCT | 82 | 14775 | 14784 | 10 |
| hsa-miR-654-3p | TATGTATACT | 83 | 15493 | 15502 | 10 |

TABLE 7-continued

Binding sites for miRNAs in the 3'UTR of UCP1 (NCBI Reference Sequence. NG_012139.1) according to several programs.

| Name | Sequence | SEQ ID NO | Minimum | Maximum | Length |
|---|---|---|---|---|---|
| 45 hsa-miR-655 | GTAATACAT | | 15593 | 15601 | 9 |
| 46 hsa-miR-767-3p | CCTGCTCAT | | 14871 | 14879 | 9 |
| 47 hsa-miR-888-3p | GACTGACTCC | 84 | 15772 | 15781 | 10 |
| 48 hsa-miR-92b-3p | ATTGCACTCC | 85 | 14181 | 14190 | 10 |
| 49 hsa-miR-941 | CACCCAGGT | | 14396 | 14404 | 9 |
| 50 hsa-miR-99a-3p | AAGCTGGCTC | 86 | 15117 | 15126 | 10 |

Figure 3:
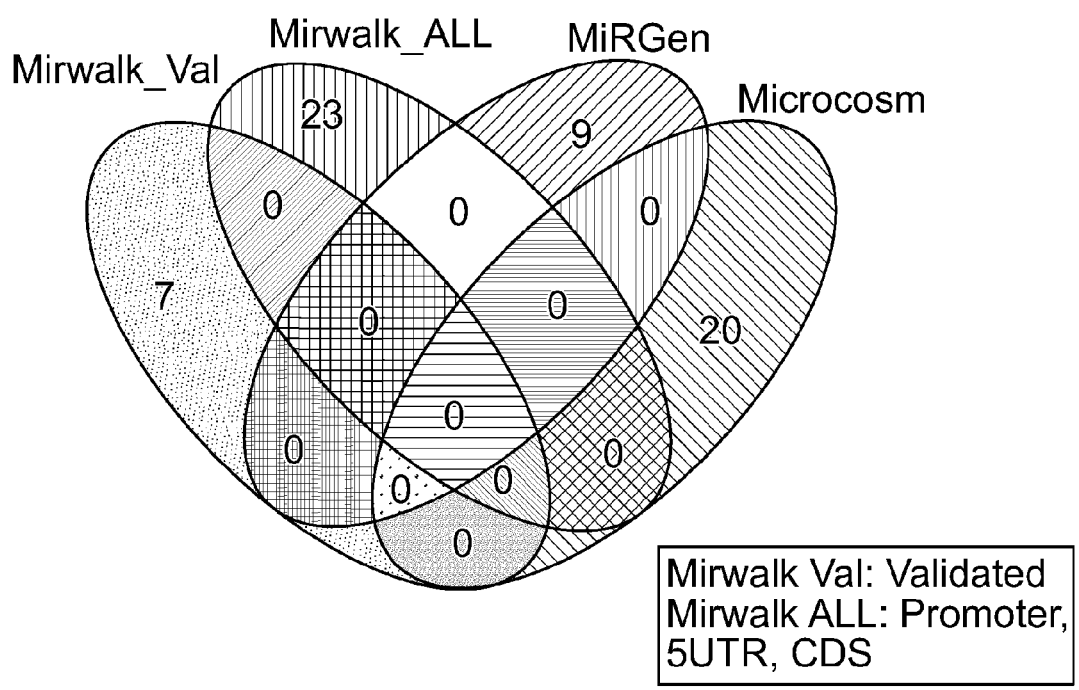
FIG. 3 is a schematic representation of the overlap between the visual inspection and alignment of nucleotide sequences set forth herein, and the results from multiple miRNA prediction programs predicting miRNA binding sites in the 5'UTR, promoter region, coding sequence and 3'UTR of the human UCP1 gene.

Alignment of the sequence of the human UCP1 gene with several miRNA sequences yielded matches in the 5'UTR, the promoter region and the coding regions of the UCP1 gene. Interrogation of the publicly available Internet tools predicting miRNAs targeting the various regions of the UCP1 gene elicited several hits. Surprisingly, the overlap between these prediction tools was zero, as shown in FIG. 3.

Nevertheless, miRNA databases were screened using the alignment program Geneious. A total of 191 human microRNAs were found which have complementary 450 binding sites in the UCP1 gene sequence (Table 8). The length of the matches goes from 7 bases to 12 bases (e.g. hsa-miR-24-2-5p and hsa-miR-192-5p). The number of hits per miRNA varies from 1 to several (e.g. 9 for hsa-miR-19b2 (an abundant adipocyte miRNA), 14 for hsa-miR-26a-2-3p, 11 for hsa-miR-181c, and 12 for hsa-miR-620).

TABLE 8 miRNAs with predicted binding sites in the UCP1 gene sequence (NCBI Reference Sequence: NG_012139.1).

| miRNA | Sequence | SEQ ID NO | Minimum | Maximum | Length | Direction |
|---|---|---|---|---|---|---|
| hsa-let-7c | TAGAGTTTC | | 5918 | 5926 | 9 | reverse |
| hsa-let-7e | GGAGGTAGG | | 13283 | 13291 | 9 | reverse |
| hsa-let-7e | TGAAGTAGG | | 7612 | 7620 | 9 | reverse |
| hsa-let-7e | AGAGGTAGG | | 3306 | 3314 | 9 | reverse |
| hsa-let-7i-3p | CTGTGCAAG | | 3588 | 3596 | 9 | reverse |
| hsa-miR-17 | CAAAGTGCT | | 12200 | 12208 | 9 | reverse |
| hsa-miR-17 | CAAAGTGCT | | 9931 | 9939 | 9 | reverse |
| hsa-miR-17 | CAAAGTGCT | | 218 | 226 | 9 | reverse |
| hsa-miR-19a | TGTGCAAAT | | 3916 | 3924 | 9 | reverse |
| hsa-miR-19a | TGTGCAAAT | | 834 | 842 | 9 | reverse |
| hsa-miR-19b-2 | ACTTTTGCGG | 87 | 14991 | 15000 | 10 | reverse |
| hsa-miR-19b-2 | AGTTTTACAA | 88 | 11998 | 12007 | 10 | reverse |
| hsa-miR-19b-2 | AGTTTTGTAT | 89 | 10023 | 10032 | 10 | reverse |
| hsa-miR-19b-2 | AGTCTTGAAG | 90 | 9399 | 9408 | 10 | reverse |
| hsa-miR-19b-2 | AGGTTTGTAG | 91 | 7758 | 7767 | 10 | reverse |
| hsa-miR-19b-2 | AGTATTGAAG | 92 | 7159 | 7168 | 10 | reverse |

TABLE 8-continued miRNAs with predicted binding sites in the UCP1 gene sequence (NCBI Reference Sequence: NG_012139.1).

| miRNA | Sequence | SEQ ID NO | Minimum | Maximum | Length | Direction |
|---|---|---|---|---|---|---|
| hsa-miR-19b-2 | AGGCTTGCAG | 93 | 3546 | 3555 | 10 | reverse |
| hsa-miR-19b-2 | AATTTGGCAG | 94 | 529 | 538 | 10 | reverse |
| hsa-miR-19b-2 | AGTTTTGGAA | 95 | 312 | 321 | 10 | reverse |
| hsa-miR-20b | CAAAGTGCT | | 12200 | 12208 | 9 | reverse |
| hsa-miR-20b | CAAAGTGCT | | 9931 | 9939 | 9 | reverse |
| hsa-miR-20b | CAAAGTGCT | | 218 | 226 | 9 | reverse |
| hsa-miR-21-5p | TAGCTTATCT | 96 | 14153 | 14162 | 10 | reverse |
| hsa-miR-22-3p | AAGCTGCCAA | 97 | 14859 | 14868 | 10 | reverse |
| hsa-miR-22-3p | AAGCTTCCAG | 98 | 1482 | 1491 | 10 | reverse |
| hsa-miR-22-5p | AGTTCTTCACA | 99 | 14203 | 14213 | 11 | reverse |
| hsa-miR-22-5p | AATTCTTCAGG | 100 | 8032 | 8042 | 11 | reverse |
| hsa-miR-22-5p | GGTTCTTCAGC | 101 | 5389 | 5399 | 11 | reverse |
| hsa-miR-24-2-5p | TGCCTACTGGCC | 102 | 8651 | 8662 | 12 | reverse |
| hsa-miR-25-3p | CATTGCAC | | 11565 | 11572 | 8 | reverse |
| hsa-miR-25-5p | AGGCGGAG | | 5963 | 5970 | 8 | reverse |
| hsa-miR-26a-2-3p | CCTTTTCATG | 103 | 15616 | 15625 | 10 | reverse |
| hsa-miR-26a-2-3p | CCAATCCTTG | 104 | 14853 | 14862 | 10 | reverse |
| hsa-miR-26a-2-3p | CATTTTCTTG | 105 | 13918 | 13927 | 10 | reverse |
| hsa-miR-26a-2-3p | CCTACTCTTC | 106 | 13505 | 13514 | 10 | reverse |
| hsa-miR-26a-2-3p | ACGATTCTTG | 107 | 13192 | 13201 | 10 | reverse |
| hsa-miR-26a-2-3p | TCTATTCTTT | 108 | 12883 | 12892 | 10 | reverse |
| hsa-miR-26a-2-3p | CATATTTTTG | 109 | 10197 | 10206 | 10 | reverse |
| hsa-miR-26a-2-3p | GCTAGTCTTG | 110 | 9978 | 9987 | 10 | reverse |
| hsa-miR-26a-2-3p | CATATTTTTG | 111 | 9890 | 9899 | 10 | reverse |
| hsa-miR-26a-2-3p | CCTTTTCTTT | 112 | 6631 | 6640 | 10 | reverse |
| hsa-miR-26a-2-3p | CCCATTCTCG | 113 | 4709 | 4718 | 10 | reverse |
| hsa-miR-26a-2-3p | TTTATTCTTG | 114 | 3893 | 3902 | 10 | reverse |
| hsa-miR-26a-2-3p | CCTTTACTTG | 115 | 1885 | 1894 | 10 | reverse |
| hsa-miR-26a-2-3p | GCGATTCTTG | 116 | 376 | 385 | 10 | reverse |
| hsa-miR-27-5p | AGAGCTTAGG | 117 | 2949 | 2958 | 10 | reverse |
| hsa-miR-30b | GTAACCTTCC | 118 | 14878 | 14887 | 10 | reverse |
| hsa-miR-30b | GTAACCATCA | 119 | 12991 | 13000 | 10 | reverse |
| hsa-miR-30b | GTAATCATAC | 120 | 12831 | 12840 | 10 | reverse |
| hsa-miR-30b | GTCAACATCA | 121 | 11401 | 11410 | 10 | reverse |
| hsa-miR-30b | GTAAACATAA | 122 | 9365 | 9374 | 10 | reverse |
| hsa-miR-30b | GTACTCATCC | 123 | 9016 | 9025 | 10 | reverse |
| hsa-miR-30b | CTATACATCC | 124 | 8586 | 8595 | 10 | reverse |

TABLE 8-continued miRNAs with predicted binding sites in the UCP1 gene sequence (NCBI Reference Sequence: NG_012139.1).

| miRNA | Sequence | SEQ ID NO | Minimum | Maximum | Length | Direction |
|---|---|---|---|---|---|---|
| hsa-miR-30b | CTAAACATCT | 125 | 7495 | 7504 | 10 | reverse |
| hsa-miR-31 | GGCTATGCC | | 7712 | 7720 | 9 | reverse |
| hsa-miR-32 | ATTGCACA | | 11564 | 11571 | 8 | reverse |
| hsa-miR-92b | ATTGCACTCC | 126 | 14181 | 14190 | 10 | reverse |
| hsa-miR-92b | ATTGCACTAG | 127 | 11282 | 11291 | 10 | reverse |
| hsa-miR-93 | CAAAGTGCTG | 128 | 12199 | 12208 | 10 | reverse |
| hsa-miR-93 | CAAAGTGCTG | 129 | 217 | 226 | 10 | reverse |
| hsa-miR-93-3p | ACTCCTGGGCT | 130 | 12356 | 12366 | 11 | reverse |
| hsa-miR-93-3p | ACTGATAAGCT | 131 | 11055 | 11065 | 11 | reverse |
| hsa-miR-93-3p | ACTCCTGACCT | 132 | 9966 | 9976 | 11 | reverse |
| hsa-miR-96-3p | AATCATGTGCC | 133 | 8659 | 8669 | 11 | reverse |
| hsa-miR-99a-3p | AAGCTGGCTC | 134 | 15117 | 15126 | 10 | reverse |
| hsa-miR-99a-3p | AAACTCTTTC | 135 | 13344 | 13353 | 10 | reverse |
| hsa-miR-99a-3p | AATCTTGTTC | 136 | 11952 | 11961 | 10 | reverse |
| hsa-miR-99a-3p | AAGCTCCTTT | 137 | 11050 | 11059 | 10 | reverse |
| hsa-miR-99a-3p | AAGCTCCTTT | 138 | 8099 | 8108 | 10 | reverse |
| hsa-miR-99a-3p | AAGCTCTGTC | 139 | 7523 | 7532 | 10 | reverse |
| hsa-miR-99b-3p | CAACCTCGAG | 140 | 13666 | 13675 | 10 | reverse |
| hsa-miR-99b-3p | CGAGCTCCTG | 141 | 13660 | 13669 | 10 | reverse |
| hsa-miR-99b-3p | GAAGCTTGTG | 142 | 6436 | 6445 | 10 | reverse |
| hsa-miR-99b-3p | CAAACTCCTG | 143 | 257 | 266 | 10 | reverse |
| hsa-miR-100 | TCCAGTAGAT | 144 | 11866 | 11875 | 10 | reverse |
| hsa-miR-100 | ACGCGCAGAT | 145 | 5634 | 5643 | 10 | reverse |
| hsa-miR-106b-5p | CAAAGTGCTG | 146 | 12199 | 12208 | 10 | reverse |
| hsa-miR-106b-5p | CAAAGTGCTG | 147 | 217 | 226 | 10 | reverse |
| hsa-miR-126-3P | TCATACAGT | | 12828 | 12836 | 9 | reverse |
| hsa-miR-126-3P | TTGTACTGT | | 11542 | 11550 | 9 | reverse |
| hsa-miR-126-3P | TGGTCCCGT | | 7922 | 7930 | 9 | reverse |
| hsa-miR-126-3P | TCATACAGT | | 932 | 940 | 9 | reverse |
| hsa-miR-130b | TTATTTTCCCT | 148 | 15161 | 15171 | 11 | reverse |
| hsa-miR-130b | CTCTTTTCAGT | 149 | 9670 | 9680 | 11 | reverse |
| hsa-miR-130b | CTCTCTTCACT | 150 | 8977 | 8987 | 11 | reverse |
| hsa-miR-130b | CTCTTTTTCCC | 151 | 8444 | 8454 | 11 | reverse |
| hsa-miR-130b | CTTTTTCCCCT | 152 | 6624 | 6634 | 11 | reverse |
| hsa-miR-130b | CTATTTTCCGT | 153 | 5742 | 5752 | 11 | reverse |
| hsa-miR-130b | TTCCTTTCCCT | 154 | 5007 | 5017 | 11 | reverse |
| hsa-miR-130b | CTCTTTGCCCC | 155 | 1845 | 1855 | 11 | reverse |

TABLE 8-continued miRNAs with predicted binding sites in the UCP1 gene sequence (NCBI Reference Sequence: NG_012139.1).

| miRNA | Sequence | SEQ ID NO | Minimum | Maximum | Length | Direction |
|---|---|---|---|---|---|---|
| hsa-miR-130b | CTCCTTTCCTT | 156 | 1033 | 1043 | 11 | reverse |
| hsa-miR-133a-1 | TTTGGTGCCC | 157 | 7393 | 7402 | 10 | reverse |
| hsa-miR-140-3p | TACCACAG | | 5893 | 5900 | 8 | reverse |
| hsa-miR-141 | TAACACTG | | 5852 | 5859 | 8 | reverse |
| hsa-miR-143 | GGTGCAGTG | 158 | 4132 | 4140 | 9 | reverse |
| hsa-miR-143-3p | TGAGATGAGG | 159 | 13727 | 13736 | 10 | reverse |
| hsa-miR-143-3p | TGAGATGGAG | 160 | 10172 | 10181 | 10 | reverse |
| hsa-miR-143-3p | TTAGATGAAG | 161 | 9572 | 9581 | 10 | reverse |
| hsa-miR-144-3p | TACAGTATT | | 12825 | 12833 | 9 | reverse |
| hsa-miR-144-3p | TACAATATA | | 8859 | 8867 | 9 | reverse |
| hsa-miR-144-3p | GACAGTATA | | 1491 | 1499 | 9 | reverse |
| hsa-miR-146a | CCTCTGAAA | | 3499 | 3507 | 9 | reverse |
| hsa-miR-146a | TGTGAACTGG | 162 | 15679 | 15688 | 10 | reverse |
| hsa-miR-146a | AGGGAACTGA | 163 | 15231 | 15240 | 10 | reverse |
| hsa-miR-146a | TGACAACTGT | 164 | 14327 | 14336 | 10 | reverse |
| hsa-miR-146a | TAAGAACTAA | 165 | 8935 | 8944 | 10 | reverse |
| hsa-miR-146a | TTAGAACAGA | 166 | 7908 | 7917 | 10 | reverse |
| hsa-miR-146a | TGAGAAGTGC | 167 | 6926 | 6935 | 10 | reverse |
| hsa-miR-146a | TGAAAACTTA | 168 | 3883 | 3892 | 10 | reverse |
| hsa-miR-146a | ACAGAACTGA | 169 | 2259 | 2268 | 10 | reverse |
| hsa-miR-146a | TGAGACCAGA | 170 | 2235 | 2244 | 10 | reverse |
| hsa-miR-146a | TGAGAAATAA | 171 | 1614 | 1623 | 10 | reverse |
| hsa-miR-147 | TGTGTGGATAA | 172 | 7223 | 7233 | 11 | reverse |
| hsa-miR-147 | TTTGTGCAAAT | 173 | 3916 | 3926 | 11 | reverse |
| hsa-miR-154 | AATCATACA | | 12830 | 12838 | 9 | reverse |
| hsa-miR-154 | AATCATACA | | 934 | 942 | 9 | reverse |
| hsa-miR-181c | AACCATAGT | | 15304 | 15312 | 9 | reverse |
| hsa-miR-181c | AACCAAAGA | | 13244 | 13252 | 9 | reverse |
| hsa-miR-181c | AACCATCAC | | 12990 | 12998 | 9 | reverse |
| hsa-miR-181c | ATCCAGCGA | | 11466 | 11474 | 9 | reverse |
| hsa-miR-181c | AACATCTA | | 7494 | 7502 | 9 | reverse |
| hsa-miR-181c | AAAAATCGA | | 6201 | 6209 | 9 | reverse |
| hsa-miR-181c | AACCCCCGA | | 5540 | 5548 | 9 | reverse |
| hsa-miR-181c | AACCCTCTA | | 3614 | 3622 | 9 | reverse |
| hsa-miR-181c | AGCCAGCGA | | 3471 | 3479 | 9 | reverse |
| hsa-miR-181c | AACCATAGG | | 2801 | 2809 | 9 | reverse |
| hsa-miR-181c | AACCATCAC | | 194 | 202 | 9 | reverse |

TABLE 8-continued miRNAs with predicted binding sites in the UCP1 gene sequence (NCBI Reference Sequence: NG_012139.1).

| miRNA | Sequence | SEQ ID NO | Minimum | Maximum | Length | Direction |
|---|---|---|---|---|---|---|
| hsa-miR-185 | TGGAGAGAA | | 2979 | 2987 | 9 | reverse |
| hsa-miR-192-5p | CTAACATATGAA | 174 | 114 | 125 | 12 | reverse |
| hsa-miR-194-1 | TGTAACAGCA | 175 | 1895 | 1904 | 10 | reverse |
| hsa-miR-196a | AGGTAGTTT | | 12139 | 12147 | 9 | reverse |
| hsa-miR-199a-5p | CCCTGTGTTC | 176 | 5753 | 5762 | 10 | reverse |
| hsa-miR-200a | TAACACTG | | 5852 | 5859 | 8 | reverse |
| hsa-miR-200b | TAATAATGCC | 177 | 11184 | 11193 | 10 | reverse |
| hsa-miR-200b | GAATACTGCC | 178 | 10340 | 10349 | 10 | reverse |
| hsa-miR-200c-3p | TAATACTGT | | 12466 | 12474 | 9 | reverse |
| hsa-miR-200c-3p | TAATAATGC | | 11185 | 11193 | 9 | reverse |
| hsa-miR-200c-3p | GAATACTGC | | 10341 | 10349 | 9 | reverse |
| hsa-miR-200c-3p | TAATACAGC | | 7594 | 7602 | 9 | reverse |
| hsa-miR-203 | TTAAATGTT | | 15584 | 15592 | 9 | reverse |
| hsa-miR-203 | TGAAATTTT | | 9782 | 9790 | 9 | reverse |
| hsa-miR-203 | TGAAAGGTT | | 4495 | 4503 | 9 | reverse |
| hsa-miR-204-5p | TTCCTCTGTC | 179 | 14648 | 14657 | 10 | reverse |
| hsa-miR-204-5p | TTCCTTTATC | 180 | 14006 | 14015 | 10 | reverse |
| hsa-miR-205 | TCCTTCATT | | 10659 | 10667 | 9 | reverse |
| hsa-miR-208b | ATAAGAAGA | | 9493 | 9501 | 9 | reverse |
| hsa-miR-208b | ATAAGAAGA | | 1770 | 1778 | 9 | reverse |
| hsa-miR-211-5p | TTCCCTATCTC | 181 | 14779 | 14789 | 11 | reverse |
| hsa-miR-211-5p | TCCCCTCTGTC | 182 | 5238 | 5248 | 11 | reverse |
| hsa-miR-211-5p | TTCCCTTGCTC | 183 | 5002 | 5012 | 11 | reverse |
| hsa-miR-211-5p | TTCCCATTCTC | 184 | 4710 | 4720 | 11 | reverse |
| hsa-miR-214 | CAGCAAGCA | | 15052 | 15060 | 9 | reverse |
| hsa-miR-214 | CAGAAGGCA | | 6918 | 6926 | 9 | reverse |
| hsa-miR-214 | CCGCAGGCA | | 5935 | 5943 | 9 | reverse |
| hsa-miR-214 | CACCAGGCA | | 2087 | 2095 | 9 | reverse |
| hsa-miR-218 | TGTGCTTGA | | 10385 | 10393 | 9 | reverse |
| hsa-miR-302c | TTTAACATG | | 2932 | 2940 | 9 | reverse |
| hsa-miR-324-5p | CGCGTCCCCT | 185 | 4876 | 4885 | 10 | reverse |
| hsa-miR-325 | CCTTGTAGGC | 186 | 15378 | 15387 | 10 | reverse |
| hsa-miR-325 | CAGAGTAGGT | 187 | 14475 | 14484 | 10 | reverse |
| hsa-miR-325 | CCAAGTAGCT | 188 | 10066 | 10075 | 10 | reverse |
| hsa-miR-325 | CCAAGTAGCT | 189 | 354 | 363 | 10 | reverse |
| hsa-miR-328 | CTGTTCCTCT | 190 | 14651 | 14660 | 10 | reverse |
| hsa-miR-328 | CTGGCTCCCT | 191 | 8215 | 8224 | 10 | reverse |

TABLE 8-continued miRNAs with predicted binding sites in the UCP1 gene sequence (NCBI Reference Sequence: NG_012139.1).

| miRNA | Sequence | SEQ ID NO | Minimum | Maximum | Length | Direction |
|---|---|---|---|---|---|---|
| hsa-miR-328 | CTGGCCCTTC | 192 | 8062 | 8071 | 10 | reverse |
| hsa-miR-328 | CTGGCACTCA | 193 | 6653 | 6662 | 10 | reverse |
| hsa-miR-328 | CTGGCTTTCT | 194 | 6496 | 6505 | 10 | reverse |
| hsa-miR-328 | CTGCCCCTCC | 195 | 6048 | 6057 | 10 | reverse |
| hsa-miR-328 | CTGGGCCGCT | 196 | 4804 | 4813 | 10 | reverse |
| hsa-miR-328 | CTGGAGCTCT | 197 | 4477 | 4486 | 10 | reverse |
| hsa-miR-328 | CTGACCCTTT | 198 | 1089 | 1098 | 10 | reverse |
| hsa-miR-330 | CAAAGCACAC | 199 | 13845 | 13854 | 10 | reverse |
| hsa-miR-330 | CAAAGCACAC | 199 | 11657 | 11666 | 10 | reverse |
| hsa-miR-331-5p | CTAGGTGTGG | 200 | 7719 | 7728 | 10 | reverse |
| hsa-miR-361-3p | CCCCCAGG |  | 5112 | 5119 | 8 | reverse |
| hsa-miR-362-5p | ATCCTTGGAT | 201 | 14850 | 14859 | 10 | reverse |
| hsa-miR-367-3p | AATTGCACTC | 202 | 14182 | 14191 | 10 | reverse |
| hsa-miR-367-3p | AAATGCACTT | 203 | 999 | 1008 | 10 | reverse |
| hsa-miR-369 | AATAATACA |  | 2266 | 2274 | 9 | reverse |
| hsa-miR-371a-3p | AAGTGCCTGC | 204 | 15435 | 15444 | 10 | reverse |
| hsa-miR-371a-3p | AAGAGCCGAC | 205 | 11455 | 11464 | 10 | reverse |
| hsa-miR-371a-3p | ACGTGCCACC | 206 | 10044 | 10053 | 10 | reverse |
| hsa-miR-371a-3p | AAGTGCCTCT | 207 | 7047 | 7056 | 10 | reverse |
| hsa-miR-371a-3p | AAGTGCACCC | 208 | 5457 | 5466 | 10 | reverse |
| hsa-miR-371a-5p | TCTCAAACTG | 209 | 14658 | 14667 | 10 | reverse |
| hsa-miR-372 | AAAGTGCTG |  | 12199 | 12207 | 9 | reverse |
| hsa-miR-372 | AAAGTGCTG |  | 217 | 225 | 9 | reverse |
| hsa-miR-374a-3p | TCATCAGATT | 210 | 10606 | 10615 | 10 | reverse |
| hsa-miR-377-3p | AGCACACAAA | 211 | 13842 | 13851 | 10 | reverse |
| hsa-miR-378a-3p | ACTGGCCTTG | 212 | 15816 | 15825 | 10 | reverse |
| hsa-miR-378a-3p | ACTGGTCTTG | 213 | 11837 | 11846 | 10 | reverse |
| hsa-miR-378a-5p | CTCCTGCCTC | 214 | 12216 | 12225 | 10 | reverse |
| hsa-miR-378a-5p | CTCCTGCCTC | 215 | 10082 | 10091 | 10 | reverse |
| hsa-miR-378a-5p | CTCCTGTCTC | 216 | 8207 | 8216 | 10 | reverse |
| hsa-miR-378a-5p | CTCCTAACTC | 217 | 7650 | 7659 | 10 | reverse |
| hsa-miR-382-3p | ATTCATTCAC | 218 | 14194 | 14203 | 10 | reverse |
| hsa-miR-383 | AGATTAGAA |  | 14545 | 14553 | 9 | reverse |
| hsa-miR-383 | AGATTAGAA |  | 7912 | 7920 | 9 | reverse |
| hsa-miR-383 | AGAACAGAA |  | 5801 | 5809 | 9 | reverse |
| hsa-miR-412 | ACTTCACCT |  | 737 | 745 | 9 | reverse |
| hsa-miR-421 | CTCAAAAGAC | 219 | 14380 | 14389 | 10 | reverse |

TABLE 8-continued miRNAs with predicted binding sites in the UCP1 gene sequence (NCBI Reference Sequence: NG_012139.1).

| miRNA | Sequence | SEQ ID NO | Minimum | Maximum | Length | Direction |
|---|---|---|---|---|---|---|
| hsa-miR-421 | ATTAACTGAC | 220 | 14333 | 14342 | 10 | reverse |
| hsa-miR-421 | AACATCAGAC | 221 | 11398 | 11407 | 10 | reverse |
| hsa-miR-421 | ATCAACTGAG | 222 | 3427 | 3436 | 10 | reverse |
| hsa-miR-421 | ATCAACAGGT | 223 | 2443 | 2452 | 10 | reverse |
| hsa-miR-421 | ATCAAAAGAT | 224 | 2333 | 2342 | 10 | reverse |
| hsa-miR-422a | ACTGGCCTT | | 15817 | 15825 | 9 | reverse |
| hsa-miR-422a | ACTGGTCTT | | 11838 | 11846 | 9 | reverse |
| hsa-miR-422a | ACTGGACGT | | 5847 | 5855 | 9 | reverse |
| hsa-miR-425 | AGCGGGAAGGT | 225 | 5167 | 5177 | 11 | reverse |
| hsa-miR-431 | TGTCTGGCA | | 14892 | 14900 | 9 | reverse |
| hsa-miR-431 | TGTCTAGCA | | 9218 | 9226 | 9 | reverse |
| hsa-miR-432-5p | TCCTGGAGT | | 13624 | 13632 | 9 | reverse |
| hsa-miR-432-5p | TATTGGAGT | | 10785 | 10793 | 9 | reverse |
| hsa-miR-432-5p | TCTTAGAGT | | 9263 | 9271 | 9 | reverse |
| hsa-miR-432-5p | TCTTAGAGT | | 6666 | 6674 | 9 | reverse |
| hsa-miR-432-5p | TCTTGGAGC | | 2180 | 2188 | 9 | reverse |
| hsa-miR-452 | ACATCTGC | | 15009 | 15016 | 8 | reverse |
| hsa-miR-452 | TCTTCTGC | | 14773 | 14780 | 8 | reverse |
| hsa-miR-452 | TTATCTGC | | 14151 | 14158 | 8 | reverse |
| hsa-miR-452 | TCCTCTGC | | 13488 | 13495 | 8 | reverse |
| hsa-miR-452 | TCATGTGC | | 8660 | 8667 | 8 | reverse |
| hsa-miR-452 | TCATCTGG | | 8221 | 8228 | 8 | reverse |
| hsa-miR-452 | TCATGTGC | | 7945 | 7952 | 8 | reverse |
| hsa-miR-452 | ACATCTGC | | 7508 | 7515 | 8 | reverse |
| hsa-miR-452 | CCATCTGC | | 6787 | 6794 | 8 | reverse |
| hsa-miR-452 | TCATCCGC | | 5912 | 5919 | 8 | reverse |
| hsa-miR-452 | TCATCTGT | | 4053 | 4060 | 8 | reverse |
| hsa-miR-452 | TCATCTCC | | 3667 | 3674 | 8 | reverse |
| hsa-miR-452 | TCCTCTGC | | 3457 | 3464 | 8 | reverse |
| hsa-miR-452 | TCTTCTGC | | 2210 | 2217 | 8 | reverse |
| hsa-miR-455-3p | CAGTCCAT | | 13893 | 13900 | 8 | reverse |
| hsa-miR-455-5p | TGTGTGCCTT | 226 | 15641 | 15650 | 10 | reverse |
| hsa-miR-455-5p | TCTGTGCCTT | 227 | 11203 | 11212 | 10 | reverse |
| hsa-miR-455-5p | TATGTGCTTT | 228 | 10522 | 10531 | 10 | reverse |
| hsa-miR-483-3p | CACTCCTC | | 13536 | 13543 | 8 | reverse |
| hsa-miR-483-3p | CACTCCTC | | 10333 | 10340 | 8 | reverse |
| hsa-miR-483-3p | CACTCCTC | | 6101 | 6108 | 8 | reverse |

TABLE 8-continued miRNAs with predicted binding sites in the UCP1 gene sequence (NCBI Reference Sequence: NG_012139.1).

| miRNA | Sequence | SEQ ID NO | Minimum | Maximum | Length | Direction |
|---|---|---|---|---|---|---|
| hsa-miR-486-5p | TCATGTACT | | 9835 | 9843 | 9 | reverse |
| hsa-miR-486-5p | TCCTGTCCT | | 6526 | 6534 | 9 | reverse |
| hsa-miR-487a | AATCATACAG | 229 | 12829 | 12838 | 10 | reverse |
| hsa-miR-487a | AATCATACAG | 229 | 933 | 942 | 10 | reverse |
| hsa-miR-491-5p | AATGGGGAAG | 230 | 14975 | 14984 | 10 | reverse |
| hsa-miR-491-5p | AGAGGGGACC | 231 | 12315 | 12324 | 10 | reverse |
| hsa-miR-491-5p | AGTTGGGCAC | 232 | 11555 | 11564 | 10 | reverse |
| hsa-miR-491-5p | AGTAGAGAAC | 233 | 6909 | 6918 | 10 | reverse |
| hsa-miR-491-5p | GGTGAGGAAC | 234 | 6005 | 6014 | 10 | reverse |
| hsa-miR-491-5p | AGCGGGGCAC | 235 | 4455 | 4464 | 10 | reverse |
| hsa-miR-491-5p | AGTGGGAAAT | 236 | 3846 | 3855 | 10 | reverse |
| hsa-miR-496 | TTAGTATTA | | 10948 | 10956 | 9 | reverse |
| hsa-miR-496 | TGAGTATAA | | 10768 | 10776 | 9 | reverse |
| hsa-miR-496 | TCAGTATTA | | 9666 | 9674 | 9 | reverse |
| hsa-miR-501-3p | ATGCATCAGG | 237 | 15547 | 15556 | 10 | reverse |
| hsa-miR-501-3p | ATCCACCGGG | 238 | 11497 | 11506 | 10 | reverse |
| hsa-miR-501-3p | AGGCACCAGG | 239 | 2089 | 2098 | 10 | reverse |
| hsa-miR-504 | AGACCCTGT | | 15325 | 15333 | 9 | reverse |
| hsa-miR-504 | AGCCCCTGG | | 12898 | 12906 | 9 | reverse |
| hsa-miR-504 | AGTCCCTGG | | 10591 | 10599 | 9 | reverse |
| hsa-miR-504 | AGACCCGGG | | 4767 | 4775 | 9 | reverse |
| hsa-miR-508-3p | TGATTATAGC | 240 | 13565 | 13574 | 10 | reverse |
| hsa-miR-508-3p | TGAGTGTAGC | 241 | 3231 | 3240 | 10 | reverse |
| hsa-miR-512-3p | CAGTGCTGTC | 242 | 13211 | 13220 | 10 | reverse |
| hsa-miR-512-3p | AAGTGCTCTC | 243 | 7688 | 7697 | 10 | reverse |
| hsa-miR-512-3p | AAGTGCTCTC | 243 | 3184 | 3193 | 10 | reverse |
| hsa-miR-512-5p | CACTCAG | | 14255 | 14261 | 7 | reverse |
| hsa-miR-512-5p | CACTCAG | | 13591 | 13597 | 7 | reverse |
| hsa-miR-512-5p | CACTCAG | | 12291 | 12297 | 7 | reverse |
| hsa-miR-512-5p | CACTCAG | | 6652 | 6658 | 7 | reverse |
| hsa-miR-512-5p | CACTCAG | | 5067 | 5073 | 7 | reverse |
| hsa-miR-514a-3p | TTGACTCTT | | 14406 | 14414 | 9 | reverse |
| hsa-miR-514a-3p | TTGACAGTT | | 13870 | 13878 | 9 | reverse |
| hsa-miR-514a-3p | TTAACACTT | | 11237 | 11245 | 9 | reverse |
| hsa-miR-514a-3p | ATGACACTT | | 10617 | 10625 | 9 | reverse |
| hsa-miR-515-3p | GTGTGCCTT | | 15641 | 15649 | 9 | reverse |
| hsa-miR-515-3p | GACTGCCTT | | 15539 | 15547 | 9 | reverse |

TABLE 8-continued miRNAs with predicted binding sites in the UCP1 gene sequence (NCBI Reference Sequence: NG_012139.1).

| miRNA | Sequence | SEQ ID NO | Minimum | Maximum | Length | Direction |
|---|---|---|---|---|---|---|
| hsa-miR-515-3p | GAGTGACTT | | 1371 | 1379 | 9 | reverse |
| hsa-miR-516a-3p | TGCTTCCT | | 10301 | 10308 | 8 | reverse |
| hsa-miR-517a-3p | ATGGTGCATT | 244 | 15650 | 15659 | 10 | reverse |
| hsa-miR-517a-3p | ATCTTGCTTC | 245 | 10303 | 10312 | 10 | reverse |
| hsa-miR-519b-3p | AAAGTGCAT | | 13782 | 13790 | 9 | reverse |
| hsa-miR-519e-3p | AAGTGCCTC | | 7048 | 7056 | 9 | reverse |
| hsa-miR-520a-5p | CTCCAGATGG | | 6274 | 6283 | 10 | reverse |
| hsa-miR-545 | CAGCAAGCACT | 246 | 15050 | 15060 | 11 | reverse |
| hsa-miR-545 | CAGAACACATT | 247 | 11639 | 11649 | 11 | reverse |
| hsa-miR-545 | CTGCAAACACT | 248 | 3450 | 3460 | 11 | reverse |
| hsa-miR-549 | TGACAACTGT | 249 | 14327 | 14336 | 10 | reverse |
| hsa-miR-551b-3p | GCTACCCAT | | 2411 | 2419 | 9 | reverse |
| hsa-miR-552 | CACAGGTGA | | 15130 | 15138 | 9 | reverse |
| hsa-miR-552 | AACAGGTCA | | 11407 | 11415 | 9 | reverse |
| hsa-miR-552 | AACATGTGA | | 9513 | 9521 | 9 | reverse |
| hsa-miR-552 | AACAGGTTA | | 2441 | 2449 | 9 | reverse |
| hsa-miR-552 | AACAGGTAA | | 1569 | 1577 | 9 | reverse |
| hsa-miR-583 | AAAAGAGGA | | 2921 | 2929 | 9 | reverse |
| hsa-miR-583 | CAAATAGGA | | 2833 | 2841 | 9 | reverse |
| hsa-miR-583 | CAACGAGGA | | 1824 | 1832 | 9 | reverse |
| hsa-miR-583 | CAAAGAAGA | | 1139 | 1147 | 9 | reverse |
| hsa-miR-593-3p | TGTCTCTGT | | 8204 | 8212 | 9 | reverse |
| hsa-miR-593-3p | TGGCTCTGC | | 6852 | 6860 | 9 | reverse |
| hsa-miR-593-3p | TGCCTCTGC | | 231 | 239 | 9 | reverse |
| hsa-miR-593-5p | AGGCACCAG | | 2090 | 2098 | 9 | reverse |
| hsa-miR-593-5p | AGGCACCAG | | 2083 | 2091 | 9 | reverse |
| hsa-miR-598 | ACGTCATC | | 11432 | 11439 | 8 | reverse |
| hsa-miR-611 | GCGAGGTCTC | 250 | 4779 | 4788 | 10 | reverse |
| hsa-miR-611 | GAGAGGCCCC | 251 | 2121 | 2130 | 10 | reverse |
| hsa-miR-611 | GAGAGGACCT | 252 | 1546 | 1555 | 10 | reverse |
| hsa-miR-616-5p | ACTCTAAAC | | 14510 | 14518 | 9 | reverse |
| hsa-miR-619 | GACCTGGA | | 5824 | 5831 | 8 | reverse |
| hsa-miR-620 | ATGAATATAG | 253 | 14560 | 14569 | 10 | reverse |
| hsa-miR-620 | ATGGAAATAT | 254 | 12111 | 12120 | 10 | reverse |
| hsa-miR-620 | TTGGATATAG | 255 | 11026 | 11035 | 10 | reverse |
| hsa-miR-620 | GTGGAGATGG | 256 | 10397 | 10406 | 10 | reverse |
| hsa-miR-620 | ATGGAGATCC | 257 | 6268 | 6277 | 10 | reverse |

TABLE 8-continued miRNAs with predicted binding sites in the UCP1 gene sequence (NCBI Reference Sequence: NG_012139.1).

| miRNA | Sequence | SEQ ID NO | Minimum | Maximum | Length | Direction |
|---|---|---|---|---|---|---|
| hsa-miR-620 | ATGGAGGGAG | 258 | 5626 | 5635 | 10 | reverse |
| hsa-miR-620 | CTGGAGAAAG | 259 | 3827 | 3836 | 10 | reverse |
| hsa-miR-620 | ATCCAGATAG | 260 | 2959 | 2968 | 10 | reverse |
| hsa-miR-620 | ATGGGGCTAG | 261 | 2843 | 2852 | 10 | reverse |
| hsa-miR-620 | AGGGAGAGAG | 262 | 1551 | 1560 | 10 | reverse |
| hsa-miR-620 | CAGGAGATAG | 263 | 1430 | 1439 | 10 | reverse |
| hsa-miR-620 | TTGGAGAGAG | 264 | 1201 | 1210 | 10 | reverse |
| hsa-miR-623 | TCCCTTGC |  | 8306 | 8313 | 8 | reverse |
| hsa-miR-623 | TCCCTTGC |  | 5004 | 5011 | 8 | reverse |
| hsa-miR-631 | CACCTGGCC |  | 9900 | 9908 | 9 | reverse |
| hsa-miR-631 | GACATGGCC |  | 8632 | 8640 | 9 | reverse |
| hsa-miR-634 | AACCAGCAC |  | 4520 | 4528 | 9 | reverse |
| hsa-miR-636 | TGTGCTTG |  | 10386 | 10393 | 8 | reverse |
| hsa-miR-638 | ACGGAGCGCG | 265 | 4905 | 4914 | 10 | reverse |
| hsa-miR-638 | AGGGAGGGCG | 266 | 4615 | 4624 | 10 | reverse |
| hsa-miR-642a-5p | ATCCCTCTC |  | 8983 | 8991 | 9 | reverse |
| hsa-miR-642a-5p | GTCCCTCCC |  | 4722 | 4730 | 9 | reverse |
| hsa-miR-643 | ACATGCATGC | 267 | 15553 | 15562 | 10 | reverse |
| hsa-miR-643 | CCTTGTAGGC | 268 | 15378 | 15387 | 10 | reverse |
| hsa-miR-643 | TCTTGTATTC | 269 | 14423 | 14432 | 10 | reverse |
| hsa-miR-643 | ACTGGTATGT | 270 | 13933 | 13942 | 10 | reverse |
| hsa-miR-643 | ACTTCTATTC | 271 | 12886 | 12895 | 10 | reverse |
| hsa-miR-643 | ACTTTTCTGC | 272 | 12044 | 12053 | 10 | reverse |
| hsa-miR-643 | GCTTGTAAGC | 273 | 11698 | 11707 | 10 | reverse |
| hsa-miR-643 | AGTTGTATGT | 274 | 10531 | 10540 | 10 | reverse |
| hsa-miR-643 | ACTTGGAAGC | 275 | 8105 | 8114 | 10 | reverse |
| hsa-miR-643 | ACTTGTGTGG | 276 | 7227 | 7236 | 10 | reverse |
| hsa-miR-643 | ACTTGTTTGA | 277 | 1880 | 1889 | 10 | reverse |
| hsa-miR-643 | ACATGTTTGC | 278 | 1695 | 1704 | 10 | reverse |
| hsa-miR-650 | AGGAGGCAC | 279 | 9647 | 9655 | 9 | reverse |
| hsa-miR-650 | AGAAGGCAG | 280 | 6917 | 6925 | 9 | reverse |
| hsa-miR-650 | AGGAGCCAG | 281 | 3474 | 3482 | 9 | reverse |
| hsa-miR-650 | ATGAGGCAG | 282 | 3052 | 3060 | 9 | reverse |
| hsa-miR-651 | TCATGATAAG | 283 | 15700 | 15709 | 10 | reverse |
| hsa-miR-651 | TTAGGTTAAA | 284 | 13993 | 14002 | 10 | reverse |
| hsa-miR-651 | TTAAAATAAG | 285 | 13988 | 13997 | 10 | reverse |
| hsa-miR-651 | TTAGCATAAC | 286 | 12788 | 12797 | 10 | reverse |

TABLE 8-continued miRNAs with predicted binding sites in the UCP1 gene sequence (NCBI Reference Sequence: NG_012139.1).

| miRNA | Sequence | SEQ ID NO | Minimum | Maximum | Length | Direction |
|---|---|---|---|---|---|---|
| hsa-miR-651 | TTATGATGAG | 287 | 12617 | 12626 | 10 | reverse |
| hsa-miR-651 | TTTGGATGAG | 288 | 11069 | 11078 | 10 | reverse |
| hsa-miR-651 | TGAGTATAAG | 289 | 10767 | 10776 | 10 | reverse |
| hsa-miR-651 | TTACAATAAG | 290 | 10546 | 10555 | 10 | reverse |
| hsa-miR-651 | TAAGGATAAA | 291 | 8265 | 8274 | 10 | reverse |
| hsa-miR-651 | TGTGGATAAG | 292 | 7222 | 7231 | 10 | reverse |
| hsa-miR-651 | GTAGGATAGG | 293 | 5553 | 5562 | 10 | reverse |
| hsa-miR-651 | CTAGGAAAAG | 294 | 2823 | 2832 | 10 | reverse |
| hsa-miR-651 | CTATGATAAG | 295 | 1635 | 1644 | 10 | reverse |
| hsa-miR-651 | TAAGGATAGG | 296 | 1562 | 1571 | 10 | reverse |
| hsa-miR-654-3p | TATGTATACT | 297 | 15493 | 15502 | 10 | reverse |
| hsa-miR-654-3p | TATCTCTTCT | 298 | 14775 | 14784 | 10 | reverse |
| hsa-miR-654-3p | TCTATCTGCT | 299 | 8354 | 8363 | 10 | reverse |
| hsa-miR-654-3p | AATGTCTGGT | 300 | 6720 | 6729 | 10 | reverse |
| hsa-miR-654-3p | TATGTTTCCT | 301 | 6638 | 6647 | 10 | reverse |
| hsa-miR-654-3p | TTTTTCTGCT | 302 | 6586 | 6595 | 10 | reverse |
| hsa-miR-654-3p | TATGTCTTTT | 303 | 6534 | 6543 | 10 | reverse |
| hsa-miR-654-3p | TATATCTGCA | 304 | 6214 | 6223 | 10 | reverse |
| hsa-miR-654-3p | TATGTAGGCT | 305 | 97 | 106 | 10 | reverse |
| hsa-miR-655 | GTAATACAT |  | 15593 | 15601 | 9 | reverse |
| hsa-miR-655 | ATAGTACAT |  | 4200 | 4208 | 9 | reverse |
| hsa-miR-655 | ATAAGACAT |  | 3642 | 3650 | 9 | reverse |
| hsa-miR-655 | ATAATACAG |  | 2265 | 2273 | 9 | reverse |
| hsa-miR-655 | ACAATACAT |  | 1757 | 1765 | 9 | reverse |
| hsa-miR-656 | AATATTATA |  | 657 | 665 | 9 | reverse |
| hsa-miR-664-3p | TATTCATTT |  | 9385 | 9393 | 9 | reverse |
| hsa-miR-765 | TGGAGGA |  | 5020 | 5026 | 7 | reverse |
| hsa-miR-766 | CTCCAGCCCC | 306 | 12901 | 12910 | 10 | reverse |
| hsa-miR-766 | CTCCAGCCCC | 307 | 5032 | 5041 | 10 | reverse |
| hsa-miR-767-3p | CCTGCTCAT |  | 14871 | 14879 | 9 | reverse |
| hsa-miR-767-3p | TCTTCTCAT |  | 9155 | 9163 | 9 | reverse |
| hsa-miR-875 | CCTGGAAATA | 308 | 5820 | 5829 | 10 | reverse |
| hsa-miR-875 | CCTAGAAACA | 309 | 5294 | 5303 | 10 | reverse |
| hsa-miR-876 | TGGATTTCT |  | 6366 | 6374 | 9 | reverse |
| hsa-miR-876 | TGGATTTCT |  | 142 | 150 | 9 | reverse |
| hsa-miR-888-3p | GACTGACTCC | 310 | 15772 | 15781 | 10 | reverse |
| hsa-miR-888-3p | GACTGACAGC | 311 | 9119 | 9128 | 10 | reverse |

TABLE 8-continued miRNAs with predicted binding sites in the UCP1 gene sequence (NCBI Reference Sequence: NG_012139.1).

| miRNA | Sequence | SEQ ID NO | Minimum | Maximum | Length | Direction |
|---|---|---|---|---|---|---|
| hsa-miR-890 | TACTTGGAAG | 312 | 8106 | 8115 | 10 | reverse |
| hsa-miR-940 | AAGGCAGTG | | 1807 | 1815 | 9 | reverse |
| hsa-miR-941 | CACCCAGGT | | 14396 | 14404 | 9 | reverse |
| hsa-miR-941 | CACCCTGCC | | 13715 | 13723 | 9 | reverse |
| hsa-miR-941 | CACCCCTCT | | 13128 | 13136 | 9 | reverse |
| hsa-miR-941 | CACTCAGCT | | 12289 | 12297 | 9 | reverse |
| hsa-miR-941 | CTCCCGGGT | | 10102 | 10110 | 9 | reverse |
| hsa-miR-941 | CAGCCTGCT | | 10034 | 10042 | 9 | reverse |
| hsa-miR-941 | CACCCACCT | | 9904 | 9912 | 9 | reverse |
| hsa-miR-941 | CACCTGGCC | | 9900 | 9908 | 9 | reverse |
| hsa-miR-941 | CATCTGGCT | | 8219 | 8227 | 9 | reverse |
| hsa-miR-941 | CACTCGACT | | 8148 | 8156 | 9 | reverse |
| hsa-miR-941 | CTCCCAGCT | | 6840 | 6848 | 9 | reverse |
| hsa-miR-941 | CTCACGGCT | | 6031 | 6039 | 9 | reverse |
| hsa-miR-941 | CAGCCCGCT | | 5928 | 5936 | 9 | reverse |
| hsa-miR-941 | CACCTGACT | | 5510 | 5518 | 9 | reverse |
| hsa-miR-941 | CACGCCGCT | | 5142 | 5150 | 9 | reverse |
| hsa-miR-941 | CTCCCTGCT | | 3983 | 3991 | 9 | reverse |
| hsa-miR-941 | CACCAGGCA | | 2087 | 2095 | 9 | reverse |
| hsa-miR-941 | CTCCCGGGT | | 390 | 398 | 9 | reverse |
| hsa-miR-941 | CACCCAGCC | | 186 | 194 | 9 | reverse |
| hsa-miR-941-2 | ATCCGACTGT | 313 | 9657 | 9666 | 10 | reverse |
| hsa-miR-941-2 | TCCCTGCTGT | 314 | 8726 | 8735 | 10 | reverse |
| hsa-miR-941-2 | TCCCAGCTGT | 315 | 6838 | 6847 | 10 | reverse |
| hsa-miR-941-2 | AGCCCGCTGT | 316 | 5926 | 5935 | 10 | reverse |
| hsa-miR-941-2 | ACCCGGGCGT | 317 | 4764 | 4773 | 10 | reverse |
| hsa-miR-1179 | AAGTATCCTTT | 318 | 15346 | 15356 | 11 | reverse |
| hsa-miR-1179 | ATGCATTCTGT | 319 | 3357 | 3367 | 11 | reverse |
| hsa-miR-1179 | ATGCATTCTCT | 320 | 1854 | 1864 | 11 | reverse |
| hsa-miR-1207-5p | TGGCAGGG | | 11441 | 11448 | 8 | reverse |
| hsa-miR-1224-3p | CTCCACCTCC | 321 | 399 | 408 | 10 | reverse |
| hsa-miR-1228-3p | TCCCACCTG | | 13637 | 13645 | 9 | reverse |
| hsa-miR-1228-3p | TCACGCCTG | | 4992 | 5000 | 9 | reverse |
| hsa-miR-1231 | GTGTCTGGC | | 12807 | 12815 | 9 | reverse |
| hsa-miR-1231 | GTGTCCGGG | | 4739 | 4747 | 9 | reverse |
| hsa-miR-1245 | AAGTGATCT | | 8341 | 8349 | 9 | reverse |
| hsa-miR-1245 | AAGTGATCT | | 2020 | 2028 | 9 | reverse |

TABLE 8-continued miRNAs with predicted binding sites in the UCP1 gene sequence (NCBI Reference Sequence: NG_012139.1).

| miRNA | Sequence | SEQ ID NO | Minimum | Maximum | Length | Direction |
|---|---|---|---|---|---|---|
| hsa-miR-1249 | CGCCCTTC | | 5907 | 5914 | 8 | reverse |
| hsa-miR-1251 | ACTCTAGGT | | 12854 | 12862 | 9 | reverse |
| hsa-miR-1251 | ACTCTATCT | | 8357 | 8365 | 9 | reverse |
| hsa-miR-1251 | ACTCCAGCT | | 4044 | 4052 | 9 | reverse |
| hsa-miR-1251 | AGTCTAGCT | | 457 | 465 | 9 | reverse |
| hsa-miR-1252 | AGAGGGAAAT | 322 | 3819 | 3828 | 10 | reverse |
| hsa-miR-1252 | GGAAGGAAAT | 323 | 1625 | 1634 | 10 | reverse |
| hsa-miR-1268 | CGGGCGTGG | | 4762 | 4770 | 9 | reverse |
| hsa-miR-1270 | CTGGAAATA | | 5820 | 5828 | 9 | reverse |
| hsa-miR-1270 | CTGGAGATG | | 5055 | 5063 | 9 | reverse |
| hsa-miR-1270 | CTGGAGAAA | | 3828 | 3836 | 9 | reverse |
| hsa-miR-1270 | CAGGAGATA | | 1431 | 1439 | 9 | reverse |
| hsa-miR-1272 | GATGATGA | | 10622 | 10629 | 8 | reverse |
| hsa-miR-1275 | GTAGGGGAGA | 324 | 1189 | 1198 | 10 | reverse |
| hsa-miR-1302 | ATGGGACACA | 325 | 15021 | 15030 | 10 | reverse |
| hsa-miR-1302 | TTTGGATATA | 326 | 11027 | 11036 | 10 | reverse |
| hsa-miR-1302 | TTAGGGCATA | 327 | 8421 | 8430 | 10 | reverse |
| hsa-miR-1302 | TTGGAACAGA | 328 | 6076 | 6085 | 10 | reverse |
| hsa-miR-1302 | CTGGGACTTA | 329 | 4819 | 4828 | 10 | reverse |
| hsa-miR-1302 | GTGGGAAATA | 330 | 3845 | 3854 | 10 | reverse |
| hsa-miR-1302 | TTGTGAGATA | 331 | 1944 | 1953 | 10 | reverse |
| hsa-miR-1302 | CTGGGAAATA | 332 | 867 | 876 | 10 | reverse |
| hsa-miR-1324 | TCAAGACAGA | 333 | 9426 | 9435 | 10 | reverse |
| hsa-miR-1827 | TGAGGCAGT | | 3051 | 3059 | 9 | reverse |
| hsa-miR-1911-3p | CACCAGGCA | | 2087 | 2095 | 9 | reverse |
| hsa-miR-1915 | CCCCAGGG | | 5111 | 5118 | 8 | reverse |
| hsa-miR-2909 | TTTAGGGCC | | 3728 | 3736 | 9 | reverse |

B. Another Exemplary Multiple miRNAs-One mRNA Paradigm Involves UCP2.

UCP2 is a mitochondrial transporter protein expressed in WAT, skeletal muscle, pancreatic islets and the central nervous system. Like UCP1, it creates proton leaks across the inner mitochondrial membrane, thus uncoupling oxidative phosphorylation from ATP synthesis (adaptive thermogenesis, see FIG. 5) (Lowell et al., Nature (2000)).

Two recent meta-analyses report an association between polymorphisms in the promoter region of UCP2 and obesity (Liu et al., Gene (2013); Andersen et al., Int J. Obes. (2013)). The first meta-analysis included 14 studies (7,647 cases and 11,322 controls) and concluded that there is a significant association of the A allele of the UCP2-866G/A polymorphism with reduced risk of obesity, especially in European populations. In the second meta-analysis including 12,984 subjects, the common UCP2-866G allele is associated with obesity. The same UCP2-866G allele is associated with decreased insulin sensitivity in 17,636 Danish subjects. In a study, UCP2 mRNA levels in visceral fat were decreased in subjects with the GG phenotype (Esterbauer et al., Nat. Genet. (2001)). A trend toward a negative correlation between subcutaneous adipocyte UCP2 mRNA and percent body fat was found in another study (Wang et al., American Journal of Physiol. (2004)). This information supports targeting UCP2 expression and activity as a meaningful way to alter adaptive thermogenesis and consequently treat human obesity. Many strategies could be implemented to achieve this goal, however, the one employed in the methods of the invention uses miRNA agents to modulate simultaneously several elements within the thermogenic pathways to increase UCP2 synthesis and activity. Both direct and indirect interactions between miRNAs and the UCP2 gene are considered. Direct interaction means the direct binding of miRNAs to the various regions of the UCP2 gene, resulting in alterations of the transcription, translation, stability and/or degradation of the UCP1 mRNA. Indirect interaction means that miRNAs alter the transcription, translation, stability and/or degradation of thermogenic mRNAs, whose expressed proteins alter the transcription of the UCP2 gene. Furthermore, indirect interaction means that miRNAs alter the transcription, translation, stability and/or degradation of other miRNAs that modify the transcription of the UCP2 gene.

The promoter region of the human UCP2 gene (ENSG00000175567, *Homo sapiens* uncoupling protein 2 (mitochondrial, proton carrier) (UCP2), RefSeqGene on chromosome 11) is rich is regulatory element motifs:

UCP2 Gene Regulatory Elements:

1. RXR/T3RE Motif: AGGTCA
Eight
Length: 6, Interval: 1,074 -> 1,079; 3,083 -> 3,088; 3,239 -> 3,244; 4,304 -> 4,309; 6,965 -> 6,970; 7,420 -> 7,425; 7,677 -> 7,682; 13,319 -> 13,324; Mismatches: 0.
2. GC Box 1 Motif: CGCCC
Sixteen
Length: 5, Interval: 2,605 -> 2,609; 4,323 -> 4,327; 4,523 -> 4,527; 4,933 -> 4,937; 4,959 -> 4,963; 5,048 -> 5,052; 5,066 -> 5,070; 5,146 -> 5,150; 5,155 -> 5,159; 5,387 -> 5,391; 5,483 -> 5,487; 6,067 -> 6,071; 8,523 -> 8,527; 9,790 -> 9,794; 10,819 -> 10,823; 11,754 -> 11,758; Mismatches: 0.
3. GC Box 2 Motif: GCGGG
Five
Length: 5, Interval: 4,263 -> 4,267; 4,757 -> 4,761; 4,860 -> 4,864; 7,619 -> 7,623; 11,262 -> 11,266; Mismatches: 0.
4. GT Box 1 Motif: CACCC
Thirty
Length: 5, Interval: 1,421 -> 1,425; 1,677 -> 1,681; 1,761 -> 1,765; 1,825 -> 1,829; 1,833 -> 1,837; 2,036 -> 2,040; 3,003 -> 3,007; 4,903 -> 4,907; 4,947 -> 4,951; 5,210 -> 5,214; 6,204 -> 6,208; 6,247 -> 6,251; 6,469 -> 6,473; 6,828 -> 6,832; 7,681 -> 7,685; 8,048 -> 8,052; 8,437 -> 8,441; 8,572 -> 8,576; 8,599 -> 8,603; 8,702 -> 8,706; 11,077 -> 11,081; 11,235 -> 11,239; 12,006 -> 12,010; 12,374 -> 12,378; 13,475 -> 13,479; 13,666 -> 13,670; 13,687 -> 13,691; 13,838 -> 13,842; 14,410 -> 14,414; 14,545 -> 14,549; Mismatches: 0.
5. GT Box 2 Motif: GTGGG
Twenty Six
Length: 5, Interval: 123 -> 127; 1,006 -> 1,010; 2,105 -> 2,109; 4,562 -> 4,566; 5,793 -> 5,797; 6,029 -> 6,033; 6,034 -> 6,038; 6,040 -> 6,044; 6,150 -> 6,154; 7,271 -> 7,275; 7,392 -> 7,396; 9,040 -> 9,044; 9,697 -> 9,701; 10,227 -> 10,231; 10,238 -> 10,242; 10,247 -> 10,251; 11,817 -> 11,821; 12,410 -> 12,414; 12,414 -> 12,418; 12,678 -> 12,682; 13,047 -> 13,051; 13,238 -> 13,742; 13,743 -> 13,747; 14,252 -> 14,256; 14,969 -> 14,973; 15,104 -> 15,108; Mismatches: 0.
6. CpG Methylation Island Motif: CG
Two hundred and Ninety Five, including many between positions 4,071 to 5,212.

Figure 8B:
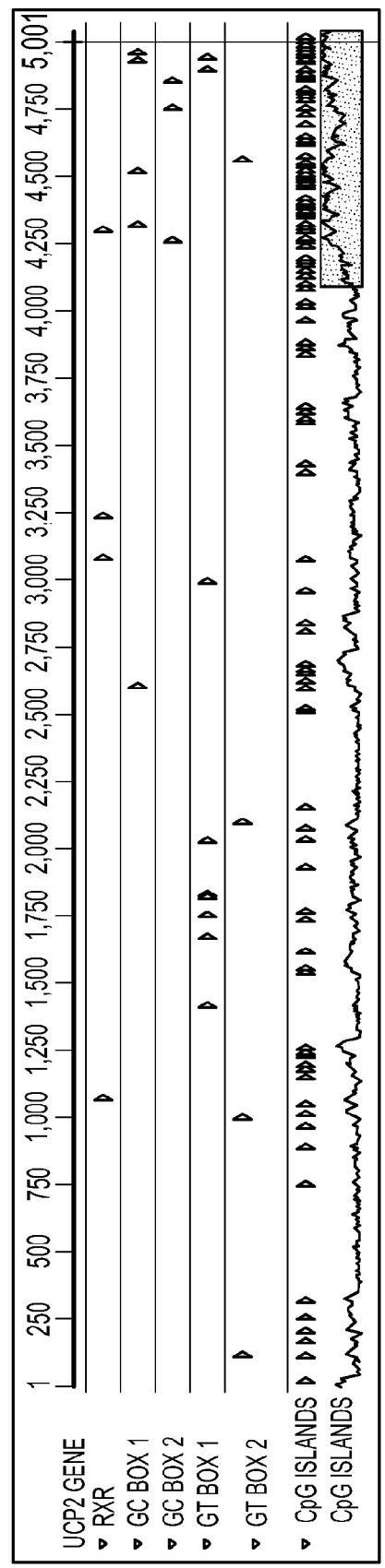
FIG. 8B depicts the location of various regulatory elements in reference to the transcription start site in the 15,174 bp of the human UCP2 gene (ENSG00000175567), including 5,000 bp 5'UTR and 2,000 bp 3'UTR on chromosome 11.

FIG. 8B depicts the location of these various regulatory elements in reference to the UCP2 transcription start site at nucleotide position 5,001 of the 15,174 base pair human UCP2 gene. Direct or indirect activation or repression of these regulatory elements by miRNAs will result in alterations of UCP2 gene expression and activity.

A survey of miRNAs targeting the human UCP2 3'UTR with several prediction programs, using the UCP2 Ensembl 2,113 base pair transcript ENST00000310473 as a target revealed binding sites for 161 miRNAs as shown in Table 9.

TABLE 9 miRNAs with predicted binding sites in the 3'UTR of UCP2 transcript sequence.

| | | |
|---|---|---|
| hsa-miR-1 | hsa-miR-1302-5 | hsa-miR-23b |
| hsa-miR-1-2 | hsa-miR-1302-6 | hsa-miR-24-1 |
| hsa-miR-101-1 | hsa-miR-1302-7 | hsa-miR-24-2 |
| hsa-miR-101-2 | hsa-miR-1302-8 | hsa-miR-27b-5p |
| hsa-miR-103 | hsa-miR-1302-9 | hsa-miR-28 |
| hsa-miR-105-1 | hsa-miR-1303 | hsa-miR-296-3p |
| hsa-miR-105-2 | hsa-miR-130a | hsa-miR-296-5p |
| hsa-miR-106b | hsa-miR-1321 | hsa-miR-3064 |
| hsa-miR-107 | hsa-miR-138-1 | hsa-miR-323a |
| hsa-miR-1204 | hsa-miR-138-2 | hsa-miR-328 |
| hsa-miR-1207 | hsa-miR-149 | hsa-miR-330 |
| hsa-miR-1208 | hsa-miR-150-3p | hsa-miR-331 |
| hsa-miR-1226 | hsa-miR-150-5p | hsa-miR-338 |
| hsa-miR-1246 | hsa-miR-1538 | hsa-miR-342 |
| hsa-miR-1252 | hsa-miR-155 | hsa-miR-3619 |
| hsa-miR-1253 | hsa-miR-15a | hsa-miR-370 |
| hsa-miR-1255a | hsa-miR-15b | hsa-miR-377 |
| hsa-miR-1255b-1 | hsa-miR-16-1 | hsa-miR-378a |
| hsa-miR-1255b-2 | hsa-miR-16-2 | hsa-miR-383 |
| hsa-miR-1260a | hsa-miR-184 | hsa-miR-411 |
| hsa-miR-1262 | hsa-miR-185-3p | hsa-miR-412 |
| hsa-miR-1263 | hsa-miR-185-5p | hsa-miR-422a |
| hsa-miR-1265 | hsa-miR-186 | hsa-miR-424 |
| hsa-miR-1275 | hsa-miR-188 | hsa-miR-425 |
| hsa-miR-1276 | hsa-miR-18a | hsa-miR-4291 |
| hsa-miR-1278 | hsa-miR-18b | hsa-miR-432-3p |
| hsa-miR-1285-1 | hsa-miR-193a | hsa-miR-4505 |
| hsa-miR-1286 | hsa-miR-195 | hsa-miR-450b |
| hsa-miR-1293 | hsa-miR-199b | hsa-miR-453 |
| hsa-miR-1300 | hsa-miR-200a | hsa-miR-4533 |
| hsa-miR-1302-1 | hsa-miR-203 | hsa-miR-4539 |
| hsa-miR-1302-10 | hsa-miR-206 | hsa-miR-4745 |

TABLE 9-continued miRNAs with predicted binding sites in the 3'UTR of UCP2 transcript sequence.

| | | |
|---|---|---|
| hsa-miR-1302-11 | hsa-miR-214 | hsa-miR-4747 |
| hsa-miR-1302-2 | hsa-miR-219-1 | hsa-miR-485-5p |
| hsa-miR-1302-3 | hsa-miR-219-2 | hsa-miR-486 |
| hsa-miR-1302-4 | hsa-miR-221-5p | hsa-miR-490 |
| hsa-miR-491 | hsa-miR-584 | hsa-miR-663b |
| hsa-miR-493 | hsa-miR-608 | hsa-miR-664-5p |
| hsa-miR-497 | hsa-miR-612 | hsa-miR-675 |
| hsa-miR-498 | hsa-miR-613 | hsa-miR-7-1 |
| hsa-miR-503 | hsa-miR-615-3p | hsa-miR-7-2 |
| hsa-miR-505 | hsa-miR-618 | hsa-miR-7-3 |
| hsa-miR-508-3p | hsa-miR-625 | hsa-miR-708 |
| hsa-miR-532 | hsa-miR-626 | hsa-miR-761 |
| hsa-miR-539 | hsa-miR-634 | hsa-miR-765 |
| hsa-miR-541 | hsa-miR-635 | hsa-miR-769 |
| hsa-miR-5481 | hsa-miR-638 | hsa-miR-770 |
| hsa-miR-552 | hsa-miR-645 | hsa-miR-876 |
| hsa-miR-563 | hsa-miR-646 | hsa-miR-877 |
| hsa-miR-575 | hsa-miR-647 | hsa-miR-921 |
| hsa-miR-577 | hsa-miR-652 | hsa-miR-922 |
| hsa-miR-580 | hsa-miR-654 | hsa-miR-92a-1 |
| hsa-miR-583 | hsa-miR-658 | hsa-miR-92a-2-5p |
| | hsa-miR-663a | hsa-miR-92b |

Moreover, a survey of miRNAs targeting the human UCP2 5'UTR with several prediction programs, using the human UCP2 gene (ENSG00000175567, 15,174 base pair (bp) of the, including 5,000 bp 5'UTR as a target revealed binding sites for 54 miRNAs in UCP2 5'UTR as shown in Table 10.

TABLE 10 miRNAs with predicted binding sites in the 5'UTR of UCP2 gene sequence.

| MicroRNA | Seed Length | Start | Sequence | SEQ ID NO | End | P value |
|---|---|---|---|---|---|---|
| hsa-let-7c | 9 | 3052 | UAGAGUUAC | | 3044 | 0.0374 |
| hsa-let-7i-3p | 9 | 3051 | CUGCGCAAG | | 3043 | 0.0374 |
| hsa-miR-1228-5p | 9 | 3419 | UGGGCGGGG | | 3411 | 0.0374 |
| hsa-miR-1229-3p | 9 | 3419 | UCUCACCAC | | 3411 | 0.0374 |
| hsa-miR-129-1-3p | 10 | 2784 | AGCCCUUACC | 334 | 2775 | 0.0095 |
| hsa-miR-1302 | 9 | 4219 | UGGGACAUA | | 4211 | 0.0374 |
| hsa-miR-1303 | 9 | 2159 | UUAGAGACG | | 2151 | 0.0374 |
| hsa-miR-136 | 9 | 4486 | CUCCAUUUG | | 4478 | 0.0374 |
| hsa-miR-155 | 9 | 2160 | UUAAUGCUA | | 2152 | 0.0374 |
| hsa-miR-16 | 10 | 3603 | UAGCAGCACG | 335 | 3594 | 0.0095 |
| hsa-miR-18a-3p | 10 | 3603 | ACUGCCCUAA | 336 | 3594 | 0.0095 |
| hsa-miR-190 | 9 | 2428 | UGAUAUGUU | | 2420 | 0.0374 |
| hsa-miR-191 | 9 | 3052 | CAACGGAAU | | 3044 | 0.0374 |
| hsa-miR-192 | 9 | 4390 | CUGACCUAU | | 4382 | 0.0374 |
| hsa-miR-194 | 9 | 1643 | UGUAACAGC | | 1635 | 0.0374 |
| hsa-miR-197 | 9 | 5001 | UCACCACCU | | 4993 | 0.0374 |
| hsa-miR-19b-2-5p | 10 | 3052 | AGUUUUGCAG | 337 | 3043 | 0.0095 |
| hsa-miR-203 | 9 | 3051 | UGAAAUGUU | | 3043 | 0.0374 |
| hsa-miR-218 | 10 | 3603 | UUGUGCUUGA | 338 | 3594 | 0.0095 |
| hsa-miR-218-1-3p | 9 | 5001 | UGGUUCCGU | | 4993 | 0.0374 |
| hsa-miR-219-1-3p | 9 | 3614 | AGAGUUGAG | | 3606 | 0.0374 |
| hsa-miR-26a-2-3p | 9 | 2163 | CCUAUUCUU | | 2155 | 0.0374 |
| hsa-miR-27a-3p | 10 | 3603 | UUCACAGUGG | 339 | 3594 | 0.0095 |
| hsa-miR-27a-5p | 11 | 3336 | AGGGCUUAGCU | 340 | 3326 | 0.0024 |
| hsa-miR-28-5p | 10 | 3603 | AAGGAGCUCA | 341 | 3594 | 0.0095 |
| hsa-miR-331-3p | 9 | 4134 | GCCCCUGGG | | 4126 | 0.0374 |

TABLE 10-continued miRNAs with predicted binding sites in the 5'UTR of UCP2 gene sequence.

| MicroRNA | Seed Length | Start | Sequence | SEQ ID NO | End | P value |
|---|---|---|---|---|---|---|
| hsa-miR-337-5p | 10 | 115 | GAACGGCUUC | 342 | 106 | 0.0095 |
| hsa-miR-340-3p | 9 | 1872 | CCGUCUCAG | | 1864 | 0.0374 |
| hsa-miR-34c-3p | 11 | 2162 | AAUCACUAACC | 343 | 2152 | 0.0024 |
| hsa-miR-373-5p | 11 | 530 | ACUCAAAAUGG | 344 | 520 | 0.0024 |
| hsa-miR-425 | 9 | 1013 | AAUGACACG | | 1005 | 0.0374 |
| hsa-miR-497 | 9 | 3661 | AGCAGCACA | | 3653 | 0.0374 |
| hsa-miR-501-5p | 9 | 4164 | AUCCUUUGU | | 4156 | 0.0374 |
| hsa-miR-505 | 9 | 1015 | GUCAACACU | | 1007 | 0.0374 |
| hsa-miR-508-3p | 9 | 1274 | GAUUGUAGC | | 1266 | 0.0374 |
| hsa-miR-509-3p | 12 | 2554 | UGAUUGGUACGU | 345 | 2543 | 0.0006 |
| hsa-miR-512-5p | 10 | 987 | ACUCAGCCUU | 346 | 978 | 0.0095 |
| hsa-miR-514 | 9 | 5001 | UUGACACUU | | 4993 | 0.0374 |
| hsa-miR-515-5p | 9 | 59 | UUCUCCAAA | | 51 | 0.0374 |
| hsa-miR-518a-3p | 9 | 19 | GAAAGCGCU | | 11 | 0.0374 |
| hsa-miR-519e-5p | 11 | 2525 | UCUCCAAAAGG | 347 | 2515 | 0.0024 |
| hsa-miR-548a-3p | 10 | 680 | CAAAACUGGC | 348 | 671 | 0.0095 |
| hsa-miR-550a-3p | 9 | 4312 | GUCUUACUC | | 4304 | 0.0374 |
| hsa-miR-571 | 9 | 739 | UGAGUUGGC | | 731 | 0.0374 |
| hsa-miR-578 | 9 | 1377 | CUUCUUGUG | | 1369 | 0.0374 |
| hsa-miR-606 | 9 | 4420 | AACUACUGA | | 4412 | 0.0374 |
| hsa-miR-615-5p | 10 | 1140 | GGGGGUCCCC | 349 | 1131 | 0.0095 |
| hsa-miR-638 | 9 | 2710 | GGGAUCGCG | | 2702 | 0.0374 |
| hsa-miR-657 | 12 | 1316 | GCAGGUUCUCAC | 350 | 1305 | 0.0006 |
| hsa-miR-658 | 9 | 3673 | GGCGGAGGG | | 3665 | 0.0374 |
| hsa-miR-877-3p | 9 | 4349 | UCCUCUUCU | | 4341 | 0.0374 |
| hsa-miR-93-3p | 9 | 799 | ACUGCUGAG | | 791 | 0.0374 |
| hsa-miR-96-3p | 9 | 799 | AAUCAUGUG | | 791 | 0.0374 |
| hsa-miR-99b-3p | 9 | 2163 | CAAGCUCGU | | 2155 | 0.0374 | c) A Multiple microRNAs-Multiple mRNAs Paradigm.

Figure 4:
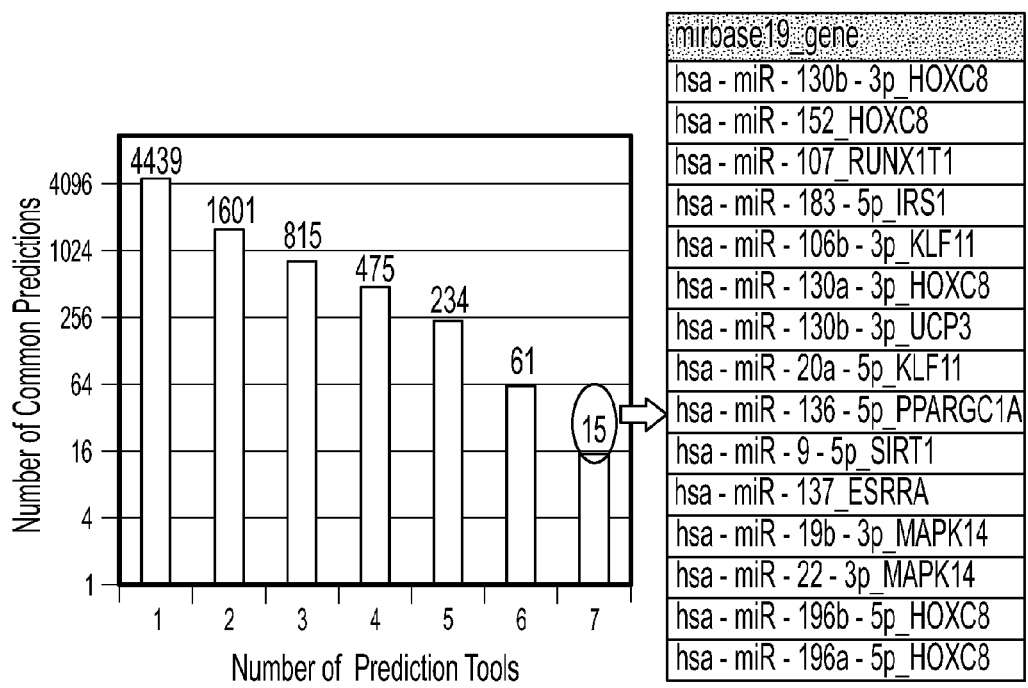
FIG. 4 is a schematic representation of the overlap of results from multiple miRNA prediction programs predicting miRNA binding sites in the 5'UTR, promoter region, coding sequence and 3'UTR of the genes of 83 thermogenic regulators.

The 83 thermogenic regulator molecules selected in Table 1 were screened for high stringency Multiple miRNAs-Multiple mRNAs associations. The results of these analyses with 7 major prediction tools are shown in FIG. 4. The union of these 7 tools produces 4439 miRNA-gene couples. Overlap between these tools decreases as the number of tools increases, reaching only 15 miRNA-gene couples when 7 tools are considered.

d) An Over-Representation of One microRNA Seed Sequence Motif Among Co-Regulated mRNA Targets Paradigm.

Several approaches can be used to identify pathway-specific miRNAs. For example, searching the 3'-UTRs of putatively co-regulated genes for an over-represented sequence from a miRNA seed region could identify a common regulatory miRNA. To determine if particular miRNA seed sequences were overrepresented among the 3' UTR of the chosen 83 thermogenesis targets, the miRvestigator web application (mirvestigator.systemsbiology.net/) was employed. Using the following parameters (motif size of 8 bp, default Weeder model, seed model of 8mer, 100% complementarity homology and 0.25 wobble base-pairing allowed), it was determined that that the motif 5'-UUU-GUACA-3' recognized by hsa-miR-19a/-19b is overrepresented among 15 of the 83 thermogenesis targets with a complementarity p value of $1.7 \times 10^{-04}$ as shown in Table 11. Of note is that hsa-miR-19 has been reported as an abundant adipocyte miRNA.

TABLE 11

Complementarity between the common motif UUUGUACA and hsa-miR-19a/19b.

| miRNA Name | miRNA Seed | Seed Model | Length of Complementarity | Complementary Base-Pairing | Complementarity P-Value |
|---|---|---|---|---|---|
| hsa-miR-19a hsa-miR-19b | UGUGCAAA | 8mer | 8 | Motif 5' UUUGUACA 3'<br>\|\|\|\|\|\|\|\|<br>3' AAACGUGU 5' miRNA Seed | 1.7e-04 |

The Minimum Free Energy levels of the hsa-miR-19 mRNA/miRNA duplexes identified by miRvestigator were quite low, favoring tight binding. Accordingly, the miRvestigator analysis was repeated with less stringent levels of complementarity. This analysis identified a further 10 additional targets (CEBPD, PRKAA1, TWIST1, IRS1, NCOA1, NCOA2, NCOA3, KLF5, RPS6KB1, NRIP1) with 95% similarity to the consensus hsa-miR-19 motif. Interestingly, hsa-miR-19 is among the most abundant miRNAs in adipose tissue. The genes identified as containing a sequence complementary to hsa-miR-19 seed region are set forth in Table 12.

TABLE 12

Thermogenic regulators identified as targets for hsa-miR-19.

| Gene | Gene symbol | Sequence of Site | Start Relative to Stop Codon (bp) | % Similarity to Consensus Motif (Quality = High\|Medium\|Fair) | Minimum Free Energy (MFE) of mRNA-miRNA Duplex |
|---|---|---|---|---|---|
| 650 | BMP2 | UUUGUACA | 386 | 100.00 | -6.80 |
| 1052 | CEBPD | UUUGUAAA | 263 | 95.44 | -3.40 |
| 7132 | TNFRSF1A | UUUGUACA | 510 | 100.00 | -6.80 |
| 5562 | PRKAA1 | UUUGUAAA | 2400 | 95.44 | -3.40 |
| 5563 | PRKAA2 | UUUGUACA | 542 | 100.00 | -6.80 |
| 655 | BMP7 | UUUGUACA | 1927 | 100.00 | -6.80 |
| 652 | BMP4 | UUUGUACA | 770 | 100.00 | -6.80 |
| 133522 | PPARGC1B | UUUGUACA | 7199 | 100.00 | -6.80 |
| 7474 | WNT5A | UUUGUACA | 1414 | 100.00 | -6.80 |
| 6720 | SREBF1 | UUUGUACA | 510 | 100.00 | -6.80 |
| 7291 | TWIST1 | UUUGUAAA | 649 | 95.44 | -3.40 |
| 3667 | IRS1 | UUUGUAAA | 992 | 95.44 | -3.40 |
| 10499 | NCOA2 | UUUGUAAA | 1381 | 95.44 | -3.40 |
| 8204 | NRIP1 | UUUGUACA | 1718 | 100.00 | -6.80 |
| 8204 | NRIP1 | UUUGUAAA | 1935 | 95.44 | -3.40 |
| 8202 | NCOA3 | UUUGUAAA | 965 | 95.44 | -3.40 |
| 1385 | CREB1 | UUUGUAAA | 1973 | 95.44 | -3.40 |
| 1385 | CREB1 | UUUGUACA | 2822 | 100.00 | -6.80 |
| 1385 | CREB1 | UUUGUACA | 2822 | 100.00 | -6.80 |
| 1385 | CREB1 | UUUGUAAA | 4175 | 95.44 | -3.40 |
| 3643 | INSR | UUUGUAAA | 2105 | 95.44 | -3.40 |
| 8013 | NR4A3 | UUUGUACA | 2347 | 100.00 | -6.80 |
| 860 | RUNX2 | UUUGUACA | 2425 | 100.00 | -6.80 |
| 6776 | STAT5A | UUUGUACA | 1214 | 100.00 | -6.80 |
| 1874 | E2F4 | UUUGUACA | 755 | 100.00 | -6.80 |
| 688 | KLF5 | UUUGUAAA | 549 | 95.44 | -3.40 |
| 8648 | NCOA1 | UUUGUAAA | 381 | 95.44 | -3.40 |
| 6198 | RPS6KB1 | UUUGUAAA | 2531 | 95.44 | -3.40 |

Accordingly, the miRvestigator analysis was repeated with less stringent levels of complementarity (motif size of 8 bp, default Weeder model, seed model of 8mer, 95% complementarity homology and 0.25 wobble base-pairing allowed). This analysis identified a further 10-12 additional targets (CEBPD, CREB1, PRKAA1, TWIST1, INSR, IRS1, NCOA1, NCOA2, NCOA3, KLF5, RPS6 KB1, NRIP1) with 95% similarity to the consensus hsa-miR-19 motif. Interestingly, hsa-miR-19 is among the most abundant miRNAs in adipose tissue. The genes identified as containing a sequence complementary to hsa-miR-19 seed region are set forth in Table 13.

TABLE 13

Thermogenic regulators identified as targets for hsa-miR-19a/b with 95% to 100% similarity to consensus motif.

| Gene | Gene symbol | Sequence of Site | Start Relative to Stop Codon (bp) | % Similarity to Consensus Motif (Quality = High\|Medium\|Fair) | Minimum Free Energy (MFE) of mRNA-miRNA Duplex |
|---|---|---|---|---|---|
| 650 | BMP2 | UUUGUACA | 386 | 100.00 | -6.80 |
| 1052 | CEBPD | UUUGUAAA | 263 | 95.44 | -3.40 |

TABLE 13 -continued

Thermogenic regulators identified as targets for hsa-miR-19a/b with 95% to 100% similarity to consensus motif.

| Gene | Gene symbol | Sequence of Site | Start Relative to Stop Codon (bp) | % Similarity to Consensus Motif (Quality = High\|Medium\|Fair) | Minimum Free Energy (MFE) of mRNA-miRNA Duplex |
|---|---|---|---|---|---|
| 7132 | TNFRSF1A | UUUGUACA | 510 | 100.00 | -6.80 |
| 4040 | LRP6 | UUUGUACA | 151 | 100.00 | -6.80 |
| 4040 | LRP6 | UUUGUAAA | 4965 | 95.42 | -3.40 |
| 5562 | PRKAA1 | UUUGUAAA | 2400 | 95.42 | -3.40 |
| 5563 | PRKAA2 | UUUGUACA | 542 | 100.00 | -6.80 |
| 655 | BMP7 | UUUGUACA | 1927 | 100.00 | -6.80 |
| 652 | BMP4 | UUUGUACA | 770 | 100.00 | -6.80 |
| 133522 | PPARGC1B | UUUGUACA | 7199 | 100.00 | -6.80 |
| 1874 | E2F4 | UUUGUACA | 755 | 100.00 | -6.80 |
| 7474 | WNT5A | UUUGUACA | 1414 | 100.00 | -6.80 |
| 6720 | SREBF1 | UUUGUACA | 510 | 100.00 | -6.80 |
| 7291 | TWIST1 | UUUGUAAA | 649 | 95.44 | -3.40 |
| 3667 | IRS1 | UUUGUAAA | 992 | 95.42 | -3.40 |
| 10499 | NCOA2 | UUUGUAAA | 1381 | 95.42 | -3.40 |
| 8204 | NRIP1 | UUUGUACA | 1718 | 100.00 | -6.80 |
| 8204 | NRIP1 | UUUGUAAA | 1935 | 95.42 | -3.40 |
| 8202 | NCOA3 | UUUGUAAA | 965 | 95.42 | -3.40 |
| 3643 | INSR | UUUGUAAA | 2105 | 95.42 | -3.40 |
| 8013 | NR4A3 | UUUGUACA | 2347 | 100.00 | -6.80 |
| 6776 | STAT5A | UUUGUACA | 1214 | 100.00 | -6.80 |
| 688 | KLF5 | UUUGUAAA | 549 | 95.42 | -3.40 |
| 8648 | NCOA1 | UUUGUAAA | 381 | 95.42 | -3.40 |
| 860 | RUNX2 | UUUGUACA | 2425 | 100.00 | -6.80 |
| 1385 | CREB1 | UUUGUAAA | 1973 | 95.42 | -3.40 |
| 1385 | CREB1 | UUUGUACA | 2822 | 100.00 | -6.80 |
| 1385 | CREB1 | UUUGUAAA | 4175 | 95.42 | -3.40 |
| 6198 | RPS6KB1 | UUUGUAAA | 2531 | 95.42 | -3.40 |

Without wobbling, the same motif 5'-UUUGUACA-3' is overrepresented among targets of hsa-miR-1283 with a complementarity p value of $1.4 \times 10^{-4}$. Furthermore, hsa-miR-1283 binds to other mRNAs of interest like ABCA1 (cholesterol transporter), the adiponectin receptor and the transcription factor TCF7L2 that is implicated in genetic human obesity.

Similarly, other miRNA over-represented seed sequences were identified for miRNAs expressed in adipocytes. They include the universal hsa-let-7 family (sequence CUAUA-CAA, p value=7.5e-04) and the adipocyte-rich hsa-miR-30 family (sequence UGUAAACA, p value=$1.9 \times 10^{-3}$) to name a few.

With respect to PRDM16, CIDEA, NRIP1, KDM3A, CEPPB, PPARG, PPARGC1A, and PPKAA2, which according to the STRING software package are directly linked to UCP1, it appears that all of them share (at motif size 8 bp, default weeder model, seed model 8mer, 95% complementarity homology and 0.25 wobble base-pairing allowed) a consensus sequence with several miRNAs, including hsa-miR-3658 (p value=1.9e-003) and the hsa-miR-30 family (p value=6.3e-003) as follows:

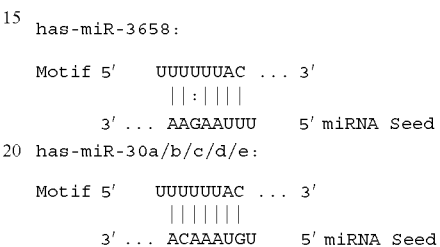

e) An Intronic miRNA-Multiple mRNAs Pathway-Specific Paradigm.

Many mammalian miRNAs are located within introns of protein-coding genes rather than in their own unique transcription units. Intronic miRNAs are typically expressed and processed with the precursor mRNA in which they reside. Although the intronic miRNAs and their host genes can be regulated independently, an intronic miRNA can down-regulate its own host protein-coding gene by targeting the host gene's UTR. Feedback regulation on host protein-coding genes could be achieved by selecting the transcription factors that are miRNA targets or by protein-protein interactions between intronic miRNA host gene product and miRNA target gene products. As an example, miR-33 acts in concert with the SREBP host genes to control cholesterol homeostasis and the pharmacological inhibition of miR-33a and miR-33b is a promising therapeutic strategy to raise plasma HDL and lower VLDL triglyceride levels for the treatment of dyslipidaemias.

Examination of the 83 thermogenic target genes reveals two intronic miRNAs: miR-378 located in the PPARGC1B gene and miR-4251 located in the PRDM16 gene.

Mining of the Internet tools predicting miRNA targets indicates that miR-378 targets include BMP2, PPARA, PPARGC1A, PRDM16, STATS and WNT10A as well as ADIPOQ and IGFR1; and that miR-4251 targets include BMP2, CTBP1, CTBP2, MAPK14, NCOA3, PLAC8, PPARA, PPARD, TRPM8, as well as ABCA5, ABCA13, ADIPOQR2, KDM5B, KLF-12, KLF-14 and TCF7L2.

Example 3

High-Content Cellular Phenotypic Screening

High-content screening methods are used to screen for novel miRNA agents that modulate the activity of thermogenic regulators (e.g., UCP1 and UCP2). High-content screening is a drug discovery method that uses images of living cells to facilitate molecule discovery. Such automated image based screening methods are particularly suitable for identifying agents which alter cellular phenotypes.

WAT cells which contain a single large lipid droplet, whereas, in contrast, BAT cells contain numerous smaller droplets and a much higher number of mitochondria, which contain iron and make them appear brown. The large number of mitochondria in BAT leads to an increased oxygen consumption, when compared to WAT. Accordingly, it is possible to distinguish between BAT and WAT cells visually based on their cellular phenotype.

Accordingly, high-content screening methods were used to screen for novel miRNA agents that modulate the activity of thermogenic regulators. Specifically, the phenotypic appearance of cultured human adipocytes and adipose tissue derived mesenchymal stem cells grown in the presence and absence of miRNA agonists or antagonists was assessed over two weeks by phase contrast microscopy of the cultured cells, measurement of the cellular lipid content (using Oil Red O Staining or Nile Red fluorescence); mitochondrial content (e.g., using Life Technologies Mito-Tracker Red FM), and/or oxygen consumption in vitro (e.g., using the Seahorse Bioscience Extra-Cellular Flux Instrument). mRNA expression is measured by targeted q-RT-PCR and universal RNA-Sequencing. Protein expression is measured by targeted Western Blotting and universal proteomic profiling.

A. Differentiation of Human Pre-Adipocytes into Adipocytes.

1. Differentiation Protocol.

In order to assess the effect of miRNA analogs on human pre-adipocytes differentiation into mature adipocytes, human subcutaneous pre-adipocytes (SuperLot 0048 from 8 female donors, ZenBio, N.C.) were plated on Day 0 into 96-well plates and allowed to attach overnight in preadipocyte medium (DMEM/Ham's F-12 (1:1, v/v), HEPES buffer, Fetal bovine serum and Antibiotics). The next day (Day 1), the medium was removed and replaced with differentiation medium (DMEM/Ham's F-12 (1:1, v/v), 100 µM Ascorbic Acid, 0.85 µM insulin, 20 nM sodium selenite, 0.2 nM, triiodothryonine, 1 µM dexamethasone, 100 µM isobutyl-methylxanthine, 100 nM Rosiglitazone and Antibiotics). The cells were allowed to incubate for 2 days at 37°, 5% $CO_2$. After 2 days (Day 3), the medium was removed and replaced with fresh maintenance medium (DMEM/Ham's F-12 (1:1, v/v), 100 µM Ascorbic Acid, 0.85 µM insulin, 20 nM sodium selenite, 0.2 nM triiodothryonine, and Antibiotics). On Day 3, the cells were transfected with miRNA analogs (Dharmacon specific miRIDIAN Mimics and Hairpin Inhibitors) using the transfecting agent Dharmafect1. All treatments were in triplicate. Post transfection, the negative control was maintenance medium only and the positive control was maintenance medium with 100 nM of the PPARG agonist rosiglitazone. After 2 days, medium was removed and replaced with fresh maintenance medium. The maintenance medium then changed every two days until the end of the treatment period (Day 15). At the end of the treatment (total of 15 days in culture) cells were processed for Phenotyping and Genotyping Screening.

1. Transfection of Pre-Adipocytes.

Transfection reagents are used to facilitate the penetration of miRNA analogs into target cells. As an example, the extent of transfection efficiency we achieved in pre-adipocytes with the transfecting agent Dharmafect 1 (Dharmacon, Colo.) is depicted herein. Transfection efficiency was assessed in two ways:

a. Measurement of Cellular Epifluorescence after Transfection with Fluorescent miRNA Analogs.

Figure 9:
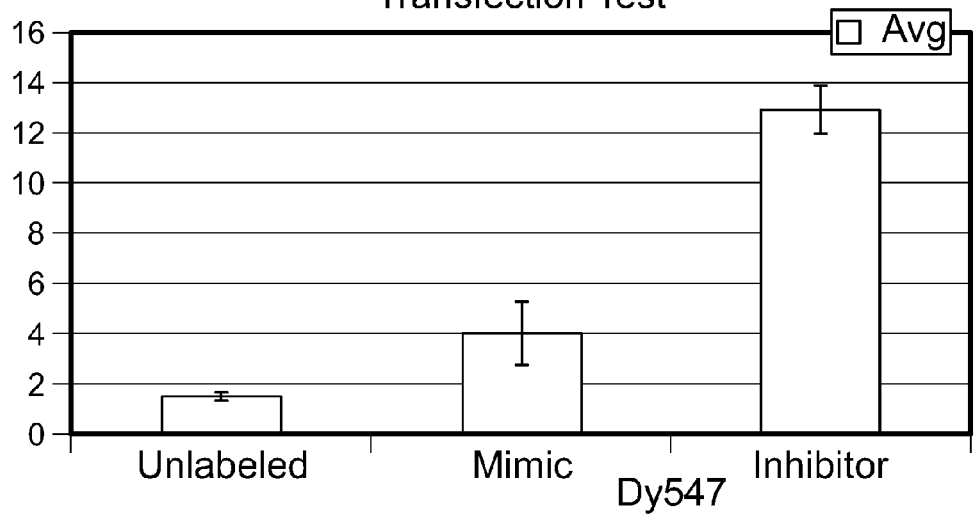
FIG. 9 is a bar graph showing relative fluorescence in unlabeled cells or cells transfected with a Dy547 labeled non-targeting miRIDIAN mimic and hairpin inhibitor.

Fluorescence was measured on Day 15 (540 excitation/590 emission) in cells transfected on Day 3 with the Dy547-labeled non-targeting miRIDIAN Mimic and Hairpin Inhibitor (100 nM). As shown in FIG. 9, there was a significantly greater fluorescence of cells transfected with the fluorescent miRNA analogs, even 12 days after transfection:

b. Reduction of Control Gene Expression.

Figure 10:
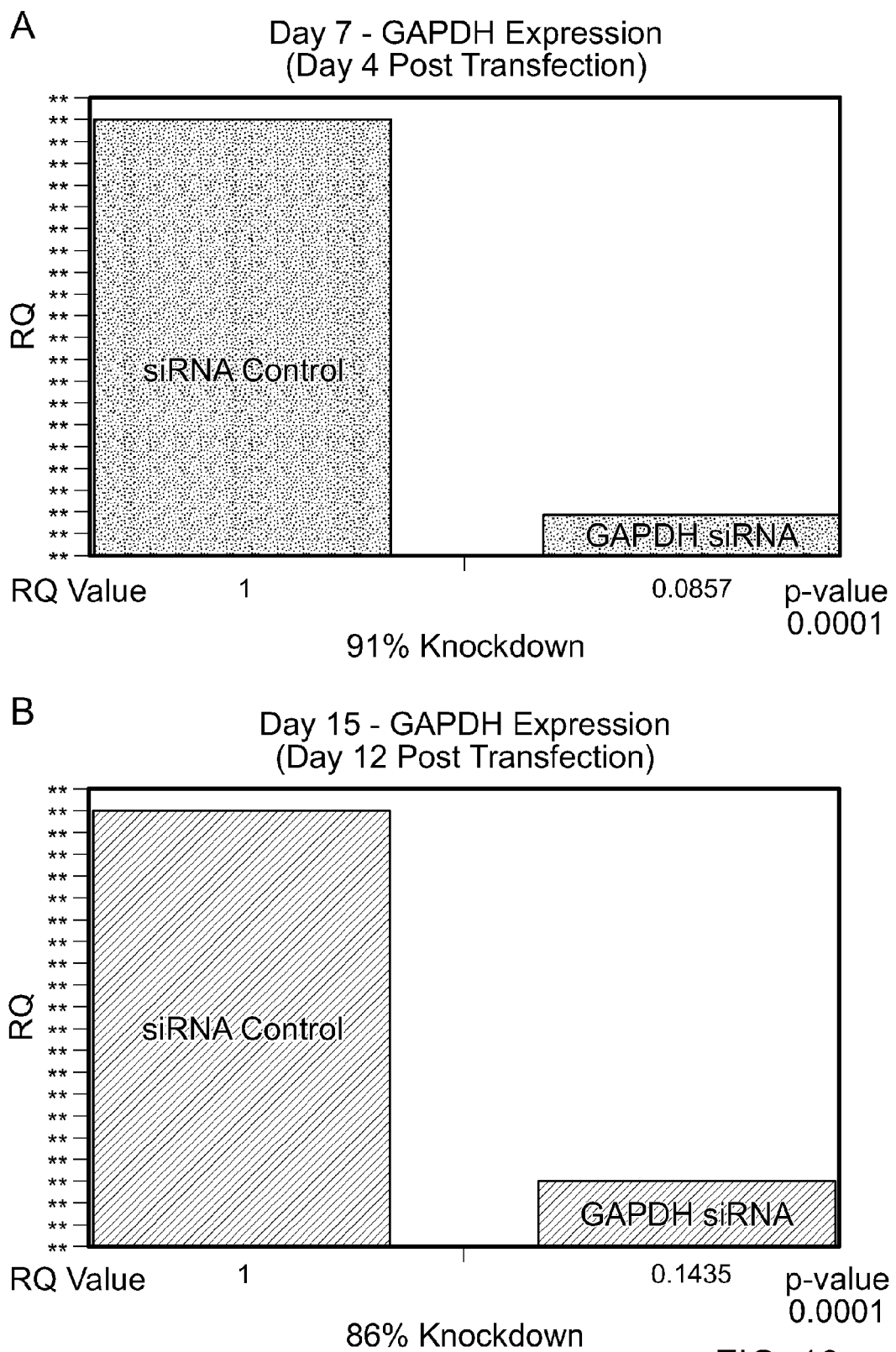
FIG. 10A is a bar graph showing the reduction of GAPDH expression in cells transfected with siRNA control and a GAPDH siRNA 4 days after transfection.
FIG. 10B is a bar graph showing the reduction of GAPDH expression in cells transfected with siRNA control and a GAPDH siRNA 12 days after transfection.

To confirm successful transfection of pre-adipocytes, the reduction of expression of the control gene GAPDH ("housekeeping gene") was measured 4 days (Day 7) (FIG. 10A) and 12 days (Day 15) (FIG. 10B) after transfection of pre-adipocytes with a GAPDH-specific siRNA. Cell lysates were obtained and RT-PCR was conducted using pure RNA obtained by Cells-to-Ct reagents. 91% and 86% knockdowns of the GAPDH mRNA expression were observed at Day 4 and Day 12 post transfection, both highly significant, as shown in FIG. 10.

c. Phenotypic Changes During Human Preadipocytes Differentiation into Adipocytes.

Figure 11:
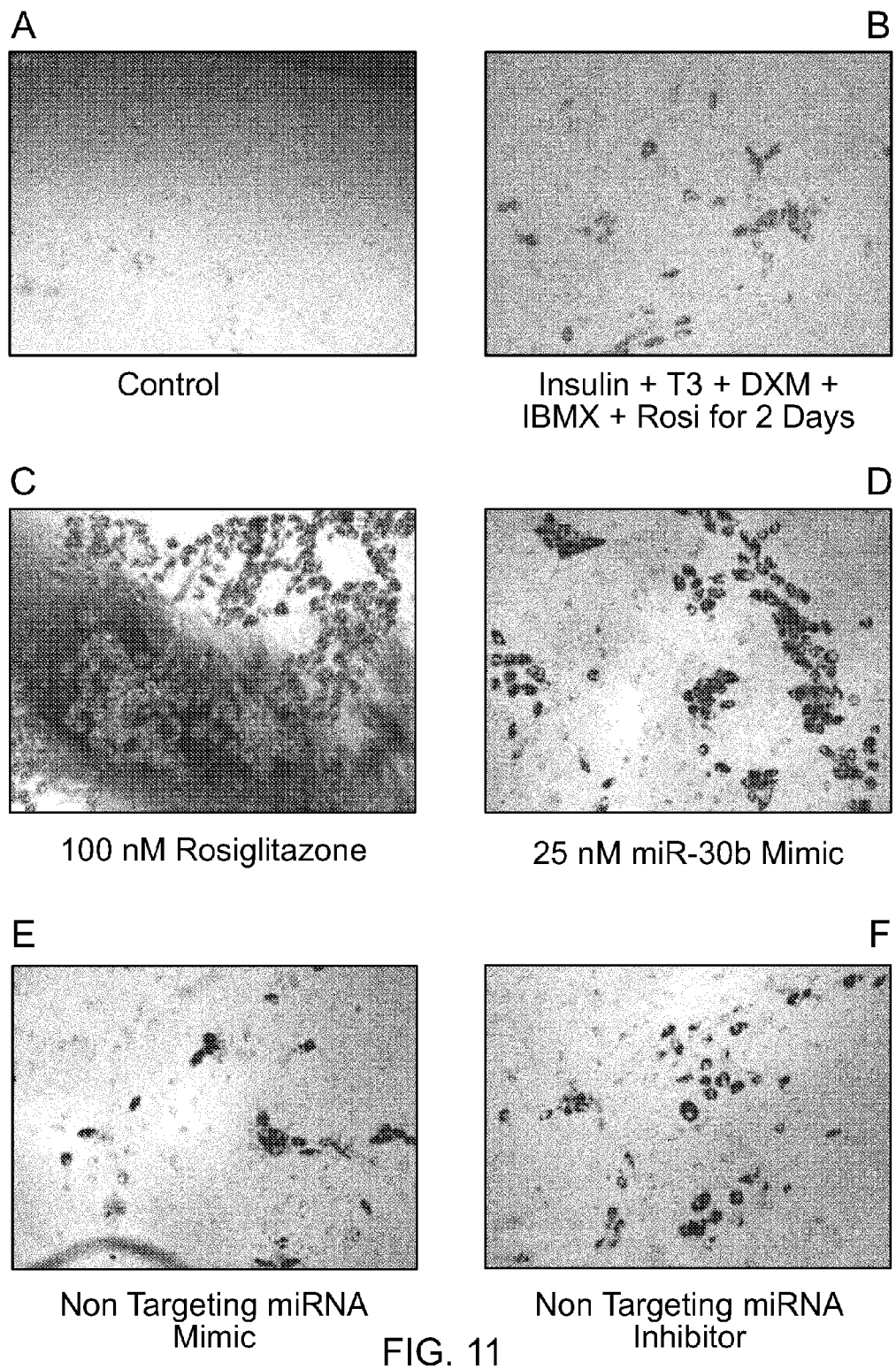
FIG. 11A is a light micrograph of preadipocytes stained with Oil Red O cultured for 2 weeks in maintenance medium without rosiglitazone.
FIG. 11B is a light micrograph of preadipocytes stained with Oil Red O cultured in the presence of insulin, triiodothyronine, dexamethasone, isobutyl-methylxanthine and rosiglitazone for two days followed by maintenance medium for 12 days.
FIG. 11C is a light micrograph of preadipocytes stained with Oil Red O cultured in the presence of insulin, triiodothyronine, dexamethasone, isobutyl-methylxanthine and rosiglitazone throughout the experiment.
FIG. 11D is a light micrograph of preadipocytes stained with Oil Red O cultured in the presence of hsa-miR-30b mimic.
FIG. 11E is a light micrograph of preadipocytes stained with Oil Red O cultured in the presence of non targeting miRNA mimic.
FIG. 11F is a light micrograph of preadipocytes stained with Oil Red O cultured in the presence of non targeting miRNA inhibitor.

At the end of treatment (15 days in culture) cells were stained with Oil Red O for assessment of lipid content. As shown in FIG. 11, in the presence of medium without rosiglitazone, the preadipocytes show little differentiation into lipid-loaded mature adipocytes. In the presence of differentiation medium including 100 nM Rosiglitazone for 2 days followed by maintenance medium for 12 days (negative control), some differentiation into lipid-loaded mature adipocytes is noted. In the presence of 100 nM rosiglitazone throughout the experiment (positive control), most of the cells became lipid-loaded mature adipocytes. As an example, in the presence of 25 nM hsa-miR-30b mimic, about half of the cells became lipid-loaded mature adipocytes. The non targeting miRNA mimic and inhibitor showed patterns similar to the negative control.

d. Genotypic Changes During Human Pre-Adipocyte Differentiation into Adipocytes.

Profiling of mRNA changes occurring during the differentiation of human pre-adipocyte into mature adipocyte induced by rosiglitazone or miRNA analogs was performed by RNA-Seq technology. Small RNA sequencing (RNA-Seq) is a high-throughput next-generation sequencing platform which now allows transcriptome-wide profiling of all small RNAs, known and unknown, with no need for prior sequence or secondary structure information.

RNA samples were extracted from pre-adipocytes (pre-adipocyte negative control) and from pre-adipocytes cultured in the presence of 100 nM rosiglitazone (differentiation positive control) or 25 nM miRNA mimics or inhibitors for 12 days. RNA sequencing was performed on the Illumina Hi-Seq 2000 equipment. The results were mapped against Human Genome 19 (http://genome.ucsc.edu/). It appears that in the presence of a miRNA analog, between 313 and 449 mRNA are significantly differentially expressed in reference to pre-adipocytes. In reference to Rosiglitazone, the number of significantly differentially expressed genes is reduced between 111 and 216, thus suggesting common pathways of activation of adipocyte differentiation between miRNAs and the PPARG analog.

Figure 12A:
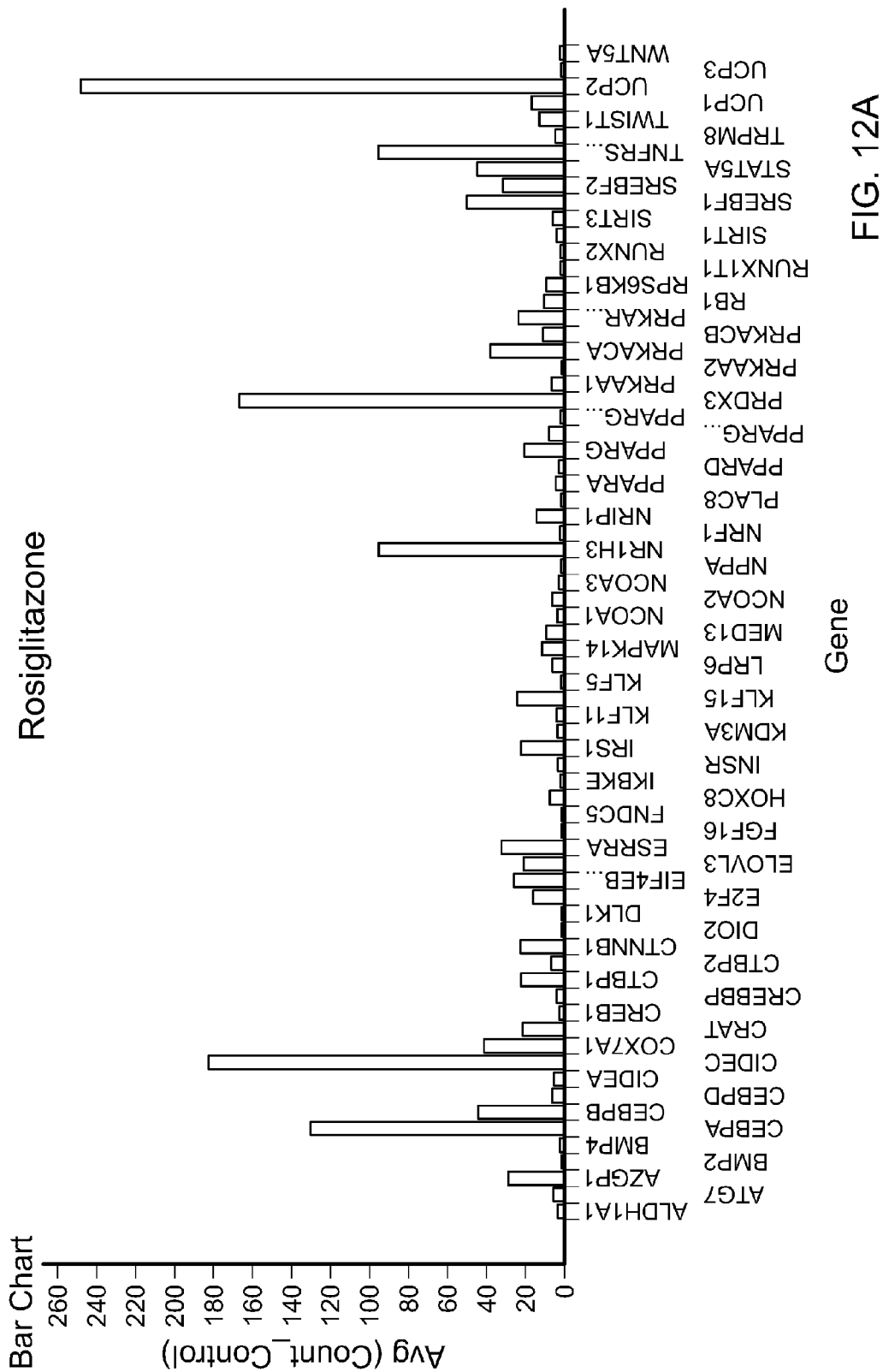
FIG. 12A is a bar graph showing mRNA expression of thermogenesis targets in the presence of rosiglitazone.
Figure 12B:
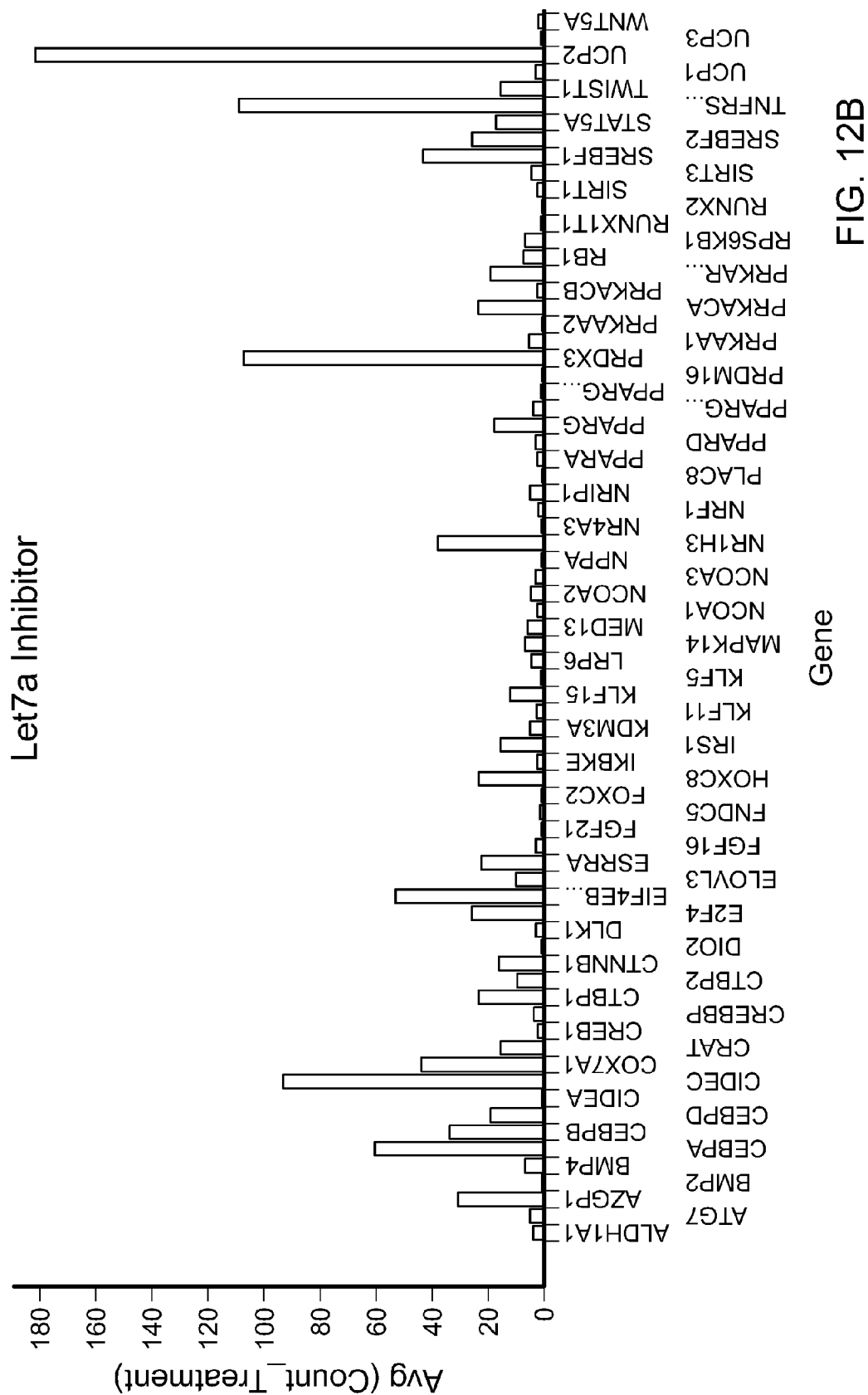
FIG. 12B is a bar graph showing mRNA expression of thermogenesis targets in the presence of hsa-let-7a inhibitor.
Figure 12C:
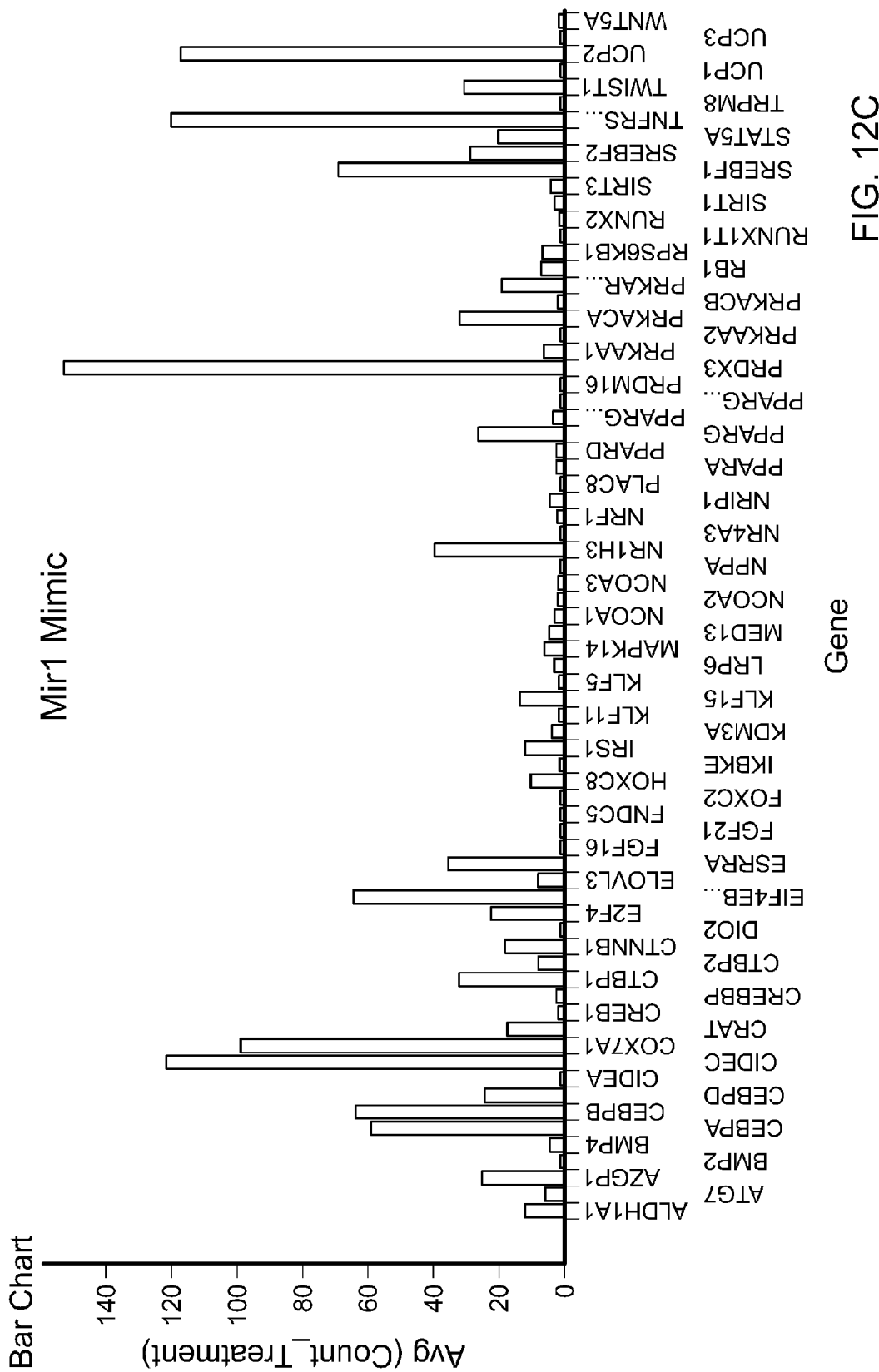
FIG. 12C is a bar graph showing mRNA expression of thermogenesis targets in the presence of hsa-miR-1 mimic.
Figure 12D:
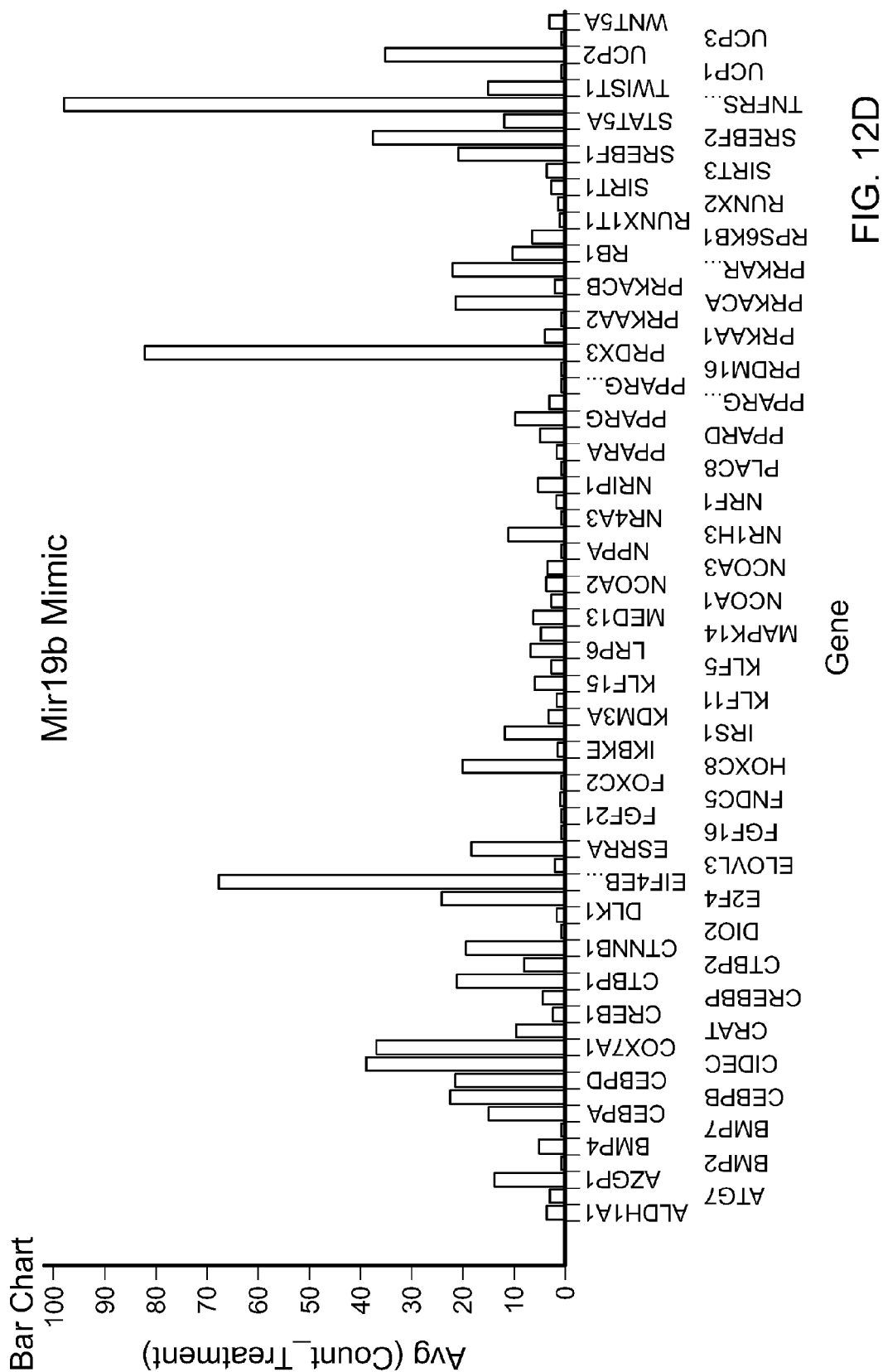
FIG. 12D is a bar graph showing mRNA expression of thermogenesis targets in the presence of hsa-miR-19b mimic.
Figure 12F:
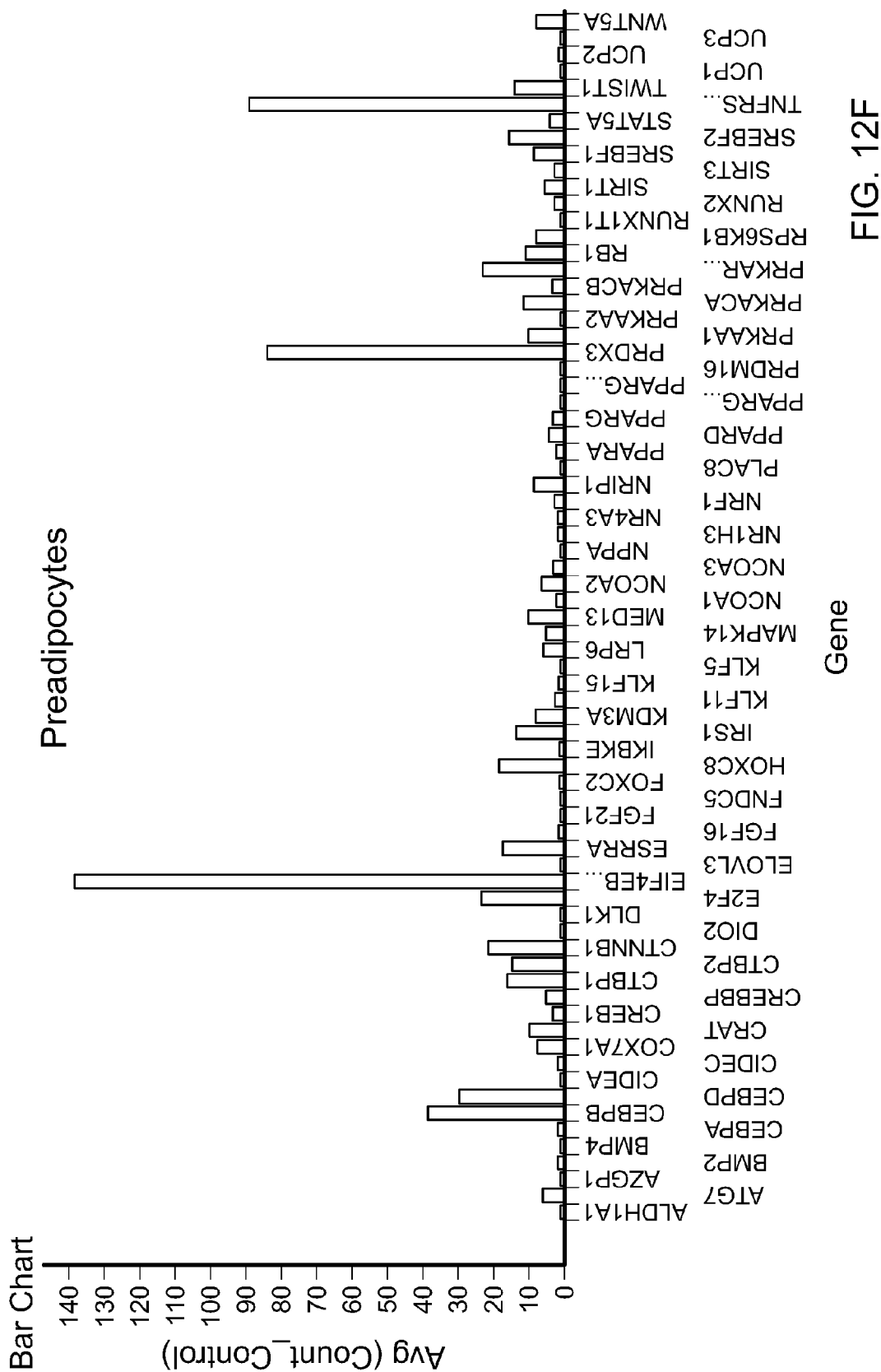
FIG. 12F is a bar graph showing mRNA expression of thermogenesis targets in untreated preadipocytes.

Regarding our 83 thermogenic activators and inhibitors, the expression of 73 of them is altered in the presence of rosiglitazone or miRNA analogs. The changes of mRNA expression of the thermogenesis targets in the presence of rosiglitazone (FIG. 12A) or miRNA analogs hsa-let-7a inhibitor, hsa-miR-1 mimic, hsa-miR-19b mimic, hsa-miR-30b mimic or control adipocytes are shown on FIGS. 12B-F, respectively).

Changes in mRNA expression of UCP1, 2 and 3 were also measured in the presence of rosiglitazone or miRNA analogs, as shown below in Table 14.

TABLE 14

Changes in thermogenic mRNA expression.

| Agent | mRNA Expression changes (log ratios) | | |
|---|---|---|---|
| | UCP1 | UCP2 | UCP3 |
| Rosiglitazone | 15.70 | 263 | 0.26 |
| hsa-let-7a inhibitor | 2.23 | 173 | 0.65 |
| hsa-miR-1 mimic | 0.41 | 110 | 0.40 |
| hsa-miR-19b mimic | 0.18 | 33 | 0.26 |
| hsa-miR-30b mimic | 0.76 | 119 | 0.28 |
| Baseline level in pre-adipocytes | 0.02 | 1.35 | 0.30 |

The expression levels of the three Uncoupling Proteins were low in pre-adipocytes. The expression of UCP1 was significantly increased in the presence of rosiglitazone 100 nM which was renewed with the culture medium every other day. The magnitude of UCP1 mRNA rise with the miRNA analogs was lower than with rosiglitazone, but one has to keep in mind the miRNA analogs concentration used (25 nM) and the fact that only one transfection was performed 12 days before RNA extraction. A major finding is the dramatic increase of UCP2 expression in the presence of rosiglitazone as well as the miRNA analogs. The expression of UCP3 did not change in any condition, as expected for a gene that is mainly expressed in myocytes. This increase in UCP1 and UCP2 expression suggests that administration of these miRNA produces adipocytes with greater potential for thermogenesis and thus are likely effective pharmaceuticals for the treatment of obesity and other metabolic diseases and disorders.

Figure 16:
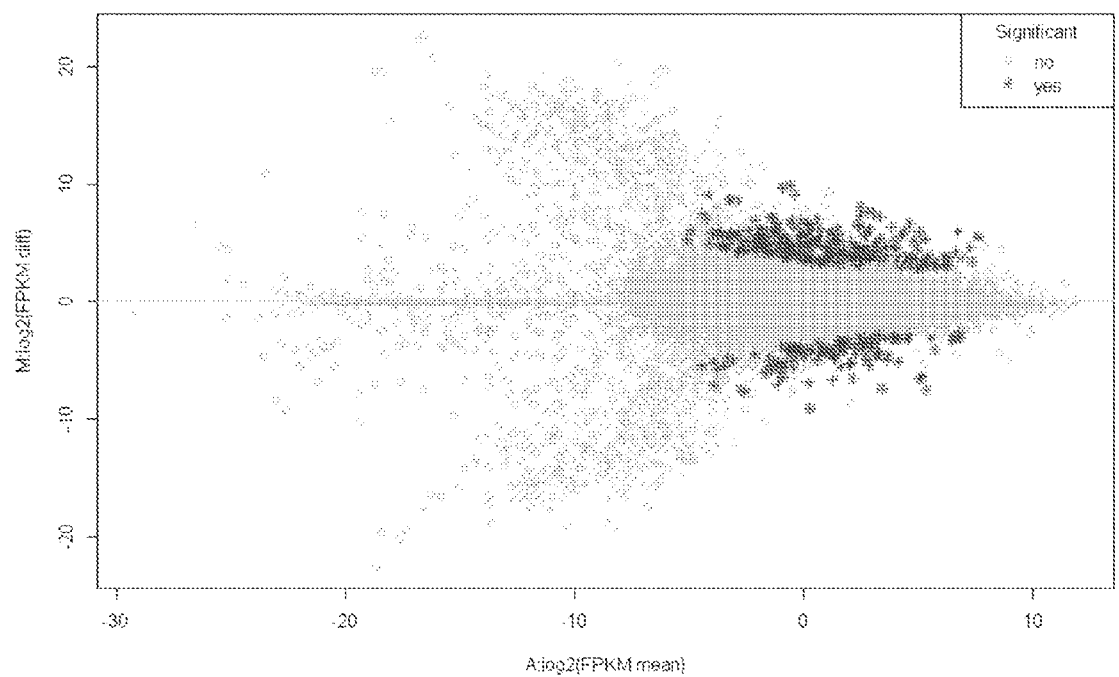
FIG. 16 is an M-A plot showing the mean gene expression on the x-axis and the difference between pairs in logarithmic scale on the y-axis.

Furthermore, we looked at genes differentially expressed during pre-adipocyte culture in the presence of miRNA analogs. As an example shown on FIG. 16, an M-A plot was created to visualize the differences of mRNA expression between pre-adipocytes grown in maintenance medium and pre-adipocytes grown in the presence of hsa-miR-19b mimic. The x-axis is the mean gene expression and the y-axis is the difference between pairs in logarithmic scale. The red dots are the differentially expressed genes (up regulated above zero and down regulated below zero). The gray dots are the genes not differentially expressed between control and hsa-miR-19b mimic (up regulated above zero and down regulated below zero).

Figure 17:
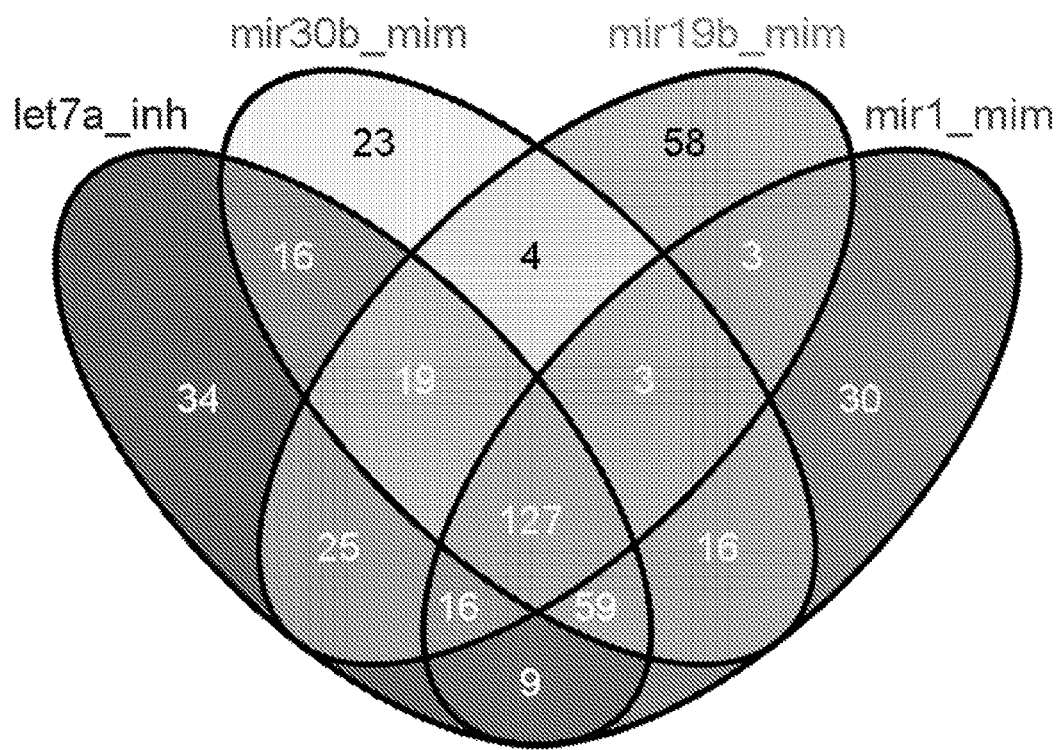
FIG. 17 is a schematic showing a Venn Diagram showing that the numbers of genes significantly upregulated in the presence of the miRNA analogs hsa-let-7a inhibitor, hsa-miR-1 mimic, hsa-miR-19b mimic and hsa-miR-30b mimic were respectively 305, 247, 255 and 267. A set of 127 genes was commonly upregulated by the listed miRNA analogs.

As an example shown on FIG. 17, in reference to pre-adipocytes cultured in maintenance medium only, the numbers of significantly differentially expressed genes in the presence of the miRNA analogs hsa-let-7a inhibitor, hsa-miR-1 mimic, hsa-miR-19b mimic and hsa-miR-30b mimic were respectively 406, 382, 370 and 433. A set of 127 genes was commonly upregulated by these 4 miRNA analogs (Venn Diagram, FIG. 17).

They include not only some of our 83 thermogenic targets like ALDH1A1, AZGP1, CEBPA, PPARGC1A, UCP1 and UCP2 highlighted in green, but also numerous genes involved in lipid metabolism and adipocyte differentiation, highlighted in yellow (Table 15).

TABLE 15

Set of 127 genes commonly upregulated by 4 miRNA analogs.

| | | | |
|---|---|---|---|
| ABCC6 | CHI3L2 | KCNE3 | PPL |
| ABCD2 | CILP | KCNK3 | PPP1R1A |
| ACACB | CKB | KIT | PRKAR2B |
| ACHE | CKMT1B | KLB | PTGDS |
| ACSF2 | CLCA2 | LBP | QPRT |
| ACSM5 | CLMN | LEP | RASL12 |
| ACSS2 | COL14A1 | LGALS12 | RNF157 |
| ADH1B | COL21A1 | LIPE | S100B |
| AIF1L | CPB1 | LPL | SDPR |
| AKR1C3 | CYB5A | LRRC4C | SELENBP1 |
| ALDH1A1 | CYP4F12 | LRRN4CL | SEMA3G |
| AOC3 | CYP4F22 | MAN1C1 | SEPP1 |
| AOC4 | DARC | MAOA | SLC2A4 |
| APCDD1 | DGAT2 | MAOB | SLC2A5 |
| APOC1 | DHCR24 | MARCO | SLC40A1 |
| AQP3 | DPT | MCAM | SLCO4C1 |
| AQP7 | DTX4 | METTL7A | SMOC2 |
| AQP9 | EPHB6 | MGP | SNCG |
| AZGP1 | FABP4 | MLXIPL | SPARCL1 |
| BBOX1 | FADS2 | MOBKL2B | SPRY1 |
| BHLHE22 | FAM65C | MOSC1 | SVEP1 |
| C11orf87 | FMO1 | MVD | TF |
| C14orf180 | FMO2 | NAT8L | TM7SF2 |
| C1orf115 | G0S2 | NKD2 | TMEM132C |
| C1orf95 | GPD1 | PCSK9 | TMEM176B |
| C3 | GPR109A | PFKFB1 | TMEM37 |
| CA2 | GPR109B | PKD1L2 | TNMD |
| CADM3 | HAVCR2 | PLA2G2A | TPRG1 |
| CDO1 | HRASLS5 | PLIN1 | TRIL |
| CEBPA | IGSF10 | PLIN4 | UCP1 |
| CFD | ITIH1 | PLXDC1 | UCP2 |
| CFHR1 | ITIH5 | PPARGC1A | |

Figure 18:
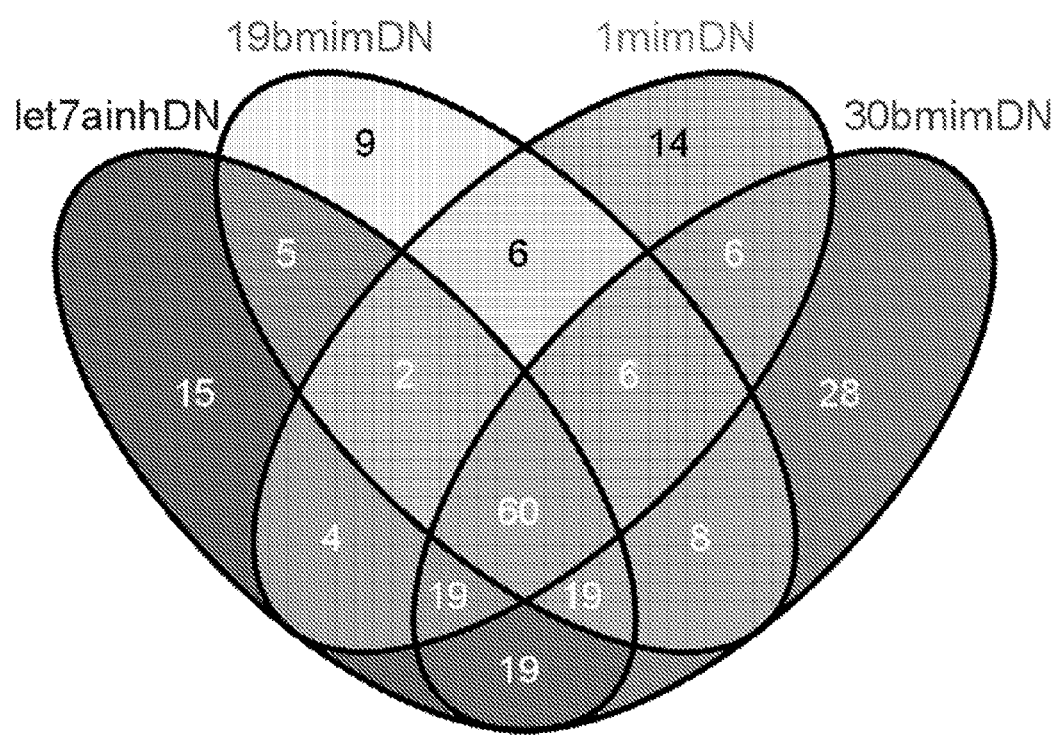
FIG. 18 is a schematic showing a Venn diagram showing that the numbers of genes significantly downpregulated in the presence of the miRNA analogs hsa-let-7a inhibitor, hsa-miR-1 mimic, hsa-miR-19b mimic and hsa-miR-30b mimic were respectively 143, 177, 115 and 165. A set of 60 genes that was commonly downregulated by the listed miRNA analogs.

A set of 60 genes was commonly downregulated by these 4 miRNA analogs (Venn Diagram, FIG. 18).

They include numerous chemokines genes and genes involved in cell proliferation and (Table 16).

TABLE 16

Set of 60 genes commonly downregulated by 4 miRNA analogs.

| | | | |
|---|---|---|---|
| ACTC1 | CENPF | ID1 | KRTAP2-1 |
| ANLN | CKAP2L | ID3 | MALL |
| ARSI | CXCL1 | IER3 | MMP3 |
| ATOH8 | CXCL2 | IL13RA2 | NCAPH |
| AURKB | CXCL3 | IL6 | PHLDA1 |
| BLM | CXCL5 | IL8 | PLK1 |
| BRCA2 | CXCL6 | INHBA | PPAPDC1A |
| BUB1 | E2F7 | IQGAP3 | PTGS2 |
| BUB1B | ESCO2 | KIAA1244 | RELN |
| CASC5 | FAM83D | KIF11 | SHCBP1 |
| CCL26 | GABBR2 | KIF14 | SLC17A9 |
| CDC6 | GREM2 | KIF18B | SLC6A17 |
| CDCA5 | GTSE1 | KIF2C | THBD |
| CDCA8 | HAS1 | KIFC1 | TMSL3 |
| CDH15 | HJURP | KRT34 | TOP2A |

B. Differentiation of Human White Adipocytes into Brown Adipocytes.

1. Differentiation Protocol.

In order to assess the effect of miRNA analogs on human white adipocytes differentiation into brown adipocytes, human subcutaneous pre-adipocytes (SuperLot 0048 from 8 female donors, ZenBio, N.C.) were plated on Day 0 into 96-well plates and allowed to attach overnight in preadipocyte medium (DMEM/Ham's F-12 (1:1, v/v), HEPES buffer, Fetal bovine serum and Antibiotics). The next day (Day 1), the medium was removed and replaced with differentiation medium-2 (DMEM/Ham's F-12 (1:1, v/v), HEPES buffer, Fetal bovine serum, Biotin, Pantothenate, Human insulin, Dexamethasone, Isobutyl-methylxanthine, Proprietary PPARG agonist and Antibiotics. The cells were allowed to incubate for 7 days at 37° C., 5% $CO_2$. After 7 days (Day 7), a partial medium exchange was performed with AM-1 adipocyte maintenance medium (DMEM/Ham's F-12 (1:1, v/v), HEPES buffer, Fetal bovine serum, Biotin, Pantothenate, Human insulin, Dexamethasone and Antibiotics). The cells were allowed to incubate for an additional 7 days at 37° C., 5% $CO_2$. On Day 17, the cells were transfected with miRNA analogs (Dharmacon specific miRIDIAN Mimics and Hairpin Inhibitors) using the transfecting agent Dharmafect 3. All treatments were in triplicate. Post transfection, the negative control was maintenance medium only and the positive control was maintenance medium with 100 nM of the PPARG agonist rosiglitazone. After 2 days, medium was removed and replaced with fresh maintenance medium. The maintenance medium then changed every two to three days until the end of the treatment period (Day 30). At the end of the treatment (total of 30 days in culture) cells were processed for Phenotyping and Genotyping Screening.

2. Transfection of Adipocytes.

Transfection reagents are used to facilitate the penetration of miRNA analogs into target cells.
As an example, the extent of transfection efficiency we achieved in adipocytes with the transfecting agent Dharmafect 3 (Dharmacon, Colo.) is depicted herein. Transfection efficiency was assessed in two ways:

a. Measurement of Cellular Epifluorescence after Transfection with Fluorescent miRNA Analogs.

Figure 13:
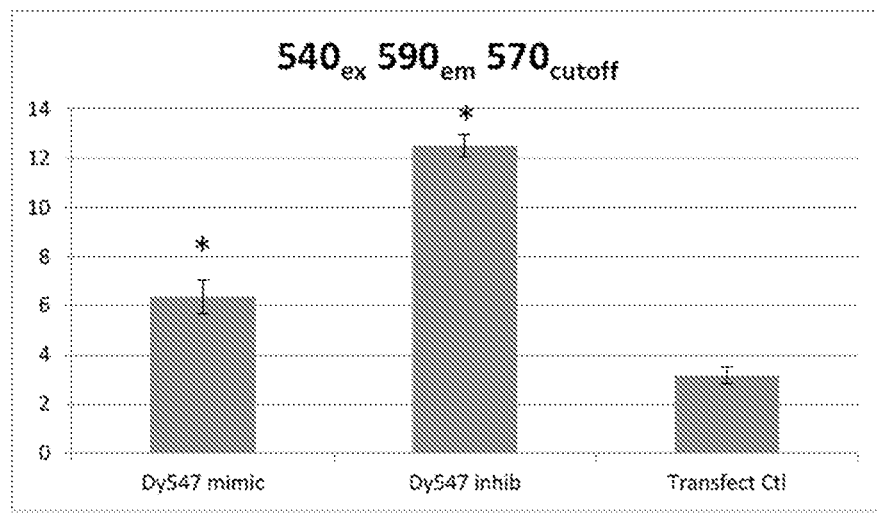
FIG. 13 is a bar graph showing relative fluorescence in unlabeled cells and cells transfected with a Dy547 labeled non-targeting miRIDIAN mimic or hairpin inhibitor.

Fluorescence was measured on Day 30 (540 excitation/590 emission) in cells transfected on Day 17 with the Dy547-labeled non-targeting miRIDIAN Mimic and Hairpin Inhibitor (100 nM). As shown in FIG. 13, there was a significantly greater fluorescence of cells transfected with the fluorescent miRNA analogs, even 12 days after transfection:

b. Reduction of Control Gene Expression.

Figure 14:
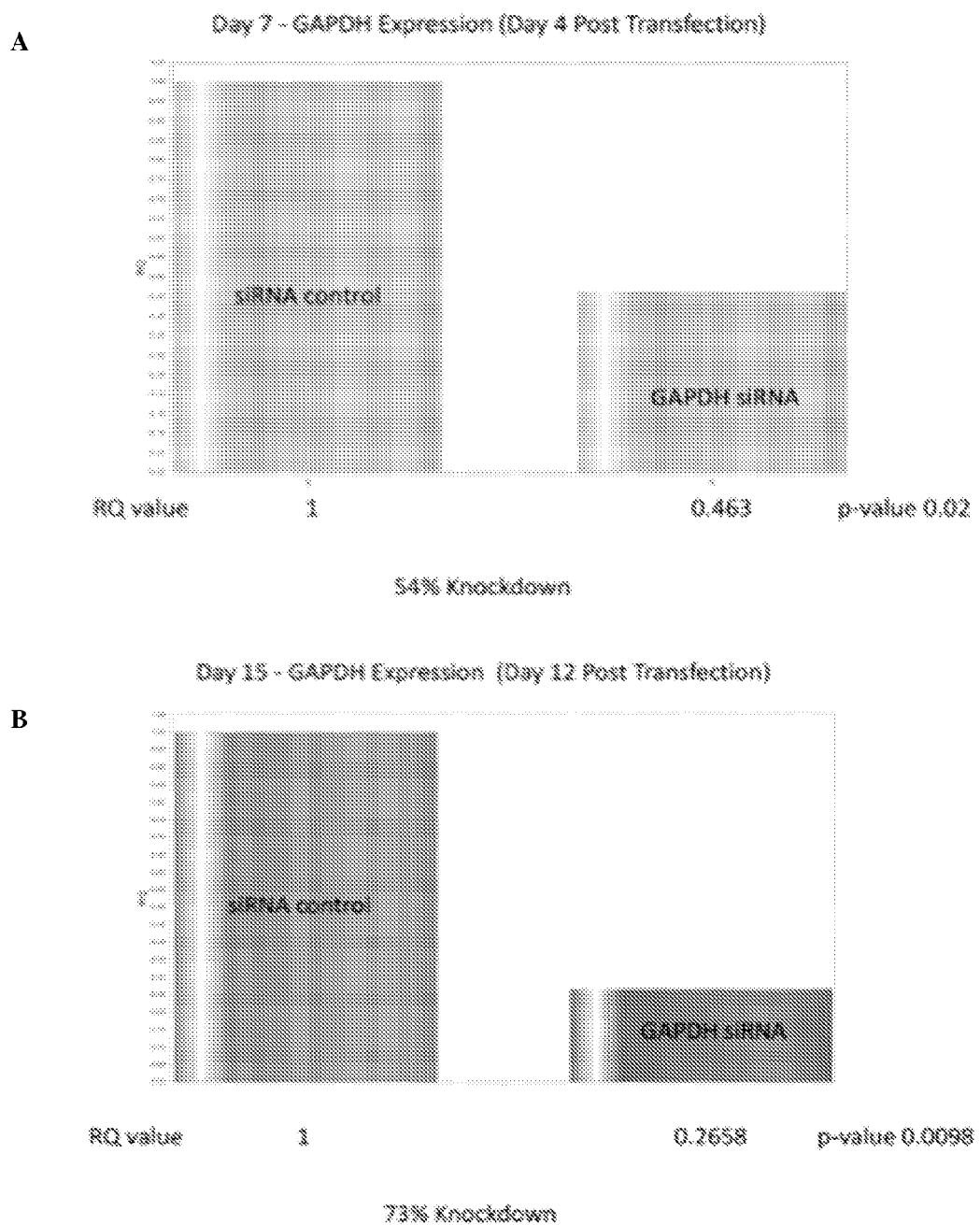
FIG. 14A is a bar graph showing the reduction of GAPDH expression in cells transfected with siRNA control and a GAPDH siRNA 4 days after transfection.
FIG. 14B is a bar graph showing the reduction of GAPDH expression in cells transfected with siRNA control and a GAPDH siRNA 12 days after transfection.

To confirm successful transfection of adipocytes, the reduction of expression of the control gene GAPDH ("housekeeping gene") was measured 4 days (Day 22) and 12 days (Day 30) after Dharmafect 3 (Dharmacon, Colo.) mediated transfection of adipocytes with a GAPDH-specific siRNA. Cell lysates were obtained and RT-PCR was conducted using pure RNA obtained by Cells-to-Ct reagents. Efficient transfection of mature adipocytes (a cell type known to be difficult to transfect) was achieved with the transfecting agent Dharmafect 3.54% and 73% knockdowns of the GAPDH mRNA expression were observed at Day 4 and Day 12 post transfection, both highly significant, as shown in FIG. 14.

c. Optimization of Human Mature Adipocyte Transfection.

As efficient transfection of mature adipocytes is known to be difficult to achieve, we tested eleven different transfecting agents and assessed the degree of reduction of mRNA expression of the control gene GAPDH. Human subcutaneous preadipocytes were plated in 6-wll plates and differentiated for two weeks following the protocol described above. Subsequently, a miRNA mimic (50 nM) targeting GAPDH was introduced into the differentiated adipocytes using transfecting agents following their manufactures' protocol. The transfected cells were incubated for 72 hours with reagents and miRNA mimic, then switched to maintenance medium. Fourteen days post-transfection, RNA was isolated using RNeasy Mini kit and RT-PCR reactions for the control gene GAPDH and the reference gene 18S were performed in triplicate using 100 ng of cDNA per well.

Figure 19:
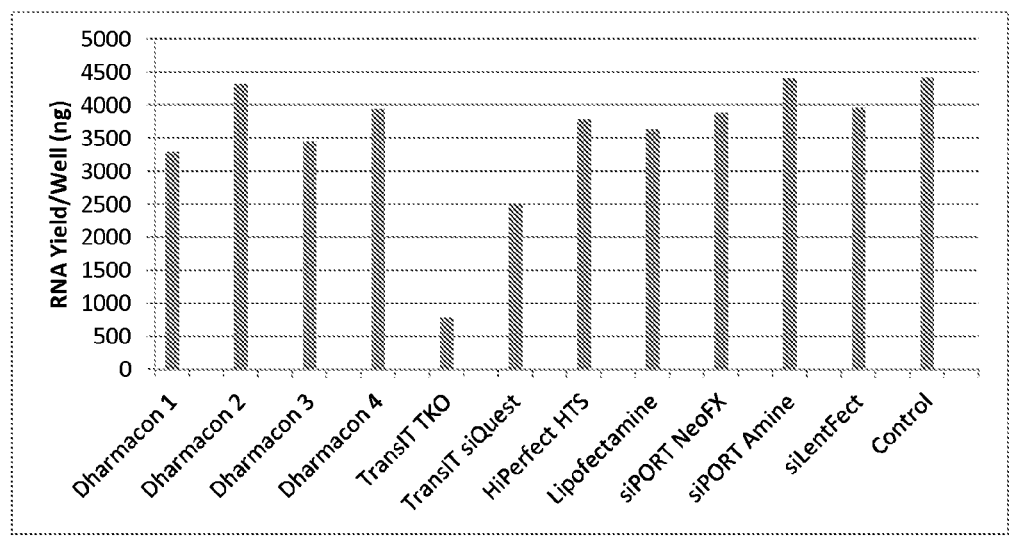
FIG. 19 is a bar graph showing the amounts of RNA extracted from mature adipocytes exposed to various transfecting agents.

The amounts of RNA extracted per well were very similar, except for the transfecting agents TransIT TKO and TransIT siQuest which may produce potential cellular toxicity in the conditions of the experiment (FIG. 19).

Figure 20:
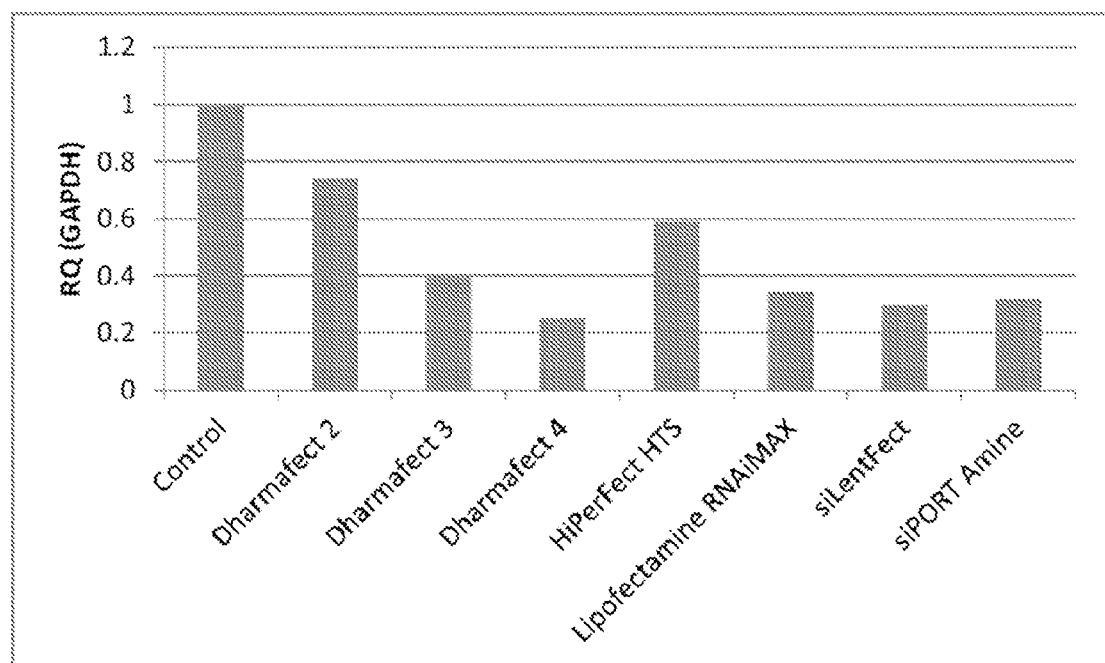
FIG. 20 is a bar graph showing reduction of GAPDH expression in mature adipocytes transfected with a GAPDH-specific miRNA mimic using various transfecting agents.

The cells transfected with Dharmacon 1 and siPORT NeoFX had significantly reduced levels of 18S expression and were excluded from the RT-PCR experiment analysis. Among the remaining 7 transfecting agents analyzed, the often-used transfecting agent Lipofectamine RNAiMAX led to a 66% reduction of GAPDH expression at day 14 post-transfection, Dharmafect 3 and Dharmafect 4 respectively produced 60% and 75% reduction of GAPDH expression (FIG. 20).

3. Phenotypic Changes During Maintenance of Human Adipocytes in Culture for Two More Weeks.

At the end of treatment (total of 30 days in culture) cells were stained with Oil Red O for assessment of lipid content. In the presence of medium without rosiglitazone from Day 16 to Day 30, the adipocytes appear loaded with large lipid droplets. In the presence of differentiation medium including 100 nM Rosiglitazone for 2 days followed by maintenance medium for 12 days (negative control), little change in appearance of the lipid-loaded mature adipocytes is noted. In the presence of 100 nM rosiglitazone throughout the experiment (positive control), the intensity of the red staining seems reduced. As an example, in the presence of 25 nM hsa-miR-30b mimic, the intensity of the red staining seems also reduced and the lipid droplets appear smaller.

Figure 15:
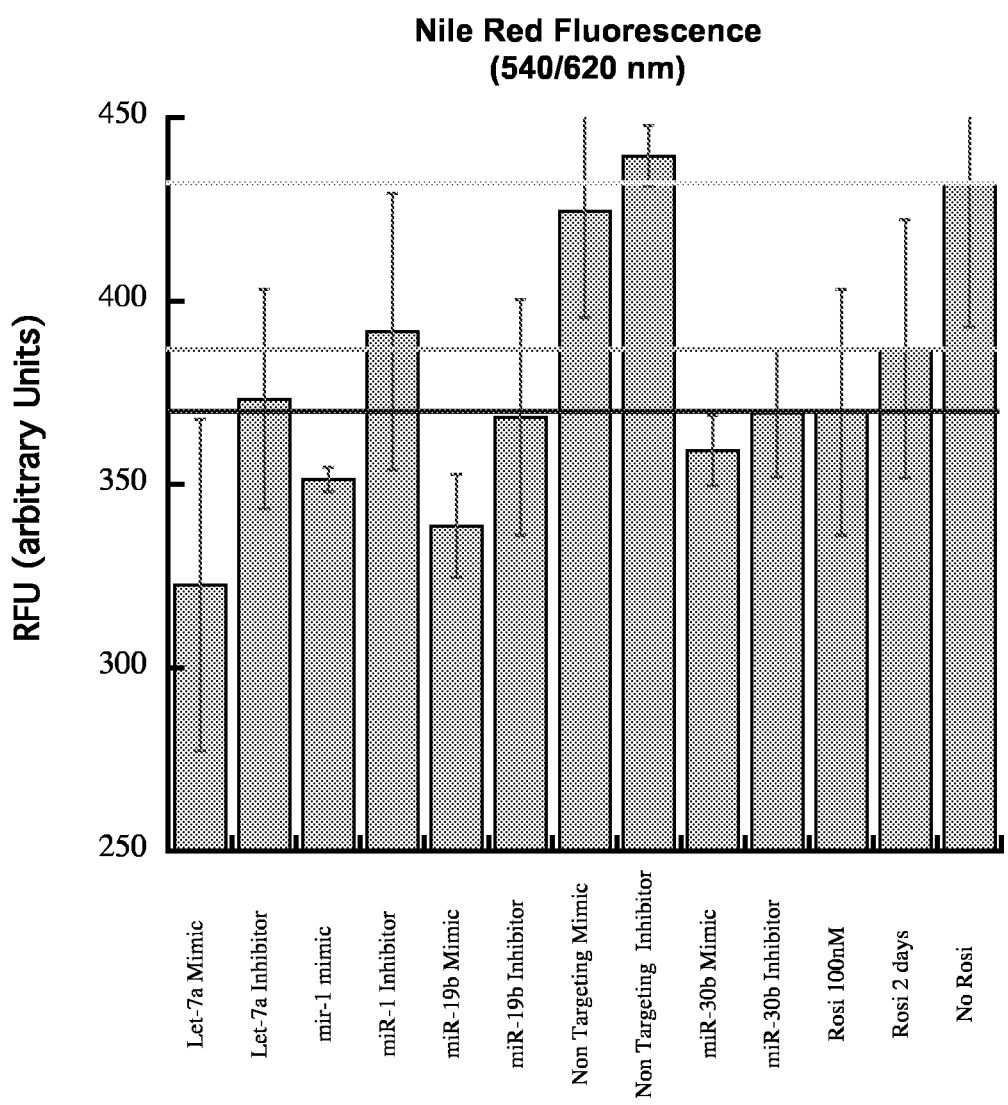
FIG. 15 is a bar graph showing the amount of lipids in mature adipocytes using Nile Red Dye exposed to various miRNAs.

The amount of lipids present in the mature adipocytes at Day 30 was measured with the fluorescent Nile Red Dye. As shown in FIG. 15, the highest fluorescence was noted in the adipocytes which were not exposed to rosiglitazone from Day 15 to day 30. A similar fluorescence level was noted in the cells which were transfected with the non targeting miRNA mimic and inhibitor. When the cells were exposed to rosiglitazone for two days, the fluorescence dropped significantly and was further reduced in the presence of rosiglitazone from Day 15 to Day 30. It appears that in the presence of the miRNA inhibitors tested, the level of fluorescence is within the range observed with rosiglitazone 2 day to throughout. In the presence of miRNA mimics, the level of fluorescence appears lower, an indication of lower lipid content.

Example 4

High-Throughput miRNA Target Screening by Luciferase Activity and qRT-PCR

High-throughput screening using luciferase reporter assay constructs are used to identify novel miRNA targets involved in thermogenesis.

Luciferase is commonly used as a reporter to assess the transcriptional activity in cells that are transfected with a genetic construct containing the luciferase gene under the control of a promoter of interest. SwitchGear Genomics has created a genome-wide library of over 18,000 human promoters and 12,000 human 3' UTR regions cloned into an optimized luciferase reporter vector system containing SwitchGear's RenSP reporter cassette (GoClone™) as a component of the LightSwitch™ Luciferase Assay System. This modified form of luciferase greatly facilitates detailed kinetic studies, especially those focusing on repression, which might otherwise be obscured by reporter protein accumulation.

The multiple microRNAs-one mRNA paradigm was tested with the SwitchGear Genomic GoClone system, using UCP1 as the single thermogenic target gene. In order to explore the possible interactions between various huma miRNAs and the 3'UTR region, the 5'UTR region and the promoter/enhancer region of the human UCP1 gene in Hela and HepG2 cells, three reporter constructs were made:

1. A human UCP1 3'UTR construct containing a reporter gene driven by a strong constitutive promoter (RPL10_prom) with a 2,218 bp 3'UTR fragment of the human UCP1 sequence cloned in the 3'UTR region of the reporter gene. The effects of a specific miRNA mimic, inhibitor, or non-targeting control on this reporter's activity are compared to those of an empty__3'UTR and an Actin Beta__3'UTR to identify effects that are specific to the putative UCP1 3'UTR construct.
2. A human UCP1 Promoter construct containing a reporter gene driven by a 4,147 bp 5'UTR fragment of the human UCP1 sequence that spans the Transcription Start Site and upstream region covering the methylation region and the enhancer region of the human UCP1 gene sequence. The effects of a specific miRNA mimic, inhibitor, or non-targeting control on this reporter's activity are compared to those of an Actin Beta Promoter to identify effects that are specific to the putative UCP1 5'UTR construct.
3. A human UCP1 Enhancer Region construct containing a reporter gene driven by a short minimal promoter from the HSV-TK locus with a 601 bp 5'UTR fragment of the human UCP1 sequence that spans the Enhancer Region of the human UCP1 gene sequence. The effects of a specific miRNA mimic, inhibitor, or non-targeting control on this reporter's activity are compared to those of an empty 5'Enhancer Region to identify effects that are specific to the putative UCP1 5'Enhancer construct.

In addition, miRNAxxx__3'UTR constructs were made. They contain the reporter gene driven by a strong promoter (RPL10_prom) with a perfect match to the target sequence of miRNAxxx cloned into the 3'UTR region of the reporter gene. The effect of a miRNA mimic, inhibitor, or non-targeting control on this reporter's activity can be compared to EMPTY__3'UTR and Actin B__3'UTR to determine whether a miRNA mimic's or inhibitor's activity can be reasonably detected in the experimental cell type. If the cell type has no endogenous expression of the miRNA in question, the addition of a mimic should knock down the activity of this reporter, and the addition of an inhibitor should have no significant effect. If the cell type has high endogenous expression of the miRNA in question, the addition of an inhibitor should increase the activity of this reporter, and the addition of a mimic should have no significant effect. The range of endogenous miRNA expression in Hela and HepG2 cell types is broad, so the synthetic target activity changes are likely to reflect this variability.

For each miRNA candidate (38 in total), the following conditions were tested:
- miRNA mimic (specific)*8 reporter constructs in Hela cells
- miRNA mimic (specific)*8 reporter constructs in HepG2 cells
- miRNA mimic non-targeting control*8 reporter constructs in Hela cells
- miRNA mimic non-targeting control*8 reporter constructs in HepG2 cells
- miRNA inhibitor (specific)*8 reporter constructs in Hela cells
- miRNA inhibitor (specific)*8 reporter constructs in HepG2 cells
- miRNA inhibitor non-targeting control*8 reporter constructs in Hela cells
- miRNA inhibitor non-targeting control*8 reporter constructs in HepG2 cells To the extensive list of miRNAs that may bind to the UCP1 sequence, 8 filters were applied (in addition to required binding to UCP1 3'UTR region) to reduce the number of miRNA candidates to be tested. These filters were length of binding sites, number of binding sites, binding to the 5'UTR region, chromosomal clustering with other miRNAs, intronic location, binding to the Enhancer Region, binding to the Methylation Region and proof of experimental evidence of a relation to UCP1. 38 miRNAs that met at least 3 of these criteria were tested (Table 17).

TABLE 17 miRNA with putative binding sites in the UCP1 gene sequence.

| miRNA | # of criteria | Binding length | # of sites | 3'UTR | 5'UTR | Clustering | Intronic | Enhancer | Methylation | Exp. Evidence |
|---|---|---|---|---|---|---|---|---|---|---|
| 1 hsa-miR-130b-5p | 7 | 11 | 3 | + | + | 22 | | + | + | + |
| 2 hsa-miR-328 | 6 | 10 | 4 | + | + | | | + | + | + |
| 3 hsa-miR-655 | 6 | 10 | 5 | + | + | 14 | | | + | + |
| 4 hsa-miR-19b-2-5p | 5 | 10 | 4 | + | + | X | | | | + |
| 5 hsa-miR-26a-2-3p | 5 | 10 | 7 | + | + | | | | + | + |
| 6 hsa-miR-367-3p | 5 | 10 to 18 | 3 | + | + | 4 | | + | | |
| 7 hsa-miR-371a-5p | 5 | 10 to 12 | 9 | + | + | 19 | | | | + |
| 8 hsa-miR-377-3p | 5 | 10 to 14 | 5 | + | + | 14 | | | | + |
| 9 hsa-miR-378a-3p | 5 | 7 to 13 | 19 | + | + | | + | | | + |
| 10 hsa-miR-382-3p/5p | 5 | 15 | 2 | + | + | 14 | | | | |
| 11 hsa-miR-421 | 5 | 10 | 5 | + | + | X | | | | + |
| 12 hsa-miR-515-3p | 5 | 9 | 3 | + | + | 19 | | + | | + |
| 13 hsa-miR-620 | 5 | 10 | 7 | + | + | | | + | | + |
| 14 hsa-miR-941/2 | 5 | 9 | 5 | + | + | 20 | | | + | |
| 15 hsa-miR-1179 | 4 | 11 | 3 | + | + | 15 | | | | |
| 16 hsa-miR-1302 | 4 | 10 | 5 | + | + | | | | + | |
| 17 hsa-miR-146a | 4 | 9 to 10 | 8 | + | + | | | | | + |
| 18 hsa-miR-181c | 4 | 9 | 5 | + | + | 19 | | | | + |
| 19 hsa-miR-203 | 4 | 9 | 1 | + | | 14 | | | + | + |
| 20 hsa-miR-331-5p | 4 | 8 to 15 | 6 | + | + | 12 | | | | |
| 21 hsa-miR-422a | 4 | 7 to 14 | 6 | + | + | | | | | + |
| 22 hsa-miR-452 | 4 | 8 | 7 | + | + | X | | | | + |
| 23 hsa-miR-491-5p | 4 | 10 | 3 | + | + | | | | | |
| 24 hsa-miR-501-3p | 4 | 10 | 2 | + | + | X | | | | + |
| 25 hsa-miR-543 | 4 | 10 to 14 | 4 | + | + | 14 | | | | |
| 26 hsa-miR-545 | 4 | 11 | 2 | + | + | X | | | | + |

TABLE 17-continued miRNA with putative binding sites in the UCP1 gene sequence.

| | miRNA | # of criteria | Binding length | # of sites | 3'UTR | 5'UTR | Clustering | Intronic | Enhancer | Methylation | Exp. Evidence |
|---|---|---|---|---|---|---|---|---|---|---|---|
| 27 | hsa-miR-549 | 4 | 13 to 14 | 3 | + | + | | | | | + |
| 28 | hsa-miR-643 | 4 | 10 to 14 | 9 | + | + | | | | | + |
| 29 | hsa-miR-651 | 4 | 10 | 6 | + | + | | | | | + |
| 30 | hsa-miR-654-3p | 4 | 8 to 10 | 11 | + | + | 14 | | | | |
| 31 | hsa-miR-21-5p | 3 | 10 to 14 | 2 | + | + | | | | | + |
| 32 | hsa-miR-211-5p | 3 | 11 | 1 | + | | | | | + | + |
| 33 | hsa-miR-22-3p | 3 | 9 | 5 | + | + | | | | | + |
| 34 | hsa-miR-30h-5p | 3 | 10 | 1 | + | | 8 | | | | + |
| 35 | hsa-miR-325 | 3 | 7 to 8 | 11 | + | + | | | | | + |
| 36 | hsa-miR-362-5p | 3 | 10 | 1 | + | | X | | | | + |
| 37 | hsa-miR-504 | 3 | 9 | 2 | + | + | | | | + | + |
| 38 | hsa-miR-552 | 3 | 9 | 3 | + | + | | | | | + |

In these Luciferase reporter gene assay experiments, a miRNA candidate was considered to interact with UCP1 if both the specific miRNA inhibitor increases the luciferase signal and the specific miRNA mimic decreases the luciferase signal with an Inhibitor/Mimic Ratio≥1.5 and or/a p value<0.05. These selection criteria identify 9 miRNAs (miR-19b-2-5p, miR-21-5p, miR-130b-5p, miR-211, miR-325, miR-382-3p/5p, miR-543, miR-515-3p, and miR-545) (Table 18). A few more barely missed these selection criteria; they are miR-331-5p, miR-552, miR-620, and miR-1179.

TABLE 18 miRNA identified as regulators of UCP1 by luciferase reporter assay.

| | Cell Line | miRNA | # of criteria | Binding length | # of sites | 3'UTR | 5'UTR | Clustering | Intronic | Enhancer | Methylation | Exp. Evidence |
|---|---|---|---|---|---|---|---|---|---|---|---|---|
| 1 | Hela | hsa-miR-130b-5p | 7 | 11 | 3 | + | + | 22 | | + | + | + |
| 2 | | hsa-miR-328 | 6 | 10 | 4 | + | + | | | + | + | + |
| 3 | | hsa-miR-655 | 6 | 10 | 5 | + | + | 14 | | + | | + |
| 4 | Hela + HepG2 | hsa-miR-19b-2-5p | 5 | 10 | 4 | + | + | X | | | | + |
| 5 | | hsa-miR-26a-2-3p | 5 | 10 | 7 | + | + | | | | + | + |
| 6 | | hsa-miR-367-3p | 5 | 10 to 18 | 3 | + | + | 4 | + | | | + |
| 7 | | hsa-miR-371a-5p | 5 | 10 to 12 | 9 | + | + | 19 | | | | + |
| 8 | | hsa-miR-377-3p | 5 | 10 to 14 | 5 | + | + | 14 | | | | + |
| 9 | | hsa-miR-378a-3p | 5 | 7 to 13 | 19 | + | + | | + | | | + |
| 10 | HepG2 | hsa-miR-382-3p/5p | 5 | 15 | 2 | + | + | 14 | | | | |
| 11 | | hsa-miR-421 | 5 | 10 | 5 | + | + | X | | | | + |
| 12 | Hela | hsa-miR-515-3p | 5 | 9 | 3 | + | + | 19 | | + | | + |
| 13 | | hsa-miR-620 | 5 | 10 | 7 | + | + | | | + | | + |
| 14 | | hsa-miR-941/2 | 5 | 9 | 5 | + | + | 20 | | | + | |
| 15 | | hsa-miR-1179 | 4 | 11 | 3 | + | + | 15 | | | | |
| 16 | | hsa-miR-1302 | 4 | 10 | 5 | + | + | | | | + | |
| 17 | | hsa-miR-I46a | 4 | 9 to 10 | 8 | + | + | | | | | + |
| 18 | | hsa-miR-181c | 4 | 9 | 5 | + | + | 19 | | | | + |
| 19 | | hsa-miR-203 | 4 | 9 | 1 | + | | 14 | | | + | + |
| 20 | | hsa-miR-331-5p | 4 | 8 to 15 | 6 | + | + | 12 | | | | |
| 21 | | hsa-miR-422a | 4 | 7 to 14 | 6 | + | + | | | | | + |
| 22 | | hsa-miR-452 | 4 | 8 | 7 | + | + | X | | | | + |
| 23 | | hsa-miR-491-5p | 4 | 10 | 3 | + | + | | | | | |
| 24 | | hsa-miR-501-3p | 4 | 10 | 2 | + | + | X | | | | + |
| 25 | Hela | hsa-miR-543 | 4 | 10 to 14 | 4 | + | + | 14 | | | | |
| 26 | | hsa-miR-545 | 4 | 11 | 2 | + | + | X | | | | + |
| 27 | | hsa-miR-549 | 4 | 13 to 14 | 3 | + | + | | | | | + |
| 28 | | hsa-miR-643 | 4 | 10 to 14 | 9 | + | + | | | | | + |
| 29 | | hsa-miR-651 | 4 | 10 | 6 | + | + | | | | | + |
| 30 | | hsa-miR-654-3p | 4 | 8 to 10 | 11 | + | + | 14 | | | | |
| 31 | Hela + HepG2 | hsa-miR-21-5p | 3 | 10 to 14 | 2 | + | + | | | | | + |
| 32 | Hela | hsa-miR-211-5p | 3 | 11 | 1 | + | | | | | + | + |
| 33 | | hsa-miR-22-3p | 3 | 9 | 5 | + | + | | | | | + |
| 34 | | hsa-miR-30b-5p | 3 | 10 | 1 | + | | 8 | | | | + |
| 35 | Hela + HepG2 | hsa-miR-325 | 3 | 7 to 8 | 11 | + | + | | | | | + |
| 36 | | hsa-miR-362-5p | 3 | 10 | 1 | + | | X | | | | + |
| 37 | | hsa-miR-504 | 3 | 9 | 2 | + | + | | | | + | + |
| 38 | | hsa-miR-552 | 3 | 9 | 3 | + | + | | | | | + |

Out of these 9 selected miRNAs, 3 appear to bind to the 3 regions of UCP1 which were studied (miR-21-5p, miR-211, and miR-515-3p); 3 appear to bind to 2 regions of UCP1 (miR-19b-2-5p, miR-130b-5p, and miR-325), and 3 bind to a single region of UCP1 (miR-331-5p, miR-543, and miR-545). All but miR-331-5p appear to bind to the 3'UTR region of UCP1 (Table 19).

TABLE 19 miRNA identified as regulators of UCP1 by luciferase reporter assay.

| | miRNA | UCP1 3' UTR | UCP1 Enhancer | UCP1 Promoter |
|---|---|---|---|---|
| 1 | mir-21-5p | X | X | X |
| 2 | miR-211 | X | X | X |
| 3 | mir-515-3p | X | X | X |
| 4 | mir-19b-2-5p | X | | X |
| 5 | mir-130b-5p | X | X | |
| 6 | mir-325 | X | X | |
| 7 | miR-331-5P | | X | |
| 8 | mir-543 | X | | |
| 9 | mir-545 | X | | |

Further screening is performed by transfection of the promoter/3'UTR library into human adipocytes or adipose-derived mesenchymal stem cells in cell culture, followed by addition of miRNA agents (e.g., agomirs or antagomirs) to the cell culture. Measurement of luciferase activity and identification of mRNAs is performed 24 hours after transfection and addition of miRNA agents.

In order to confirm the results of the transfection experiments set forth above over a longer time frame, lentiviral transduction experiments are performed using lentiviral vectors containing the miRNA agents of interest (from System Biosciences (SBI) collection of miRNA precursors expressed in the pMIRNA1 SBI vectors allowing the expression of the copGFP fluorescent marker). Specifically, cells containing the promoter/3'UTR library are transduced with lentiviral particles at an MOI of 1:10 and GFP-positive cells are sorted by FACS, according to the supplier's instructions. The level of expression of the mature miRNAs and their targeted mRNAs is assessed at several time points (0, 3, and 6 hr.; 1, 4, and 7 days) by Taqman Quantitative Real-time PCR in control cells (HEK293 cells), Human Adipose-Derived Mesenchymal Stem Cells, Human Subcutaneous Preadipocytes, and Human Proliferating Subcutaneous Adipocytes. Pooling of RNAs from 5 different time points after transduction is optionally employed to reduce the complexity of the qRT-PCR based screening approach while preserving the detection sensitivity.

Example 5

Proteomic Profiling

Proteomic Profiling is also used to identify novel miRNA targets involved in thermogenesis.

Shotgun proteomics is a method of identifying proteins in complex mixtures using high performance liquid chromatography (HPLC) combined with mass spectrometry (MS). Transfected and transduced cells with miRNA agents and promoter/3'UTR library (as described in Example 4) are harvested and lysed to produce crude soluble (cytosolic) and insoluble (nuclear) fractions. Peptides are from these fractions are then separated by HPLC and analyzed using nano-electrospray-ionization tandem MS using the isotopic labeling technique SILAC to quantify protein abundance. Spectra are searched against the Ensembl release 54 human protein-coding sequence database using Sequest (Bioworks version 3.3.1, Thermo Scientific).

To avoid missing low abundance proteins, a targeted proteomics approach is also employed to accurately quantify a set of proteins that are known regulators of adipogenesis, adipocyte differentiation and BAT function. Some examples include UCP1, KDM3A, PRDM16, PPARA, PPARGC1A, CEBPB, CIDEA, BMP7, COX7A1, SIRT1, SIRT3, DIO2, FABP4, ADIPOQ. These proteins are analyzed via ELISA based or Luminex based immunoassays using commercially available antibodies.

Optionally, the protein fractions are analyzed using Multiple Reaction Monitoring-Mass Spectrometry on a proteomics platform, whereby only one protein (e.g. UCP1) of the thermogenic pathway is accurately quantified using LC-MS-MS.

Example 6

Reconciliation of the Phenotypic, Luciferase/qRT-PCR, and Proteomic Datasets

The results of the in vitro experiments set forth in Examples 3-5, herein, are reconciled. Specifically, to narrow further the initial set of microRNAs, mRNAs and target proteins and pathways to a relevant yet manageable number of targets, the experimental data is integrated with Network Searches and Analyses Packages (DAVID, Ingenuity Systems IPA and ARIADNE Pathway Studio.

Global analysis of the results of the in vitro experiments set forth in Examples 3-5, herein, is performed the Business Intelligence tool TIBCO Spotfire. This allows for a visualization of the relationships between the miRNA agents and target gene.

Example 7

Animal Models of Obesity

Several animal models of obesity have been developed and validated (Kanasaki K et al., J Biomed Biotechnol., 2011: 197636 (2011); Speakman J et al., Obesity reviews: an official journal of the International Association for the Study of Obesity, 8 Suppl 1:55-61 (2007)). The most commonly used are the Leptin Signaling Defects Lep$^{ob/ob}$ and Lepr$^{db/db}$ Mouse Models as well as the High-Fat Diet model in C57BL/6J mice (Wang C Y et al., Methods in molecular biology, 821:421-433 (2012). This diet-induced obesity (DIO) model closely mimics the increased availability of the high-fat/high-density foods in modern society.

A DIO mouse model is used for in vivo validation of the effectiveness of the miRNA analogs described herein for the increase in thermogenesis and/or the treatment of obesity and other metabolic disorders (Yin H et al., Cell Metab., 17(2): 210-224 (2013)).

DIO mice are administered one or more of an hsa-let-7a agomir, hsa-let-7a antagomir, hsa-miR-1 agomir, hsa-miR-1 antagomir, hsa-miR-19b agomir, hsa-miR-19b antagomir, hsa-miR-30b agomir, and hsa-miR-30b antagomir. Rosiglitazone is used as a positive control. Food intake, blood metabolic parameters, body composition (body weight, body fat, bone mineral and lean mass, body fat distribution, body temperature, O2 consumption and CO2 production, exercise induced thermogenesis, cold induced thermogenesis and resting thermogenesis are measured in the mice prior to treatment and after treatment. A reduction in body mass or body fat or an increase in body temperature or any kind of thermogenesis indicate the in vivo effectiveness of the administered composition.

Example 8

Nucleic Acid Sequences of Human UCP1 and UCP2 Genes and Transcripts

The nucleic acid sequence of the 1,462 base pair (bp) transcript ENST00000262999 of the human UCP1 gene is as follows (Exons in capital letters) [SEQ ID NO: FROM 351-363]

| No | Exon/ Intron | Start | End | Start Phase | End Phase | Length | Sequence | SEQ ID NO: |
|---|---|---|---|---|---|---|---|---|
| | 5' upstream sequence | | | | | | ...gtcggttcaaaaaacagaaatcgg gtttgctgcccggcggacaggcgtga | 351 |
| 1 | ENSE00001 081761 | 141,489,959 | 141,489,758 | — | 0 | 202 | AGAGCAAGGG AAAGGAACTT CCTCCACCTT CGGGGCTGGA GCCCTTTTCC TCTGCATCTC CAGTCTCTGA GTGAAGATGG GGGGCCTGAC AGCCTCGGAC GTACACCCGA CCCTGGGGGT CCAGCTCTTC TCAGCTGGAA TAGCGGCGTG CTTGGCGGAC GTGATCACCT TCCCGCTGGA CACGGCCAAA GTCCGGCTCC AG | 352 |
| | Intron 1-2 | 141,489,757 | 141,489,132 | | | 626 | gtagctaggc agagggtaa dacaa...tgttc tgcacctttc ttatttccag | 353 |
| 2 | ENSE00001 009006 | 141,489,131 | 141,488,933 | 0 | 1 | 199 | GTCCAAGGTG AATGCCCGAC GTCCAGTGTT ATTAGGTATA AAGGTGTCCT GGGAACAATC ACCGCTGTGG TAAAAACAGA AGGGCGGATG AAACTCTACA GCGGGCTGCC TGCGGGGCTT CAGCGGCAAA TCAGCTCCGC CTCTCTCAGG ATCGGCCTCT ACGACACGGT CCAGGAGTTC CTCACCGCAG GGAAAGAAA | 354 |
| | Intron 2-3 | 141,488,932 | 141,484,673 | | | 4,260 | gtaagccgtg agcgttcctg ggagg...aataa ttttttttct ctctggatag | 355 |
| 3 | ENSE00001 081759 | 141,484,672 | 141,484,472 | 1 | 1 | 201 | CAGCACCTAG TTTAGGAAGC AAGATTTTAG CTGGTCTAAC GACTGGAGGA GTGGCAGTAT TCATTGGGCA ACCCACAGAG GTCGTGAAAG TCAGACTTCA AGCACAGCCA TCTCCACGGA ATCAAACCTC GCTACACGGG GACTTATAAT GCGTACAGAA TAATAGCAAC AACCGAAGGC TTGACGGGTC TTTGGAAAG | 356 |
| | Intron 3-4 | 141,484,471 | 141,484,366 | | | 106 | gtaactaact tcaaaatggg tttta...acatt tctttttttt ttttccccag | 357 |
| 4 | ENSE00001 081762 | 141,484,365 | 141,484,264 | 1 | 1 | 102 | GGACTACTCC CAATCTGATG AGAAGTGTCA TCATCAATTG TACAGAGCTA GTAACATATG ATCTAATGAA GGAGGCCTTT GTGAAAAACA ACATATTAGC AG | 358 |
| | Intron 4-5 | 141,484,263 | 141,483,528 | | | 736 | gtaacttccc atttcatata acaaa...gac- c tgtttcatcg g atccatttta | 359 |
| 5 | ENSE00001 081763 | 141,483,527 | 141,483,347 | 1 | 2 | 181 | ATGACGTCCC CTGCCACTTG GTGTCGGCTC TTATCGCTGG ATTTTGCGCA ACAGCTATGT CCTCCCCGGT GGATGTAGTA AAAACCAGAT TTATTAATTC TCCACCAGGA CAGTACAAAA GTGTGCCCAA CTGTGCAATG AAAGTGTTCA CTAACGAAGG ACCAACGGCT TTCTTCAAGG G | 360 |
| | Intron 5-6 | 141,483,346 | 141,481,165 | | | 2,182 | gtaagatatg atcttgtgta tctgt...cgaac gatgacatgc acttttctag | 361 |
| 6 | ENSE00001 081760 | 141,481,164 | 141,480,586 | 2 | — | 577 | GTTGGTACCT TCCTTCTTGC GACTTGGATC CTGGAACGTC ATTATGTTTG TGTGCTTTGA CAACTGAAA CGAGAACTGT CAAAGTCAAG GCAGACTATG GACTGTGCCA CATAATCAGC TTCAAGAAAA TGATGTAACA TACCAGTGGG AATCTTGCTG ACTGGATCAT AAAAACAAAC AAAACTTATT CACTTATTTT AACCTAAAAA GATAAAGGAA TTTTGGCAGA GAATTTTGGA CTTTTTTATA TAAAAAGAG GAAAATTAAT GCCTATTTCA TATAACTTTT TTTTTTTCTC AGTGTCTTAA GAAGGGGAAA GCAAAACATT CAGCATATAC CCTGGCAAAT GTAATGCAGA TAAGCTACTG CATTTGACCA TTTCTGGAGT GCAATTGTGT GAATGAATGT GAAGAACTTT AACATGTTTT AATTACAATT CCAACTGGTG GAAAAGAAAC TGAGTGAAAT GCAGTTTATA TTTATAAATA CTTAAAAATG AAGTTATTAA AAATATTAGT TTTTATTAAC CACAGTTGTC | 362 |

| No | Exon/ Intron | Start | End | Start Phase | End Phase | Length | Sequence | SEQ ID NO: |
|---|---|---|---|---|---|---|---|---|
| | 3' down- stream sequence | | | | | | AGTTAATATA TTCAATAAAA GTATTGCTAA TACCTTTT aaagtttgtcttttgagatctatacct gggtgtaagagtcaagttcacta... | 363 |

The nucleic acid sequence of the 9,371 base pair (bp) of the human UCP1 gene (ENSG00000109424) is as follows (Exons are highlighted) [SEQ ID NO: 364]:

```
>chromosome: GRCh37:4:141479988:141490559:-1
AGAGAAGGCC GCAAGGTGCC TGCAAGATGT CTGGGGAGTT GGAGGAATGG AAGAGTGCCC    60
CGCTCTTCCT TCTGGGAGAG CTCCAGCTAG GCAGAACCTT TCACCAAGGC TCTGATATCG   120
TGCTGGTTTC CGAAAGCCCC AGCCGAAGGT GTGCAGCCAA AGGGTGACAG AAGGTGAGGC   180
ACGTGCGGGG GCGCGGGTGC TGACCGCCGC GGTGCGCCCT CCCTCCGACG TGCGGTGTGC   240
GGGGCGCAGA CAACCAGCGG CCGGCCCAGG GCTTTCGGGG AGCGAAGCAG GGCTCCCGAG   300
GCACCGAGCG AGAATGGGAA TGGGAGGGAC CCGGTGCTCC CGGACACGCC CCCGGCAGGT   360
CCCACGCCCG GGTCTTCTGA GACCTCGCGC GGCCCAGCCC GGGAGCGGCC CAGCTATATA   420
AGTCCCAGCG GAAGACCGGA ACGCAGAGGG TCCTGCTGGC GCGAGGGTGG GTAGGAGGGG   480
ACGCGGGGAC TCGGCCCCCA ACACCGCGCT CCGTCTGCAG CCGCCGCCTC TGCACCGCCG   540
CTGCCCGGCG GTCGGTTCAA AAAACAGAAA TCGGGTTTGC TGCCCGGCGG ACAGGCGTGA   600
AGAGCAAGGG AAAGGAACTT CCTCCACCTT CGGGGCTGGA GCCCTTTTCC TCTGCATCTC   660
CAGTCTCTGA GTGAAGATGG GGGGCCTGAC AGCCTCGGAC GTACACCCGA CCCTGGGGGT   720
CCAGCTCTTC TCAGCTGGAA TAGCGGCGTG CTTGGCGGAC GTGATCACCT TCCCGCTGGA   780
CACGGCCAAA GTCCGGCTCC AGGTAGCTAG GCAGAGGGGT AAGACAAGGG GTCTCAGGAC   840
AGAGGGGACG CTGTTGCGTG CATTCCATTT ATTCTCTGCT TTGGTGTAAC CACTGTTTCT   900
AGGTAGGGTA GGTGACCTTC CAAAGCAGTC TGGCCTTGTC CCAGGGCTGG TGCTTTAGGA   960
TGGGAAACTG GAACTTTTTC TGGGATTAGC TGAAGAACCA CCAGGGCCAC AGAGAATGGG  1020
TTGACCATGA CTACTACCAA ATTCTCCCAA AATTTAGGGT GCACTTAGTA TTTTAAGAGC  1080
TGAGAATATT GGCCTCTCCT GAGTTTACTA GTCAGGTGCT TTTTCCTTTC TTTGATTCTT  1140
CGGGGGTTCT GTCCTATCCT ACTGCCCTAG GGGTTCTGGA GAGTTCCTGG GGAGGGGAT   1200
ATTCAAAATG TGCATTGTAG CCAGCCTCCC TCCATCTGCG CGTGAGCGAA CACACACACA  1260
CACACACACA CACACACACA CACACACACA CACACACGGT AGAGGGAGGT GGATGGAAGA  1320
GGAATGTTGC TGAGAAAAGA AACGGAAAAT AGGAACACAG GGGGAAATCT TGGCTTAAGA  1380
GTGAACTCAA TTTCGCTCCC TTCTGTTCTG CACCTTTCTT ATTTCCAGGT CCAAGGTGAA  1440
TGCCCGACGT CCAGTGTTAT TAGGTATAAA GGTGTCCTGG GAACAATCAC CGCTGTGGTA  1500
AAAACAGAAG GGCGGATGAA ACTCTACAGC GGGCTGCCTG CGGGGCTTCA GCGGCAAATC  1560
AGCTCCGCCT CTCTCAGGAT CGGCCTCTAC GACACGGTCC AGGAGTTCCT CACCGCAGGG  1620
AAAGAAAGTA AGCCGTGAGC GTTCCTGGGA GGGGCAGAAA AGCCTTGGGC TCCGCTCTGT  1680
TCCAAAAAGT GTAACACACA GAGGAGTGGT TTTCATAACA AATTGGCGAG AAAACATTCA  1740
TATTTGAACT CTCCCTTCCC CAAACATTAG CTCATTGTTC ATAGAAAAAA GTATGCAAAA  1800
```

```
TCGATTTTTT AGATGCAGAT ATATACTTGT AAAGGTCACC CAGTCATGGA AGTTTTGTGC    1860

CCAGTTTGGA TCTCCATCTG GAGAATATGG GTGGGCTACA GAAAAATGTT AACTTAAAG    1920

TTCTCCAAAG AGGGAAGTAT ATCAGAAACA TCTATGGAGC TTGTCAGAAA TCCAAACGAG    1980

GACTACCATG GTCCTCTGAG TCTGAATCCT CAGGCTAGAG ACCAGAGTGT CTTTCCACAA    2040

GCTTCCCTCA TCATTTGTGT ATGCAACAAA GTTCAAAGCC TTCTGTTTGA AGCAAAGAAA    2100

GCCAGACTTT GTGAAGAGAG TTGAAAGGAC AGGAAAAGAC ATATTTCCTC TTAAGAGGTT    2160

CCTCATCAGG TCCAGGAAAG ACCAGAGCAG AAAAAGTGGA CGAATGCTGC AGGGAGTTTG    2220

TTTAGGGGAA AAAGAAAAGG AAACATATTT CCTGAGTGCC AGTGCACTCT AAGAATTCCT    2280

GTCACTTTAG GTAGCATTTA TTTGAGGGCT TAACTATGAA CCAGACATTG TTCTAAGTGC    2340

TTCAGATACA TTATAACTGG AAGGGTATTA GTACCATTAT CCCTTGGCAG ATGGGAAAAC    2400

TGAACACAGA GCAGATTCAT CACTTGCCCA AGGTCACACA GCTGGGAGGG GGCAGAGCCA    2460

GGGTTCAAAC CCAGGCAGTC TGGCCTCGGA CTCCAGGCTC CTAACCCTGT TCTCTACTGC    2520

CTTCTGCACT TCTCATATGA TTCTGCCCAT CATTCAAACC GCACAACACT GCTGTGAGTA    2580

AAAAGTGTTA GCCGAATATC AGGGTAGTTA AGTAACATGC ACAAAATCAC ACAGCTAATC    2640

AACATCAGAG GCACTTTCAT GTGGAGTAGA CAAGCCAGAG AGAAGATGTG CTGATGGCAC    2700

AATGAATACA TTAAGTGAAA TCCACCTTGT AGATTTCATC ATTTCTGCTG TGAGTAACCT    2760

TCAATACTAT AATTTTATGG GATAATTTAT AAATGTTGTC TATACAAATA TATAAGTTAT    2820

ACTTATCCAC ACAAGTACTT TCAAAGTGAA GATAAAGTCT GGATGTTACT AGATCAAAAC    2880

TGCATTTTTT TATTTATAGA TGTAGCAAGA GAGGAAACAC AAAGGAGGTA AAGCTGCCCG    2940

TTCAGGTGGT TTTCTTCACA GATTGACTGT TCTACCAATT GTTGTGGACT TTGGGCACCA    3000

AATTAATAGG ATATATGTTG GCAGTGTTCT ATGTTATATA GATTCAGTTT ATTTAGTAGG    3060

CTTTATTGAA CTGCCATGTG CCAGTAACTA TGTTAGATGT TTAGATGGCA GATGTGTCTC    3120

TAGACAGAGC TTACAGTTGA GAGTATGGGT TGTGTGGGGA GAAGTGAATA GATGACTATA    3180

TTCCATGATA CATGCTGTAT TACAATACAG TCCTACTTCA CTTAACGATG GGGATACATT    3240

CTCAGAAATG AGTTAGGAGG CAAATTGGTT GTTGAATGAA CATCACAGAG AGCACTTACA    3300

CAAACCTAGA TGGCATAGCC ACACCTAGGC TATATGGTAT AATCTATTGC TCCTAGGCTA    3360

CAAACCTGTG CAGCATGTTG GTATTGAATA CTACAGGCAA TTGTTACATA AAGTTAAGTG    3420

TTTGTGTACC TAAAAATAGA AAAGGTAATG CATTACACTA CAGTCTTATG GGGCTGGGAT    3480

GTCACTAGGT GATAGGAATT TTTCAGCTCT GTTCTAATCT TACGGACCA CCATCATGTA    3540

TGCAGCACAT GACTAACTGT AATTACAAGA TGGTGGCTAT ATTAAACAGA ACTACTTAAG    3600

CTAGCCATGG AGGTATGGTC CGTGAGATTT TCCTGAAGAA TTAACGTCTG GATCAATTCT    3660

GGAAGGGCCA GCAGGAGTAC TCCAGGCAAA GGGGTGAGAA AGGAGCTTCC AAGTAGAGTG    3720

AAGGTCATGT GCAAAGACTC AGTGAGGAGT CGAGTGAACA TAGCACAGGG AGGACATGTT    3780

GGTGAGGAAG GAGGGGTGAA GCCACAGAGA CAGGAGGGAG CCAGATGACA GAAGGCCTTG    3840

CAGGCGGTGC TAAGGAGTTT GGATTTTATC CTTACAGTGG TGGGAAGTCA TTGTAAAAAT    3900

ATTAAGCAAG GGAGTGGCAT AAACAATTTA CATTTTCAAA AGATCACTTT GGCAGCAGAT    3960

AGAGTATATA TGTAAAAGGA GTAAGAAAGA GGTAAGTTAG AAAGCAAGAA ATGATCAGGG    4020

TATGCCCTAA AACACTGGCA ATAGGGAAAA AGAGATGTCA ATCAGAAAGA TTGAGAAAGT    4080

ATAATTGAAT TGACTTGGTG AACAAATAGA AGTAAGGCAT AAGGGACAGG TAGAAATATG    4140

AGATGACTTC CAAGTTTCTG TTTAAAGATA CCCTTTATTG AGAGAGGATG TATAGAAGCT    4200
```

```
GTCTTAGGGG GAAGACAAGA AATTTGGTTT AGGCCATGTC AACAGGTAAT GGCCAGTAGG    4260

CACATGATTC AGTTTATTTA GTGGGCTCCT TTTAGGAGAA AATCTGAGCC AGATTCCAGG    4320

AAGTCACAGC AGGGACTACC AATAGGGTCA AACAGCAGAG AGTGTGGAAA GGACTGAAAA    4380

GTGATCATTG TACATAACAA ATAGAAGCTC ACTGATTTTC TAGCAAAAAC ATCTTCAGCA    4440

GAGTAGCGTG GTATAAGCTA TATTGTAGGG GACTGAGGAA GAAATGGGCT CTGAGAAGTA    4500

AAGACAAACA ATATGTTTTG TAAATAAATT TCTTTTAGTT CTTAAAAAAA AAGCCTCTTT    4560

TCCAGCTTGA TTGGGAAGTG AAGAGAGGGA TTTGAAAGTT GGAGATTGGA GGATAGGATG    4620

AGTACATCAA GATACACTAC GTTGTAGTGC AGTGCATTAC AAATGTGAGC TAAAAGTGAA    4680

GGCATTTGTA ATCATATGAT ATTGCTAATT AAAAGACAGC TGTCAGTCAT ATGCCCAGCT    4740

CCTGGTAAAG CATGATGAGA AGAGTACAAT CATGGTAGTG ATTTAAAAAT TGCTGCCAGT    4800

TTTGTGGATT TTCTTTATGC TAGACAGTGT AAGCTCTTTA TCAATATTAT TTAACTCACA    4860

CAACTCTAAG AGGTAGATAT TATTATCCCT TTTTGACAAA TTAGGAAACA GAATTATAAT    4920

GACTGAGAAA GTCTCTGCTG AGTAAATGTT ACTGAACCTT AATTTTATGT TTACTTAATG    4980

ATAGAAATGA ATATTGGGCT TCAAGACTAT TTGTACTTAA TGAAATCTGT CTTGAGCAAC    5040

ATAAGCTATT TTTTTCAAAA TTTTAAGACA AAAATCACTT TCTTCTCTCC TGTCTTCTTA    5100

TTTTTGTTCC CTTCACATGT TGTAGCCTAA CACTACTTGA TGGCCCATTT TGGTGCAGTT    5160

TGTCCACTGG GCTTCATCTA AGGCCACCAA GTCCCATAAT TAACATGATC ATTCGTGGGA    5220

GAAAGATCAA GCCTCATTGG TGATGGGTGC CTCCTCACAG TCGGATAATA CTGAAAAGAG    5280

AGCTAAATGT GGGAAAGAAC CAAGTTGAAC ACAGGAAAGA ATCAGGCCAC TGTGAAAATA    5340

AGCATTGTGT TTTCTTGTTC CTTGAAAGTC TTCATTTTTA AAAAATTTCA GACACCTGAA    5400

GTTTTCTAGC CTTACTCTGA GTTGACGCAC ATTTAGTACA TGATCAACAC ATAAACAAGC    5460

ATTAGAGAAA TAGAAAAGCT GTAAGAATAC AAAAATATGG GCCAGGTGGG TGGCTCATAC    5520

CTGTAATCCT AGCACTTTGG GAGGCCGAGG CAGACGGATC ACCTGAGGTC AGGAGTTCAA    5580

GACTAGCCTG GCCAATATAG TGAAACCCTG TCTCTACTAA AAATACAAAA CTTAGCAGGC    5640

TGTGGTGGCA CGTGCCTATA ATCCCAGCTA CTTGGGAGGC TGAGGCAGGA GAATCTCTTG    5700

AACCCGGGAG GCGGAGATTG CAGTGAGCCA AGATCACACC ACTGCACTCT AGCCTAGATA    5760

ACAGAGCAAG ACTCCATCTC AAATACAAAA AAAATACAAA AATATGAACC ACTGAAAATT    5820

AAAAAGACAT GCATGCATTC TAGGTCTTTA ATTTTTTTTC TTAATAATTT TTTTTCTCTC    5880

TGGATAGCAG CACCTAGTTT AGGAAGCAAG ATTTTAGCTG GTCTAACGAC TGGAGGAGTG    5940

GCAGTATTCA TTGGGCAACC CACAGAGGTC GTGAAAGTCA GACTTCAAGC ACAGAGCCAT    6000

CTCCACGGAA TCAAACCTCG CTACACGGGG ACTTATAATG CGTACAGAAT AATAGCAACA    6060

ACCGAAGGCT TGACGGGTCT TTGGAAAGGT AACTAACTTC AAAATGGGTT TTATAACCAC    6120

CAAAGCACAT ACATACAACT AGCAACTTAT TGTAAAGTAG AGTTAATAAA CATTTTCTTT    6180

TTTTTTTTCC CCAGGGACTA CTCCCAATCT GATGAGAAGT GTCATCATCA ATTGTACAGA    6240

GCTAGTAACA TATGATCTAA TGAAGGAGGC CTTTGTGAAA AACAACATAT TAGCAGGTAA    6330

CTTCCCATTT CATATAACAA ACAGGTCTGC ACCTTTAGAA GTTCATCTTG GAGCTTCTGC    6360

AGCCACCTTA TACTCAATCT CTTAACTCCA ATAGTTTTCT CTTTTTAAAA ATTAAGTAAT    6420

TTTGAACCAT ATATAACTTT GTGAGAAGCA GGAAAAGACC AAAATATTAA GTTTAAGAAG    6480

TTTTGCCACA ACAAAAATAT TTTGCAACAA AAATAACAGG CAATTTCATG TCAGCATTAT    6540

TCTCATTTAA TACTAATATA TGGGACTTTT GTTAGAATCT TATTCTTTAT ACAGCAGAAT    6600
```

```
TCAGGAGGTA AGTCCATCCT GCATACTATA TCCAAAAGAT CTAGTTATAA AAGGAGCTTA    6660

TCAGTGGTCT CATCCAAAAA GTAATACCAT AAGATAGGTT CTTAAAAATA ATATTCTAAC    6720

AACTTCTAGA GACATTGAAA TTTCCCTTAT TTCAATAAAA AAGTATTAGA TGCTCATATA    6780

TTAGGCATTA TTACAGGCCT TAAAGGCACA GAGGAAACTA ACAGTTTACT TTCCTAAAGT    6840

GTTAACAATC TATTAAGCCA TTTACTCTTT ACCTTCTTTT TCTAGTGCAA TACCTTTCTT    6900

ATTTTATTTT ATTTATTTAT AAGACATCTT CATTGACCTA CTGTTATCAA TAGGTTTATA    6960

AAGATATGAC AGATAACTAA ATTGCAAGCC CCCAAAAGTC TGATGTTGAC CTGTTTCATC    7020

GATCCATTTT AGATGACGTC CCCTGCCACT TGGTGTCGGC TCTTATCGCT GGATTTTGCG    7080

CAACAGCTAT GTCCTCCCCG GTGGATGTAG TAAAAACCAG ATTTATTAAT TCTCCACCAG    7140

GACAGTACAA AAGTGTGCCC AACTGTGCAA TGAAAGTGTT CACTAACGAA GGACCAACGG    7200

CTTTCTTCAA GGGGTAAGAT ATGATCTTGT GTATCTGTAA TGTGTTCTGG CTGTCTGTGT    7260

GCTTTGGGAC ACTCTCATGT CAAGCAACCG ACATTTAGCT TACAAGCCTT AGTATATTCA    7320

TATACTTAGT ATTGACTTTT CCTTGCCACA GATTTCTCCA ATCCACCAAT TCCACTGTGC    7380

CAGAAAGTAA AAAGCCATGA TATTCAAATT TTCTCAACTT TGATCAAAGG CTCATTCAAG    7440

ACCAGTGCCT TTTCCACTGG TCCCAATCTA CTGGAAATGC AGACAGTATT TTGCCTTCTC    7500

TGGGCAAGAA AGTTATAAAG TAGAGGGAAA TCATAATAGA GAGCTATGAG AGAACAAGAT    7560

TTGATTTGAT TTAATTTGAT GGACTCAAGT TTTAACATTG TAAAACTAGA GATAAGACAT    7620

CACCACCAAT CTAGAAAAGT GATGCAGAAA AGTATTTGAT TTGGGTAATT ATTACACTCA    7680

CCTAGAAACA AGTGTTGTGT AATAGATTAC ATATTTCCAT AATGCAATGT TGTATCAGAA    7740

ACTACCTTCC TAAGAAAATA TAGTATGGGC TCGGCGTGGT GGCTCGCACC TGTAATCCCA    7800

GCACTTTGGG AGATGGAGGC AGGAGGATCA CTTGAGCCCA GACTGGGCAA CAAAGCGAGA    7860

CCCTGTCTCA ACAAAAAATT TAAAAATTAG CTGAGTGTGG TGGCACGCAC TGATGGTCCC    7920

CTCTACTTGG GAAGCTGAGG CAAGAGGATC TCCTGAGCCC AGGAGTTCAA GGTTTCAGCG    7980

AGCTATGATT GTGCCACTGC ACTCCAGCCT GGGAGACAGA GCAAGTCCCT GTCTCAAAAA    8040

AGAAGAAGGA GAAGGAGGAG AAAATACAGT ATTAAGTAAT CTGTCAATAT ATTCCACAAG    8100

GATTACACTA GTGGTTTAAT AATAAAATTA TATTACCTTT TTAAATTGTA AGGCCATTCC    8160

TCAAGCTTTA TAAATTAAGC ATGAATGCAT CATACACATT TTATAAAAAG TTCCAACTCA    8220

TCATAATCTG TACTTATGAT ACATTAATAC AAATGAAGTT CATTATAAAA TTAACTTAAA    8280

ATGGATATAC CAGTTATTAA ACCATTAACC ATTTAATAAT TTTATTTTTT TCAAATTTAA    8340

AAACCTTTTG GGGAAGAAAT ACTACAACAT GGATGAACCT TGAAAACGTT ATGCTAAGTG    8400

AAATAAGCCA GACACAAAAG GACAAATACT GTATGATTAC ACTTAAATGA GGTACCTAGA    8460

GTAGTCAAAT TCATAGAGAC AGAAAGAATA GAAGTTACCA GGGGCTGGAG GTAGGAAAAA    8520

ATGGAGAGCT GTTTAATGGG TAGAGAGTTT CTTTTTGGGG TGACAAAAAG GTTCTAGAGA    8580

TGGATAGTGG TGATGGTTAC ACACAATGTG TGTGTACTTA ATGCTACTGA AATGTAATTT    8640

TATGATTTTT TTTTTTTGCA GCAAAATACC CCACATTGGG AAGTGAAGAG AAACATGTTA    8700

AGAGACTTGA AGGAAAAAAA TTGGGGCAGA GGGGTGTTTT TTATAGGTTA AACAATAAAA    8760

GCCATTTAAA CAGTAACAAT TTCTCTAAGG ACAAGAATCG TCAAGATTGA GACAGCACTG    8820

ATTTCTTGAC TCTACTCAAT ACTTCTTTGG TTTCTCTTCT TCCTTCCCCC TTCTAATAGT    8880

TTCCTACCTC CCATTCAGAA AGCAAAGCAA AACAAGCAAA AATTCCCCCT TCCCTCAAAA    8940

AAGGAAAGAG TTTTTGAAAA AGTTCATGTC AGTGAAGAAA AGACATGTTT TGGGAGTGAA    9000
```

-continued

```
GGATATTTGT GGATTTGTAT AGATGTGATC ATCAGGGCTG TGTTGTTTTG AAGTAATATA    9060

GGACATCTAG AGGAAAATTT ATTTTCAGCA GAGGAGGGAA AGATGAAGAG TAGGTACTTT    9120

TAAGCATCTT CACTTGAGGA GTGGCAAAAT GAGAAGCATA ACCTGCTATA ATCACTTTAA    9180

GAATTTCAGG CTGAGTGTGG TGGTGCAGTC TCTAGTCCCA GTTACTCCAG GAGGCTCAGG    9240

TGGGAGGATC ACTTAAGCCC AGGAGCTCGA GGTTGCAGTG AGCTATGATT ACACTACTGC    9300

ATTCCAGCCT GGGCGGCAGG GTGAAGCCTC ATCTCAAAAA TTAAAAAAAA AAAAAATCAA    9360

ACAAATTAAT CGAACGATGA CATGCACTTT TCTAGGTTGG TACCTTCCTT CTTGCGACTT    9420

GGATCCTGGA ACGTCATTAT GTTTGTGTGC TTTGAACAAC TGAAACGAGA ACTGTCAAAG    9480

TCAAGGCAGA CTATGGACTG TGCCACATAA TCAGCTTCAA GAAAATGATG TAACATACCA    9540

GTGGGAATCT TGCTGACTGG ATCATAAAAA CAAACAAAAC TTATTCACTT ATTTTAACCT    9600

AAAAAGATAA AGGAATTTTG GCAGAGAATT TTGGACTTTT TTATATAAAA AAGAGGAAAA    9660

TTAATGCCTA TTTCATATAA CTTTTTTTTT TTCTCAGTGT CTTAAGAAGG GGAAAGCAAA    9720

ACATTCAGCA TATACCCTGG CAAATGTAAT GCAGATAAGC TACTGCATTT GACCATTTCT    9780

GGAGTGCAAT TGTGTGAATG AATGTGAAGA ACTTTAACAT GTTTTAATTA CAATTCCAAC    9840

TGGTGGAAAA GAAACTGAGT GAAATGCAGT TTATATTTAT AAATACTTAA AAATGAAGTT    9900

ATTAAAAATA TTAGTTTTTA TTAACCACAG TTGTCAGTTA ATATATTCAA TAAAGTATTG    9960

CTAATACCTT TTAAAGTTTG TCTTTTGAGA TCTATACCTG GGTGTAAGAG TCAAGTTCAC   10020

TAGAATACAA GACTGCCCAA TAGCAAATGC AGGTCTTTAG AATCATAGGC ATGAACCTAC   10080

TCTGAATGTT ATTAGTATAG ATTTTTAATG TTTAGAGTCC AGATTTGATG ACATCTCTAA   10140

CAACTTCTAA TCTAAGACAC TATATTCATT TTGGCAGGAT TGCTACTAGA GTCTTGGTAT   10200

CTGTGCTAGC ATCACATAAT TTTAGAGCTG GAGGGTACTT CTGGGAAGAC AGAGGAACAG   10260

TTTGAGATTC CTACTGAGAT GAAAACGAAT CTTCATGGAA TCTTTCAGCA AAGCCAAATT   10320

CAAATTCATC ATTAGCACCT GTAGTAACCT TTTCAATGCC TACAAACTGC ATGCAGAAGA   10380

GATAGGGAAA CAGTAAAACA GATATTAAAA GAAGTTTTTA AGACAAAGCC CAGCCTGATT   10440

TTAAGCTAAA TCCAAGGATT GGCAGCTTGG ATGAGCAGGA AGGTTACAGG CTGCCAGACA   10500

TCATTCTAGT TCTGTTTTAA TCAACTCCAT GTTACATTTA CTATCAGGGA TTCTCACCTC   10560

ACCCTCATGC AT                                                      10572
```

The nucleic acid sequence of the 15,901 base pair (bp) human UCP1 sequence (gi|237858805|ref|NG_012139.1| *Homo sapiens* uncoupling protein 1 (mitochondrial, proton carrier) (UCP1), RefSeqGene on chromosome 4) is as follows [SEQ ID NO: 365]:

```
CTGTACAGCT CTCCGACAAT CCCACATCTA GATGCCAAGC TGAGGTTGGC ATTCTCACTA      60

ATTTGCTGTT ATAAATATTA AGCTATCATA AGCGTTAGCC TACATATGAC TCTTTCATAT     120

GTTAGTTAAT TATTTTAGGG TAGAAATCCA AAAGTGGAGT TACCAGAAGT GGATATAGAC     180

ATTCTGGCTG GGTGTGATGG TTCATGCCTG TAATCCCAGC ACTTTGGGAG GCAGAGGCAG     240

GCGGATCACT TGAGGCCAGG AGTTTGAGAT CAGCCTGGGC AACACAGCG AAACCCCATC     300

TCTACTAAAA ATTCCAAAAC TAGCCAGGCA TAGTGGCACA TGCCTGTACT CCCAGCTACT     360

TGGGAGGCTA AGACACAAGA ATCGCTTGAA CCCGGGAGGG AGGTGGAGGT TGCGGTGAGC     420

TGAGATTGTG CCACCGTACT CCAGCCTGGG TGACACAGCT AGACTCTGTT TCAAAAAAA     480
```

-continued

```
AAAGAAAAAG AAAAGAAAAA AATAGACTTT CTCTTGGCTC AGTGTATACT GCCAAATTGT      540

TTTCCAAAAA AATTGTGTCA ATGTATAACA CCATCACTAA TATAGTATTG ATATTATGGT      600

TATTACATTT TAAAATTCAT AATTTGTAAT TATAACATTC ATAATTTATT ACTATTTATA      660

ATATTAATGT AAATGTATAT TATATATAAA TGTTATAGTA ATTATAACTT TGGTAGTGAC      720

AAAGTATTAA TTTATTAGGT GAAGTATATG CTTTTTTATT AGTGATAATA AATATATCCT      780

CTCTCCCATT ATAAAAGTTT GTATTCTTC TTTTAGAAAT TGATTCTTCT GTCATTTGCA       840

CATTTATCTG TATAATTATA ACAGGGTATT TCCCAGTGGT GGCTAATGAG AGAATTATGG      900

GAAAGTATAG AACACTATTC AAATGCAAAG CACTGTATGA TTTTTATTTA ATAGGAAGAC      960

ATTTTGTGCA GCGATTTCTG ATTGACCACA GTTTGATCAA GTGCATTTGT TAATGTGTTC     1020

TACATTTTCA AAAAGGAAAG GAGAATTTGT TACATTCAGA ACTTGCTGCC ACTCCTTTGC     1080

TACGTCATAA AGGGTCAGTT GCCCTTGCTC ATACTGACCT ATTCTTTACC TCTCTGCTTC     1140

TTCTTTGTGC CAGAAGAGTA GAAATCTGAC CCTTTGGGGA TACCACCCTC TCCCCTACTG     1200

CTCTCTCCAA CCTGAGGCAA ACTTTCTCCT ACTTCCCAGA GCCTGTCAGA AGTGGTGAAG     1260

CCAGCCTGCT CCTTGGAATC CAGAACTACT TTCAGAATCT TGAACTTCTG TGACCTCTCA     1320

GGGTCCCCTT GTGTGAAGTT TTTGACGTCA GCTTCTCCTG TGACCCTTAG AAGTCACTCT     1380

TGTGTCTAGC ACATCCCAGG TGCTCAGTCA CCATTGAACT ACAGTCATAC TATCTCCTGG     1440

CAAAGGCTCT TAACTGTCCA TGTTAGCCTG ATATTAATAT CCTGGAAGCT TATACTGTCG     1500

TTCTTCCTTC CAGGTTTAAA TAAGGCAGCC CCTTTATCCT GTCACAGGTC CTCTCTCCCT     1560

ACCTATCCTT ACCTGTTTTG GATAACAACC TTTCTTATTT CTAATAGATT TATTTATTTC     1620

TCACATTTCC TTCCCTTATC ATAGTTTTCC TCTCACTTTC TCCTCTAGTT TGTCATACTC     1680

TGGCTTTAAA ACATGCAAAC ATGTGCCTTA TGGGGAAAAA AAGACAATTT TAATTTACCT     1740

TGCTTCTTCT TTACAAATGT ATTGTGGCTT CTTCTTATAG TCCAAATCTA AAACTCTTTA     1800

CCCACCCACT GCCTTGAACT CCTTCCTCGT TGTGAAAGTA GGATGGGGCA AAGAGAGAAT     1860

GCATGCCCCT CCCAACTGCT CAAACAAGTA AAGGTGCTGT TACAGTTATC TTTTGCTACC     1920

TTAATACAAT AATTATTTTA TTATATCTCA CAATTTTATG GATCAGGAAT TTAGACTGGG     1980

CTCAGCTAGG CGATTCTTCT GCTTTACTGA CATCATAGGA GATCACTTGG TGGTATTCAA     2040

CTGTCAGGTA GGCTTATCTG GAGGGTCCAA GATAGCTGTA CTCTGGTGCC TGGTGCCTTG     2100

GTAAAGAGGG ATGATGATGT GGGGCCTCTC CAGCATGAAC AGCCTCAGAG AAGTTTGCTT     2160

TCTTACATGC TGGCCCAGGG CTCCAAGAGC AAATGTTGCA GTGAGTAAAG CAGAAGATAC     2220

AAGGACTTTT ATAATCTGGT CTCAGAAGCC ACATGGCATC AGTTCTGTAT TATTCTATTG     2280

GTCAAAACAT TCATAAGCCT GCCAGATGCA AGGGGAAGGC ATATGTACCC TCATCTTTTG     2340

ATGGGAGGAA TGTGATGGAT TTGCAATTAT GTTTTAAAAC TACTACAGAC AGAACCACTG     2400

AGAAAGATTC ATGGGTAGCT TTGGGGTGAG GACTGGGAAT TAACCTGTTG ATAGCAGAGG     2460

TTCACTAGAG TCAACAAGGA ATAAGGTCTC CTCTTGTACA CTTTAGTCAT ACTATACCAA     2520

CATTCTTAAC CACTGCTTAG CCATCAGCCT CACAACATAA CAACTCCATC ATAGTTGTAC     2580

TCCCTAAGAT CACCAACAAT GTTAGAGTCA AATCCGGTAG GTTTTTCTTT GTTTTTGTCC     2640

TCCTGACATT TTTTCTAAAC TTGACACTGG TCAGACCCAA TCTTTCTTTA ATCATATTCT     2700

TAAATACCAG TTCTATCACT GGATATGTTA CTGTTTCTTG TTCTCACTCT ACCTTTGACA     2760

AAGCCATTCT TTCCAGACTA TAACTCTGGG TCTGGGTCCC CTATGGTTT GGCCCTTGAA      2820

TTCTTTTCCT AGTCCTATTT GACTAGCCCC ATTTTCCCGT GAAAAGCATG CCCCTTTCAT     2880

TGCATCCATA TCATGACTAC CAAATACCTC CTCTATTTCT TCCTCTTTTA GCATGTTAAA    2940
```

```
TGCAGCTTCC TAAGCTCTCT ATCTGGATAT CAACAGTATT CTCTCCAAAT AATTCTAAGA    3000

CTTTAAAAAT TGGTTTAATC TTCTTACCCC TAAAATCACC CCCCTTACCA ACTGCCTCAT    3060

GACAATCATT GGTACTGTCA CTGAGCTTGC AACCCATGTT CTTAAACATA GAGTAATCTT    3120

TGACTCCACA TCTAATCATT CATAAAGCTG TATTGTCTAT CAAATTAAAT CTGACATTTA    3180

TGTGAGAGCA CTTCATAGTC TGTAAAGCAC TACACAGGTG ATAACATGAA GCTACACTCA    3240

TAATGGATTT GCAGGCTCTG CTTCTCATTT GGCTTCTACA GCCTCATCCC TCACCAACTT    3300

CTTGCCCTAC CTCTCTCTTT CTTCCCCATC ACCCAATTTC CCAGTCAGTC AGGCCAACAG    3360

AATGCATTCT ATATACGCGA CTTGCTTTCC CCAACATCTT TGCCTGTATG CATGCCACTT    3420

ATTTGCCTCA GTTGATCTTT ATTTCAACAA GTGTTTGCAG AGGAGAAACC TCGCTGGCTC    3480

CTTCTCCTTT CTATTTTTTT TCAGAGGCTA CCCGTCAGGT CAACATTGCC TTTTTCAGGG    3540

AAGCTCTGCA AGCCTGACCT CCCTTGGAAG TGCCTTAGGA CTGGCTTCTT GCACAGTACA    3600

CAACCTTTAC TTATAGAGGG TTTGGAGATT ATTCTTTATT CATGTCTTAT TTCTCCTGCT    3660

CCTGGAGGAG ATGACTCTGA CTTCCACTGA CTCTTTTGGG GGGCTTAAGT CAGGGTTGAG    3720

TACCAGAGGC CCTAAATAGC TGGACGTGGA TTCTGGTAAT ATCAAATCCA TCTTTGGCTT    3780

AACTGAGAGG TTCTGAAAGC TGGGACCTGA CCTTGTCCAT TTCCCTCTTT CTCCAGTTTC    3840

CTATTATTTC CCACTGTTTT TTTTAAAAGT TTTTTGTTTT CTTAAGTTTT CACAAGAATA    3900

AACATTGAAA ATAAAATTTG CACAAAGATC GAACTAGGAA AGGCCACACA ACCAACACAT    3960

ATTACATCAT TATAGGTAAG TTAGCAGGGA GATTTCAGAC CTGGGCTAGC TCTGGAACCA    4020

CATTTTACAC TGTTGAAAAT AAAAGCTGGA GTACAGATGA CTTTCCCAGG TTCACAGAGT    4080

TGGTAAGCTG GAGAGCTGCA CCTGGAGCCA AGCAACCTGC CCTGTCCTTT CCACTGCACC    4140

CTCTAAGAAA TCTAATTAGA AGGAACAGGT GGTATCTCAT TTTGTACGGT GCTTTAGCAA    4200

TGTACTATTT GCTTTCTAGT GTGTCTATTG TCTCGTTTGA CATCTTCTCT CAAAAAGTGA    4260

TGAAACGAAA CGCTCTTTTT GACAAGTTCA GAGTGCTCTT GGTTCCTGTG TGGGATTCTT    4320

CCAAGTCTGA ATTTGGTAGT GGGAAGAGAA GGAATCCGGA GGAAGGAGGA TGAGAAGTTT    4380

AAAGGAGAGG AAAGGGAAGC AGAGAAGGCC GCAAGGTGCC TGCAAGATGT CTGGGGAGTT    4440

GGAGGAATGG AAGAGTGCCC CGCTCTTCCT TCTGGGAGAG CTCCAGCTAG CAGAACCTT    4500

TCACCAAGGC TCTGATATCG TGCTGGTTTC CGAAAGCCCC AGCCGAAGGT GTGCAGCCAA    4560

AGGGTGACAG AAGGTGAGGC ACGTGCGGGG GCGCGGGTGC TGACCGCCGC GGTGCGCCCT    4620

CCCTCCGACG TGCGGTGTGC GGGGCGCAGA CAACCAGCGG CCGGCCCAGG GCTTTCGGGG    4680

AGCGAAGCAG GGCTCCCGAG GCACCGAGCG AGAATGGGAA TGGGAGGGAC CCGGTGCTCC    4740

CGGACACGCC CCCGGCAGGT CCCACGCCCG GGTCTTCTGA GACCTCGCGC GGCCCAGCCC    4800

GGGAGCGGCC CAGCTATATA AGTCCCAGCG GAAGACCGGA ACGCAGAGGG TCCTGCTGGC    4860

GCGAGGGTGG GTAGGAGGGG ACGCGGGGAC TCGGCCCCCA ACACCGCGCT CCGTCTGCAG    4920

CCGCCGCCTC TGCACCGCCG CTGCCCGGCG GTCGGTTCAA AAAACAGAAA TCGGGTTTGC    4980

TGCCCGGCGG ACAGGCGTGA AGAGCAAGGG AAAGGAACTT CCTCCACCTT CGGGGCTGGA    5040

GCCCTTTTCC TCTGCATCTC CAGTCTCTGA GTGAAGATGG GGGGCCTGAC AGCCTCGGAC    5100

GTACACCCGA CCCTGGGGGT CCAGCTCTTC TCAGCTGGAA TAGCGGCGTG CTTGGCGGAC    5160

GTGATCACCT TCCCGCTGGA CACGGCCAAA GTCCGGCTCC AGGTAGCTAG GCAGAGGGGT    5220

AAGACAAGGG GTCTCAGGAC AGAGGGGACG CTGTTGCGTG CATTCCATTT ATTCTCTGCT    5280

TTGGTGTAAC CACTGTTTCT AGGTAGGGTA GGTGACCTTC CAAAGCAGTC TGGCCTTGTC    5340
```

```
CCAGGGCTGG TGCTTTAGGA TGGGAAACTG GAACTTTTTC TGGGATTAGC TGAAGAACCA       5400

CCAGGGCCAC AGAGAATGGG TTGACCATGA CTACTACCAA ATTCTCCCAA AATTTAGGGT       5460

GCACTTAGTA TTTTAAGAGC TGAGAATATT GGCCTCTCCT GAGTTTACTA GTCAGGTGCT       5520

TTTTCCTTTC TTTGATTCTT CGGGGGTTCT GTCCTATCCT ACTGCCCTAG GGGTTCTGGA       5580

GAGTTCCTGG GGAGGGGGAT ATTCAAAATG TGCATTGTAG CCAGCCTCCC TCCATCTGCG       5640

CGTGAGCGAA CACACACACA CACACACACA CACACACACA CACACACACA CACACACGGT       5700

AGAGGGAGGT GGATGGAAGA GGAATGTTGC TGAGAAAAGA AACGGAAAAT AGGAACACAG       5760

GGGGAAATCT TGGCTTAAGA GTGAACTCAA TTTCGCTCCC TTCTGTTCTG CACCTTTCTT       5820

ATTTCCAGGT CCAAGGTGAA TGCCCGACGT CCAGTGTTAT AGGTATAAA GGTGTCCTGG        5880

GAACAATCAC CGCTGTGGTA AAACAGAAG GGCGGATGAA ACTCTACAGC GGGCTGCCTG        5940

CGGGGCTTCA GCGGCAAATC AGCTCCGCCT CTCTCAGGAT CGGCCTCTAC GACACGGTCC       6000

AGGAGTTCCT CACCGCAGGG AAAGAAAGTA AGCCGTGAGC GTTCCTGGGA GGGGCAGAAA       6060

AGCCTTGGGC TCCGCTCTGT TCCAAAAAGT GTAACACACA GAGGAGTGGT TTTCATAACA       6120

AATTGGCGAG AAAACATTCA TATTTGAACT CTCCCTTCCC CAAACATTAG CTCATTGTTC       6180

ATAGAAAAAA GTATGCAAAA TCGATTTTTT AGATGCAGAT ATATACTTGT AAAGGTCACC       6240

CAGTCATGGA AGTTTTGTGC CCAGTTTGGA TCTCCATCTG GAGAATATGG GTGGGCTACA       6300

GAAAAATGTT TAACTTAAAG TTCTCCAAAG AGGGAAGTAT ATCAGAAACA TCTATGGAGC       6360

TTGTCAGAAA TCCAAACGAG GACTACCATG GTCCTCTGAG TCTGAATCCT CAGGCTAGAG       6420

ACCAGAGTGT CTTTCCACAA GCTTCCCTCA TCATTTGTGT ATGCAACAAA GTTCAAAGCC       6480

TTCTGTTTGA AGCAAAGAAA GCCAGACTTT GTGAAGAGAG TTGAAAGGAC AGGAAAAGAC       6540

ATATTTCCTC TTAAGAGGTT CCTCATCAGG TCCAGGAAAG ACCAGAGCAG AAAAAGTGGA       6600

CGAATGCTGC AGGGAGTTTG TTTAGGGGAA AAAGAAAAGG AAACATATTT CCTGAGTGCC       6660

AGTGCACTCT AAGAATTCCT GTCACTTTAG GTAGCATTTA TTTGAGGGCT TAACTATGAA       6720

CCAGACATTG TTCTAAGTGC TTCAGATACA TTATAACTGG AAGGGTATTA GTACCATTAT       6780

CCCTTGGCAG ATGGGAAAAC TGAACACAGA GCAGATTCAT CACTTGCCCA AGGTCACACA       6840

GCTGGGAGGG GGCAGAGCCA GGGTTCAAAC CCAGGCAGTC TGGCCTCGGA CTCCAGGCTC       6900

CTAACCCTGT TCTCTACTGC CTTCTGCACT TCTCATATGA TTCTGCCCAT CATTCAAACC       6960

GCACAACACT GCTGTGAGTA AAAGTGTTA GCCGAATATC AGGGTAGTTA AGTAACATGC        7020

ACAAAATCAC ACAGCTAATC AACATCAGAG GCACTTTCAT GTGGAGTAGA CAAGCCAGAG       7080

AGAAGATGTG CTGATGGCAC AATGAATACA TTAAGTGAAA TCCACCTTGT AGATTTCATC       7140

ATTTCTGCTG TGAGTAACCT TCAATACTAT AATTTTATGG GATAATTTAT AAATGTTGTC       7200

TATACAAATA TATAAGTTAT ACTTATCCAC ACAAGTACTT TCAAAGTGAA GATAAAGTCT       7260

GGATGTTACT AGATCAAAAC TGCATTTTTT TATTTATAGA TGTAGCAAGA GAGGAAACAC       7320

AAAGGAGGTA AAGCTGCCCG TTCAGGTGGT TTTCTTCACA GATTGACTGT TCTACCAATT       7380

GTTGTGGACT TTGGGCACCA AATTAATAGG ATATATGTTG GCAGTGTTCT ATGTTATATA       7440

GATTCAGTTT ATTTAGTAGG CTTTATTGAA CTGCCATGTG CCAGTAACTA TGTTAGATGT       7500

TTAGATGGCA GATGTGTCTC TAGACAGAGC TTACAGTTGA GAGTATGGGT TGTGTGGGGA       7560

GAAGTGAATA GATGACTATA TTCCATGATA CATGCTGTAT TACAATACAG TCCTACTTCA       7620

CTTAACGATG GGGATACATT CTCAGAAATG AGTTAGGAGG CAAATTGGTT GTTGAATGAA       7680

CATCACAGAG AGCACTTACA CAAACCTAGA TGGCATAGCC ACACCTAGGC TATATGGTAT       7740

AATCTATTGC TCCTAGGCTA CAAACCTGTG CAGCATGTTG GTATTGAATA CTACAGGCAA       7800
```

-continued

```
TTGTTACATA AAGTTAAGTG TTTGTGTACC TAAAAATAGA AAAGGTAATG CATTACACTA      7860

CAGTCTTATG GGGCTGGGAT GTCACTAGGT GATAGGAATT TTTCAGCTCT GTTCTAATCT      7920

TACGGGACCA CCATCATGTA TGCAGCACAT GACTAACTGT AATTACAAGA TGGTGGCTAT      7980

ATTAAACAGA ACTACTTAAG CTAGCCATGG AGGTATGGTC CGTGAGATTT TCCTGAAGAA      8040

TTAACGTCTG GATCAATTCT GGAAGGGCCA GCAGGAGTAC TCCAGGCAAA GGGGTGAGAA      8100

AGGAGCTTCC AAGTAGAGTG AAGGTCATGT GCAAAGACTC AGTGAGGAGT CGAGTGAACA      8160

TAGCACAGGG AGGACATGTT GGTGAGGAAG GAGGGGTGAA GCCACAGAGA CAGGAGGGAG      8220

CCAGATGACA GAAGGCCTTG CAGGCGGTGC TAAGGAGTTT GGATTTTATC CTTACAGTGG      8280

TGGGAAGTCA TTGTAAAAAT ATTAAGCAAG GGAGTGGCAT AAACAATTTA CATTTTCAAA      8340

AGATCACTTT GGCAGCAGAT AGAGTATATA TGTAAAAGGA GTAAGAAAGA GGTAAGTTAG      8400

AAAGCAAGAA ATGATCAGGG TATGCCCTAA AACACTGGCA ATAGGGAAAA AGAGATGTCA      8460

ATCAGAAAGA TTGAGAAAGT ATAATTGAAT TGACTTGGTG AACAAATAGA AGTAAGGCAT      8520

AAGGGACAGG TAGAAATATG AGATGACTTC CAAGTTTCTG TTTAAAGATA CCCTTTATTG      8580

AGAGAGGATG TATAGAAGCT GTCTTAGGGG GAAGACAAGA AATTTGGTTT AGGCCATGTC      8640

AACAGGTAAT GGCCAGTAGG CACATGATTC AGTTTATTTA GTGGGCTCCT TTTAGGAGAA      8700

AATCTGAGCC AGATTCCAGG AAGTCACAGC AGGGACTACC AATAGGGTCA ACAGCAGAG      8760

AGTGTGGAAA GGACTGAAAA GTGATCATTG TACATAACAA ATAGAAGCTC ACTGATTTTC      8820

TAGCAAAAAC ATCTTCAGCA GAGTAGCGTG GTATAAGCTA TATTGTAGGG GACTGAGGAA      8880

GAAATGGGCT CTGAGAAGTA AAGACAAACA ATATGTTTTG TAAATAAATT TCTTTTAGTT      8940

CTTAAAAAAA AAGCCTCTTT TCCAGCTTGA TTGGGAAGTG AAGAGAGGGA TTTGAAAGTT      9000

GGAGATTGGA GGATAGGATG AGTACATCAA GATACACTAC GTTGTAGTGC AGTGCATTAC      9060

AAATGTGAGC TAAAGTGAA GGCATTTGTA ATCATATGAT ATTGCTAATT AAAAGACAGC      9120

TGTCAGTCAT ATGCCCAGCT CCTGGTAAAG CATGATGAGA AGAGTACAAT CATGGTAGTG      9180

ATTTAAAAAT TGCTGCCAGT TTTGTGGATT TTCTTTATGC TAGACAGTGT AAGCTCTTTA      9240

TCAATATTAT TTAACTCACA CAACTCTAAG AGGTAGATAT TATTATCCCT TTTTGACAAA      9300

TTAGGAAACA GAATTATAAT GACTGAGAAA GTCTCTGCTG AGTAAATGTT ACTGAACCTT      9360

AATTTTATGT TTACTTAATG ATAGAAATGA ATATTGGGCT TCAAGACTAT TTGTACTTAA      9420

TGAAATCTGT CTTGAGCAAC ATAAGCTATT TTTTTCAAAA TTTTAAGACA AAAATCACTT      9480

TCTTCTCTCC TGTCTTCTTA TTTTTGTTCC CTTCACATGT TGTAGCCTAA CACTACTTGA      9540

TGGCCCATTT TGGTGCAGTT TGTCCACTGG GCTTCATCTA AGGCCACCAA GTCCCATAAT      9600

TAACATGATC ATTCGTGGGA GAAAGATCAA GCCTCATTGG TGATGGGTGC CTCCTCACAG      9660

TCGGATAATA CTGAAAAGAG AGCTAAATGT GGGAAAGAAC CAAGTTGAAC ACAGGAAAGA      9720

ATCAGGCCAC TGTGAAAATA AGCATTGTGT TTTCTTGTTC CTTGAAAGTC TTCATTTTTA      9780

AAAAATTTCA GACACCTGAA GTTTTCTAGC CTTACTCTGA GTTGACGCAC ATTTAGTACA      9840

TGATCAACAC ATAAACAAGC ATTAGAGAAA TAGAAAAGCT GTAAGAATAC AAAAATATGG      9900

GCCAGGTGGG TGGCTCATAC CTGTAATCCT AGCACTTTGG GAGGCCGAGG CAGACGGATC      9960

ACCTGAGGTC AGGAGTTCAA GACTAGCCTG GCCAATATAG TGAAACCCTG TCTCTACTAA     10020

AAATACAAAA CTTAGCAGGC TGTGGTGGCA CGTGCCTATA ATCCCAGCTA CTTGGGAGGC     10080

TGAGGCAGGA GAATCTCTTG AACCCGGGAG GCGGAGATTG CAGTGAGCCA AGATCACACC     10140

ACTGCACTCT AGCCTAGATA ACAGAGCAAG ACTCCATCTC AAAAAAAAAA AAAATACAAA     10200
```

```
                              -continued
AATATGAACC ACTGAAAATT AAAAAGACAT GCATGCATTC TAGGTCTTTA ATTTTTTTTC    10260

TTAATAATTT TTTTTCTCTC TGGATAGCAG CACCTAGTTT AGGAAGCAAG ATTTTAGCTG    10320

GTCTAACGAC TGGAGGAGTG GCAGTATTCA TTGGGCAACC CACAGAGGTC GTGAAAGTCA    10380

GACTTCAAGC ACAGAGCCAT CTCCACGGAA TCAAACCTCG CTACACGGGG ACTTATAATG    10440

CGTACAGAAT AATAGCAACA ACCGAAGGCT TGACGGGTCT TTGGAAAGGT AACTAACTTC    10500

AAAATGGGTT TTATAACCAC CAAAGCACAT ACATACAACT AGCAACTTAT TGTAAAGTAG    10560

AGTTAATAAA CATTTTCTTT TTTTTTTTCC CCAGGGACTA CTCCCAATCT GATGAGAAGT    10620

GTCATCATCA ATTGTACAGA GCTAGTAACA TATGATCTAA TGAAGGAGGC CTTTGTGAAA    10680

AACAACATAT TAGCAGGTAA CTTCCCATTT CATATAACAA ACAGGTCTGC ACCTTTAGAA    10740

GTTCATCTTG GAGCTTCTGC AGCCACCTTA TACTCAATCT CTTAACTCCA ATAGTTTTCT    10800

CTTTTTAAAA ATTAAGTAAT TTTGAACCAT ATATAACTTT GTGAGAAGCA GGAAAAGACC    10860

AAAATATTAA GTTTAAGAAG TTTTGCCACA ACAAAAATAT TTTGCAACAA AATAACAGG     10920

CAATTTCATG TCAGCATTAT TCTCATTTAA TACTAATATA TGGGACTTTT GTTAGAATCT    10980

TATTCTTTAT ACAGCAGAAT TCAGGAGGTA AGTCCATCCT GCATACTATA TCCAAAGAT     11040

CTAGTTATAA AAGGAGCTTA TCAGTGGTCT CATCCAAAAA GTAATACCAT AAGATAGGTT    11100

CTTAAAAATA ATATTCTAAC AACTTCTAGA GACATTGAAA TTTCCCTTAT TTCAATAAAA    11160

AAGTATTAGA TGCTCATATA TTAGGCATTA TTACAGGCCT TAAAGGCACA GAGGAAACTA    11220

ACAGTTTACT TTCCTAAAGT GTTAACAATC TATTAAGCCA TTTACTCTTT ACCTTCTTTT    11280

TCTAGTGCAA TACCTTTCTT ATTTTATTTT ATTTATTTAT AAGACATCTT CATTGACCTA    11340

CTGTTATCAA TAGGTTTATA AAGATATGAC AGATAACTAA ATTGCAAGCC CCCAAAAGTC    11400

TGATGTTGAC CTGTTTCATC GATCCATTTT AGATGACGTC CCCTGCCACT TGGTGTCGGC    11460

TCTTATCGCT GGATTTTGCG CAACAGCTAT GTCCTCCCCG GTGGATGTAG TAAAAACCAG    11520

ATTTATTAAT TCTCCACCAG GACAGTACAA AAGTGTGCCC AACTGTGCAA TGAAAGTGTT    11580

CACTAACGAA GGACCAACGG CTTTCTTCAA GGGGTAAGAT ATGATCTTGT GTATCTGTAA    11640

TGTGTTCTGG CTGTCTGTGT GCTTTGGGAC ACTCTCATGT CAAGCAACCG ACATTTAGCT    11700

TACAAGCCTT AGTATATTCA TATACTTAGT ATTGACTTTT CCTTGCCACA GATTTCTCCA    11760

ATCCACCAAT TCCACTGTGC CAGAAAGTAA AAAGCCATGA TATTCAAATT TTCTCAACTT    11820

TGATCAAAGG CTCATTCAAG ACCAGTGCCT TTTCCACTGG TCCCAATCTA CTGGAAATGC    11880

AGACAGTATT TTGCCTTCTC TGGGCAAGAA AGTTATAAAG TAGAGGGAAA TCATAATAGA    11940

GAGCTATGAG AGAACAAGAT TTGATTTGAT TTAATTTGAT GGACTCAAGT TTTAACATTG    12000

TAAAACTAGA GATAAGACAT CACCACCAAT CTAGAAAAGT GATGCAGAAA AGTATTTGAT    12060

TTGGGTAATT ATTACACTCA CCTAGAAACA AGTGTTGTGT AATAGATTAC ATATTTCCAT    12120

AATGCAATGT TGTATCAGAA ACTACCTTCC TAAGAAAATA TAGTATGGGC TCGGCGTGGT    12180

GGCTCGCACC TGTAATCCCA GCACTTTGGG AGATGGAGGC AGGAGGATCA CTTGAGCCCA    12240

GACTGGGCAA CAAAGCGAGA CCCTGTCTCA CAAAAAATT TAAAAATTAG CTGAGTGTGG     12300

TGGCACGCAC TGATGGTCCC CTCTACTTGG GAAGCTGAGG CAAGAGGATC TCCTGAGCCC    12360

AGGAGTTCAA GGTTTCAGCG AGCTATGATT GTGCCACTGC ACTCCAGCCT GGGAGACAGA    12420

GCAAGTCCCT GTCTCAAAAA AGAAGAAGGA GAAGGAGGAG AAAATACAGT ATTAAGTAAT    12480

CTGTCAATAT ATTCCACAAG GATTACACTA GTGGTTTAAT AATAAAATTA TATTACCTTT    12540

TTAAATTGTA AGGCCATTCC TCAAGCTTTA TAAATTAAGC ATGAATGCAT CATACACATT    12600

TTATAAAAAG TTCCAACTCA TCATAATCTG TACTTATGAT ACATTAATAC AAATGAAGTT    12660
```

```
CATTATAAAA TTAACTTAAA ATGGATATAC CAGTTATTAA ACCATTAACC ATTTAATAAT    12720

TTTATTTTTT TCAAATTTAA AAACCTTTTG GGGAAGAAAT ACTACAACAT GGATGAACCT    12780

TGAAAACGTT ATGCTAAGTG AAATAAGCCA GACACAAAAG GACAAATACT GTATGATTAC    12840

ACTTAAATGA GGTACCTAGA GTAGTCAAAT TCATAGAGAC AGAAAGAATA GAAGTTACCA    12900

GGGGCTGGAG GTAGGAAAAA ATGGAGAGCT GTTTAATGGG TAGAGAGTTT CTTTTTGGGG    12960

TGACAAAAAG GTTCTAGAGA TGGATAGTGG TGATGGTTAC ACACAATGTG TGTGTACTTA    13020

ATGCTACTGA AATGTAATTT TATGATTTTT TTTTTTTGCA GCAAAATACC CCACATTGGG    13080

AAGTGAAGAG AAACATGTTA AGAGACTTGA AGGAAAAAAA TTGGGGCAGA GGGGTGTTTT    13140

TTATAGGTTA AACAATAAAA GCCATTTAAA CAGTAACAAT TTCTCTAAGG ACAAGAATCG    13200

TCAAGATTGA GACAGCACTG ATTTCTTGAC TCTACTCAAT ACTTCTTTGG TTTCTCTTCT    13260

TCCTTCCCCC TTCTAATAGT TTCCTACCTC CCATTCAGAA AGCAAAGCAA AACAAGCAAA    13320

AATTCCCCCT TCCCTCAAAA AAGGAAAGAG TTTTTGAAAA AGTTCATGTC AGTGAAGAAA    13380

AGACATGTTT TGGGAGTGAA GGATATTTGT GGATTTGTAT AGATGTGATC ATCAGGGCTG    13440

TGTTGTTTTG AAGTAATATA GGACATCTAG AGGAAAATTT ATTTTCAGCA GAGGAGGGAA    13500

AGATGAAGAG TAGGTACTTT TAAGCATCTT CACTTGAGGA GTGGCAAAAT GAGAAGCATA    13560

ACCTGCTATA ATCACTTTAA GAATTTCAGG CTGAGTGTGG TGGTGCAGTC TCTAGTCCCA    13620

GTTACTCCAG GAGGCTCAGG TGGGAGGATC ACTTAAGCCC AGGAGCTCGA GGTTGCAGTG    13680

AGCTATGATT ACACTACTGC ATTCCAGCCT GGGCGGCAGG GTGAAGCCTC ATCTCAAAAA    13740

TTAAAAAAAA AAAAAATCAA ACAAATTAAT CGAACGATGA CATGCACTTT TCTAGGTTGG    13800

TACCTTCCTT CTTGCGACTT GGATCCTGGA ACGTCATTAT GTTTGTGTGC TTTGAACAAC    13860

TGAAACGAGA ACTGTCAAAG TCAAGGCAGA CTATGGACTG TGCCACATAA TCAGCTTCAA    13920

GAAAATGATG TAACATACCA GTGGGAATCT TGCTGACTGG ATCATAAAAA CAAACAAAAC    13980

TTATTCACTT ATTTTAACCT AAAAAGATAA AGGAATTTTG GCAGAGAATT TTGGACTTTT    14040

TTATATAAAA AAGAGGAAAA TTAATGCCTA TTTCATATAA CTTTTTTTTT TTCTCAGTGT    14100

CTTAAGAAGG GGAAAGCAAA ACATTCAGCA TATACCCTGG CAAATGTAAT GCAGATAAGC    14160

TACTGCATTT GACCATTTCT GGAGTGCAAT TGTGTGAATG AATGTGAAGA ACTTTAACAT    14220

GTTTTAATTA CAATTCCAAC TGGTGGAAAA GAAACTGAGT GAAATGCAGT TTATATTTAT    14280

AAATACTTAA AAATGAAGTT ATTAAAAATA TTAGTTTTTA TTAACCACAG TTGTCAGTTA    14340

ATATATTCAA TAAAGTATTG CTAATACCTT TTAAAGTTTG TCTTTTGAGA TCTATACCTG    14400

GGTGTAAGAG TCAAGTTCAC TAGAATACAA GACTGCCCAA TAGCAAATGC AGGTCTTTAG    14460

AATCATAGGC ATGAACCTAC TCTGAATGTT ATTAGTATAG ATTTTAATG TTTAGAGTCC     14520

AGATTTGATG ACATCTCTAA CAACTTCTAA TCTAAGACAC TATATTCATT TTGGCAGGAT    14580

TGCTACTAGA GTCTTGGTAT CTGTGCTAGC ATCACATAAT TTTAGAGCTG GAGGGTACTT    14640

CTGGGAAGAC AGAGGAACAG TTTGAGATTC CTACTGAGAT GAAAACGAAT CTTCATGGAA    14700

TCTTTCAGCA AAGCCAAATT CAAATTCATC ATTAGCACCT GTAGTAACCT TTTCAATGCC    14760

TACAAACTGC ATGCAGAAGA GATAGGGAAA CAGTAAAACA GATATTAAAA GAAGTTTTTA    14820

AGACAAAGCC CAGCCTGATT TTAAGCTAAA TCCAAGGATT GGCAGCTTGG ATGAGCAGGA    14880

AGGTTACAGG CTGCCAGACA TCATTCTAGT TCTGTTTTAA TCAACTCCAT GTTACATTTA    14940

CTATCAGGGA TTCTCACCTC ACCCTCATGC ATGTCTTCCC CATTCATTAC CCGCAAAAGT    15000

GTCTTGTAGC AGATGTCTTC TGTGTCCCAT ACATACCATT TTGCTCTTTA GTGCTTGCTG    15060
```

-continued

```
GCCTGACTTC CTATTGTCAT GTCAGCATCT GCCCTTTTTA GGGTCTCTGG CCACCAGAGC     15120

CAGCTTTACT CACCTGTGCA TGGCATTCTA GAAGAGCAGC AGGGAAAATA ACACAGCCCC     15180

AGTGCAGCCC TTAACCACCA ATAACTGGTA GTAGTTGGTG TACAAATATC TCAGTTCCCT     15240

CAACTGTCAG GTGGAATACC GCTGAGGGAT CAAACTCTAG TAACACACAG TAGTGTTTTG     15300

CTTACTATGG TTAACTAAAA AATCACAGGG TCTTCATGCA TTTGGAAAGG ATACTTTATT     15360

TCTTACAAAG GGTTACAGCC TACAAGGTGG TCATTCTGCA GGCTAGAAAG CGTAACCTCC     15420

AGCAAAGACC GGAGGCAGGC ACTTCTAGGG AAGGAAGAGT AAGACAGAAA TTTAAATTGA     15480

ATGGGTTGGC CAAGTATACA TATTCAACAG GCTACAGGTG GATTCATGAA TATTCATGAA     15540

GGCAGTCCTG ATGCATGCAT GTTACACCTT GGGGTGGAGG CTTAACATTT AAATGTATTA     15600

CAGTTAGGCC CTATACATGA AAAGGTGAAG CAGTAACACG AAGGCACACA ATGCACCATT     15660

TCTGTAAACA GGCCAGAGCC AGTTCACAGT GGTTGGTCTC TTATCATGAG AAAGCTACTA     15720

AAATCCTCTT GTCCAGTTAA AACTGTAGTT ATGGCTGGTG GAAAATGGGC TGGAGTCAGT     15780

CAACACTTGG TGAAGCTGCA GTTGCTTCAG ACACTCAAGG CCAGTGTTTG TTTAGCTGCT     15840

CGAGAAAAAG AAAAATCTTG TGGCAGTTAG AACATAGTTT ATTCTTTAAG TGTAGGAGTG     15900

TGTGACTTAA //
```

The nucleic acid sequence of the 2,113 base pair (bp) transcript ENST00000310473 of the human UCP2 gene is as follows (Eight Coding Exons in capital letters) (SEQ ID NO: 366-382):

| No | Exon/<br>Intron | Start | End | Start<br>Phase | End<br>Phase | Length | Sequence | SEQ<br>ID<br>NO |
|----|------|------|------|------|------|------|------|------|
|  | 5'<br>upstream<br>sequence |  |  |  |  |  | ...aatcgacagc gaggccggtc gcgaggcccc agtcccgccc tgcaggagcc | 366 |
| 1 | ENSE00002<br>287650 | 73,694,352 | 73,693,766 | — | — | 587 | AGCCGCGCGC TCGCTCGCAG GAGGGTGGGT AGTTTGCCCAGCGTAGGGGG<br>GCTGGGCCCA TAAAAGAGGA AGTGCACTTA AGACACGGCC<br>CCGCTGGACG CTGTTAGAAA CCGTCCTGGC TGGGAAGGCA<br>AGAGGTGTGT GACTGGACAA GACTTGTTTC TGGCGGTCAG<br>TCTTGCCATC<br>CTCACAGAGG TTGGCGGCCC GAGAGAGTGT GAGGCAGAGG<br>CGGGGAGTGG CAAGGGAGTG ACCATCTCGG GGAACGAAGG<br>AGTAAACGCG GTGATGGGAC GCACGGAAAC GGGAGTGGAG<br>AAAGTCATGG AGAGAACCCT AGGCGGGGCG GTCCCCGCGG<br>AAAGGCGGCT GCTCCAGGGT CTCCGCACCC AAGTAGGAGC<br>TGGCAGGCCC GGCCCCGCCC CGCAGGCCCC ACCCCGGGCC<br>CCGCCCCCGA GGCTTAAGCC GCGCCGCCGC CTGCGCGGAG<br>CCCCACTGCG<br>AAGCCCAGCT GCGCGCGCCT TGGGATTGAC TGTCCACGCT<br>CGCCCGGCTC<br>GTCCGACGCG CCCTCCGCCA GCCGACAGAC ACAGCCGCAC<br>GCACTGCCGT GTTCTCCCTG CGGCTCG | 367 |
|  | Intron<br>1-2 | 73,693,765 | 73,692,678 |  |  | 1,088 | gtgagcctgg ccccagccct gcgcc...actct ctgcctttgc tcacccacag | 368 |
| 2 | ENSE00001<br>184362 | 73,692,677 | 73,692,521 | — | — | 157 | GACACATAGT ATGACCATTA GGTGTTTCGT CTCCCACCCA TTTTCTATGG<br>AAAACCAAGG GGATCGGGCC ATGATAGCCA CTGGCAGCTT<br>TGAAGAACGG GACACCTTTA GAGAAGCTTG ATCTTGGAGG<br>CCTCACCGTG AGACCTTACA AAGCCGG | 369 |
|  | Intron<br>2-3 | 73,692,520 | 73,689,523 |  |  | 2,998 | gtaagagtcc agtccaagga agagg...tgggg cttttctcct cttggcttag | 370 |
| 3 | ENSE00001<br>184370 | 73,689,522 | 73,689,298 | — | 0 | 225 | ATTCCGGCAG AGTTCCTCTA TCTCGTCTTG TTGCTGATTA AAGGTGCCCC<br>TGTCTCCAGT TTTTCTCCAT CTCCTGGGAC GTAGCAGGAA ATCAGCATCA | 371 |

| No | Exon/Intron | Start | End | Start Phase | End Phase | Length | Sequence | SEQ ID NO |
|---|---|---|---|---|---|---|---|---|
| | | | | | | | TGGTTGGGTT CAAGGCCACA GATGTGCCCC CTACTGCCAC TGTGAAGTTT CTTGGGGCTG GCACAGCTGC CTGCATCGCA GATCTCATCA CCTTTCCTCT GGATACTGCT AAAGTCCGGT TACAG | |
| | Intron 3-4 | 73,689,298 | 73,689,142 | | | 156 | gtgaggggat gaagcctggg agtct...tagct accctgtctt ggccttgcag | 372 |
| 4 | ENSE00001 252503 | 73,689,141 | 73,688,931 | 0 | 1 | 211 | ATCCAAGGAG AAAGTCAGGG GCCAGTGCGC GCTACAGCCA GCGCCCAGTA CCGCGGTGTG ATGGGCACCA TTCTGACCAT GGTGCGTACT GAGGGCCCCC GAAGCCTCTA CAATGGGCTG GTTGCCGGCC TGCAGCGCCA AATGAGCTTT GCCTCTGTCC GCATCGGCCT GTATGATTCT GTCAAACAGT TCTACACCAA GGGCTCTGAG C | 373 |
| | Intron 4-5 | 73,688,930 | 73,688,063 | | | 868 | gtgagtatga agcaagggtg taggc...cactg accccatggc tcgcccacag | 374 |
| 5 | ENSE00001 184355 | 73,688,062 | 73,687,868 | 1 | 1 | 195 | ATGCCAGCAT TGGGAGCCGC CTCCTAGCAG GCAGCACCAC AGGTGCCCTG GCTGTGGCTG TGGCCCAGCC CACGGATGTG GTAAAGGTCC GATTCCAAGC TCAGGCCCGG GCTGGAGGTG GTCGGAGATA CCAAAGCACC GTCAATGCCT ACAAGACCAT TGCCCGAGAG GAAGGGTTCC GGGGCCTCTG GAAAG | 375 |
| | Intron 5-6 | 73,687,867 | 73,687,788 | | | 80 | gtgtgtacca gttgtttttcc cttcc...accca ggatcttcct cctcctacag | 376 |
| 6 | ENSE00003 147097 | 73,687,787 | 73,687,686 | 1 | 1 | 102 | GGACCTCTCC CAATGTTGCT CGTAATGCCA TTGTCAACTG TGCTGAGCTG GTGACCTATG ACCTCATCAA GGATGCCCTC CTGAAAGCCA ACCTCATGAC AG | 377 |
| | Intron 6-7 | 73,687,685 | 73,686,717 | | | 969 | gtgagtcatg aggtagacgg tgctg...tgcct tgcctgctcc tccttggcag | 378 |
| 7 | ENSE00001 184349 | 73,686,716 | 73,686,536 | 1 | 2 | 181 | ATGACCTCCC TTGCCACTTC ACTTCTGCCT TTGGGGCAGG CTTCTGCACC ACTGTCATCG CCTCCCCTGT AGACGTGGTC AAGACGAGAT ACATGAACTC TGCCCTGGGC CAGTACAGTA GCGCTGGCCA CTGTGCCCTT ACCATGCTCC AGAAGGAGGG GCCCCGAGCC TTCTACAAAGG | 379 |
| | Intron 7-8 | 73,685,535 | 73,686,167 | | | 369 | gtgagcctct ggtcctcccc accca...atgac ctgtgattt tctcctctag | 380 |
| 8 | ENSE00001 184368 | 73,685,166 | 73,685,712 | 2 | — | 455 | GTTCATGCCC TCCTTTCTCC GCTTGGGTTC CTGGAACGTG GTGATGTTCG TCACCTATGA GCAGCTGAAA CGAGCCCTCA TGGCTGCCTG CACTTCCCGA GAGGCTCCCT TCTGAGCCTC TCCTGCTGCT GACCTGATCA CCTCTGGCTT TGTCTCTAGC CGGGCCATGC TTTCCTTTTC TTCCTTCTTT CTCTTCCCTC CTTCCCTTCT CTCCTTCCCT CTTTCCCCAC CTCTTCCTTC CGCTCCTTTA CCTACCACCT TCCCTCTTTC TACATTCTCA TCTACTCATT GTCTCAGTGC TGGTGGAGTT GACATTTGAC AGTGTGGGAG GCCTCGTACC AGCCAGGATC CCAAGCGTCC CGTCCCTTGG AAAGTTCAGC CAGAATCTTC GTCCTGCCCC CGACAGCCCA GCCTAGCCCA CTTGTCATCC ATAAAGCAAG CTCAACCTTG GCGTC | 381 |
| | 3' down-stream sequence | | | | | | tcctccctct cttgtagctc ttaccagagg tcttggtcca atggccttt... | 382 |

The nucleic acid sequence of the 15,174 base pair (bp) of the human UCP2 gene (ENSG00000175567), including 5,000 bp 5'UTR and 2,000 bp 3'UTR, is as follows (Exons are highlighted) [SEQ ID NO: 383]:

```
TCCAGCCTGG GCAACAAGAG TGAAACTCGG TCTCAAAAAA AAAAAAAAGA GAAGAAGAAG      60
AAAGAAAACT AGGTGGAGTG TGGTGGCTTG CACCTATAAT CCCAGCACTT TGGGAGGCCG     120
AGGTGGGTGG ATCTATTGAG CTAGGAGTT  CAAGATCAAC CTGCCAACAT GACGAAACCC     180
CACCTCTACT AAAAATACAA AAAATTAGCA CGGCGTGGTG TGTGTGCCTG TAATCCTAGC     240
TACTTGGAAG GCTGAGGCAG GAATCGCTTG AACCTGGGGG GCAGAGGTTG CAGTGAGCCA     300
AGATCTTGCC ACTGCACTCC AGGCTGGGCG ACACAGCACA ACTCTATCTC AAAAATACAA     360
AGAAAAAACA AAGAAAACT  AATATATCAA ATAATTTCT  AGTTAGTTGG ATTCACTCAC     420
TTATTCATTC AATGACTTAT TGAATTATCA TATATTACTA GTGCTTTTTA ATACATACCT     480
TCTACAATTT TTCAACTGAA AATTACTTCA TTGATCAGGG CTCTTTAAAC TGATCTCCAT     540
TTGCATTGTT TTACTAACTA TAGTTATTAT TCATGTATTA GCACTCTGAG CCTACTGTAA     600
TGATGTGTAC CTTAATAAAG AACTGAATAT TTGTAATGGC TGGCAGTGAA TTTAGTAGTT     660
CTTGAATTTA GAGCTCAAAA TATGGGAGTA ATTTGCTGCT TTATTTCCTT TGAGAGGTAA     720
TAGAGGAAAA ACAGAATCTA ATAACAATCA CAGATTTTCG GGAAAGCACT GTAAAACCAT     780
ATGATCAATT CTAGCTTCTT ATGTAAACAT GGAAAGATTG CCAGCTGAAC ACCTGTCATG     840
CTCTAAGAAG TTGGGGAGAA TTTGCATTTT TAGAACTGTG AGCAAAATGA GAACGACTGC     900
TATGTTCATG CTTTGTGAAT TTAGCTTTAT TTCATTCACA CAATTCATGG GAAAAAATGC     960
ATCTTTTAAC TCGGTGTTTT TCAATTCAAC TTTTAAAATA CAGGAGTGGG CCAGACCCGG    1020
TGGCTCACAC CTGTAATCTC ATCACTTTGG GAGGCCGAGG CAGGTGGACC ACAAGGTCAA    1080
GAGATAGACA CCATCCTGGC CAACATGGTG AAACCCCATC TCCACTAAAA ATACAAAAAT    1140
TAGCTGGGCA TGTTGGCACG TACCTGTAAT CCCAGCTACT CGGGAGACTG AGGCAGGAGA    1200
ATCGCTTGAA CCTGGGAGAT GGAGGTTACA GTAAGCCGAG ATCGCGCCAC TGCACTCCAG    1260
CCTGGCGACA GAGCAAGACT CCATCTCAAA AAAAATACAA AAAAATACAA AAAAATACAA    1320
AAAAAACCAG GATGTGTTAC CAAGGAAAAT TCATTTACAA TGGTTAATTA TGTGACAAAC    1380
ATGTCAAGTA ATTCCATCTG GCTTTGTGTC ACCATTTCCC CACCCTTTTT TCAGAAACCA    1440
AAACCAAGAA GAAGAACAAA CATCAAAATG GACATGGAAA TTAACAAATA TATGATTCAA    1500
TTTAATCTCC TAAGAGGTTT TTTAAAATTA TTTTATTTTG AGACGGAGTC TTGCTCTGTC    1560
GCCAGGCTGG AGTGCAGTGG CAGGATCTCA GCTCACTGCA ACCTCCATCT CCCAGGTTCA    1620
AGCGATTCTC CTGCTTCAGC CTCCCAAGTA GCTGGAACTA CAGGCAAGCA CCACCACACC    1680
CAGCTAATGT TTGTATTTTT GGTAGAGATG GGGTTTCACC ATGTTGGCCA GGATGGTCTC    1740
GATCTCTTGA CCTCATGATC CACCCGCCTT GGCCTCCCAA AGTGCTGGGA TTACAGGTAT    1800
TTTTTATTTT TTTTGAGACA GGGTCACCCT GTCACCCAGG CTGGAGTGTA GTGGCACAAT    1860
CATGGCTCAC TGCAGCCTCA ACCTCCCAGG CTCAGGTGAT CCTCCATGTC AGCCTCCCAA    1920
GTAGCTGGAA CTATAGGCGT GCAACACCAT GCCCAGCTAA TTTTTGTATT TTTTGTAGAG    1980
ACAGGGATTT GCCATGTTGG CCAGGCTGGT CTTCAACTCC TGGCCTCAAG TGATCCACCC    2040
GTCTCAACCT CCCAAACTGC TAGGATTACA GGTGTGAGCC ACCGTGCCCC ATCTCATCTG    2100
CTAAGTGGGT TTAAAGAAAT TCAGTTTCAT GTCAATTTTT AAAATGTATG GTTATCAAAT    2160
TCGACTTCTT TTTAAAAATG CAATCAGATA ACTGTATGCT TGTTTGATGA GGGGAGGAAA    2220
GTTAATATAG CCAATCTACT CAATATTTTT AGCAGAAATT ATCAGAGACT AAGGAAATGT    2280
TTAAGTTTTT CTCATGTTGG TTTTAATTAC CTAATGTTTT CAGTTTTCTC TTTCATTCTT    2340
GTGTCTTTTT TTCATTTTCA GTGTTTCAAA TACAGTTTGT ATTTAAAGAT TTAGAAGTTC    2400
CAAAACTGTA AGCACAGTGG ATTGTTTCCT GGGATGATGT TAAAATTATA CAACAAAATA    2460
```

```
TATGAAACTT TGTCAATTTG GTTATTGGCA CATACAAAAT ATTTACAAAT AAACGTGTGT    2520

GTGTGTGCGT GTACACACAA TTCAATGAAA TAGATGTGAA ACAAGTTTTC TTTTTTTTTT    2580

TTTTGAGACA GAGTCTTGCT CTGTCGCCCA GGCTGGAGTG CAATGTCGCA GTCTCAGCTC    2640

ACTGCAACCT CTGCCTCCCG GGTTCAAGCG ATTCTCCTGC CTCAGCCTCC CGAGTAGCTG    2700

GGACTACAGG CACCTACCAC CACTCCCAGC TAATTTTTGT GTTTTAGTA GAGACAGGGT     2760

TTCACCATGT TAGCCAGGCT AGTCTCCAAC TCCTGACCTC AGGTGATCTG CCCGCCTCAG    2820

CCTCCCAAAG TGCTGGGATT GCAGGCGTGA GCCACCTCAC CTGGCTACAA GTTTTCAAAA    2880

TACATTTATC TGTACCCATA CATTCTCCAG TTTGTCCACA GGACATCTTA TGACTTGAGC    2940

AAGCTGCTAA AAATCCAAGG GTGCAGCGTT TGTATGTCTA TAGGATTGCT CAGATCTGCC    3000

CCCACCCTGA AAGAATTTAA GAGAATTTCT TGAGGCCAGG CACAGTGGCT CACACCTGTA    3060

ATTCCAGTAC TGTGAGAGTC CGAGGTCAGA GGACTGCTTG AGGCCAGGAG TTCAAGAGCA    3120

GCCTGGACAA CATAGGGAGA CCTGTCACTA CAAAGAATAA ATAAATTAGC CAGGCTTAGT    3180

GGCTCATCCC TGTGGTCCCA GCTACTAGGG AGGCAGAAGT AGGACTGCTT GTCCCAGGAG    3240

GTCAAGACTG CAGTGAGCTG AGACCCAGCC ACCTGCATTC CAGCCTGGGC AACAAAAGA     3300

GACCCTGTCT CAAAAAATAA GTTAAATAAA TAAATAATAA AAATAGTTTA AACCCTAAAC    3360

ACATCTTCTT TTTCAAAGAG GACTTCTTAA GGACTTCATG CTGCGTCCTG TTGATCTCCA    3420

CTTCCCTTTT TCAGCGTCCA CACTTTTAAC AGTCTCTTTT GCCAAGGATA ATAAGTATAT    3480

AGTTTCTGGA ATCCAGATTC TTCCCTGTTT GGACAGCCAG GGGGACAATT TTTGGTCTGC    3540

AGGCCTTTGC ATCTGTTCTG CTGTTGCTCA GCAATCTCAC AGCAAATTTG CCGAGCCTCT    3600

CCGGAATGCA CAGCCAGACA GAGCTCAGCG CAAAAGCTAG AGAACCTGGC GGAGGGAGAC    3660

TCACAGTGCC ACAAAAAAAC TTTATCTTTT CTTTTTTTTT TTCTTTTCTT TCTTTCTCTT    3720

TCTTTCTTGT CTTTCTGTCT TTCCTCTCTC TCTCTCTGTC TTTCTTTCCT CTCTTTCTTT    3780

CTTTTTTCCT ACATGGCAAG ATCTCCTCAT GGCAGAAATA ATCTGCCTTG ACTTCTGTTT    3840

CCACGCTGCT TCTGCCAGGA CCATGCGCTC GGCGTGTTTT TCTTTCCGCT ATAATTATCC    3900

AGGCCCATCC CAGCTCTGGT CCCCTCAGCT GTTCCCTGGC AGTCCCTTCT GCTGGTGAAA    3960

ACACATATGG CGCCGGCCTG ACCAGGGTGT AAGTGTGTGA ATATCAGGAA GATGACTGAA    4020

CGTCTTTGGG ACTCCGTTTC CTCATTGTAA AATGGAGGTT AATACCAGCC TTCTTCTACT    4080

CCCCAAACGC ACGTGTTTGT CCCGGCCAGA GGGCCCAATT GTTGGCTGTT CACGCGTCAG    4140

TTACCCCCAC AGGACGGGTC AGCCAATTAA AGGCGAACCA GGCCCGGTCC ATCTCCTGAC    4200

GCCTTTTCTC ATCCCAGGGC TGGACAGGCA GCTGGCCTGG GCCCGGCTCT GCCTTGTCAC    4260

GTGCGGGGGC CGGCCCGTTT GCTTGTCTGT GTGTAGGAGC GTGAGGTCAC GCTGGGTGCT    4320

CCCGCCCCGC CGGGGCCTTT AGTGTCCTGG TCCCTAAACG CCAGGCCGCT CCACCGGGGG    4380

AGAAGGCGCG AACCCCAGCC GAGCCCAACG GCTGTTGTCG GTTGCCGGGC CACCTGTTGC    4440

TGCAGTTCTG ATTGGTTCCT TCCCCCGACA ACGCGGCGGC TGTAACCAAT CGACAGCGAG    4500

GCCGGTCGCG AGGCCCAGT CCCGCCCTGC AGGAGCCAGC CGCGCGCTCG CTCGCAGGAG     4560

GGTGGGTAGT TTGCCCAGCG TAGGGGGGCT GGGCCCATAA AAGAGGAAGT GCACTTAAGA    4620

CACGGCCCCG CTGGACGCTG TTAGAAACCG TCCTGGCTGG GAAGGCAAGA GGTGTGTGAC    4680

TGGACAAGAC TTGTTTCTGG CGGTCAGTCT TGCCATCCTC ACAGAGGTTG GCGGCCCGAG    4740

AGAGTGTGAG GCAGAGGCGG GGAGTGGCAA GGGAGTGACC ATCTCGGGGA ACGAAGGAGT    4800

AAACGCGGTG ATGGGACGCA CGGAAACGGG AGTGGAGAAA GTCATGGAGA GAACCCTAGG    4860
```

```
CGGGGCGGTC CCCGCGGAAA GGCGGCTGCT CCAGGGTCTC CGCACCCAAG TAGGAGCTGG    4920

CAGGCCCGGC CCCGCCCCGC AGGCCCCACC CCGGGCCCCG CCCCCGAGGC TTAAGCCGCG    4980

CCGCCGCCTG CGCGGAGCCC CACTGCGAAG CCCAGCTGCG CGCGCCTTGG GATTGACTGT    5040

CCACGCTCGC CCGGCTCGTC CGACGCGCCC TCCGCCAGCC GACAGACACA GCCGCACGCA     5100

CTGCCGTGTT CTCCCTGCGG CTCGGTGAGC CTGGCCCCAG CCCTGCGCCC TTTGCGCCCC    5160

CCACGCTTGT TCTGCGTGCG CTGCCCGCTC TTCCATTTAC CTTCTCTCCC ACCCAAGTTT    5220

GTACTCTTTT CTTTCTCTCG GTTTTATTTT TTGTTTTTGT TTGTTTGTTT GAGACAGGCT    5280

TTCGCTCTGT CTCCCAGGCT GGAGTGCAGT GGCGCGATCT CGGCTCACTG CAGCCTCCAC    5340

CTCCCAGGTT CAAGCGATCC GCCTGCCGAG TAGCTGGGAT TACAGGCGCC CGCCACCACG    5400

CCTGGCTAAT TTTTGTGTTT TGTAGAGATG GGGTTTCGCC ATGTTGGCCA GGCTGGCCTC    5460

GAACTGCTGA GCTCAAGCAA TCCGCCCGCC TCGGCCTCAC AAAGTCCTAG AATTTTAGGC    5520

ATGAGCCTCC GGGTCCGGCC TGTGCTAATC CTTTCTGTCC TTGGTTCTTT ATTTCTCTTC    5580

TCTCTTTTTC TTAGTCCCTT TTGTTCTTTC CCTCTCCCGT TCAGTTGGCT GTCGTTTGAG    5640

CCTCCACCTT TTCACTCCCT CCTTTCCACC ACGATGCCGA GCCCTGCCTT GGATGGGGAC    5700

CATCAGCGAT GACCACAATG ACCTCTCCCT TACCAGGCAG CTCCAGGCAG TGTTCCTGCA    5760

CCGCCTTTCC CAGGGCTTGG GGGCTTTTTC TAGTGGGCTT TGAGCTGCTC AATCTGGCCT    5820

CTGCAGGGCC GGCTCCCAGC CCTTCCAACC TCCTCACAGC CCGACCTGGG ACCTAGCCAA    5880

TTCCCGGAGA GTCTCTGTCC CATCGTGACC CCCTCACAAC TCTCCCACTC ACCAAAGTCT    5940

GATGACTGTG CTAGGGGGTG CTTATATAGA GTACTGAGTG TTACAAAAGC AGAAGTCTGG    6000

ATGAGAACCA ATTTGTGATA TTAAGCAGGT GGGGTGGGGG TGGGGAGTGT ACCTAGGTTC    6060

ATTTTCCGCC CTGCTTTTCC CCTTTCCAGT GTGTGCACTT AACCAGTCCC TGGGCCCTGT    6120

TCCCCATCCC CCTCCAAGGC ATGGATTGGG TGGGCTTGTG TGTCTTGGGG CAGGTGGCCC    6180

TTTCTAAACT CTCTGCCTTT GCTCACCCAC AGGACACATA GTATGACCAT TAGGTGTTTC    6240

GTCTCCCACC CATTTTCTAT GGAAAACCAA GGGGATCGGG CCATGATAGC CACTGGCAGC    6300

TTTGAAGAAC GGGACACCTT TAGAGAAGCT TGATCTTGGA GGCCTCACCG TGAGACCTTA    6360

CAAAGCCGGG TAAGAGTCCA GTCCAAGGAA GAGGTCTCTT GCTGCCTCCT AACCCTGTGG    6420

TCTAGGGGCA GGAGTCAGCA GGGCATTAAC AAAAATAATT ACCATCCCCA CCCCCGACAG    6480

TGAAGTGGCT CTTTCCAGTT CACAGAGCAC TCTCACACCT CCCCGCTCTC ATTCTGGCCC    6540

TTCAGCTGAC TCGGACAAGC CAAGGATCTT GGTCCCCATT TTATAAAGGA GAAAACTGAG    6600

GCCCACGTGT AACAGTGATT GGCCCCAAGT CATCCCGGGA GCCAGCAGAA GAGCTAGGAC    6660

AGGAACCTAT TGTTCTAACT TCATATTGAT GCTAGCTTTT GACTATCCCT GAAACCGAGA    6720

TTGGTAATCA GCCCGGCTCT GAAACTGGTT ATTTGCTGGG GACTGTAAAA TAGGATTAAC    6780

TATTTCTAGT CCTGCATTTT AATTGCTGTT AGTAGGGCCA TCTTACCCAC CCTCTGAAGG    6840

ACCTGACTTG GCAAGCCCAA GGCAACATTC AGAATATGGC AGCTGAACCT CTGTGCACTT    6900

GTCTTTGGGC AGCAGCTGGG TCTTATTCTT CTCTGGCCTT CACAACATCC TGCAACCCAG    6960

CTCAAGGTCA GGAATGTGAC AGACTCATGT CATCATATCT CTGATGCCCA GAGAAGGGAT    7020

ACCATTTGCC TGAGCCTTCT CAGTACTGTT AATCAGCCT GTGAGAACTT TCCTTGTGAA    7080

AGGCCCTGTC TGTGCCTGGG GCTGATAAAA CAGCAAGAAC GAACTGAGGA GCTGGGCAGC    7140

AGTGCAAAGC AAATACTACC AGCTTTGGTG CCTGTAAGTG TGGCTCTTAC TCATCTCACA    7200

TGGAAATAAG GGCAGCCACC TTGCAGGGCT GCTCTGAGGA TTGAGCTAAT ACAGTGCCCT    7260
```

-continued

```
GGGCGTTGGG GTGGGGAAAG TTGTGGAGCA CCTCCTGGGG GAAGGGGGTG TCAGAGCAGG    7320

GAATCTGGGG AGTCCGAGGG CACCTTCATC AACCCAATCT GTCATTTGAG CACCAGTCTT    7380

CACTGAGCCT CGTGGGCAAG CTGGAGGGAA ACAGGAATAA GGTCAGGCCC TGTTCTATAG    7440

GTCCCAGTGT AGTTGCTATG GTGAGTATCT TCATTTCCCT GCTTGCCCCA GCCACCTGGA    7500

GTGAGAAGCC CAAGAGGAAG CTGGGTGAGC TGTTTGTTTC CATGGGTCTC TGTGTTCACA    7560

GCTGACTCCC TTCACCAGCC AGCCCTTTCA CCTGAGCCCC AGCAACAAAG GCAGTCAGGC    7620

GGGGCTCAAA GCAGCTGCTC CAATGAAGTC AAAGAAATAA GCTCAGGGGA AGAAGCAGGT    7680

CACCCTCCCC CACTAGGGTG CTGGGCTCAC TTCCTCCTGG GGCAGTGGAG GAGGGTGTGG    7740

TTCCAACTCA GAACAAAATG GGGCTTTTGG TTTACTTTAT CACTCTTCAC AGCTCTGACC    7800

TGGACCCCTC ATCCCTGCCT GTCTTGTGGT GTAAGTGCGG ATCCCCCTAA GTTGGAGGAA    7860

AGGAAACTGG CCCAAACAAA AAGGAGAGCA GTTTTCTCTG CATCACATGG TAGGCCAGGA    7920

GGAGTCTAAT GCCCCAGAGT TTACTCTCAG CCCCCAAAAT CACCTAGCTA AATGTTACCT    7980

TATCTAAGAA GTCCTTAGGT TTTTTGGGGT TTGTTTTTTT TTTTTTGAG ACAAGGTCTC     8040

ACTCTCTCAC CCAGACTGGA GCACAGTGGC ACAATCACAG CTCACTGCAG CCTCAACCTC    8100

CTGGGCTCAA GCAATCGTCC CAAGTAGCTG GGACTATAGG CCTGCACCAC CATGTCCAGC    8160

TAATTTATTT TTATTTATAT TTTTTAGACA GGGTCTCATT ATGTTGCCCT GGCTGGTCTT    8220

GAACTCCTGG GTTCAAGCAG TCCTCCCACC TCTGCCTCCC AAAGTGCTAG GTTTTTTTT     8280

GTTTGTTTGT CTGTTTTTTG AAACAGAGTC TTGCTCTGTC GCCTAGGCTG GAGTGCAGTG    8340

GCACGATCTC AGCTACTGCA ACCTCCACCT CCTGGGTTCA AGTGATTCTC CTGCCTCAGC    8400

CTCCTAAGTA GTTGGGAATA CAGGCGTGTG CCAACACACC CAGCTCATTT TGTATTTTT    8460

AGCGGAGATG GGGTTTTGCC ATGTTGGCCA AGCTGGTCTC AAACTCCTGA CCTCAGGTGA    8520

TTCGCCCGCC TCAGCCTCCC AAAGTGCTGG GTTTACAGGC GTGAGCCACC ACACCCAGCC    8580

CAAGAAGTCT TTTCTGATCA CCCACTCTTC CTTCTCTCCC AATGGCATTA GTTGTTCCCT    8640

CCTTTGCATT TTGAGAGTAT GTCCTGTAAG CCCCAAATGC AGCTTGAATC ATCTGCCCAT    8700

CCACCCCCTG TGCCCAACAG TAAGCCTCCT CTAGAGTAGA TACTATCTCC TGCATCTCAG    8760

TGAACCACTG CCCAGCAAAG CAGTCTTGCT AAAACAATGA CTCTAGAGAT CCTAAGCTGT    8820

GTGAGAGCTG GAGGAGAGAA TTAGACTGAT GGTCTGGGAA GGGATTGAAT TAGTCATCTT    8880

GTACCTTTTC TTCTTGACTT AAGTTCCAGA CCTGTAGCAA CCATTCCTGC TTAGACATCC    8940

AGAACATAAG CCTATGGGTC TGTGCCTGTT GGGTCTTAGT CTGGGTGAAA CTTTTCTCTA    9000

CTTCTGTCAG CTCTCCAGAT GAACCACAGA AGCAGGAATG TGGGCATCAT CAGTGAAATC    9060

TCTGCATACA GCAGACAAAG GGCTGGTCCA GTGGCTGTTT ATGAGGCAGC GCTAGGAGAG    9120

CTCTGATCCA GACTCTCCCT GCAGTGAAAG GGAGGGAGCC CTTCATGAAG TATTGACTGC    9180

TTGAGCAGGA ATTGCTTCAC CAGCACCTAA CTGAGTGCCT CTCGAGCTCA CATCGGTTTT    9240

CCCTCATGAG GCCACTTGGA GTCTTGCTGA GGGACTTGGT TCTATTAGGG AAGGTGAGTT    9300

TGGGGATGGT GAGCAGGGAG GGCCTGGGGA CATTGTGGCT AATGGGGCTT TTCTCCTCTT    9360

GGCTTAGATT CCGGCAGAGT TCCTCTATCT CGTCTTGTTG CTGATTAAAG GTGCCCCTGT    9420

CTCCAGTTTT TCTCCATCTC CTGGGACGTA GCAGGAAATC AGCATCATGG TTGGGTTCAA    9480

GGCCACAGAT GTGCCCCCTA CTGCCACTGT GAAGTTTCTT GGGGCTGGCA CAGCTGCCTG    9540

CATCGCAGAT CTCATCACCT TTCCTCTGGA TACTGCTAAA GTCCGGTTAC AGGTGAGGGG    9600

ATGAAGCCTG GGAGTCTTGA TGGTGTCTAC TCTGTTCCCT CCCCAAAGAC ACAGACCCCT    9660
```

```
CAAGGGCCAG TGTTTGGAGC ATCGAGATGA CTGGAGGTGG GAAGGGCAAC ATGCTTATCC    9720

CTGTAGCTAC CCTGTCTTGG CCTTGCAGAT CCAAGGAGAA AGTCAGGGGC CAGTGCGCGC    9780

TACAGCCAGC GCCCAGTACC GCGGTGTGAT GGGCACCATT CTGACCATGG TGCGTACTGA    9840

GGGCCCCCGA AGCCTCTACA ATGGGCTGGT TGCCGGCCTG CAGCGCCAAA TGAGCTTTGC    9900

CTCTGTCCGC ATCGGCCTGT ATGATTCTGT CAAACAGTTC TACACCAAGG GCTCTGAGCG    9960

TGAGTATGGA GCAAGGGTGT AGGCCCCTTG GCCCTTTTTT CTCAGTGATG ATTGATCTTA   10020

GTTCATTCAG CCATATAGTT TTTTAGGCCC CACGATCCCT AGGAAGATCA GGGAACAGA    10080

GAACTGGAAG GGGCCCTGGT CCTCCACATA GTTCCTAAGC ACCTGGGCTA TACCAGGCTC   10140

TGAGCAGGGC GTCATCCCAT CACAGTCTTC AACACCACCT TGGGAGTAGG TAGTATCATC   10200

CCAGTGTTAT AGAAGAAGAG ACTGAGGTGG GAAGGCAGTG GGTAGAGTGG GGACTTGGCC   10260

AGGGGCACAC AGTAGAGAGC CAGAAAACAC ACAGTAGAGA GCCAGGACAC TCGTCTCTAA   10320

GGCCAGCGTT CTTCCCTTTC ACCTCCTTAG TATGCCATGC CAACCCTCCA TTTTACACAT   10380

GACGAAACAG AGCCCCAGAC AAAAGGTTGT CTTTCCCAGA TCACATGGCA GGAAGAAGTA   10440

AAGCTGACCT GAGATCCCAA GTCTTAGGAA TCCCAGTCCT CAGAAAGCCA CTTCTCTCTG   10500

AGCCTTGGTT TTCACATTTG TCAGATGGAA ATGATTGTGA TTTCTCAGGG CTGTTGAGCA   10560

GGTAAATGAA AATGTTTTAT GAAAGAAAGC ACCAAGTTTC ATTTTGGTCT TAGCCCTTGC   10620

TATGTCCCTA GCAAGAAGTA GATATTCATA GGGATATTTT GTTTGATGTG AGGAGTTCTT   10680

ACAGCAAGAG CTTGTAGAAG GCCAAAAGCT TCTGGATTCT ATTCCCAAAA GCAGGAGATG   10740

ACAGTGACAG GGTGGTTTTG GTGAGGAGAG ATGAGGTAGA AAATGAGTGC AAGCCCGCTG   10800

GCCACTGACC CCATGGCTCG CCCACAGATG CCAGCATTGG GAGCCGCCTC CTAGCAGGCA   10860

GCACCACAGG TGCCCTGGCT GTGGCTGTGG CCCAGCCCAC GGATGTGGTA AAGGTCCGAT   10920

TCCAAGCTCA GGCCCGGGCT GGAGGTGGTC GGAGATACCA AAGCACCGTC AATGCCTACA   10980

AGACCATTGC CCGAGAGGAA GGGTTCCGGG GCCTCTGGAA AGGTGTGTAC CAGTTGTTTT   11040

CCCTTCCCCT TTTCCTCCTC CCCGATACTC TGGTCTCACC CAGGATCTTC CTCCTCCTAC   11100

AGGGACCTCT CCCAATGTTG CTCGTAATGC CATTGTCAAC TGTGCTGAGC TGGTGACCTA   11160

TGACCTCATC AAGGATGCCC TCCTGAAAGC CAACCTCATG ACAGGTGAGT CATGAGGTAG   11220

ACGGTGCTGG GTCTCACCCT TCCCCCATGC CAGGAGCAGG TGCGGGGGTC TAGCTGACAC   11280

CAGAAGACCA CATCTTTTCA TCCTATTTGC CCTTTGCAGG GAGAGTAAGA TATCTCTTAC   11340

TTGCCATATT GAAGCCAATT GGGATGAAGC TCCCACTTTG CACATTGAGG AACTGAGGCT   11400

AGATTGGCAA AATGACTCTT TCAGGTCCTC AGAAGATGTC TCAGCTGGAG TCCCTGTCTG   11460

TTTTTGTTTT TTTGTTTGTT TGTTTTTTGT TTTTTTGAG ATAGAGTCTC ACTCTGTTAC    11520

CCGTGTAATC TCAGCTCACT GCAACCTTCT CCTCCTGGGT TCAAGCGATT CTTGTGCCTC   11580

AGCCTCCCGA GTAGCTGGGA TGACAGGTGT GCACCAGCAC ACTGGCTAAT TTTTGTATTT   11640

TTAGTAGAGA TGGAGTTTCA CCATGTTAGC CAGGCTGGTC TCGAACTCCT GGCCTCAAGT   11700

GATCTGCCCA CCTTGGCCTC CCAATGTGCT GGGATTACAG GTGTGAGCCT CTGCGCCCCA   11760

TCCTCTTGTT TGTTTTTGA GACAGGGTCT TGCTCGGTTG CCCAGGCTGG AGTGCAGTGG    11820

GGTGATTAAT GGCTCATTGC AGCCTCGACC TCCCTGACTC AAGCAATCCT CCCACCTCAG   11880

CCTCCTGAGT AGCTGGGGCT GACTACAGGC ATGCACACTG TGCCTGGCTA ATTTTTGTAT   11940

TTTGTAGAGA CAGGGTTTTT GCCATGTTAC CCAGTCTGGT CTTGAACTCC TGGGCTCAAG   12000

TGATCCACCC ACCTCGGCCT CCAAAAGAAG TCCTGGATTA CAGGCATGAG ACATTGTGCC   12060
```

```
CAGCCTCTCT GTCTCTTTAA AATCATGAAA ACTCGTAGCT ACTTAAGTAA TTCTCCTGCC    12120

TTCTGGAATG ATGGGTGAAG ATCTTGACTG CCTTGCCTGC TCCTCCTTGG CAGATGACCT    12180

CCCTTGCCAC TTCACTTCTG CCTTTGGGGC AGGCTTCTGC ACCACTGTCA TCGCCTCCCC    12240

TGTAGACGTG GTCAAGACGA GATACATGAA CTCTGCCCTG GGCCAGTACA GTAGCGCTGG    12300

CCACTGTGCC CTTACCATGC TCCAGAAGGA GGGGCCCCGA GCCTTCTACA AAGGGTGAGC    12360

CTCTGGTCCT CCCCACCCAG TTCAGGCCTC TTGGCTATGC ATGTCTATTG TGGGTGGGAG    12420

AGAACCACCT GGAAGTGAGT AGCAGCCAAG TGTGACTATT TCTGATCCTG GTCCTGGCAT    12480

TTCACCAGCA TTCACCTATC CCCTTAATTC CTTCCTCCCA GAATTGCTAC CATCACTGTT    12540

TATTAGGTGT TAAATGGAGA CTCAAAGGGA ATTCATGCTT ATAGCCAAGC AGCTGTGAGC    12600

TCAGTTCATT GAGTCCTCCC AGCCTCCTTT GGGACAGAGC AACTGGGTTG GATTGAATAC    12660

CAGGCCCAGT GAGGGAAGTG GGAGGTGGAG GTGCCCCCAT GACCTGTGAT TTTTCTCCTC    12720

TAGGTTCATG CCCTCCTTTC TCCGCTTGGG TTCCTGGAAC GTGGTGATGT TCGTCACCTA    12780

TGAGCAGCTG AAACGAGCCC TCATGGCTGC CTGCACTTCC CGAGAGGCTC CCTTCTGAGC    12840

CTCTCCTGCT GCTGACCTGA TCACCTCTGG CTTTGTCTCT AGCCGGGCCA TGCTTTCCTT    12900

TTCTTCCTTC TTTCTCTTCC CTCCTTCCCT TCTCTCCTTC CCTCTTTCCC CACCTCTTCC    12960

TTCCGCTCCT TTACCTACCA CCTTCCCTCT TTCTACATTC TCATCTACTC ATTGTCTCAG    13020

TGCTGGTGGA GTTGACATTT GACAGTGTGG GAGGCCTCGT ACCAGCCAGG ATCCCAAGCG    13080

TCCCGTCCCT TGGAAAGTTC AGCCAGAATC TTCGTCCTGC CCCCGACAGC CCAGCCTAGC    13140

CCACTTGTCA TCCATAAAGC AAGCTCAACC TTGGCGTCTC CTCCCTCTCT TGTAGCTCTT    13200

ACCAGAGGTC TTGGTCCAAT GGCCTTTTTG GTACCTGGTG GGCAGGGGAG GAACCACCTG    13260

ACTTTGAAAA TGGGTGTGAT CCACCTTCCA CCTCCAGCAT CCAATCTGAA GCCCGTGTAG    13320

GTCATCTGGT CCATTTCTCT CTAGACCCAG GCCCTGTACT AACATGGGGA GTGCAGGAGC    13380

CACCTGAGAG ACAGCAGTGC CTCCCCTTCC TTTGCCGGGC CACTTGAGCT CTTACTCAGA    13440

ATCTGGTACT CTAGTGCCTG CCATCCCAAC CCCCCACCCC AGCCGCAGGC CTGTTTATCT    13500

GCACAACAAG AGTGCTCCTG TGTGCCCTGC ATCTCCTGCA GTTCCAGAGG AACATGAGAC    13560

TCTTAGATGC TGTTGACTTT ATTTTATTCC ATTTTACAAA TGGAAGGAAG ACCCACCTCC    13620

CCCAAAGTCC CAGACCTTGT GAGAACAAGT CAGTCAGCCT CCTTCCACCC TCCACAGCCA    13680

CAGCCACACC CACAGAGGAA ATGTTACTGA ACTGGGTGGA GCAGGCCCTG ACTCCACAGA    13740

GGGTGGGTGG AGGCTGCAGG GCAAACATCT GGTCTCTGCC TGAGGATACT TTCCATTTGT    13800

GTTTTTTGTT GTTTTGAGAC AGAGTCTCAC TTGCTGTCAC CCAGGCTGGA GTGCAGTGGT    13860

GCAATCTTGG CTCACTGCAA CCTCTCCCAG GTTCAGGCGA TTCTCCTGCC TCAGCCTCCC    13920

AAGTAGCTGG GATTACAGGC ATACACCATC ATACCTGGCT AATTTTTGTG TTTTTGGTAG    13980

AAACGGGGTT TTGCCATGTT GGCCAGGCTG GTCTCAAACT CCTGACCTCA AGTGATCCAC    14040

CTACCTCAGC CTCCCAAAGT GCTGGGATTA CAGGCATGAG CCACTGTGCC TGGCCAGGAT    14100

ATTTTCCATT TGGAGTCTCA CCACCACAAC CCCCCTCCAC CTGCCCCTGC CCCAGCTAGG    14160

CATCCAAGGA GGCCGCAAGA AGCCAGGGCC TTGGCTGCAC AGGGGTCTCC GCTTCTCTGT    14220

CCCTGTTCTT ATCACCTGCA CTCAGAGGCA GGTGGGCAGG GGTACTACAA TTTCAAGGAG    14280

TGGAGACTGT GAGGTCCTGG AATCCCAAGG CATCTCCTGT AGGGCTGGGC CCTTAGAATT    14340

ATGTCACTCA GACCCAGTTT GTAGGTGTCT GAAGAAACTG AGGCCTGACA CAGGTGATGC    14400
```

-continued

```
AGGCAAGAAC ACCCAGAAAG TCCACTACTG AACTGGGACC GGGACCCAGT CCTCCTTCCC    14460

CTTGTGGACT CCCCCAGAGA CCAGTGCTGG GGTCCTTGGG GAAGCCTGTT TGGCAGCTGT    14520

GGAGCTAGGC CCTGAGAACA CGACCACCCT CCCTCTTCCC TCAGCCTCAA GCCGCTGAAG    14580

CCACTGCTGC TTCGCCGCCT CGTAAGCCCA ATGGTCAGAG CTGGAGGCTA GACCCTTCAG    14640

TGCTTGGGTT GAGGGCCAGG GTGTTAGATT GGTTTTTGGA GAAGGAACGA GGGCCCAGGA    14700

TTCTTCAGCT TCTTAGTTTT TGACAAATTG AGCTGAGGCC CCATAGTCCT CGGGAGGGAC    14760

AGGGTTGAGT GCCATAAGTC GGCAAACCAG GGTAAAGGTG ACAGGCAGCT CAGCCAGGCT    14820

GCAGGGGGTG GCATATACAG AGGACCTGGC CACTACTTTA TGTACCTTCT TACACTAATT    14880

CTGTGAGGCA GGCTGTTTGT TAGCTCTGCT CTGGACGGGA AGAAGTAGGG GCAGTTTGGT    14940

AGGTGTGTGT CAAAGCTAAA CAGGCTGGGT GGGCATGAGC AAGTCAGCTG GTTCATTCAG    15000

CAGCCTTAAT AGACACGAGG CTACCCAACT TCACTGTGGT TCTGGGTGTG GCCTTAGGAC    15060

AATGAGCTGG GAACAGTGGT AGGAACCACT GGAAAACATA CCAGTGGGTC TCATTCATTC    15120

TGATCACAGG TAGATCACTT CTCTTTGGTT CCCAACCCTT TAATGCCTAT TAAG          15174
```

What is claimed is:

1. A method of modulating respiratory chain uncoupling in a cell or thermogenesis in a tissue, the method comprising contacting the cell or tissue with a miRNA agent that increases activity of at least one mitochondrial uncoupler selected from UCP1 or UCP2; wherein the miRNA agent is hsa-miR-515-3p or an agomir thereof.

2. The method of claim 1, wherein the cell is a pre-adipocyte, adipocyte, adipose tissue derived mesenchymal stem cell, hepatocyte, myocyte, or a precursor thereof.

3. The method of claim 1, wherein the tissue is brown fat, white fat, subcutaneous adipose tissue, liver or muscle.

4. The method of claim 3, wherein the tissue is contacted with the miRNA agent ex vivo.

5. The method of claim 1, wherein the mitochondrial uncoupler is UCP1 or UCP2.

6. The method of claim 1, wherein the miRNA agent is linked to targeting moiety.

7. The method of claim 6, wherein the targeting moiety is an aptamer.

8. The method of claim 6, wherein the targeting moiety delivers the miRNA agent to a specific cell type or tissue.

9. The method of claim 1, wherein the miRNA agent directly binds to the mRNA, 3'UTR, 5'UTR, coding, or promoter regions of UCP1 or UCP2.

10. The method of claim 1, wherein the miRNA agent modulates the activity of an activator or repressor of a mitochondrial uncoupling protein.

11. The method of claim 10, wherein the miRNA agent directly binds to the mRNA, 3'UTR, 5'UTR, coding, or promoter regions of the activator or repressor.

12. The method of claim 1, wherein the agent is an agomir of hsa-miR-515-3p.

* * * * *

UNITED STATES PATENT AND TRADEMARK OFFICE
CERTIFICATE OF CORRECTION

PATENT NO. : 9,034,839 B2
APPLICATION NO. : 13/826775
DATED : May 19, 2015
INVENTOR(S) : Marc Thibonnier Page 1 of 1

It is certified that error appears in the above-identified patent and that said Letters Patent is hereby corrected as shown below:

On the Title page in items (71) Applicant and (72) Inventor, delete "Naples, FL" and insert --Austin, TX-- therefor.

Signed and Sealed this
First Day of September, 2015

Michelle K. Lee
*Director of the United States Patent and Trademark Office*

SEQUENCE LISTING

<160> NUMBER OF SEQ ID NOS: 383

<210> SEQ ID NO 1
<211> LENGTH: 16
<212> TYPE: DNA
<213> ORGANISM: Homo sapiens

<400> SEQUENCE: 1
cctctctgct tcttct                                                    16

<210> SEQ ID NO 2
<211> LENGTH: 10
<212> TYPE: DNA
<213> ORGANISM: Homo sapiens

<400> SEQUENCE: 2
ctccttggaa                                                           10

<210> SEQ ID NO 3
<211> LENGTH: 13
<212> TYPE: DNA
<213> ORGANISM: Homo sapiens

<400> SEQUENCE: 3
ttgcccttgc tca                                                       13

<210> SEQ ID NO 4
<211> LENGTH: 16
<212> TYPE: DNA
<213> ORGANISM: Homo sapiens

<400> SEQUENCE: 4
acgtcataaa gggtca                                                    16

<210> SEQ ID NO 5
<211> LENGTH: 16
<212> TYPE: DNA
<213> ORGANISM: Homo sapiens
<220> FEATURE:
<221> NAME/KEY: misc_feature
<222> LOCATION: (7)..(10)

<223> OTHER INFORMATION: n is an a, t, g, c, other or unknown

<400> SEQUENCE: 5
rgktcannnn rgktca                                               16

<210> SEQ ID NO 6
<211> LENGTH: 14
<212> TYPE: DNA
<213> ORGANISM: Homo sapiens

<400> SEQUENCE: 6
gctcatactg acct                                                 14

<210> SEQ ID NO 7
<211> LENGTH: 13
<212> TYPE: DNA
<213> ORGANISM: Homo sapiens

<400> SEQUENCE: 7
gttaatgtgt tct                                                  13

<210> SEQ ID NO 8
<211> LENGTH: 17
<212> TYPE: DNA
<213> ORGANISM: Homo sapiens

<400> SEQUENCE: 8
tgaccacagt ttgatca                                              17

<210> SEQ ID NO 9
<211> LENGTH: 20
<212> TYPE: DNA
<213> ORGANISM: Homo sapiens

<400> SEQUENCE: 9
aatgtaatgc agataagcta                                           20

<210> SEQ ID NO 10
<211> LENGTH: 20
<212> TYPE: DNA
<213> ORGANISM: Homo sapiens

<400> SEQUENCE: 10
acatgtttta attacaattc                                           20

<210> SEQ ID NO 11
<211> LENGTH: 12
<212> TYPE: DNA
<213> ORGANISM: Homo sapiens

<400> SEQUENCE: 11
gattggcagc tt                                                   12

<210> SEQ ID NO 12
<211> LENGTH: 23
<212> TYPE: DNA
<213> ORGANISM: Homo sapiens

<400> SEQUENCE: 12
gatttttaat gtttagagtc cag                                       23

<210> SEQ ID NO 13
<211> LENGTH: 20

```
<212> TYPE: DNA
<213> ORGANISM: Homo sapiens

<400> SEQUENCE: 13
tttagagctg gagggtactt                                          20

<210> SEQ ID NO 14
<211> LENGTH: 20
<212> TYPE: DNA
<213> ORGANISM: Homo sapiens

<400> SEQUENCE: 14
tttagagctg gagggtactt                                          20

<210> SEQ ID NO 15
<211> LENGTH: 19
<212> TYPE: DNA
<213> ORGANISM: Homo sapiens

<400> SEQUENCE: 15
gacagaggaa cagtttgag                                           19

<210> SEQ ID NO 16
<211> LENGTH: 22
<212> TYPE: DNA
<213> ORGANISM: Homo sapiens

<400> SEQUENCE: 16
attttggcag gattgctact ag                                       22

<210> SEQ ID NO 17
<211> LENGTH: 19
<212> TYPE: DNA
<213> ORGANISM: Homo sapiens

<400> SEQUENCE: 17
ttttgagatc tatacctgg                                           19

<210> SEQ ID NO 18
<211> LENGTH: 23
<212> TYPE: DNA
<213> ORGANISM: Homo sapiens

<400> SEQUENCE: 18
attttaagct aaatccaagg att                                      23

<210> SEQ ID NO 19
<211> LENGTH: 22
<212> TYPE: DNA
<213> ORGANISM: Homo sapiens

<400> SEQUENCE: 19
tgaccatttc tggagtgcaa tt                                       22

<210> SEQ ID NO 20
<211> LENGTH: 10
<212> TYPE: DNA
<213> ORGANISM: Homo sapiens

<400> SEQUENCE: 20
acagtttgat                                                     10

<210> SEQ ID NO 21
```

```
<211> LENGTH: 10
<212> TYPE: DNA
<213> ORGANISM: Homo sapiens

<400> SEQUENCE: 21
acagtttgag                                                              10

<210> SEQ ID NO 22
<211> LENGTH: 19
<212> TYPE: DNA
<213> ORGANISM: Homo sapiens

<400> SEQUENCE: 22
ctggagtgca attgtgtga                                                    19

<210> SEQ ID NO 23
<211> LENGTH: 20
<212> TYPE: DNA
<213> ORGANISM: Homo sapiens

<400> SEQUENCE: 23
ttttaatgtt tagagtccag                                                   20

<210> SEQ ID NO 24
<211> LENGTH: 22
<212> TYPE: DNA
<213> ORGANISM: Homo sapiens

<400> SEQUENCE: 24
tgatgacatc tctaacaact tc                                                22

<210> SEQ ID NO 25
<211> LENGTH: 20
<212> TYPE: DNA
<213> ORGANISM: Homo sapiens

<400> SEQUENCE: 25
agaaactgag tgaaatgcag                                                   20

<210> SEQ ID NO 26
<211> LENGTH: 17
<212> TYPE: DNA
<213> ORGANISM: Homo sapiens

<400> SEQUENCE: 26
tgaccatttc tggagtg                                                      17

<210> SEQ ID NO 27
<211> LENGTH: 13
<212> TYPE: DNA
<213> ORGANISM: Homo sapiens

<400> SEQUENCE: 27
tactctgaat gtt                                                          13

<210> SEQ ID NO 28
<211> LENGTH: 16
<212> TYPE: DNA
<213> ORGANISM: Homo sapiens

<400> SEQUENCE: 28
ttaaccacag ttgtca                                                       16
```

```
<210> SEQ ID NO 29
<211> LENGTH: 20
<212> TYPE: DNA
<213> ORGANISM: Homo sapiens

<400> SEQUENCE: 29
caagttcact agaatacaag                                              20

<210> SEQ ID NO 30
<211> LENGTH: 22
<212> TYPE: DNA
<213> ORGANISM: Homo sapiens

<400> SEQUENCE: 30
aaggttacag gctgccagac at                                           22

<210> SEQ ID NO 31
<211> LENGTH: 13
<212> TYPE: DNA
<213> ORGANISM: Homo sapiens

<400> SEQUENCE: 31
gtgtgaatga atg                                                     13

<210> SEQ ID NO 32
<211> LENGTH: 23
<212> TYPE: DNA
<213> ORGANISM: Homo sapiens

<400> SEQUENCE: 32
taggcatgaa cctactctga atg                                          23

<210> SEQ ID NO 33
<211> LENGTH: 20
<212> TYPE: DNA
<213> ORGANISM: Homo sapiens

<400> SEQUENCE: 33
aaactgagtg aaatgcagtt                                              20

<210> SEQ ID NO 34
<211> LENGTH: 20
<212> TYPE: DNA
<213> ORGANISM: Homo sapiens

<400> SEQUENCE: 34
aaactgagtg aaatgcagtt                                              20

<210> SEQ ID NO 35
<211> LENGTH: 23
<212> TYPE: DNA
<213> ORGANISM: Homo sapiens

<400> SEQUENCE: 35
tttattaacc acagttgtca gtt                                          23

<210> SEQ ID NO 36
<211> LENGTH: 11
<212> TYPE: DNA
<213> ORGANISM: Homo sapiens

<400> SEQUENCE: 36
aagtatcctt t                                                       11
```

```
<210> SEQ ID NO 37
<211> LENGTH: 10
<212> TYPE: DNA
<213> ORGANISM: Homo sapiens

<400> SEQUENCE: 37
atgggacaca                                                              10

<210> SEQ ID NO 38
<211> LENGTH: 11
<212> TYPE: DNA
<213> ORGANISM: Homo sapiens

<400> SEQUENCE: 38
ttattttccc t                                                            11

<210> SEQ ID NO 39
<211> LENGTH: 10
<212> TYPE: DNA
<213> ORGANISM: Homo sapiens

<400> SEQUENCE: 39
tgacaactgt                                                              10

<210> SEQ ID NO 40
<211> LENGTH: 10
<212> TYPE: DNA
<213> ORGANISM: Homo sapiens

<400> SEQUENCE: 40
agggaactga                                                              10

<210> SEQ ID NO 41
<211> LENGTH: 10
<212> TYPE: DNA
<213> ORGANISM: Homo sapiens

<400> SEQUENCE: 41
tgtgaactgg                                                              10

<210> SEQ ID NO 42
<211> LENGTH: 10
<212> TYPE: DNA
<213> ORGANISM: Homo sapiens

<400> SEQUENCE: 42
acttttgcgg                                                              10

<210> SEQ ID NO 43
<211> LENGTH: 10
<212> TYPE: DNA
<213> ORGANISM: Homo sapiens

<400> SEQUENCE: 43
ttcctttatc                                                              10

<210> SEQ ID NO 44
<211> LENGTH: 10
<212> TYPE: DNA
<213> ORGANISM: Homo sapiens

<400> SEQUENCE: 44
ttcctctgtc                                                              10
```

```
<210> SEQ ID NO 45
<211> LENGTH: 10
<212> TYPE: DNA
<213> ORGANISM: Homo sapiens

<400> SEQUENCE: 45
tagcttatct                                                              10

<210> SEQ ID NO 46
<211> LENGTH: 11
<212> TYPE: DNA
<213> ORGANISM: Homo sapiens

<400> SEQUENCE: 46
ttccctatct c                                                            11

<210> SEQ ID NO 47
<211> LENGTH: 9
<212> TYPE: DNA
<213> ORGANISM: Homo sapiens

<400> SEQUENCE: 47 cagcaagca                                                                9

<210> SEQ ID NO 48
<211> LENGTH: 10
<212> TYPE: DNA
<213> ORGANISM: Homo sapiens

<400> SEQUENCE: 48
aagctgccaa                                                              10

<210> SEQ ID NO 49
<211> LENGTH: 11
<212> TYPE: DNA
<213> ORGANISM: Homo sapiens

<400> SEQUENCE: 49
agttcttcac a                                                            11

<210> SEQ ID NO 50
<211> LENGTH: 10
<212> TYPE: DNA
<213> ORGANISM: Homo sapiens

<400> SEQUENCE: 50
cattttcttg                                                              10

<210> SEQ ID NO 51
<211> LENGTH: 10
<212> TYPE: DNA
<213> ORGANISM: Homo sapiens

<400> SEQUENCE: 51
ccaatccttg                                                              10

<210> SEQ ID NO 52
<211> LENGTH: 10
<212> TYPE: DNA
<213> ORGANISM: Homo sapiens

<400> SEQUENCE: 52
```

```
ccttttcatg                                                                10

<210> SEQ ID NO 53
<211> LENGTH: 10
<212> TYPE: DNA
<213> ORGANISM: Homo sapiens

<400> SEQUENCE: 53
gtaaccttcc                                                                10

<210> SEQ ID NO 54
<211> LENGTH: 10
<212> TYPE: DNA
<213> ORGANISM: Homo sapiens

<400> SEQUENCE: 54
cagagtaggt                                                                10

<210> SEQ ID NO 55
<211> LENGTH: 10
<212> TYPE: DNA
<213> ORGANISM: Homo sapiens

<400> SEQUENCE: 55
ccttgtaggc                                                                10

<210> SEQ ID NO 56
<211> LENGTH: 10
<212> TYPE: DNA
<213> ORGANISM: Homo sapiens

<400> SEQUENCE: 56
ctgttcctct                                                                10

<210> SEQ ID NO 57
<211> LENGTH: 10
<212> TYPE: DNA
<213> ORGANISM: Homo sapiens

<400> SEQUENCE: 57
atccttggat                                                                10

<210> SEQ ID NO 58
<211> LENGTH: 10
<212> TYPE: DNA
<213> ORGANISM: Homo sapiens

<400> SEQUENCE: 58
aattgcactc                                                                10

<210> SEQ ID NO 59
<211> LENGTH: 10
<212> TYPE: DNA
<213> ORGANISM: Homo sapiens

<400> SEQUENCE: 59
aagtgcctgc                                                                10

<210> SEQ ID NO 60
<211> LENGTH: 10
<212> TYPE: DNA
<213> ORGANISM: Homo sapiens

<400> SEQUENCE: 60
```

```
tctcaaactg                                                                10

<210> SEQ ID NO 61
<211> LENGTH: 10
<212> TYPE: DNA
<213> ORGANISM: Homo sapiens

<400> SEQUENCE: 61
actggccttg                                                                10

<210> SEQ ID NO 62
<211> LENGTH: 10
<212> TYPE: DNA
<213> ORGANISM: Homo sapiens

<400> SEQUENCE: 62
attcattcac                                                                10

<210> SEQ ID NO 63
<211> LENGTH: 15
<212> TYPE: DNA
<213> ORGANISM: Homo sapiens

<400> SEQUENCE: 63
gaagttgtta gagat                                                          15

<210> SEQ ID NO 64
<211> LENGTH: 9
<212> TYPE: DNA
<213> ORGANISM: Homo sapiens

<400> SEQUENCE: 64 agattagaa                                                                  9

<210> SEQ ID NO 65
<211> LENGTH: 10
<212> TYPE: DNA
<213> ORGANISM: Homo sapiens

<400> SEQUENCE: 65
attaactgac                                                                10

<210> SEQ ID NO 66
<211> LENGTH: 10
<212> TYPE: DNA
<213> ORGANISM: Homo sapiens

<400> SEQUENCE: 66
ctcaaaagac                                                                10

<210> SEQ ID NO 67
<211> LENGTH: 10
<212> TYPE: DNA
<213> ORGANISM: Homo sapiens

<400> SEQUENCE: 67
tgtgtgcctt                                                                10

<210> SEQ ID NO 68
<211> LENGTH: 10
<212> TYPE: DNA
<213> ORGANISM: Homo sapiens
```

-continued

```
<400> SEQUENCE: 68
aatggggaag                                                            10

<210> SEQ ID NO 69
<211> LENGTH: 10
<212> TYPE: DNA
<213> ORGANISM: Homo sapiens

<400> SEQUENCE: 69
atgcatcagg                                                            10

<210> SEQ ID NO 70
<211> LENGTH: 23
<212> TYPE: DNA
<213> ORGANISM: Homo sapiens

<400> SEQUENCE: 70
tattctagtg aacttgactc tta                                             23

<210> SEQ ID NO 71
<211> LENGTH: 10
<212> TYPE: DNA
<213> ORGANISM: Homo sapiens

<400> SEQUENCE: 71
atggtgcatt                                                            10

<210> SEQ ID NO 72
<211> LENGTH: 11
<212> TYPE: DNA
<213> ORGANISM: Homo sapiens

<400> SEQUENCE: 72
cagcaagcac t                                                          11

<210> SEQ ID NO 73
<211> LENGTH: 10
<212> TYPE: DNA
<213> ORGANISM: Homo sapiens

<400> SEQUENCE: 73
tgacaactgt                                                            10

<210> SEQ ID NO 74
<211> LENGTH: 10
<212> TYPE: DNA
<213> ORGANISM: Homo sapiens

<400> SEQUENCE: 74
atgaatatag                                                            10

<210> SEQ ID NO 75
<211> LENGTH: 10
<212> TYPE: DNA
<213> ORGANISM: Homo sapiens

<400> SEQUENCE: 75
actggtatgt                                                            10

<210> SEQ ID NO 76
<211> LENGTH: 10
<212> TYPE: DNA
<213> ORGANISM: Homo sapiens
```

```
<400> SEQUENCE: 76
tcttgtattc                                                            10

<210> SEQ ID NO 77
<211> LENGTH: 10
<212> TYPE: DNA
<213> ORGANISM: Homo sapiens

<400> SEQUENCE: 77
ccttgtaggc                                                            10

<210> SEQ ID NO 78
<211> LENGTH: 10
<212> TYPE: DNA
<213> ORGANISM: Homo sapiens

<400> SEQUENCE: 78
acatgcatgc                                                            10

<210> SEQ ID NO 79
<211> LENGTH: 10
<212> TYPE: DNA
<213> ORGANISM: Homo sapiens

<400> SEQUENCE: 79
ttaaaataag                                                            10

<210> SEQ ID NO 80
<211> LENGTH: 10
<212> TYPE: DNA
<213> ORGANISM: Homo sapiens

<400> SEQUENCE: 80
ttaggttaaa                                                            10

<210> SEQ ID NO 81
<211> LENGTH: 10
<212> TYPE: DNA
<213> ORGANISM: Homo sapiens

<400> SEQUENCE: 81
tcatgataag                                                            10

<210> SEQ ID NO 82
<211> LENGTH: 10
<212> TYPE: DNA
<213> ORGANISM: Homo sapiens

<400> SEQUENCE: 82
tatctcttct                                                            10

<210> SEQ ID NO 83
<211> LENGTH: 10
<212> TYPE: DNA
<213> ORGANISM: Homo sapiens

<400> SEQUENCE: 83
tatgtatact                                                            10

<210> SEQ ID NO 84
<211> LENGTH: 10
<212> TYPE: DNA
```

```
<213> ORGANISM: Homo sapiens

<400> SEQUENCE: 84
gactgactcc                                                              10

<210> SEQ ID NO 85
<211> LENGTH: 10
<212> TYPE: DNA
<213> ORGANISM: Homo sapiens

<400> SEQUENCE: 85
attgcactcc                                                              10

<210> SEQ ID NO 86
<211> LENGTH: 10
<212> TYPE: DNA
<213> ORGANISM: Homo sapiens

<400> SEQUENCE: 86
aagctggctc                                                              10

<210> SEQ ID NO 87
<211> LENGTH: 10
<212> TYPE: DNA
<213> ORGANISM: Homo sapiens

<400> SEQUENCE: 87
acttttgcgg                                                              10

<210> SEQ ID NO 88
<211> LENGTH: 10
<212> TYPE: DNA
<213> ORGANISM: Homo sapiens

<400> SEQUENCE: 88
agttttacaa                                                              10

<210> SEQ ID NO 89
<211> LENGTH: 10
<212> TYPE: DNA
<213> ORGANISM: Homo sapiens

<400> SEQUENCE: 89
agttttgtat                                                              10

<210> SEQ ID NO 90
<211> LENGTH: 10
<212> TYPE: DNA
<213> ORGANISM: Homo sapiens

<400> SEQUENCE: 90
agtcttgaag                                                              10

<210> SEQ ID NO 91
<211> LENGTH: 10
<212> TYPE: DNA
<213> ORGANISM: Homo sapiens

<400> SEQUENCE: 91
aggtttgtag                                                              10

<210> SEQ ID NO 92
<211> LENGTH: 10
```

-continued

<210> SEQ ID NO 92
<211> LENGTH: 10
<212> TYPE: DNA
<213> ORGANISM: Homo sapiens

<400> SEQUENCE: 92
agtattgaag                                                          10

<210> SEQ ID NO 93
<211> LENGTH: 10
<212> TYPE: DNA
<213> ORGANISM: Homo sapiens

<400> SEQUENCE: 93
aggcttgcag                                                          10

<210> SEQ ID NO 94
<211> LENGTH: 10
<212> TYPE: DNA
<213> ORGANISM: Homo sapiens

<400> SEQUENCE: 94
aatttggcag                                                          10

<210> SEQ ID NO 95
<211> LENGTH: 10
<212> TYPE: DNA
<213> ORGANISM: Homo sapiens

<400> SEQUENCE: 95
agttttggaa                                                          10

<210> SEQ ID NO 96
<211> LENGTH: 10
<212> TYPE: DNA
<213> ORGANISM: Homo sapiens

<400> SEQUENCE: 96
tagcttatct                                                          10

<210> SEQ ID NO 97
<211> LENGTH: 10
<212> TYPE: DNA
<213> ORGANISM: Homo sapiens

<400> SEQUENCE: 97
aagctgccaa                                                          10

<210> SEQ ID NO 98
<211> LENGTH: 10
<212> TYPE: DNA
<213> ORGANISM: Homo sapiens

<400> SEQUENCE: 98
aagcttccag                                                          10

<210> SEQ ID NO 99
<211> LENGTH: 11
<212> TYPE: DNA
<213> ORGANISM: Homo sapiens

<400> SEQUENCE: 99
agttcttcac a                                                        11

<210> SEQ ID NO 100

```
<211> LENGTH: 11
<212> TYPE: DNA
<213> ORGANISM: Homo sapiens

<400> SEQUENCE: 100
aattcttcag g                                                          11

<210> SEQ ID NO 101
<211> LENGTH: 11
<212> TYPE: DNA
<213> ORGANISM: Homo sapiens

<400> SEQUENCE: 101
ggttcttcag c                                                          11

<210> SEQ ID NO 102
<211> LENGTH: 12
<212> TYPE: DNA
<213> ORGANISM: Homo sapiens

<400> SEQUENCE: 102
tgcctactgg cc                                                         12

<210> SEQ ID NO 103
<211> LENGTH: 10
<212> TYPE: DNA
<213> ORGANISM: Homo sapiens

<400> SEQUENCE: 103
cctttcatg                                                             10

<210> SEQ ID NO 104
<211> LENGTH: 10
<212> TYPE: DNA
<213> ORGANISM: Homo sapiens

<400> SEQUENCE: 104
ccaatccttg                                                            10

<210> SEQ ID NO 105
<211> LENGTH: 10
<212> TYPE: DNA
<213> ORGANISM: Homo sapiens

<400> SEQUENCE: 105
cattttcttg                                                            10

<210> SEQ ID NO 106
<211> LENGTH: 10
<212> TYPE: DNA
<213> ORGANISM: Homo sapiens

<400> SEQUENCE: 106
cctactcttc                                                            10

<210> SEQ ID NO 107
<211> LENGTH: 10
<212> TYPE: DNA
<213> ORGANISM: Homo sapiens

<400> SEQUENCE: 107
acgattcttg                                                            10
```

```
<210> SEQ ID NO 108
<211> LENGTH: 10
<212> TYPE: DNA
<213> ORGANISM: Homo sapiens

<400> SEQUENCE: 108
tctattcttt                                                          10

<210> SEQ ID NO 109
<211> LENGTH: 10
<212> TYPE: DNA
<213> ORGANISM: Homo sapiens

<400> SEQUENCE: 109
catatttttg                                                          10

<210> SEQ ID NO 110
<211> LENGTH: 10
<212> TYPE: DNA
<213> ORGANISM: Homo sapiens

<400> SEQUENCE: 110
gctagtcttg                                                          10

<210> SEQ ID NO 111
<211> LENGTH: 10
<212> TYPE: DNA
<213> ORGANISM: Homo sapiens

<400> SEQUENCE: 111
catatttttg                                                          10

<210> SEQ ID NO 112
<211> LENGTH: 10
<212> TYPE: DNA
<213> ORGANISM: Homo sapiens

<400> SEQUENCE: 112
cctttctttt                                                          10

<210> SEQ ID NO 113
<211> LENGTH: 10
<212> TYPE: DNA
<213> ORGANISM: Homo sapiens

<400> SEQUENCE: 113
cccattctcg                                                          10

<210> SEQ ID NO 114
<211> LENGTH: 10
<212> TYPE: DNA
<213> ORGANISM: Homo sapiens

<400> SEQUENCE: 114
tttattcttg                                                          10

<210> SEQ ID NO 115
<211> LENGTH: 10
<212> TYPE: DNA
<213> ORGANISM: Homo sapiens

<400> SEQUENCE: 115
cctttacttg                                                          10
```

```
<210> SEQ ID NO 116
<211> LENGTH: 10
<212> TYPE: DNA
<213> ORGANISM: Homo sapiens

<400> SEQUENCE: 116
gcgattcttg                                                          10

<210> SEQ ID NO 117
<211> LENGTH: 10
<212> TYPE: DNA
<213> ORGANISM: Homo sapiens

<400> SEQUENCE: 117
agagcttagg                                                          10

<210> SEQ ID NO 118
<211> LENGTH: 10
<212> TYPE: DNA
<213> ORGANISM: Homo sapiens

<400> SEQUENCE: 118
gtaaccttcc                                                          10

<210> SEQ ID NO 119
<211> LENGTH: 10
<212> TYPE: DNA
<213> ORGANISM: Homo sapiens

<400> SEQUENCE: 119
gtaaccatca                                                          10

<210> SEQ ID NO 120
<211> LENGTH: 10
<212> TYPE: DNA
<213> ORGANISM: Homo sapiens

<400> SEQUENCE: 120
gtaatcatac                                                          10

<210> SEQ ID NO 121
<211> LENGTH: 10
<212> TYPE: DNA
<213> ORGANISM: Homo sapiens

<400> SEQUENCE: 121
gtcaacatca                                                          10

<210> SEQ ID NO 122
<211> LENGTH: 10
<212> TYPE: DNA
<213> ORGANISM: Homo sapiens

<400> SEQUENCE: 122
gtaaacataa                                                          10

<210> SEQ ID NO 123
<211> LENGTH: 10
<212> TYPE: DNA
<213> ORGANISM: Homo sapiens

<400> SEQUENCE: 123
gtactcatcc                                                          10
```

<210> SEQ ID NO 124
<211> LENGTH: 10
<212> TYPE: DNA
<213> ORGANISM: Homo sapiens

<400> SEQUENCE: 124
ctatacatcc                                                           10

<210> SEQ ID NO 125
<211> LENGTH: 10
<212> TYPE: DNA
<213> ORGANISM: Homo sapiens

<400> SEQUENCE: 125
ctaaacatct                                                           10

<210> SEQ ID NO 126
<211> LENGTH: 10
<212> TYPE: DNA
<213> ORGANISM: Homo sapiens

<400> SEQUENCE: 126
attgcactcc                                                           10

<210> SEQ ID NO 127
<211> LENGTH: 10
<212> TYPE: DNA
<213> ORGANISM: Homo sapiens

<400> SEQUENCE: 127
attgcactag                                                           10

<210> SEQ ID NO 128
<211> LENGTH: 10
<212> TYPE: DNA
<213> ORGANISM: Homo sapiens

<400> SEQUENCE: 128
caaagtgctg                                                           10

<210> SEQ ID NO 129
<211> LENGTH: 10
<212> TYPE: DNA
<213> ORGANISM: Homo sapiens

<400> SEQUENCE: 129
caaagtgctg                                                           10

<210> SEQ ID NO 130
<211> LENGTH: 11
<212> TYPE: DNA
<213> ORGANISM: Homo sapiens

<400> SEQUENCE: 130
actcctgggc t                                                         11

<210> SEQ ID NO 131
<211> LENGTH: 11
<212> TYPE: DNA
<213> ORGANISM: Homo sapiens

<400> SEQUENCE: 131
actgataagc t    11

<210> SEQ ID NO 132
<211> LENGTH: 11
<212> TYPE: DNA
<213> ORGANISM: Homo sapiens

<400> SEQUENCE: 132
actcctgacc t    11

<210> SEQ ID NO 133
<211> LENGTH: 11
<212> TYPE: DNA
<213> ORGANISM: Homo sapiens

<400> SEQUENCE: 133
aatcatgtgc c    11

<210> SEQ ID NO 134
<211> LENGTH: 10
<212> TYPE: DNA
<213> ORGANISM: Homo sapiens

<400> SEQUENCE: 134
aagctggctc    10

<210> SEQ ID NO 135
<211> LENGTH: 10
<212> TYPE: DNA
<213> ORGANISM: Homo sapiens

<400> SEQUENCE: 135
aaactctttc    10

<210> SEQ ID NO 136
<211> LENGTH: 10
<212> TYPE: DNA
<213> ORGANISM: Homo sapiens

<400> SEQUENCE: 136
aatcttgttc    10

<210> SEQ ID NO 137
<211> LENGTH: 10
<212> TYPE: DNA
<213> ORGANISM: Homo sapiens

<400> SEQUENCE: 137
aagctccttt    10

<210> SEQ ID NO 138
<211> LENGTH: 10
<212> TYPE: DNA
<213> ORGANISM: Homo sapiens

<400> SEQUENCE: 138
aagctccttt    10

<210> SEQ ID NO 139
<211> LENGTH: 10
<212> TYPE: DNA
<213> ORGANISM: Homo sapiens

<400> SEQUENCE: 139

```
aagctctgtc                                                          10

<210> SEQ ID NO 140
<211> LENGTH: 10
<212> TYPE: DNA
<213> ORGANISM: Homo sapiens

<400> SEQUENCE: 140
caacctcgag                                                          10

<210> SEQ ID NO 141
<211> LENGTH: 10
<212> TYPE: DNA
<213> ORGANISM: Homo sapiens

<400> SEQUENCE: 141
cgagctcctg                                                          10

<210> SEQ ID NO 142
<211> LENGTH: 10
<212> TYPE: DNA
<213> ORGANISM: Homo sapiens

<400> SEQUENCE: 142
gaagcttgtg                                                          10

<210> SEQ ID NO 143
<211> LENGTH: 10
<212> TYPE: DNA
<213> ORGANISM: Homo sapiens

<400> SEQUENCE: 143
caaactcctg                                                          10

<210> SEQ ID NO 144
<211> LENGTH: 10
<212> TYPE: DNA
<213> ORGANISM: Homo sapiens

<400> SEQUENCE: 144
tccagtagat                                                          10

<210> SEQ ID NO 145
<211> LENGTH: 10
<212> TYPE: DNA
<213> ORGANISM: Homo sapiens

<400> SEQUENCE: 145
acgcgcagat                                                          10

<210> SEQ ID NO 146
<211> LENGTH: 10
<212> TYPE: DNA
<213> ORGANISM: Homo sapiens

<400> SEQUENCE: 146
caaagtgctg                                                          10

<210> SEQ ID NO 147
<211> LENGTH: 10
<212> TYPE: DNA
<213> ORGANISM: Homo sapiens
```

<400> SEQUENCE: 147
caaagtgctg                                                          10

<210> SEQ ID NO 148
<211> LENGTH: 11
<212> TYPE: DNA
<213> ORGANISM: Homo sapiens

<400> SEQUENCE: 148
ttattttccc t                                                        11

<210> SEQ ID NO 149
<211> LENGTH: 11
<212> TYPE: DNA
<213> ORGANISM: Homo sapiens

<400> SEQUENCE: 149
ctcttttcag t                                                        11

<210> SEQ ID NO 150
<211> LENGTH: 11
<212> TYPE: DNA
<213> ORGANISM: Homo sapiens

<400> SEQUENCE: 150
ctctcttcac t                                                        11

<210> SEQ ID NO 151
<211> LENGTH: 11
<212> TYPE: DNA
<213> ORGANISM: Homo sapiens

<400> SEQUENCE: 151 ctcttttcc c                                                         11

<210> SEQ ID NO 152
<211> LENGTH: 11
<212> TYPE: DNA
<213> ORGANISM: Homo sapiens

<400> SEQUENCE: 152
cttttccccc t                                                        11

<210> SEQ ID NO 153
<211> LENGTH: 11
<212> TYPE: DNA
<213> ORGANISM: Homo sapiens

<400> SEQUENCE: 153
ctattttccg t                                                        11

<210> SEQ ID NO 154
<211> LENGTH: 11
<212> TYPE: DNA
<213> ORGANISM: Homo sapiens

<400> SEQUENCE: 154
ttcctttccc t                                                        11

<210> SEQ ID NO 155
<211> LENGTH: 11
<212> TYPE: DNA
<213> ORGANISM: Homo sapiens

```
<400> SEQUENCE: 155
ctctttgccc c                                                    11

<210> SEQ ID NO 156
<211> LENGTH: 11
<212> TYPE: DNA
<213> ORGANISM: Homo sapiens

<400> SEQUENCE: 156
ctcctttcct t                                                    11

<210> SEQ ID NO 157
<211> LENGTH: 10
<212> TYPE: DNA
<213> ORGANISM: Homo sapiens

<400> SEQUENCE: 157
tttggtgccc                                                      10

<210> SEQ ID NO 158
<211> LENGTH: 9
<212> TYPE: DNA
<213> ORGANISM: Homo sapiens

<400> SEQUENCE: 158 ggtgcagtg                                                        9

<210> SEQ ID NO 159
<211> LENGTH: 10
<212> TYPE: DNA
<213> ORGANISM: Homo sapiens

<400> SEQUENCE: 159
tgagatgagg                                                      10

<210> SEQ ID NO 160
<211> LENGTH: 10
<212> TYPE: DNA
<213> ORGANISM: Homo sapiens

<400> SEQUENCE: 160
tgagatggag                                                      10

<210> SEQ ID NO 161
<211> LENGTH: 10
<212> TYPE: DNA
<213> ORGANISM: Homo sapiens

<400> SEQUENCE: 161
ttagatgaag                                                      10

<210> SEQ ID NO 162
<211> LENGTH: 10
<212> TYPE: DNA
<213> ORGANISM: Homo sapiens

<400> SEQUENCE: 162
tgtgaactgg                                                      10

<210> SEQ ID NO 163
<211> LENGTH: 10
<212> TYPE: DNA
```

```
<213> ORGANISM: Homo sapiens

<400> SEQUENCE: 163
agggaactga                                                          10

<210> SEQ ID NO 164
<211> LENGTH: 10
<212> TYPE: DNA
<213> ORGANISM: Homo sapiens

<400> SEQUENCE: 164
tgacaactgt                                                          10

<210> SEQ ID NO 165
<211> LENGTH: 10
<212> TYPE: DNA
<213> ORGANISM: Homo sapiens

<400> SEQUENCE: 165
taagaactaa                                                          10

<210> SEQ ID NO 166
<211> LENGTH: 10
<212> TYPE: DNA
<213> ORGANISM: Homo sapiens

<400> SEQUENCE: 166
ttagaacaga                                                          10

<210> SEQ ID NO 167
<211> LENGTH: 10
<212> TYPE: DNA
<213> ORGANISM: Homo sapiens

<400> SEQUENCE: 167
tgagaagtgc                                                          10

<210> SEQ ID NO 168
<211> LENGTH: 10
<212> TYPE: DNA
<213> ORGANISM: Homo sapiens

<400> SEQUENCE: 168
tgaaaactta                                                          10

<210> SEQ ID NO 169
<211> LENGTH: 10
<212> TYPE: DNA
<213> ORGANISM: Homo sapiens

<400> SEQUENCE: 169
acagaactga                                                          10

<210> SEQ ID NO 170
<211> LENGTH: 10
<212> TYPE: DNA
<213> ORGANISM: Homo sapiens

<400> SEQUENCE: 170
tgagaccaga                                                          10

<210> SEQ ID NO 171
<211> LENGTH: 10
```

```
<212> TYPE: DNA
<213> ORGANISM: Homo sapiens

<400> SEQUENCE: 171
tgagaaataa                                                           10

<210> SEQ ID NO 172
<211> LENGTH: 11
<212> TYPE: DNA
<213> ORGANISM: Homo sapiens

<400> SEQUENCE: 172
tgtgtggata a                                                         11

<210> SEQ ID NO 173
<211> LENGTH: 11
<212> TYPE: DNA
<213> ORGANISM: Homo sapiens

<400> SEQUENCE: 173
tttgtgcaaa t                                                         11

<210> SEQ ID NO 174
<211> LENGTH: 12
<212> TYPE: DNA
<213> ORGANISM: Homo sapiens

<400> SEQUENCE: 174
ctaacatatg aa                                                        12

<210> SEQ ID NO 175
<211> LENGTH: 10
<212> TYPE: DNA
<213> ORGANISM: Homo sapiens

<400> SEQUENCE: 175
tgtaacagca                                                           10

<210> SEQ ID NO 176
<211> LENGTH: 10
<212> TYPE: DNA
<213> ORGANISM: Homo sapiens

<400> SEQUENCE: 176
ccctgtgttc                                                           10

<210> SEQ ID NO 177
<211> LENGTH: 10
<212> TYPE: DNA
<213> ORGANISM: Homo sapiens

<400> SEQUENCE: 177
taataatgcc                                                           10

<210> SEQ ID NO 178
<211> LENGTH: 10
<212> TYPE: DNA
<213> ORGANISM: Homo sapiens

<400> SEQUENCE: 178
gaatactgcc                                                           10

<210> SEQ ID NO 179
```

```
<211> LENGTH: 10
<212> TYPE: DNA
<213> ORGANISM: Homo sapiens

<400> SEQUENCE: 179
ttcctctgtc                                                                10

<210> SEQ ID NO 180
<211> LENGTH: 10
<212> TYPE: DNA
<213> ORGANISM: Homo sapiens

<400> SEQUENCE: 180
ttcctttatc                                                                10

<210> SEQ ID NO 181
<211> LENGTH: 11
<212> TYPE: DNA
<213> ORGANISM: Homo sapiens

<400> SEQUENCE: 181
ttccctatct c                                                              11

<210> SEQ ID NO 182
<211> LENGTH: 11
<212> TYPE: DNA
<213> ORGANISM: Homo sapiens

<400> SEQUENCE: 182
tcccctctgt c                                                              11

<210> SEQ ID NO 183
<211> LENGTH: 11
<212> TYPE: DNA
<213> ORGANISM: Homo sapiens

<400> SEQUENCE: 183
ttcccttgct c                                                              11

<210> SEQ ID NO 184
<211> LENGTH: 11
<212> TYPE: DNA
<213> ORGANISM: Homo sapiens

<400> SEQUENCE: 184
ttcccattct c                                                              11

<210> SEQ ID NO 185
<211> LENGTH: 10
<212> TYPE: DNA
<213> ORGANISM: Homo sapiens

<400> SEQUENCE: 185 cgcgtccect                                                                10

<210> SEQ ID NO 186
<211> LENGTH: 10
<212> TYPE: DNA
<213> ORGANISM: Homo sapiens

<400> SEQUENCE: 186
ccttgtaggc                                                                10
```

-continued

```
<210> SEQ ID NO 187
<211> LENGTH: 10
<212> TYPE: DNA
<213> ORGANISM: Homo sapiens

<400> SEQUENCE: 187
cagagtaggt                                                          10

<210> SEQ ID NO 188
<211> LENGTH: 10
<212> TYPE: DNA
<213> ORGANISM: Homo sapiens

<400> SEQUENCE: 188
ccaagtagct                                                          10

<210> SEQ ID NO 189
<211> LENGTH: 10
<212> TYPE: DNA
<213> ORGANISM: Homo sapiens

<400> SEQUENCE: 189
ccaagtagct                                                          10

<210> SEQ ID NO 190
<211> LENGTH: 10
<212> TYPE: DNA
<213> ORGANISM: Homo sapiens

<400> SEQUENCE: 190
ctgttcctct                                                          10

<210> SEQ ID NO 191
<211> LENGTH: 10
<212> TYPE: DNA
<213> ORGANISM: Homo sapiens

<400> SEQUENCE: 191
ctggctccct                                                          10

<210> SEQ ID NO 192
<211> LENGTH: 10
<212> TYPE: DNA
<213> ORGANISM: Homo sapiens

<400> SEQUENCE: 192
ctggcccttc                                                          10

<210> SEQ ID NO 193
<211> LENGTH: 10
<212> TYPE: DNA
<213> ORGANISM: Homo sapiens

<400> SEQUENCE: 193
ctggcactca                                                          10

<210> SEQ ID NO 194
<211> LENGTH: 10
<212> TYPE: DNA
<213> ORGANISM: Homo sapiens

<400> SEQUENCE: 194
ctggctttct                                                          10
```

<210> SEQ ID NO 195
<211> LENGTH: 10
<212> TYPE: DNA
<213> ORGANISM: Homo sapiens

<400> SEQUENCE: 195
ctgcccctcc                                                                  10

<210> SEQ ID NO 196
<211> LENGTH: 10
<212> TYPE: DNA
<213> ORGANISM: Homo sapiens

<400> SEQUENCE: 196
ctgggccgct                                                                  10

<210> SEQ ID NO 197
<211> LENGTH: 10
<212> TYPE: DNA
<213> ORGANISM: Homo sapiens

<400> SEQUENCE: 197
ctggagctct                                                                  10

<210> SEQ ID NO 198
<211> LENGTH: 10
<212> TYPE: DNA
<213> ORGANISM: Homo sapiens

<400> SEQUENCE: 198
ctgacccttt                                                                  10

<210> SEQ ID NO 199
<211> LENGTH: 10
<212> TYPE: DNA
<213> ORGANISM: Homo sapiens

<400> SEQUENCE: 199
caaagcacac                                                                  10

<210> SEQ ID NO 200
<211> LENGTH: 10
<212> TYPE: DNA
<213> ORGANISM: Homo sapiens

<400> SEQUENCE: 200
ctaggtgtgg                                                                  10

<210> SEQ ID NO 201
<211> LENGTH: 10
<212> TYPE: DNA
<213> ORGANISM: Homo sapiens

<400> SEQUENCE: 201
atccttggat                                                                  10

<210> SEQ ID NO 202
<211> LENGTH: 10
<212> TYPE: DNA
<213> ORGANISM: Homo sapiens

<400> SEQUENCE: 202
aattgcactc                                                                  10

```
<210> SEQ ID NO 203
<211> LENGTH: 10
<212> TYPE: DNA
<213> ORGANISM: Homo sapiens

<400> SEQUENCE: 203
aaatgcactt                                                          10

<210> SEQ ID NO 204
<211> LENGTH: 10
<212> TYPE: DNA
<213> ORGANISM: Homo sapiens

<400> SEQUENCE: 204
aagtgcctgc                                                          10

<210> SEQ ID NO 205
<211> LENGTH: 10
<212> TYPE: DNA
<213> ORGANISM: Homo sapiens

<400> SEQUENCE: 205
aagagccgac                                                          10

<210> SEQ ID NO 206
<211> LENGTH: 10
<212> TYPE: DNA
<213> ORGANISM: Homo sapiens

<400> SEQUENCE: 206
acgtgccacc                                                          10

<210> SEQ ID NO 207
<211> LENGTH: 10
<212> TYPE: DNA
<213> ORGANISM: Homo sapiens

<400> SEQUENCE: 207
aagtgcctct                                                          10

<210> SEQ ID NO 208
<211> LENGTH: 10
<212> TYPE: DNA
<213> ORGANISM: Homo sapiens

<400> SEQUENCE: 208
aagtgcaccc                                                          10

<210> SEQ ID NO 209
<211> LENGTH: 10
<212> TYPE: DNA
<213> ORGANISM: Homo sapiens

<400> SEQUENCE: 209
tctcaaactg                                                          10

<210> SEQ ID NO 210
<211> LENGTH: 10
<212> TYPE: DNA
<213> ORGANISM: Homo sapiens

<400> SEQUENCE: 210
```
tcatcagatt 10

<210> SEQ ID NO 211
<211> LENGTH: 10
<212> TYPE: DNA
<213> ORGANISM: Homo sapiens

<400> SEQUENCE: 211
agcacacaaa 10

<210> SEQ ID NO 212
<211> LENGTH: 10
<212> TYPE: DNA
<213> ORGANISM: Homo sapiens

<400> SEQUENCE: 212
actggccttg 10

<210> SEQ ID NO 213
<211> LENGTH: 10
<212> TYPE: DNA
<213> ORGANISM: Homo sapiens

<400> SEQUENCE: 213
actggtcttg 10

<210> SEQ ID NO 214
<211> LENGTH: 10
<212> TYPE: DNA
<213> ORGANISM: Homo sapiens

<400> SEQUENCE: 214
ctcctgcctc 10

<210> SEQ ID NO 215
<211> LENGTH: 10
<212> TYPE: DNA
<213> ORGANISM: Homo sapiens

<400> SEQUENCE: 215
ctcctgcctc 10

<210> SEQ ID NO 216
<211> LENGTH: 10
<212> TYPE: DNA
<213> ORGANISM: Homo sapiens

<400> SEQUENCE: 216
ctcctgtctc 10

<210> SEQ ID NO 217
<211> LENGTH: 10
<212> TYPE: DNA
<213> ORGANISM: Homo sapiens

<400> SEQUENCE: 217
ctcctaactc 10

<210> SEQ ID NO 218
<211> LENGTH: 10
<212> TYPE: DNA
<213> ORGANISM: Homo sapiens

<400> SEQUENCE: 218

```
attcattcac                                                          10

<210> SEQ ID NO 219
<211> LENGTH: 10
<212> TYPE: DNA
<213> ORGANISM: Homo sapiens

<400> SEQUENCE: 219
ctcaaaagac                                                          10

<210> SEQ ID NO 220
<211> LENGTH: 10
<212> TYPE: DNA
<213> ORGANISM: Homo sapiens

<400> SEQUENCE: 220
attaactgac                                                          10

<210> SEQ ID NO 221
<211> LENGTH: 10
<212> TYPE: DNA
<213> ORGANISM: Homo sapiens

<400> SEQUENCE: 221
aacatcagac                                                          10

<210> SEQ ID NO 222
<211> LENGTH: 10
<212> TYPE: DNA
<213> ORGANISM: Homo sapiens

<400> SEQUENCE: 222
atcaactgag                                                          10

<210> SEQ ID NO 223
<211> LENGTH: 10
<212> TYPE: DNA
<213> ORGANISM: Homo sapiens

<400> SEQUENCE: 223
atcaacaggt                                                          10

<210> SEQ ID NO 224
<211> LENGTH: 10
<212> TYPE: DNA
<213> ORGANISM: Homo sapiens

<400> SEQUENCE: 224
atcaaaagat                                                          10

<210> SEQ ID NO 225
<211> LENGTH: 11
<212> TYPE: DNA
<213> ORGANISM: Homo sapiens

<400> SEQUENCE: 225
agcgggaagg t                                                        11

<210> SEQ ID NO 226
<211> LENGTH: 10
<212> TYPE: DNA
<213> ORGANISM: Homo sapiens
```

```
<400> SEQUENCE: 226
tgtgtgcctt                                                              10

<210> SEQ ID NO 227
<211> LENGTH: 10
<212> TYPE: DNA
<213> ORGANISM: Homo sapiens

<400> SEQUENCE: 227
tctgtgcctt                                                              10

<210> SEQ ID NO 228
<211> LENGTH: 10
<212> TYPE: DNA
<213> ORGANISM: Homo sapiens

<400> SEQUENCE: 228
tatgtgcttt                                                              10

<210> SEQ ID NO 229
<211> LENGTH: 10
<212> TYPE: DNA
<213> ORGANISM: Homo sapiens

<400> SEQUENCE: 229
aatcatacag                                                              10

<210> SEQ ID NO 230
<211> LENGTH: 10
<212> TYPE: DNA
<213> ORGANISM: Homo sapiens

<400> SEQUENCE: 230
aatggggaag                                                              10

<210> SEQ ID NO 231
<211> LENGTH: 10
<212> TYPE: DNA
<213> ORGANISM: Homo sapiens

<400> SEQUENCE: 231
agaggggacc                                                              10

<210> SEQ ID NO 232
<211> LENGTH: 10
<212> TYPE: DNA
<213> ORGANISM: Homo sapiens

<400> SEQUENCE: 232
agttgggcac                                                              10

<210> SEQ ID NO 233
<211> LENGTH: 10
<212> TYPE: DNA
<213> ORGANISM: Homo sapiens

<400> SEQUENCE: 233
agtagagaac                                                              10

<210> SEQ ID NO 234
<211> LENGTH: 10
<212> TYPE: DNA
<213> ORGANISM: Homo sapiens
```

```
<400> SEQUENCE: 234
ggtgaggaac                                                            10

<210> SEQ ID NO 235
<211> LENGTH: 10
<212> TYPE: DNA
<213> ORGANISM: Homo sapiens

<400> SEQUENCE: 235
agcggggcac                                                            10

<210> SEQ ID NO 236
<211> LENGTH: 10
<212> TYPE: DNA
<213> ORGANISM: Homo sapiens

<400> SEQUENCE: 236
agtgggaaat                                                            10

<210> SEQ ID NO 237
<211> LENGTH: 10
<212> TYPE: DNA
<213> ORGANISM: Homo sapiens

<400> SEQUENCE: 237
atgcatcagg                                                            10

<210> SEQ ID NO 238
<211> LENGTH: 10
<212> TYPE: DNA
<213> ORGANISM: Homo sapiens

<400> SEQUENCE: 238
atccaccggg                                                            10

<210> SEQ ID NO 239
<211> LENGTH: 10
<212> TYPE: DNA
<213> ORGANISM: Homo sapiens

<400> SEQUENCE: 239
aggcaccagg                                                            10

<210> SEQ ID NO 240
<211> LENGTH: 10
<212> TYPE: DNA
<213> ORGANISM: Homo sapiens

<400> SEQUENCE: 240
tgattatagc                                                            10

<210> SEQ ID NO 241
<211> LENGTH: 10
<212> TYPE: DNA
<213> ORGANISM: Homo sapiens

<400> SEQUENCE: 241
tgagtgtagc                                                            10

<210> SEQ ID NO 242
<211> LENGTH: 10
<212> TYPE: DNA
```

```
<213> ORGANISM: Homo sapiens

<400> SEQUENCE: 242
cagtgctgtc                                                            10

<210> SEQ ID NO 243
<211> LENGTH: 10
<212> TYPE: DNA
<213> ORGANISM: Homo sapiens

<400> SEQUENCE: 243
aagtgctctc                                                            10

<210> SEQ ID NO 244
<211> LENGTH: 10
<212> TYPE: DNA
<213> ORGANISM: Homo sapiens

<400> SEQUENCE: 244
atggtgcatt                                                            10

<210> SEQ ID NO 245
<211> LENGTH: 10
<212> TYPE: DNA
<213> ORGANISM: Homo sapiens

<400> SEQUENCE: 245
atcttgcttc                                                            10

<210> SEQ ID NO 246
<211> LENGTH: 11
<212> TYPE: DNA
<213> ORGANISM: Homo sapiens

<400> SEQUENCE: 246
cagcaagcac t                                                          11

<210> SEQ ID NO 247
<211> LENGTH: 11
<212> TYPE: DNA
<213> ORGANISM: Homo sapiens

<400> SEQUENCE: 247
cagaacacat t                                                          11

<210> SEQ ID NO 248
<211> LENGTH: 11
<212> TYPE: DNA
<213> ORGANISM: Homo sapiens

<400> SEQUENCE: 248
ctgcaaacac t                                                          11

<210> SEQ ID NO 249
<211> LENGTH: 10
<212> TYPE: DNA
<213> ORGANISM: Homo sapiens

<400> SEQUENCE: 249
tgacaactgt                                                            10

<210> SEQ ID NO 250
<211> LENGTH: 10
```

```
<212> TYPE: DNA
<213> ORGANISM: Homo sapiens

<400> SEQUENCE: 250
gcgaggtctc                                                      10

<210> SEQ ID NO 251
<211> LENGTH: 10
<212> TYPE: DNA
<213> ORGANISM: Homo sapiens

<400> SEQUENCE: 251
gagaggcccc                                                      10

<210> SEQ ID NO 252
<211> LENGTH: 10
<212> TYPE: DNA
<213> ORGANISM: Homo sapiens

<400> SEQUENCE: 252
gagaggacct                                                      10

<210> SEQ ID NO 253
<211> LENGTH: 10
<212> TYPE: DNA
<213> ORGANISM: Homo sapiens

<400> SEQUENCE: 253
atgaatatag                                                      10

<210> SEQ ID NO 254
<211> LENGTH: 10
<212> TYPE: DNA
<213> ORGANISM: Homo sapiens

<400> SEQUENCE: 254
atggaaatat                                                      10

<210> SEQ ID NO 255
<211> LENGTH: 10
<212> TYPE: DNA
<213> ORGANISM: Homo sapiens

<400> SEQUENCE: 255
ttggatatag                                                      10

<210> SEQ ID NO 256
<211> LENGTH: 10
<212> TYPE: DNA
<213> ORGANISM: Homo sapiens

<400> SEQUENCE: 256
gtggagatgg                                                      10

<210> SEQ ID NO 257
<211> LENGTH: 10
<212> TYPE: DNA
<213> ORGANISM: Homo sapiens

<400> SEQUENCE: 257
atggagatcc                                                      10

<210> SEQ ID NO 258
```

```
<211> LENGTH: 10
<212> TYPE: DNA
<213> ORGANISM: Homo sapiens

<400> SEQUENCE: 258
atggagggag                                                          10

<210> SEQ ID NO 259
<211> LENGTH: 10
<212> TYPE: DNA
<213> ORGANISM: Homo sapiens

<400> SEQUENCE: 259
ctggagaaag                                                          10

<210> SEQ ID NO 260
<211> LENGTH: 10
<212> TYPE: DNA
<213> ORGANISM: Homo sapiens

<400> SEQUENCE: 260
atccagatag                                                          10

<210> SEQ ID NO 261
<211> LENGTH: 10
<212> TYPE: DNA
<213> ORGANISM: Homo sapiens

<400> SEQUENCE: 261
atggggctag                                                          10

<210> SEQ ID NO 262
<211> LENGTH: 10
<212> TYPE: DNA
<213> ORGANISM: Homo sapiens

<400> SEQUENCE: 262
agggagagag                                                          10

<210> SEQ ID NO 263
<211> LENGTH: 10
<212> TYPE: DNA
<213> ORGANISM: Homo sapiens

<400> SEQUENCE: 263
caggagatag                                                          10

<210> SEQ ID NO 264
<211> LENGTH: 10
<212> TYPE: DNA
<213> ORGANISM: Homo sapiens

<400> SEQUENCE: 264
ttggagagag                                                          10

<210> SEQ ID NO 265
<211> LENGTH: 10
<212> TYPE: DNA
<213> ORGANISM: Homo sapiens

<400> SEQUENCE: 265
acggagcgcg                                                          10
```

-continued

```
<210> SEQ ID NO 266
<211> LENGTH: 10
<212> TYPE: DNA
<213> ORGANISM: Homo sapiens

<400> SEQUENCE: 266
agggagggcg                                                          10

<210> SEQ ID NO 267
<211> LENGTH: 10
<212> TYPE: DNA
<213> ORGANISM: Homo sapiens

<400> SEQUENCE: 267
acatgcatgc                                                          10

<210> SEQ ID NO 268
<211> LENGTH: 10
<212> TYPE: DNA
<213> ORGANISM: Homo sapiens

<400> SEQUENCE: 268
ccttgtaggc                                                          10

<210> SEQ ID NO 269
<211> LENGTH: 10
<212> TYPE: DNA
<213> ORGANISM: Homo sapiens

<400> SEQUENCE: 269
tcttgtattc                                                          10

<210> SEQ ID NO 270
<211> LENGTH: 10
<212> TYPE: DNA
<213> ORGANISM: Homo sapiens

<400> SEQUENCE: 270
actggtatgt                                                          10

<210> SEQ ID NO 271
<211> LENGTH: 10
<212> TYPE: DNA
<213> ORGANISM: Homo sapiens

<400> SEQUENCE: 271
acttctattc                                                          10

<210> SEQ ID NO 272
<211> LENGTH: 10
<212> TYPE: DNA
<213> ORGANISM: Homo sapiens

<400> SEQUENCE: 272
acttttctgc                                                          10

<210> SEQ ID NO 273
<211> LENGTH: 10
<212> TYPE: DNA
<213> ORGANISM: Homo sapiens

<400> SEQUENCE: 273
gcttgtaagc                                                          10
```

<210> SEQ ID NO 274
<211> LENGTH: 10
<212> TYPE: DNA
<213> ORGANISM: Homo sapiens

<400> SEQUENCE: 274
agttgtatgt                                                              10

<210> SEQ ID NO 275
<211> LENGTH: 10
<212> TYPE: DNA
<213> ORGANISM: Homo sapiens

<400> SEQUENCE: 275
acttggaagc                                                              10

<210> SEQ ID NO 276
<211> LENGTH: 10
<212> TYPE: DNA
<213> ORGANISM: Homo sapiens

<400> SEQUENCE: 276
acttgtgtgg                                                              10

<210> SEQ ID NO 277
<211> LENGTH: 10
<212> TYPE: DNA
<213> ORGANISM: Homo sapiens

<400> SEQUENCE: 277
acttgtttga                                                              10

<210> SEQ ID NO 278
<211> LENGTH: 10
<212> TYPE: DNA
<213> ORGANISM: Homo sapiens

<400> SEQUENCE: 278
acatgtttgc                                                              10

<210> SEQ ID NO 279
<211> LENGTH: 9
<212> TYPE: DNA
<213> ORGANISM: Homo sapiens

<400> SEQUENCE: 279 aggaggcac                                                                9

<210> SEQ ID NO 280
<211> LENGTH: 9
<212> TYPE: DNA
<213> ORGANISM: Homo sapiens

<400> SEQUENCE: 280 agaaggcag                                                                9

<210> SEQ ID NO 281
<211> LENGTH: 9
<212> TYPE: DNA
<213> ORGANISM: Homo sapiens

<400> SEQUENCE: 281 aggagccag                                                                9

```
<210> SEQ ID NO 282
<211> LENGTH: 9
<212> TYPE: DNA
<213> ORGANISM: Homo sapiens

<400> SEQUENCE: 282 atgaggcag                                                                 9

<210> SEQ ID NO 283
<211> LENGTH: 10
<212> TYPE: DNA
<213> ORGANISM: Homo sapiens

<400> SEQUENCE: 283
tcatgataag                                                               10

<210> SEQ ID NO 284
<211> LENGTH: 10
<212> TYPE: DNA
<213> ORGANISM: Homo sapiens

<400> SEQUENCE: 284
ttaggttaaa                                                               10

<210> SEQ ID NO 285
<211> LENGTH: 10
<212> TYPE: DNA
<213> ORGANISM: Homo sapiens

<400> SEQUENCE: 285
ttaaaataag                                                               10

<210> SEQ ID NO 286
<211> LENGTH: 10
<212> TYPE: DNA
<213> ORGANISM: Homo sapiens

<400> SEQUENCE: 286
ttagcataac                                                               10

<210> SEQ ID NO 287
<211> LENGTH: 10
<212> TYPE: DNA
<213> ORGANISM: Homo sapiens

<400> SEQUENCE: 287
ttatgatgag                                                               10

<210> SEQ ID NO 288
<211> LENGTH: 10
<212> TYPE: DNA
<213> ORGANISM: Homo sapiens

<400> SEQUENCE: 288
tttggatgag                                                               10

<210> SEQ ID NO 289
<211> LENGTH: 10
<212> TYPE: DNA
<213> ORGANISM: Homo sapiens

<400> SEQUENCE: 289
```

```
tgagtataag                                                              10

<210> SEQ ID NO 290
<211> LENGTH: 10
<212> TYPE: DNA
<213> ORGANISM: Homo sapiens

<400> SEQUENCE: 290
ttacaataag                                                              10

<210> SEQ ID NO 291
<211> LENGTH: 10
<212> TYPE: DNA
<213> ORGANISM: Homo sapiens

<400> SEQUENCE: 291
taaggataaa                                                              10

<210> SEQ ID NO 292
<211> LENGTH: 10
<212> TYPE: DNA
<213> ORGANISM: Homo sapiens

<400> SEQUENCE: 292
tgtggataag                                                              10

<210> SEQ ID NO 293
<211> LENGTH: 10
<212> TYPE: DNA
<213> ORGANISM: Homo sapiens

<400> SEQUENCE: 293
gtaggatagg                                                              10

<210> SEQ ID NO 294
<211> LENGTH: 10
<212> TYPE: DNA
<213> ORGANISM: Homo sapiens

<400> SEQUENCE: 294
ctaggaaaag                                                              10

<210> SEQ ID NO 295
<211> LENGTH: 10
<212> TYPE: DNA
<213> ORGANISM: Homo sapiens

<400> SEQUENCE: 295
ctatgataag                                                              10

<210> SEQ ID NO 296
<211> LENGTH: 10
<212> TYPE: DNA
<213> ORGANISM: Homo sapiens

<400> SEQUENCE: 296
taaggatagg                                                              10

<210> SEQ ID NO 297
<211> LENGTH: 10
<212> TYPE: DNA
<213> ORGANISM: Homo sapiens

<400> SEQUENCE: 297
```

-continued

```
tatgtatact                                                          10

<210> SEQ ID NO 298
<211> LENGTH: 10
<212> TYPE: DNA
<213> ORGANISM: Homo sapiens

<400> SEQUENCE: 298
tatctcttct                                                          10

<210> SEQ ID NO 299
<211> LENGTH: 10
<212> TYPE: DNA
<213> ORGANISM: Homo sapiens

<400> SEQUENCE: 299
tctatctgct                                                          10

<210> SEQ ID NO 300
<211> LENGTH: 10
<212> TYPE: DNA
<213> ORGANISM: Homo sapiens

<400> SEQUENCE: 300
aatgtctggt                                                          10

<210> SEQ ID NO 301
<211> LENGTH: 10
<212> TYPE: DNA
<213> ORGANISM: Homo sapiens

<400> SEQUENCE: 301
tatgtttcct                                                          10

<210> SEQ ID NO 302
<211> LENGTH: 10
<212> TYPE: DNA
<213> ORGANISM: Homo sapiens

<400> SEQUENCE: 302
tttttctgct                                                          10

<210> SEQ ID NO 303
<211> LENGTH: 10
<212> TYPE: DNA
<213> ORGANISM: Homo sapiens

<400> SEQUENCE: 303
tatgtctttt                                                          10

<210> SEQ ID NO 304
<211> LENGTH: 10
<212> TYPE: DNA
<213> ORGANISM: Homo sapiens

<400> SEQUENCE: 304
tatatctgca                                                          10

<210> SEQ ID NO 305
<211> LENGTH: 10
<212> TYPE: DNA
<213> ORGANISM: Homo sapiens
```

```
<400> SEQUENCE: 305
tatgtaggct                                                              10

<210> SEQ ID NO 306
<211> LENGTH: 10
<212> TYPE: DNA
<213> ORGANISM: Homo sapiens

<400> SEQUENCE: 306
ctccagcccc                                                              10

<210> SEQ ID NO 307
<211> LENGTH: 10
<212> TYPE: DNA
<213> ORGANISM: Homo sapiens

<400> SEQUENCE: 307
ctccagcccc                                                              10

<210> SEQ ID NO 308
<211> LENGTH: 10
<212> TYPE: DNA
<213> ORGANISM: Homo sapiens

<400> SEQUENCE: 308
cctggaaata                                                              10

<210> SEQ ID NO 309
<211> LENGTH: 10
<212> TYPE: DNA
<213> ORGANISM: Homo sapiens

<400> SEQUENCE: 309
cctagaaaca                                                              10

<210> SEQ ID NO 310
<211> LENGTH: 10
<212> TYPE: DNA
<213> ORGANISM: Homo sapiens

<400> SEQUENCE: 310
gactgactcc                                                              10

<210> SEQ ID NO 311
<211> LENGTH: 10
<212> TYPE: DNA
<213> ORGANISM: Homo sapiens

<400> SEQUENCE: 311
gactgacagc                                                              10

<210> SEQ ID NO 312
<211> LENGTH: 10
<212> TYPE: DNA
<213> ORGANISM: Homo sapiens

<400> SEQUENCE: 312
tacttggaag                                                              10

<210> SEQ ID NO 313
<211> LENGTH: 10
<212> TYPE: DNA
<213> ORGANISM: Homo sapiens
```

```
<400> SEQUENCE: 313
atccgactgt                                                         10

<210> SEQ ID NO 314
<211> LENGTH: 10
<212> TYPE: DNA
<213> ORGANISM: Homo sapiens

<400> SEQUENCE: 314
tccctgctgt                                                         10

<210> SEQ ID NO 315
<211> LENGTH: 10
<212> TYPE: DNA
<213> ORGANISM: Homo sapiens

<400> SEQUENCE: 315
tcccagctgt                                                         10

<210> SEQ ID NO 316
<211> LENGTH: 10
<212> TYPE: DNA
<213> ORGANISM: Homo sapiens

<400> SEQUENCE: 316
agcccgctgt                                                         10

<210> SEQ ID NO 317
<211> LENGTH: 10
<212> TYPE: DNA
<213> ORGANISM: Homo sapiens

<400> SEQUENCE: 317
acccgggcgt                                                         10

<210> SEQ ID NO 318
<211> LENGTH: 11
<212> TYPE: DNA
<213> ORGANISM: Homo sapiens

<400> SEQUENCE: 318
aagtatcctt t                                                       11

<210> SEQ ID NO 319
<211> LENGTH: 11
<212> TYPE: DNA
<213> ORGANISM: Homo sapiens

<400> SEQUENCE: 319
atgcattctg t                                                       11

<210> SEQ ID NO 320
<211> LENGTH: 11
<212> TYPE: DNA
<213> ORGANISM: Homo sapiens

<400> SEQUENCE: 320
atgcattctc t                                                       11

<210> SEQ ID NO 321
<211> LENGTH: 10
<212> TYPE: DNA
```

```
<213> ORGANISM: Homo sapiens

<400> SEQUENCE: 321
ctccacctcc                                                           10

<210> SEQ ID NO 322
<211> LENGTH: 10
<212> TYPE: DNA
<213> ORGANISM: Homo sapiens

<400> SEQUENCE: 322
agagggaaat                                                           10

<210> SEQ ID NO 323
<211> LENGTH: 10
<212> TYPE: DNA
<213> ORGANISM: Homo sapiens

<400> SEQUENCE: 323
ggaaggaaat                                                           10

<210> SEQ ID NO 324
<211> LENGTH: 10
<212> TYPE: DNA
<213> ORGANISM: Homo sapiens

<400> SEQUENCE: 324
gtagggaga                                                            10

<210> SEQ ID NO 325
<211> LENGTH: 10
<212> TYPE: DNA
<213> ORGANISM: Homo sapiens

<400> SEQUENCE: 325
atgggacaca                                                           10

<210> SEQ ID NO 326
<211> LENGTH: 10
<212> TYPE: DNA
<213> ORGANISM: Homo sapiens

<400> SEQUENCE: 326
tttggatata                                                           10

<210> SEQ ID NO 327
<211> LENGTH: 10
<212> TYPE: DNA
<213> ORGANISM: Homo sapiens

<400> SEQUENCE: 327
ttagggcata                                                           10

<210> SEQ ID NO 328
<211> LENGTH: 10
<212> TYPE: DNA
<213> ORGANISM: Homo sapiens

<400> SEQUENCE: 328
ttggaacaga                                                           10

<210> SEQ ID NO 329
<211> LENGTH: 10
```

```
<212> TYPE: DNA
<213> ORGANISM: Homo sapiens

<400> SEQUENCE: 329
ctgggactta                                                        10

<210> SEQ ID NO 330
<211> LENGTH: 10
<212> TYPE: DNA
<213> ORGANISM: Homo sapiens

<400> SEQUENCE: 330
gtgggaaata                                                        10

<210> SEQ ID NO 331
<211> LENGTH: 10
<212> TYPE: DNA
<213> ORGANISM: Homo sapiens

<400> SEQUENCE: 331
ttgtgagata                                                        10

<210> SEQ ID NO 332
<211> LENGTH: 10
<212> TYPE: DNA
<213> ORGANISM: Homo sapiens

<400> SEQUENCE: 332
ctgggaaata                                                        10

<210> SEQ ID NO 333
<211> LENGTH: 10
<212> TYPE: DNA
<213> ORGANISM: Homo sapiens

<400> SEQUENCE: 333
tcaagacaga                                                        10

<210> SEQ ID NO 334
<211> LENGTH: 10
<212> TYPE: RNA
<213> ORGANISM: Homo sapiens

<400> SEQUENCE: 334
agcccuuacc                                                        10

<210> SEQ ID NO 335
<211> LENGTH: 10
<212> TYPE: RNA
<213> ORGANISM: Homo sapiens

<400> SEQUENCE: 335
uagcagcacg                                                        10

<210> SEQ ID NO 336
<211> LENGTH: 10
<212> TYPE: RNA
<213> ORGANISM: Homo sapiens

<400> SEQUENCE: 336
acugcccuaa                                                        10

<210> SEQ ID NO 337
```

```
<211> LENGTH: 10
<212> TYPE: RNA
<213> ORGANISM: Homo sapiens

<400> SEQUENCE: 337
aguuuugcag                                                          10

<210> SEQ ID NO 338
<211> LENGTH: 10
<212> TYPE: RNA
<213> ORGANISM: Homo sapiens

<400> SEQUENCE: 338
uugugcuuga                                                          10

<210> SEQ ID NO 339
<211> LENGTH: 10
<212> TYPE: RNA
<213> ORGANISM: Homo sapiens

<400> SEQUENCE: 339
uucacagugg                                                          10

<210> SEQ ID NO 340
<211> LENGTH: 11
<212> TYPE: RNA
<213> ORGANISM: Homo sapiens

<400> SEQUENCE: 340
agggcuuagc u                                                        11

<210> SEQ ID NO 341
<211> LENGTH: 10
<212> TYPE: RNA
<213> ORGANISM: Homo sapiens

<400> SEQUENCE: 341
aaggagcuca                                                          10

<210> SEQ ID NO 342
<211> LENGTH: 10
<212> TYPE: RNA
<213> ORGANISM: Homo sapiens

<400> SEQUENCE: 342
gaacggcuuc                                                          10

<210> SEQ ID NO 343
<211> LENGTH: 11
<212> TYPE: RNA
<213> ORGANISM: Homo sapiens

<400> SEQUENCE: 343
aaucacuaac c                                                        11

<210> SEQ ID NO 344
<211> LENGTH: 11
<212> TYPE: RNA
<213> ORGANISM: Homo sapiens

<400> SEQUENCE: 344
acucaaaaug g                                                        11
```

```
<210> SEQ ID NO 345
<211> LENGTH: 12
<212> TYPE: RNA
<213> ORGANISM: Homo sapiens

<400> SEQUENCE: 345
ugauuggauc gu                                                         12

<210> SEQ ID NO 346
<211> LENGTH: 10
<212> TYPE: RNA
<213> ORGANISM: Homo sapiens

<400> SEQUENCE: 346
acucagccuu                                                            10

<210> SEQ ID NO 347
<211> LENGTH: 11
<212> TYPE: RNA
<213> ORGANISM: Homo sapiens

<400> SEQUENCE: 347
ucuccaaaag g                                                          11

<210> SEQ ID NO 348
<211> LENGTH: 10
<212> TYPE: RNA
<213> ORGANISM: Homo sapiens

<400> SEQUENCE: 348
caaaacuggc                                                            10

<210> SEQ ID NO 349
<211> LENGTH: 10
<212> TYPE: RNA
<213> ORGANISM: Homo sapiens

<400> SEQUENCE: 349 ggggguccccc                                                           10

<210> SEQ ID NO 350
<211> LENGTH: 12
<212> TYPE: RNA
<213> ORGANISM: Homo sapiens

<400> SEQUENCE: 350
gcagguucuc ac                                                         12

<210> SEQ ID NO 351
<211> LENGTH: 50
<212> TYPE: DNA
<213> ORGANISM: Homo sapiens

<400> SEQUENCE: 351
gtcggttcaa aaaacagaaa tcgggtttgc tgcccggcgg acaggcgtga               50

<210> SEQ ID NO 352
<211> LENGTH: 202
<212> TYPE: DNA
<213> ORGANISM: Homo sapiens

<400> SEQUENCE: 352
agagcaaggg aaaggaactt cctccaccct cggggctgga gcccttttcc tctgcatctc    60
```

```
cagtctctga gtgaagatgg ggggcctgac agcctcggac gtacacccga ccctgggggt      120
ccagctcttc tcagctggaa tagcggcgtg cttggcggac gtgatcacct tcccgctgga      180
cacggccaaa gtccggctcc ag                                               202
```

<210> SEQ ID NO 353
<211> LENGTH: 50
<212> TYPE: DNA
<213> ORGANISM: Homo sapiens

<400> SEQUENCE: 353

```
gtagctaggc agaggggtaa gacaatgttc tgcacctttc ttatttccag                  50
```

<210> SEQ ID NO 354
<211> LENGTH: 199
<212> TYPE: DNA
<213> ORGANISM: Homo sapiens

<400> SEQUENCE: 354

```
gtccaaggtg aatgcccgac gtccagtgtt attaggtata aaggtgtcct gggaacaatc       60
accgctgtgg taaaaacaga agggcggatg aaactctaca gcgggctgcc tgcggggctt      120
cagcggcaaa tcagctccgc ctctctcagg atcggcctct acgacacggt ccaggagttc      180
ctcaccgcag ggaaagaaa                                                   199
```

<210> SEQ ID NO 355
<211> LENGTH: 50
<212> TYPE: DNA
<213> ORGANISM: Homo sapiens

<400> SEQUENCE: 355

```
gtaagccgtg agcgttcctg ggaggaataa ttttttttct ctctggatag                  50
```

<210> SEQ ID NO 356
<211> LENGTH: 199
<212> TYPE: DNA
<213> ORGANISM: Homo sapiens

<400> SEQUENCE: 356

```
cagcacctag tttaggaagc aagattttag ctggtctaac gactggagga gtggcagtat       60
tcattgggca acccacagag gtcgtgaaag tcagacttca agcacagcca tctccacgga     120
atcaaacctc gctacacggg gacttataat gcgtacagaa taatagcaac aaccgaaggc     180
ttgacgggtc tttggaaag                                                   199
```

<210> SEQ ID NO 357
<211> LENGTH: 50
<212> TYPE: DNA
<213> ORGANISM: Homo sapiens

<400> SEQUENCE: 357

```
gtaactaact tcaaaatggg ttttaacatt ttcttttttt ttttcccag                   50
```

<210> SEQ ID NO 358
<211> LENGTH: 102
<212> TYPE: DNA
<213> ORGANISM: Homo sapiens

<400> SEQUENCE: 358

```
ggactactcc caatctgatg agaagtgtca tcatcaattg tacagagcta gtaacatatg       60
atctaatgaa ggaggccttt gtgaaaaaca acatattagc ag                         102
```

<210> SEQ ID NO 359
<211> LENGTH: 50
<212> TYPE: DNA
<213> ORGANISM: Homo sapiens

<400> SEQUENCE: 359
gtaacttccc atttcatata acaaagacct gtttcatcga tccattttag        50

<210> SEQ ID NO 360
<211> LENGTH: 181
<212> TYPE: DNA
<213> ORGANISM: Homo sapiens

<400> SEQUENCE: 360
atgacgtccc ctgccacttg gtgtcggctc ttatcgctgg attttgcgca acagctatgt        60
cctccccggt ggatgtagta aaaaccagat ttattaattc tccaccagga cagtacaaaa       120
gtgtgcccaa ctgtgcaatg aaagtgttca ctaacgaagg accaacggct ttcttcaagg       180
g                                                                      181

<210> SEQ ID NO 361
<211> LENGTH: 50
<212> TYPE: DNA
<213> ORGANISM: Homo sapiens

<400> SEQUENCE: 361
gtaagatatg atcttgtgta tctgtcgaac gatgacatgc acttttctag        50

<210> SEQ ID NO 362
<211> LENGTH: 578
<212> TYPE: DNA
<213> ORGANISM: Homo sapiens

<400> SEQUENCE: 362
gttggtacct tccttcttgc gacttggatc ctggaacgtc attatgtttg tgtgctttga        60
acaactgaaa cgagaactgt caaagtcaag gcagactatg gactgtgcca cataatcagc       120
ttcaagaaaa tgatgtaaca taccagtggg aatcttgctg actggatcat aaaaacaaac       180
aaaacttatt cacttatttt aacctaaaaa gataaaggaa ttttggcaga gaattttgga       240
cttttttata taaaaagag gaaaattaat gcctatttca tataactttt ttttttttctc       300 agtgtcttaa gaaggggaaa gcaaaacatt cagcatatac cctggcaaat gtaatgcaga       360
taagctactg catttgacca tttctggagt gcaattgtgt gaatgaatgt gaagaacttt       420
aacatgtttt aattacaatt ccaactggtg gaaagaaac tgagtgaaat gcagtttata       480
tttataaata cttaaaaatg aagttattaa aaatattagt ttttattaac cacagttgtc       540
agttaatata ttcaataaaa gtattgctaa tacctttt                             578

<210> SEQ ID NO 363
<211> LENGTH: 50
<212> TYPE: DNA
<213> ORGANISM: Homo sapiens

<400> SEQUENCE: 363
aaagtttgtc ttttgagatc tatacctggg tgtaagagtc aagttcacta        50

<210> SEQ ID NO 364
<211> LENGTH: 10572
<212> TYPE: DNA

<213> ORGANISM: Homo sapiens

<400> SEQUENCE: 364

```
agagaaggcc gcaaggtgcc tgcaagatgt ctggggagtt ggaggaatgg aagagtgccc      60
cgctcttcct tctgggagag ctccagctag gcagaacctt tcaccaaggc tctgatatcg     120
tgctggtttc cgaaagcccc agccgaaggt gtgcagccaa agggtgacag aaggtgaggc     180
acgtgcgggg gcgcgggtgc tgaccgccgc ggtgcgccct ccctccgacg tgcggtgtgc     240
ggggcgcaga caaccagcgg ccggcccagg gctttcgggg agcgaagcag ggctcccgag     300
gcaccgagcg agaatgggaa tgggagggac ccggtgctcc cggacacgcc cccggcaggt     360
cccacgcccg ggtcttctga gacctcgcgc ggcccagccc gggagcggcc cagctatata     420
agtcccagcg gaagaccgga acgcagaggg tcctgctggc gcgagggtgg gtaggagggg     480
acgcggggac tcggccccca acaccgcgct ccgtctgcag ccgccgcctc tgcaccgccg     540
ctgcccggcg gtcggttcaa aaacagaaa tcgggtttgc tgcccggcgg acaggcgtga     600
agagcaaggg aaaggaactt cctccacctt cggggctgga gccttttcc tctgcatctc     660
cagtctctga gtgaagatgg ggggcctgac agcctcggac gtacacccga ccctgggggt     720
ccagctcttc tcagctggaa tagcggcgtg cttggcggag gtgatcacct cccgctgga     780
cacggccaaa gtccggctcc aggtagctag gcagagggt aagacaaggg gtctcaggac     840
agagggggacg ctgttgcgtg cattccattt attctctgct ttggtgtaac cactgtttct     900
aggtagggta ggtgaccttc caaagcagtc tggccttgtc ccagggctgg tgctttagga     960
tgggaaactg gaactttttc tgggattagc tgaagaacca ccaggccac agagaatggg    1020
ttgaccatga ctactaccaa attctcccaa aatttagggt gcacttagta ttttaagagc    1080
tgagaatatt ggcctctcct gagtttacta gtcaggtgct ttttccttc tttgattctt    1140
cgggggttct gtcctatcct actgccctag gggttctgga gagttcctgg ggaggggat    1200
attcaaaatg tgcattgtag ccagcctccc tccatctgcg cgtgagcgaa cacacacaca    1260
cacacacaca cacacacaca cacacacaca cacacacggt agagggaggt ggatggaaga    1320
ggaatgttgc tgagaaaaga aacggaaaat aggaacacag ggggaaatct tggcttaaga    1380
gtgaactcaa tttcgctccc ttctgttctg cacctttctt atttccaggt ccaaggtgaa    1440
tgcccgacgt ccagtgttat taggtataaa ggtgtcctgg gaacaatcac cgctgtggta    1500
aaaacagaag ggcggatgaa actctacagc gggctgcctg cggggcttca gcggcaaatc    1560
agctccgcct ctctcaggat cggcctctac gacacggtcc aggagttcct caccgcaggg    1620
aaagaaagta agccgtgagc gttcctggga ggggcagaaa agccttgggc tccgctctgt    1680
tccaaaaagt gtaacacaca gaggagtggt tttcataaca aattggcgag aaaacattca    1740
tatttgaact ctcccttccc caaacattag ctcattgttc atagaaaaaa gtatgcaaaa    1800
tcgattttt agatgcagat atatacttgt aaaggtcacc cagtcatgga agttttgtgc    1860
ccagtttgga tctccatctg gagaatatgg gtgggctaca gaaaaatgtt taacttaaag    1920
ttctccaaag agggaagtat atcagaaaca tctatggagc ttgtcagaaa tccaaacgag    1980
gactaccatg gtcctctgag tctgaatcct caggctagag accagagtgt ctttccacaa    2040
gcttccctca tcatttgtgt atgcaacaaa gttcaaagcc ttctgtttga agcaaagaaa    2100
gccagacttt gtgaagagag ttgaaaggac aggaaaagac atatttcctc ttaagaggtt    2160
cctcatcagg tccaggaaag accagagcag aaaaagtgga cgaatgctgc agggagtttg    2220
tttaggggaa aaagaaaagg aaacatattt cctgagtgcc agtgcactct aagaattcct    2280
```

```
gtcactttag gtagcattta tttgagggct taactatgaa ccagacattg ttctaagtgc    2340
ttcagataca ttataactgg aagggtatta gtaccattat cccttggcag atgggaaaac    2400
tgaacacaga gcagattcat cacttgccca aggtcacaca gctgggaggg ggcagagcca    2460
gggttcaaac ccaggcagtc tggcctcgga ctccaggctc ctaaccctgt tctctactgc    2520
cttctgcact tctcatatga ttctgcccat cattcaaacc gcacaacact gctgtgagta    2580
aaaagtgtta gccgaatatc agggtagtta agtaacatgc acaaaatcac acagctaatc    2640
aacatcagag gcactttcat gtggagtaga caagccagag agaagatgtg ctgatggcac    2700
aatgaataca ttaagtgaaa tccaccttgt agatttcatc atttctgctg tgagtaacct    2760
tcaatactat aattttatgg gataatttat aaatgttgtc tatacaaata tataagttat    2820
acttatccac acaagtactt tcaaagtgaa gataaagtct ggatgttact agatcaaaac    2880 tgcattttt tatttataga tgtagcaaga gaggaaacac aaaggaggta aagctgcccg    2940
ttcaggtggt tttcttcaca gattgactgt tctaccaatt gttgtggact ttgggcacca    3000
aattaatagg atatatgttg gcagtgttct atgttatata gattcagttt atttagtagg    3060
ctttattgaa ctgccatgtg ccagtaacta tgttagatgt ttagatgcca gatgtgtctc    3120
tagacagagc ttacagttga gagtatgggt tgtgtgggga gaagtgaata gatgactata    3180
ttccatgata catgctgtat tacaatacag tcctacttca cttaacgatg gggatacatt    3240
ctcagaaatg agttaggagg caaattggtt gttgaatgaa catcacagag agcacttaca    3300
caaacctaga tggcatagcc acacctaggc tatatggtat aatctattgc tcctaggcta    3360
caaacctgtg cagcatgttg gtattgaata ctacaggcaa ttgttacata agttaagtg    3420 tttgtgtacc taaaaataga aaaggtaatg cattacacta cagtcttatg gggctgggat    3480
gtcactaggt gataggaatt tttcagctct gttctaatct tacgggacca ccatcatgta    3540
tgcagcacat gactaactgt aattacaaga tggtggctat attaaacaga actacttaag    3600
ctagccatgg aggtatggtc cgtgagattt tcctgaagaa ttaacgtctg gatcaattct    3660
ggaagggcca gcaggagtac tccaggcaaa ggggtgagaa aggagcttcc aagtagagtg    3720
aaggtcatgt gcaaagactc agtgaggagt cgagtgaaca tagcacaggg aggacatgtt    3780
ggtgaggaag gaggggtgaa gccacagaga caggagggag ccagatgaca gaaggccttg    3840
caggcggtgc taaggagttt ggattttatc cttacagtgg tgggaagtca ttgtaaaaat    3900
attaagcaag ggagtggcat aaacaattta catttcaaa agatcacttt ggcagcagat    3960
agagtatata tgtaaaagga gtaagaaaga ggtaagttag aaagcaagaa atgatcaggg    4020
tatgccctaa aacactggca atagggaaaa agagatgtca atcagaaaga ttgagaaagt    4080
ataattgaat tgacttggtg aacaaataga agtaaggcat aagggacagg tagaaatatg    4140
agatgacttc caagtttctg tttaaagata cccttttattg agagaggatg tatagaagct    4200
gtcttagggg gaagacaaga aatttggttt aggccatgtc aacaggtaat ggccagtagg    4260
cacatgattc agtttatta gtgggctcct tttaggagaa aatctgagcc agattccagg    4320
aagtcacagc agggactacc aatagggtca aacagcagag agtgtggaaa ggactgaaaa    4380
gtgatcattg tacataacaa atagaagctc actgattttc tagcaaaaac atcttcagca    4440
gagtagcgtg gtataagcta tattgtaggg gactgaggaa gaaatgggct ctgagaagta    4500
aagacaaaca atatgttttg taaataaatt tcttttagtt cttaaaaaaa aagcctcttt    4560
tccagcttga ttgggaagtg aagagaggga tttgaaagtt ggagattgga ggataggatg    4620
```

```
agtacatcaa gatacactac gttgtagtgc agtgcattac aaatgtgagc taaaagtgaa      4680
ggcatttgta atcatatgat attgctaatt aaaagacagc tgtcagtcat atgcccagct      4740
cctggtaaag catgatgaga agagtacaat catggtagtg atttaaaaat tgctgccagt      4800
tttgtggatt ttcttttatgc tagacagtgt aagctcttta tcaatattat ttaactcaca     4860
caactctaag aggtagatat tattatccct ttttgacaaa ttaggaaaca gaattataat      4920
gactgagaaa gtctctgctg agtaaatgtt actgaacctt aattttatgt ttacttaatg      4980
atagaaatga atattgggct tcaagactat ttgtacttaa tgaaatctgt cttgagcaac      5040
ataagctatt ttttttcaaaa ttttaagaca aaaatcactt tcttctctcc tgtcttctta    5100
tttttgttcc cttcacatgt tgtagcctaa cactacttga tggcccattt tggtgcagtt     5160
tgtccactgg gcttcatcta aggccaccaa gtcccataat taacatgatc attcgtggga    5220
gaaagatcaa gcctcattgg tgatgggtgc ctcctcacag tcggataata ctgaaaagag    5280
agctaaatgt gggaaagaac caagttgaac acaggaaaga atcaggccac tgtgaaaata    5340
agcattgtgt ttcttgttc cttgaaagtc ttcatttta aaaatttca gacacctgaa       5400 gttttctagc cttactctga gttgacgcac atttagtaca tgatcaacac ataaacaagc    5460
attagagaaa tagaaaagct gtaagaatac aaaaatatgg gccaggtggg tggctcatac    5520
ctgtaatcct agcactttgg gaggccgagg cagacggatc acctgaggtc aggagttcaa    5580
gactagcctg gccaatatag tgaaaccctg tctctactaa aaatacaaaa cttagcaggc    5640
tgtggtggca cgtgcctata atcccagcta cttgggaggc tgaggcagga gaatctcttg    5700
aacccgggag gcggagattg cagtgagcca agatcacacc actgcactct agcctagata    5760
acagagcaag actccatctc aaaaaaaaaa aaaatacaaa aatatgaacc actgaaaatt    5820
aaaaagacat gcatgcattc taggtcttta attttttttc ttaataattt tttttctctc    5880
tggatagcag cacctagttt aggaagcaag attttagctg gtctaacgac tggaggagtg    5940
gcagtattca ttgggcaacc cacagaggtc gtgaaagtca gacttcaagc acagagccat    6000
ctccacggaa tcaaacctcg ctacacgggg acttataatg cgtacagaat aatagcaaca    6060
accgaaggct tgacgggtct ttggaaaggt aactaacttc aaaatgggtt ttataaccac    6120
caaagcacat acatacaact agcaacttat tgtaaagtag agttaataaa cattttcttt    6180 tttttttttcc ccaggacta ctcccaatct gatgagaagt gtcatcatca attgtacaga    6240
gctagtaaca tatgatctaa tgaaggaggc ctttgtgaaa acaacatat tagcaggtaa    6300 cttcccattt catataacaa acaggtctgc acctttagaa gttcatcttg gagcttctgc    6360 agccaccttta tactcaatct cttaactcca atagttttct cttttttaaaa attaagtaat    6420 tttgaaccat atataacttt gtgagaagca ggaaaagacc aaaatattaa gtttaagaag    6480
ttttgccaca acaaaaatat tttgcaacaa aaataacagg caatttcatg tcagcattat    6540
tctcatttaa tactaatata tgggactttt gttagaatct tattctttat acagcagaat    6600
tcaggaggta agtccatcct gcatactata tccaaaagat ctagttataa aaggagctta    6660
tcagtggtct catccaaaaa gtaataccat aagataggtt cttaaaaata atattctaac    6720
aacttctaga gacattgaaa tttcccttat ttcaataaaa aagtattaga tgctcatata    6780
ttaggcatta ttacaggcct taaaggcaca gaggaaacta acagtttact ttcctaaagt    6840
gttaacaatc tattaagcca tttactcttt accttctttt tctagtgcaa tacctttctt    6900
attttatttt atttatttat aagacatctt cattgaccta ctgttatcaa taggtttata    6960
aagatatgac agataactaa attgcaagcc cccaaaagtc tgatgttgac ctgtttcatc    7020
```

```
gatccatttt agatgacgtc ccctgccact tggtgtcggc tcttatcgct ggattttgcg     7080
caacagctat gtcctccccg gtggatgtag taaaaaccag atttattaat tctccaccag     7140
gacagtacaa aagtgtgccc aactgtgcaa tgaaagtgtt cactaacgaa ggaccaacgg     7200 cttttcttcaa ggggtaagat atgatcttgt gtatctgtaa tgtgttctgg ctgtctgtgt    7260
gctttgggac actctcatgt caagcaaccg acatttagct tacaagcctt agtatattca     7320
tatacttagt attgactttt ccttgccaca gatttctcca atccaccaat tccactgtgc     7380
cagaaagtaa aaagccatga tattcaaatt ttctcaactt tgatcaaagg ctcattcaag     7440
accagtgcct tttccactgg tcccaatcta ctggaaatgc agacagtatt ttgccttctc     7500
tgggcaagaa agttataaag tagagggaaa tcataataga gagctatgag agaacaagat     7560
ttgatttgat ttaatttgat ggactcaagt tttaacattg taaaactaga gataagacat     7620
caccaccaat ctagaaaagt gatgcagaaa agtatttgat ttgggtaatt attacactca     7680
cctagaaaca agtgttgtgt aatagattac atatttccat aatgcaatgt tgtatcagaa     7740
actaccttcc taagaaaata tagtatgggc tcggcgtggt ggctcgcacc tgtaatccca     7800
gcactttggg agatggaggc aggaggatca cttgagccca gactgggcaa caaagcgaga     7860
ccctgtctca acaaaaaatt taaaaattag ctgagtgtgg tggcacgcac tgatggtccc     7920
ctctacttgg gaagctgagg caagaggatc tcctgagccc aggagttcaa ggtttcagcg     7980
agctatgatt gtgccactgc actccagcct gggagacaga gcaagtccct gtctcaaaaa     8040
agaagaagga gaaggaggag aaaatacagt attaagtaat ctgtcaatat attccacaag     8100
gattacacta gtggtttaat aataaaatta tattacccttt ttaaattgta aggccattcc    8160
tcaagcttta taaattaagc atgaatgcat catacacatt ttataaaaag ttccaactca     8220
tcataatctg tacttatgat acattaatac aaatgaagtt cattataaaa ttaacttaaa     8280
atggatatac cagttattaa accattaacc atttaataat tttattttttt tcaaatttaa    8340 aaaccttttg gggaagaaat actacaacat ggatgaacct tgaaaacgtt atgctaagtg     8400
aaataagcca gacacaaaag gacaaatact gtatgattac acttaaatga ggtacctaga     8460
gtagtcaaat tcatagagac agaaagaata gaagttacca ggggctggag gtaggaaaaa     8520
atggagagct gtttaatggg tagagagttt ctttttgggg tgacaaaaag gttctagaga     8580
tggatagtgg tgatggttac acacaatgtg tgtgtactta atgctactga aatgtaatttt    8640 tatgattttt ttttttttgca gcaaaatacc ccacattggg aagtgaagag aaacatgtta    8700
agagacttga aggaaaaaaa ttggggcaga ggggtgtttt ttataggtta aacaataaaa     8760
gccatttaaa cagtaacaat ttctctaagg acaagaatcg tcaagattga gacagcactg     8820
atttcttgac tctactcaat acttctttgg tttctcttct tccttccccc ttctaatagt     8880
ttcctacctc ccattcagaa agcaaagcaa acaagcaaa aattccccct tccctcaaaa      8940
aaggaaagag ttttttgaaaa agttcatgtc agtgaagaaa agacatgttt tgggagtgaa    9000
ggatatttgt ggatttgtat agatgtgatc atcagggctg tgttgttttg aagtaatata     9060
ggacatctag aggaaaattt attttcagca gaggagggaa agatgaagag taggtacttt     9120
taagcatctt cacttgagga gtggcaaaat gagaagcata acctgctata atcactttaa     9180
gaatttcagg ctgagtgtgg tggtgcagtc tctagtccca gttactccag gaggctcagg     9240
tgggaggatc acttaagccc aggagctcga ggttgcagtg agctatgatt acactactgc     9300
attccagcct gggcggcagg gtgaagcctc atctcaaaaa ttaaaaaaaa aaaaaatcaa     9360
```

| | | | | |
|---|---|---|---|---|
| acaaattaat | cgaacgatga | catgcacttt | tctaggttgg | taccttcctt cttgcgactt | 9420 |
| ggatcctgga | acgtcattat | gtttgtgtgc | tttgaacaac | tgaaacgaga actgtcaaag | 9480 |
| tcaaggcaga | ctatggactg | tgccacataa | tcagcttcaa | gaaaatgatg taacatacca | 9540 |
| gtgggaatct | tgctgactgg | atcataaaaa | caaacaaaac | ttattcactt attttaacct | 9600 |
| aaaaagataa | aggaattttg | gcagagaatt | ttggactttt | ttatataaaa aagaggaaaa | 9660 |
| ttaatgccta | tttcatataa | cttttttttt | ttctcagtgt | cttaagaagg ggaaagcaaa | 9720 |
| acattcagca | tatacccctgg | caaatgtaat | gcagataagc | tactgcattt gaccatttct | 9780 |
| ggagtgcaat | tgtgtgaatg | aatgtgaaga | actttaacat | gttttaatta caattccaac | 9840 |
| tggtggaaaa | gaaactgagt | gaaatgcagt | ttatatttat | aaatacttaa aaatgaagtt | 9900 |
| attaaaaata | ttagttttta | ttaaccacag | ttgtcagtta | atatattcaa taaagtattg | 9960 |
| ctaatacctt | ttaaagtttg | tcttttgaga | tctatacctg | ggtgtaagag tcaagttcac | 10020 |
| tagaatacaa | gactgcccaa | tagcaaatgc | aggtctttag | aatcataggc atgaacctac | 10080 |
| tctgaatgtt | attagtatag | atttttaatg | tttagagtcc | agatttgatg acatctctaa | 10140 |
| caacttctaa | tctaagacac | tatattcatt | ttggcaggat | tgctactaga gtcttggtat | 10200 |
| ctgtgctagc | atcacataat | tttagagctg | gagggtactt | ctgggaagac agaggaacag | 10260 |
| tttgagattc | ctactgagat | gaaaacgaat | cttcatggaa | tctttcagca aagccaaatt | 10320 |
| caaattcatc | attagcacct | gtagtaacct | tttcaatgcc | tacaaactgc atgcagaaga | 10380 |
| gatagggaaa | cagtaaaaca | gatattaaaa | gaagttttta | agacaaagcc cagcctgatt | 10440 |
| ttaagctaaa | tccaaggatt | ggcagcttgg | atgagcagga | aggttacagg ctgccagaca | 10500 |
| tcattctagt | tctgttttaa | tcaactccat | gttacattta | ctatcaggga ttctcacctc | 10560 |
| accctcatgc | at | | | | 10572 |

<210> SEQ ID NO 365
<211> LENGTH: 15910
<212> TYPE: DNA
<213> ORGANISM: Homo sapiens

<400> SEQUENCE: 365

| | | | | |
|---|---|---|---|---|
| ctgtacagct | ctccgacaat | cccacatcta | gatgccaagc | tgaggttggc attctcacta | 60 |
| atttgctgtt | ataaatatta | agctatcata | agcgttagcc | tacatatgac tctttcatat | 120 |
| gttagttaat | tattttaggg | tagaaatcca | aaagtggagt | taccagaagt ggatatagac | 180 |
| attctggctg | ggtgtgatgg | ttcatgcctg | taatcccagc | actttgggag gcagaggcag | 240 |
| gcggatcact | tgaggccagg | agtttgagat | cagcctgggc | caacacagcg aaaccccatc | 300 |
| tctactaaaa | attccaaaac | tagccaggca | tagtggcaca | tgcctgtact cccagctact | 360 |
| tgggaggcta | agacacaaga | atcgcttgaa | cccgggaggg | aggtggaggt tgcggtgagc | 420 |
| tgagattgtg | ccaccgtact | ccagcctggg | tgacacagct | agactctgtt tcaaaaaaaa | 480 |
| aaagaaaaag | aaagaaaaa | aatagacttt | ctcttggctc | agtgtatact gccaaattgt | 540 |
| tttccaaaaa | aattgtgtca | atgtataaca | ccatcactaa | tatagtattg atattatggt | 600 |
| tattacattt | taaaattcat | aatttgtaat | tataacattc | ataatttatt actatttata | 660 |
| atattaatgt | aaatgtatat | tatatataaa | tgttatagta | attataactt tggtagtgac | 720 |
| aaagtattaa | tttattaggt | gaagtatatg | ctttttttatt | agtgataata aatatatcct | 780 |
| ctctcccatt | ataaaagttt | gtatttcttc | ttttagaaat | tgattcttct gtcatttgca | 840 |
| catttatctg | tataattata | acagggtatt | tcccagtggt | ggctaatgag agaattatgg | 900 |

```
gaaagtatag aacactattc aaatgcaaag cactgtatga ttttattta ataggaagac      960
attttgtgca gcgatttctg attgaccaca gtttgatcaa gtgcatttgt taatgtgttc     1020
tacattttca aaaggaaag gagaatttgt tacattcaga acttgctgcc actcctttgc      1080
tacgtcataa agggtcagtt gcccttgctc atactgacct attctttacc tctctgcttc     1140
ttctttgtgc cagaagagta gaaatctgac cctttgggga taccaccctc tcccctactg     1200
ctctctccaa cctgaggcaa actttctcct acttcccaga gcctgtcaga agtggtgaag     1260
ccagcctgct ccttggaatc cagaactact ttcagaatct tgaacttctg tgacctctca     1320
gggtcccctt gtgtgaagtt tttgacgtca gcttctcctg tgacccttag aagtcactct     1380
tgtgtctagc acatcccagg tgctcagtca ccattgaact acagtcatac tatctcctgg     1440
caaaggctct taactgtcca tgttagcctg atattaatat cctggaagct tatactgtcg     1500
ttcttccttc caggtttaaa taaggcagcc cctttatcct gtcacaggtc ctctctccct     1560
acctatcctt acctgttttg gataacaacc tttcttattt ctaatagatt tatttatttc     1620
tcacatttcc ttcccttatc atagttttcc tctcactttc tcctctagtt tgtcatactc     1680
tggctttaaa acatgcaaac atgtgcctta tggggaaaaa aagacaattt taatttacct     1740
tgcttcttct ttacaaatgt attgtggctt cttcttatag tccaaatcta aaactcttta     1800
cccacccact gccttgaact ccttcctcgt tgtgaaagta ggatggggca aagagagaat     1860
gcatgcccct cccaactgct caaacaagta aggtgctgt tacagttatc ttttgctacc      1920
ttaatacaat aattatttta ttatatctca caattttatg gatcaggaat ttagactggg     1980
ctcagctagg cgattcttct gctttactga catcatagga gatcacttgg tggtattcaa     2040
ctgtcaggta ggcttatctg gagggtccaa gatagctgta ctctggtgcc tggtgccttg     2100
gtaaagaggg atgatgatgt ggggcctctc cagcatgaac agcctcagag aagtttgctt     2160
tcttacatgc tggcccaggg ctccaagagc aaatgttgca gtgagtaaag cagaagatac     2220
aaggactttt ataatctggt ctcagaagcc acatggcatc agttctgtat tattctattg     2280
gtcaaaacat tcataagcct gccagatgca aggggaaggc atatgtaccc tcatcttttg     2340
atgggaggaa tgtgatggat ttgcaattat gttttaaaac tactacagac agaaccactg     2400
agaaagattc atgggtagct ttggggtgag gactgggaat taacctgttg atagcagagg     2460
ttcactagag tcaacaagga ataaggtctc ctcttgtaca ctttagtcat actataccaa     2520
cattcttaac cactgcttag ccatcagcct cacaacataa caactccatc atagttgtac     2580
tccctaagat caccaacaat gttagagtca atccggtag gtttttcttt gtttttgtcc      2640
tcctgacatt ttttctaaac ttgacactgg tcagacccaa tctttcttta atcatattct     2700
taaataccag ttctatcact ggatatgtta ctgtttcttg ttctcactct accttttgaca    2760
aagccattct ttccagacta taactctggg tctgggtccc cctatggttt ggcccttgaa     2820
ttctttttcct agtcctattt gactagcccc attttcccgt gaaaagcatg ccccttcat    2880
tgcatccata tcatgactac caaataccctc tctatttct tcctcttta gcatgttaaa     2940
tgcagcttcc taagctctct atctggatat caacagtatt ctctccaaat aattctaaga    3000
ctttaaaaat tggtttaatc ttcttacccc taaaatcacc ccccttacca actgcctcat    3060
gacaatcatt ggtactgtca ctgagcttgc aacccatgtt cttaaacata gagtaatctt    3120
tgactccaca tctaatcatt cataaagctg tattgtctat caaattaaat ctgcatttta    3180
tgtgagagca cttcatagtc tgtaaagcac tacacaggtg ataacatgaa gctacactca    3240
```

```
taatggattt gcaggctctg cttctcattt ggcttctaca gcctcatccc tcaccaactt    3300
cttgccctac ctctctcttt cttccccatc acccaatttc ccagtcagtc aggccaacag    3360
aatgcattct atatacgcga cttgctttcc ccaacatctt tgcctgtatg catgccactt    3420
atttgcctca gttgatcttt atttcaacaa gtgtttgcag aggagaaacc tcgctggctc    3480
cttctccttt ctattttttt tcagaggcta cccgtcaggt caacattgcc ttttcaggg    3540
aagctctgca agcctgacct cccttggaag tgccttagga ctggcttctt gcacagtaca    3600
caacctttac ttatagaggg tttggagatt attctttatt catgtcttat ttctcctgct    3660
cctggaggag atgactctga cttccactga ctcttttggg gggcttaagt cagggttgag    3720
taccagaggc cctaaatagc tggacgtgga ttctggtaat atcaaatcca tctttggctt    3780
aactgagagg ttctgaaagc tgggacctga ccttgtccat ttccctcttt ctccagtttc    3840
ctattatttc ccactgtttt ttttaaaagt tttttgtttt cttaagtttt cacaagaata    3900
aacattgaaa ataaaatttg cacaaagatc gaactaggaa aggccacaca accaacacat    3960
attacatcat tataggtaag ttagcaggga gatttcagac ctgggctagc tctgaaacca    4020
cattttacac tgttgaaaat aaaagctgga gtacagatga cttccccagg ttcacagagt    4080
tggtaagctg gagagctgca cctggagcca agcaacctgc cctgtccttt ccactgcacc    4140
ctctaagaaa tctaattaga aggaacaggt ggtatctcat tttgtacggt gctttagcaa    4200
tgtactattt gctttctagt gtgtctattg tctcgtttga catcttctct caaaaagtga    4260
tgaaacgaaa cgctctttt gacaagttca gagtgctctt ggttcctgtg tgggattctt    4320
ccaagtctga atttggtagt gggaagagaa ggaatccgga ggaaggagga tgagaagttt    4380
aaaggagagg aaagggaagc agagaaggcc gcaaggtgcc tgcaagatgt ctggggagtt    4440
ggaggaatgg aagagtgccc cgctcttcct tctgggagag ctccagctag cagaaccttt    4500
tcaccaaggc tctgatatcg tgctggtttc cgaaagcccc agccgaaggt gtgcagccaa    4560
agggtgacag aagtgaggc acgtgcgggg gcgcgggtgc tgaccgccgc ggtgcgccct    4620
ccctccgacg tgcggtgtgc ggggcgcaga caaccagcgg ccggcccagg gctttcgggg    4680
agcgaagcag ggctcccgag gcaccgagcg agaatgggaa tgggagggac ccggtgctcc    4740
cggacacgcc cccggcaggt cccacgcccg ggtcttctga cctcgcgc ggcccagccc    4800
gggagcggcc cagctatata agtcccagcg gaagaccgga acgcagaggg tcctgctggc    4860
gcgagggtgg gtaggagggg acgcggggac tcggcccca acaccgcgct ccgtctgcag    4920
ccgccgcctc tgcaccgccg ctgcccgcg gtcggttcaa aaaacagaaa tcgggtttgc    4980
tgcccggcgg acaggcgtga agagcaaggg aaaggaactt cctccacctt cggggctgga    5040
gccctttcc tctgcatctc cagtctctga gtgaagatgg ggggcctgac agcctcggac    5100
gtacacccga ccctgggggt ccagctcttc tcagctggaa tagcggcgtg cttggcggac    5160
gtgatcacct tcccgctgga cacggccaaa gtccggctcc aggtagctag cagaggggt    5220
aagacaaggg gtctcaggac agaggggacg ctgttgcgtg cattccattt attctctgct    5280
ttggtgtaac cactgtttct aggtagggta ggtgaccttc caaagcagtc tggccttgtc    5340
ccagggctgt tgcttagga tgggaaactg gaacttttc tgggattagc tgaagaacca    5400
ccagggccac agagaatggg ttgaccatga ctactaccaa attctcccaa aatttagggt    5460
gcacttagta ttttaagagc tgagaatatt ggcctctcct gagtttacta gtcaggtgct    5520
ttttcctttc tttgattctt cggggtgtct gtcctatcct actgcctag ggttctgga    5580
gagttcctgg ggaggggat attcaaaatg tgcattgtag ccagcctccc tccatctgcg    5640
```

```
cgtgagcgaa cacacacaca cacacacaca cacacacaca cacacacaca cacacacggt    5700
agagggaggt ggatggaaga ggaatgttgc tgagaaaaga aacggaaaat aggaacacag    5760
ggggaaatct tggcttaaga gtgaactcaa tttcgctccc ttctgttctg cacctttctt    5820
atttccaggt ccaaggtgaa tgcccgacgt ccagtgttat taggtataaa ggtgtcctgg    5880
gaacaatcac cgctgtggta aaaacagaag ggcggatgaa actctacagc gggctgcctg    5940
cggggcttca gcggcaaatc agctccgcct ctctcaggat cggcctctac gacacggtcc    6000
aggagttcct caccgcaggg aaagaaagta agccgtgagc gttcctggga ggggcagaaa    6060
agccttgggc tccgctctgt tccaaaaagt gtaacacaca gaggagtggt tttcataaca    6120
aattggcgag aaaacattca tatttgaact ctcccttccc caaacattag ctcattgttc    6180
atagaaaaaa gtatgcaaaa tcgattttt agatgcagat atatacttgt aaaggtcacc    6240
cagtcatgga agttttgtgc ccagtttgga tctccatctg gagaatatgg gtgggctaca    6300
gaaaaatgtt taacttaaag ttctccaaag agggaagtat atcagaaaca tctatggagc    6360
ttgtcagaaa tccaaacgag gactaccatg gtcctctgag tctgaatcct caggctagag    6420
accagagtgt ctttccacaa gcttccctca tcatttgtgt atgcaacaaa gttcaaagcc    6480
ttctgtttga agcaaagaaa gccagacttt gtgaagagag ttgaaaggac aggaaaagac    6540
atatttcctc ttaagaggtt cctcatcagg tccaggaaag accagagcag aaaaagtgga    6600
cgaatgctgc agggagtttg tttaggggaa aaagaaaagg aaacatattt cctgagtgcc    6660
agtgcactct aagaattcct gtcactttag gtagcattta tttgagggct taactatgaa    6720
ccagacattg ttctaagtgc ttcagataca ttataactgg aagggtatta gtaccattat    6780
cccttggcag atgggaaaac tgaacacaga gcagattcat cacttgccca aggtcacaca    6840
gctgggaggg ggcagagcca gggttcaaac ccaggcagtc tggcctcgga ctccaggctc    6900
ctaaccctgt tctctactgc cttctgcact tctcatatga ttctgcccat cattcaaacc    6960
gcacaacact gctgtgagta aaaagtgtta gccgaatatc agggtagtta agtaacatgc    7020
acaaaatcac acagctaatc aacatcagag gcactttcat gtggagtaga caagccagag    7080
agaagatgtg ctgatggcac aatgaataca ttaagtgaaa tccaccttgt agatttcatc    7140
atttctgctg tgagtaacct tcaatactat aattttatgg gataatttat aaatgttgtc    7200
tatacaaata tataagttat acttatccac acaagtactt tcaaagtgaa gataaagtct    7260
ggatgttact agatcaaaac tgcattttt tatttataga tgtagcaaga gaggaaacac    7320
aaaggaggta aagctgcccg ttcaggtggt tttcttcaca gattgactgt tctaccaatt    7380
gttgtggact ttgggcacca aattaatagg atatatgttg gcagtgttct atgttatata    7440
gattcagttt atttagtagg ctttattgaa ctgccatgtg ccagtaacta tgttagatgt    7500
ttagatggca gatgtgtctc tagacagagc ttacagttga gagtatgggt tgtgtgggga    7560
gaagtgaata atgactata ttccatgata catgctgtat tacaatacag tcctacttca    7620
cttaacgatg gggatacatt ctcagaaatg agttaggagg caaattggtt gttgaatgaa    7680
catcacagag agcacttaca caaacctaga tggcatagcc acacctaggc tatatggtat    7740
aatctattgc tcctaggcta caaacctgtg cagcatgttg gtattgaata ctacaggcaa    7800
ttgttacata agttaagtg tttgtgtacc taaaaataga aaaggtaatg cattacacta    7860
cagtcttatg gggctgggat gtcactaggt gataggaatt tttcagctct gttctaatct    7920
tacgggacca ccatcatgta tgcagcacat gactaactgt aattacaaga tggtggctat    7980
```

```
attaaacaga actacttaag ctagccatgg aggtatggtc cgtgagattt tcctgaagaa   8040
ttaacgtctg gatcaattct ggaagggcca gcaggagtac tccaggcaaa ggggtgagaa   8100
aggagcttcc aagtagagtg aaggtcatgt gcaaagactc agtgaggagt cgagtgaaca   8160
tagcacaggg aggacatgtt ggtgaggaag gaggggtgaa gccacagaga caggagggag   8220
ccagatgaca gaaggccttg caggcggtgc taaggagttt ggattttatc cttacagtgg   8280
tgggaagtca ttgtaaaaat attaagcaag ggagtggcat aaacaattta cattttcaaa   8340
agatcacttt ggcagcagat agagtatata tgtaaaagga gtaagaaaga ggtaagttag   8400
aaagcaagaa atgatcaggg tatgccctaa aacactggca atagggaaaa agagatgtca   8460
atcagaaaga ttgagaaagt ataattgaat tgacttggtg aacaaataga agtaaggcat   8520
aagggacagg tagaaatatg agatgacttc caagtttctg tttaaagata cccttattg    8580
agagaggatg tatagaagct gtcttagggg gaagacaaga aatttggttt aggccatgtc   8640
aacaggtaat ggccagtagg cacatgattc agtttattta gtgggctcct tttaggagaa   8700
aatctgagcc agattccagg aagtcacagc agggactacc aatagggtca aacagcagag   8760
agtgtggaaa ggactgaaaa gtgatcattg tacataacaa atagaagctc actgattttc   8820
tagcaaaaac atcttcagca gagtagcgtg gtataagcta tattgtaggg gactgaggaa   8880
gaaatgggct ctgagaagta aagacaaaca atatgttttg taaataaatt tcttttagtt   8940
cttaaaaaaa aagcctcttt tccagcttga ttggaagtg aagagaggga tttgaaagtt   9000
ggagattgga ggataggatg agtacatcaa gatacactac gttgtagtgc agtgcattac   9060
aaatgtgagc taaagtgaa ggcatttgta atcatatgat attgctaatt aaaagacagc     9120
tgtcagtcat atgcccagct cctggtaaag catgatgaga agagtacaat catggtagtg   9180
atttaaaaat tgctgccagt tttgtggatt ttctttatgc tagacagtgt aagctcttta   9240
tcaatattat ttaactcaca caactctaag aggtagatat tattatccct ttttgacaaa   9300
ttaggaaaca gaattataat gactgagaaa gtctctgctg agtaaatgtt actgaacctt   9360
aattttatgt ttacttaatg atagaaatga atattgggct tcaagactat ttgtacttaa   9420
tgaaatctgt cttgagcaac ataagctatt ttttcaaaa tttttaagaca aaaatcacttt  9480
tcttctctcc tgtcttctta tttttgttcc cttcacatgt tgtagcctaa cactacttga   9540
tggcccattt tggtgcagtt tgtccactgg gcttcatcta aggccaccaa gtcccataat   9600
taacatgatc attcgtggga gaaagatcaa gcctcattgg tgatgggtgc ctcctcacag   9660
tcggataata ctgaaaagag agctaaatgt gggaagaac caagttgaac acaggaaaga   9720
atcaggccac tgtgaaaata agcattgtgt tttcttgttc cttgaaagtc ttcatttta    9780
aaaaatttca gacacctgaa gttttctagc cttactctga gttgacgcac atttagtaca   9840
tgatcaacac ataaacaagc attagagaaa tagaaaagct gtaagaatac aaaaatatgg   9900
gccaggtggg tggctcatac ctgtaatcct agcactttgg gaggccgagg cagacggatc   9960
acctgaggtc aggagttcaa gactagcctg gccaatatag tgaaaccctg tctctactaa   10020
aaatacaaaa cttagcaggc tgtggtggca cgtgcctata atcccagcta cttgggaggc   10080
tgaggcagga gaatctcttg aacccgggag gcggagattg cagtgagcca agatcacacc   10140
actgcactct agcctagata acagagcaag actccatctc aaaaaaaaaa aaaatacaaa   10200
aatatgaacc actgaaaatt aaaaagacat gcatgcattc taggtctta atttttttc      10260
ttaataattt ttttctctc tggatagcag cacctagttt aggaagcaag attttagctg    10320
gtctaacgac tggaggagtg gcagtattca ttgggcaacc cacagaggtc gtgaaagtca   10380
```

```
gacttcaagc acagagccat ctccacggaa tcaaacctcg ctacacgggg acttataatg    10440
cgtacagaat aatagcaaca accgaaggct tgacgggtct ttggaaaggt aactaacttc    10500
aaaatgggtt ttataaccac caaagcacat acatacaact agcaacttat tgtaaagtag    10560
agttaataaa cattttcttt tttttttttcc ccagggacta ctcccaatct gatgagaagt    10620
gtcatcatca attgtacaga gctagtaaca tatgatctaa tgaaggaggc ctttgtgaaa    10680
aacaacatat tagcaggtaa cttcccattt catataacaa acaggtctgc acctttagaa    10740
gttcatcttg gagcttctgc agccaccttta tactcaatct cttaactcca atagttttct    10800 cttttttaaaa attaagtaat tttgaaccat atataacttt gtgagaagca ggaaaagacc    10860
aaaatattaa gtttaagaag ttttgccaca acaaaaatat tttgcaacaa aataacagg     10920 caatttcatg tcagcattat tctcatttaa tactaatata tgggactttt gttagaatct    10980
tattctttat acagcagaat tcaggaggta agtccatcct gcatactata tccaaaagat    11040
ctagttataa aaggagctta tcagtggtct catccaaaaa gtaataccat aagataggtt    11100
cttaaaaata atattctaac aacttctaga gacattgaaa tttcccttat ttcaataaaa    11160
aagtattaga tgctcatata ttaggcatta ttacaggcct taaaggcaca gaggaaacta    11220
acagtttact ttcctaaagt gttaacaatc tattaagcca tttactcttt accttctttt    11280
tctagtgcaa tacctttctt atttttatttt atttatttat aagacatctt cattgaccta    11340
ctgttatcaa taggtttata aagatatgac agataactaa attgcaagcc cccaaaagtc    11400
tgatgttgac ctgtttcatc gatccatttt agatgacgtc ccctgccact tggtgtcggc    11460
tcttatcgct ggattttgcg caacagctat gtcctccccg gtggatgtag taaaaaccag    11520
atttattaat tctccaccag gacagtacaa aagtgtgccc aactgtgcaa tgaaagtgtt    11580
cactaacgaa ggaccaacgg cttttcttcaa ggggtaagat atgatcttgt gtatctgtaa    11640
tgtgttctgg ctgtctgtgt gctttgggac actctcatgt caagcaaccg acatttagct    11700
tacaagcctt agtatattca tatacttagt attgactttt ccttgccaca gatttctcca    11760
atccaccaat tccactgtgc cagaaagtaa aaagccatga tattcaaatt ttctcaactt    11820
tgatcaaagg ctcattcaag accagtgcct tttccactgg tcccaatcta ctggaaatgc    11880
agacagtatt ttgccttctc tgggcaagaa agttataaag tagagggaaa tcataataga    11940
gagctatgag agaacaagat ttgatttgat ttaatttgat ggactcaagt tttaacattg    12000
taaaactaga gataagacat caccaccaat ctagaaaagt gatgcagaaa agtatttgat    12060
ttgggtaatt attacactca cctagaaaca agtgttgtgt aatagattac atatttccat    12120
aatgcaatgt tgtatcagaa actaccttcc taagaaaata tagtatgggc tcggcgtggt    12180
ggctcgcacc tgtaatccca gcactttggg agatggaggc aggaggatca cttgagccca    12240
gactgggcaa caaagcgaga ccctgtctca acaaaaaatt taaaaattag ctgagtgtgg    12300
tggcacgcac tgatggtccc ctctacttgg gaagctgagg caagaggatc tcctgagccc    12360
aggagttcaa ggtttcagcg agctatgatt gtgccactgc actccagcct gggagacaga    12420
gcaagtccct gtctcaaaaa agaagaagga gaaggaggag aaaatacagt attaagtaat    12480
ctgtcaatat attccacaag gattacacta gtggtttaat aataaaatta tattaccttt    12540
ttaaattgta aggccattcc tcaagcttta taaattaagc atgaatgcat catacacatt    12600
ttataaaaag ttccaactca tcataatctg tacttatgat acattaatac aaatgaagtt    12660
cattataaaa ttaacttaaa atggatatac cagttattaa accattaacc atttaataat    12720
```

```
tttatttttt tcaaatttaa aaaccttttg gggaagaaat actacaacat ggatgaacct    12780
tgaaaacgtt atgctaagtg aaataagcca gacacaaaag gacaaatact gtatgattac    12840
acttaaatga ggtacctaga gtagtcaaat tcatagagac agaaagaata gaagttacca    12900
ggggctggag gtaggaaaaa atggagagct gtttaatggg tagagagttt cttttttgggg   12960 tgacaaaaag gttctagaga tggatagtgg tgatggttac acacaatgtg tgtgtactta    13020
atgctactga aatgtaattt tatgattttt ttttttgca gcaaaatacc ccacattggg     13080
aagtgaagag aaacatgtta agagacttga aggaaaaaaa ttggggcaga ggggtgtttt    13140
ttataggtta aacaataaaa gccatttaaa cagtaacaat ttctctaagg acaagaatcg    13200
tcaagattga gacagcactg atttcttgac tctactcaat acttctttgg tttctcttct    13260 tccttcccc ttctaatagt ttcctacctc ccattcagaa agcaaagcaa aacaagcaaa     13320 aattcccct tccctcaaaa aaggaaagag ttttgaaaa agttcatgtc agtgaagaaa      13380
agacatgttt tgggagtgaa ggatatttgt ggatttgtat agatgtgatc atcagggctg    13440
tgttgttttg aagtaatata ggacatctag aggaaaattt attttcagca gaggagggaa    13500
agatgaagag taggtacttt taagcatctt cacttgagga gtggcaaaat gagaagcata    13560
acctgctata atcactttaa gaatttcagg ctgagtgtgg tggtgcagtc tctagtccca    13620
gttactccag gaggctcagg tgggaggatc acttaagccc aggagctcga ggttgcagtg    13680
agctatgatt acactactgc attccagcct gggcggcagg gtgaagcctc atctcaaaaa    13740
ttaaaaaaaa aaaaaatcaa acaaattaat cgaacgatga catgcacttt tctaggttgg    13800
taccttcctt cttgcgactt ggatcctgga acgtcattat gtttgtgtgc tttgaacaac    13860
tgaaacgaga actgtcaaag tcaaggcaga ctatggactg tgccacataa tcagcttcaa    13920
gaaaatgatg taacatacca gtgggaatct tgctgactgg atcataaaaa caaacaaaac    13980
ttattcactt attttaacct aaaaagataa aggaattttg gcagagaatt ttggactttt    14040
ttatataaaa aagaggaaaa ttaatgccta tttcatataa cttttttttt ttctcagtgt    14100
cttaagaagg ggaaagcaaa acattcagca tataccctgg caaatgtaat gcagataagc    14160
tactgcattt gaccatttct ggagtgcaat tgtgtgaatg aatgtgaaga actttaacat    14220
gttttaatta caattccaac tggtggaaaa gaaactgagt gaaatgcagt ttatatttat    14280
aaatacttaa aaatgaagtt attaaaaata ttagttttta ttaaccacag ttgtcagtta    14340
atatattcaa taaagtattg ctaatacctt ttaaagtttg tcttttgaga tctataccctg   14400 ggtgtaagag tcaagttcac tagaatacaa gactgcccaa tagcaaatgc aggtctttag    14460
aatcataggc atgaacctac tctgaatgtt attagtatag attttaatg tttagagtcc     14520 agatttgatg acatctctaa caacttctaa tctaagacac tatattcatt ttggcaggat    14580
tgctactaga gtcttggtat ctgtgctagc atcacataat tttagagctg gagggtactt    14640
ctgggaagac agaggaacag tttgagattc ctactgagat gaaaacgaat cttcatggaa    14700
tctttcagca aagccaaatt caaattcatc attagcacct gtagtaacct tttcaatgcc    14760
tacaaactgc atgcagaaga gatagggaaa cagtaaaaca gatattaaaa gaagttttta    14820
agacaaagcc cagcctgatt ttaagctaaa tccaaggatt ggcagcttgg atgagcagga    14880
aggttacagg ctgccagaca tcattctagt tctgttttaa tcaactccat gttacattta    14940
ctatcagggg ttctcacctc accctcatgc atgtcttccc cattcattac ccgcaaaagt    15000
gtcttgtagc agatgtcttc tgtgtcccat acataccatt ttgctctttta gtgcttgctg    15060 gcctgacttc ctattgtcat gtcagcatct gccctttta gggtctctgg ccaccagagc      15120
```

```
cagctttact cacctgtgca tggcattcta gaagagcagc agggaaaata acacagcccc      15180
agtgcagccc ttaaccacca ataactggta gtagttggtg tacaaatatc tcagttccct      15240
caactgtcag gtggaatacc gctgagggat caaactctag taacacacag tagtgttttg      15300
cttactatgg ttaactaaaa aatcacaggg tcttcatgca tttggaaagg atactttatt      15360
tcttacaaag ggttacagcc tacaaggtgg tcattctgca ggctagaaag cgtaacctcc      15420
agcaaagacc ggaggcaggc acttctaggg aaggaagagt aagacagaaa tttaaattga      15480
atgggttggc caagtataca tattcaacag gctacaggtg gattcatgaa tattcatgaa      15540
ggcagtcctg atgcatgcat gttacacctt ggggtggagg cttaacattt aaatgtatta      15600
cagttaggcc ctatacatga aaaggtgaag cagtaacacg aaggcacaca atgcaccatt      15660
tctgtaaaca ggccagagcc agttcacagt ggttggtctc ttatcatgag aaagctacta      15720
aaatcctctt gtccagttaa aactgtagtt atggctggtg gaaaatgggc tggagtcagt      15780
caacacttgg tgaagctgca gttgcttcag acactcaagg ccagtgtttg tttagctgct      15840
cgagaaaaag aaaaatcttg tggcagttag aacatagttt attctttaag tgtaggagtg      15900
tgtgacttaa                                                              15910

<210> SEQ ID NO 366
<211> LENGTH: 50
<212> TYPE: DNA
<213> ORGANISM: Homo sapiens

<400> SEQUENCE: 366
aatcgacagc gaggccggtc gcgaggcccc agtcccgccc tgcaggagcc                  50

<210> SEQ ID NO 367
<211> LENGTH: 587
<212> TYPE: DNA
<213> ORGANISM: Homo sapiens

<400> SEQUENCE: 367
agccgcgcgc tcgctcgcag gagggtgggt agtttgccca gcgtaggggg gctgggccca       60
taaaagagga agtgcactta agacacggcc ccgctggacg ctgttagaaa ccgtcctggc      120
tgggaaggca agaggtgtgt gactggacaa gacttgtttc tggcggtcag tcttgccatc      180
ctcacagagg ttggcggccc gagagagtgt gaggcagagg cggggagtgg caagggagtg      240
accatctcgg ggaacgaagg agtaaacgcg gtgatgggac gcacggaaac gggagtggag      300
aaagtcatga agagaaccct aggcggggcg gtccccgcgg aaaggcggct gctccagggt      360
ctccgcaccc aagtaggagc tggcaggccc ggccccgccc cgcaggcccc accccgggcc      420
ccgcccccga ggcttaagcc gcgccgccgc ctgcgcggag ccccactgcg aagcccagct      480
gcgcgcgcct tgggattgac tgtccacgct cgccggctc gtccgacgcg ccctccgcca       540
gccgacagac acagccgcac gcactgccgt gttctccctg cggctcg                    587

<210> SEQ ID NO 368
<211> LENGTH: 50
<212> TYPE: DNA
<213> ORGANISM: Homo sapiens

<400> SEQUENCE: 368
gtgagcctgg ccccagccct gcgccactct ctgcctttgc tcacccacag                  50

<210> SEQ ID NO 369
```

```
<211> LENGTH: 157
<212> TYPE: DNA
<213> ORGANISM: Homo sapiens

<400> SEQUENCE: 369
gacacatagt atgaccatta ggtgtttcgt ctcccaccca ttttctatgg aaaaccaagg    60
ggatcgggcc atgatagcca ctggcagctt tgaagaacgg gacaccttta gagaagcttg   120
atcttggagg cctcaccgtg agaccttaca aagccgg                           157

<210> SEQ ID NO 370
<211> LENGTH: 50
<212> TYPE: DNA
<213> ORGANISM: Homo sapiens

<400> SEQUENCE: 370
gtaagagtcc agtccaagga agaggtgggg cttttctcct cttggcttag               50

<210> SEQ ID NO 371
<211> LENGTH: 225
<212> TYPE: DNA
<213> ORGANISM: Homo sapiens

<400> SEQUENCE: 371
attccggcag agttcctcta tctcgtcttg ttgctgatta aaggtgcccc tgtctccagt    60
ttttctccat ctcctgggac gtagcaggaa atcagcatca tggttgggtt caaggccaca   120
gatgtgcccc ctactgccac tgtgaagttt cttggggctg cacagctgc ctgcatcgca    180 gatctcatca cctttcctct ggatactgct aaagtccggt tacag                   225

<210> SEQ ID NO 372
<211> LENGTH: 50
<212> TYPE: DNA
<213> ORGANISM: Homo sapiens

<400> SEQUENCE: 372
gtgaggggat gaagcctggg agtcttagct accctgtctt ggccttgcag               50

<210> SEQ ID NO 373
<211> LENGTH: 211
<212> TYPE: DNA
<213> ORGANISM: Homo sapiens

<400> SEQUENCE: 373
atccaaggag aaagtcaggg gccagtgcgc gctacagcca gcgcccagta ccgcggtgtg    60
atgggcacca ttctgaccat ggtgcgtact gagggccccc gaagcctcta caatgggctg   120
gttgccggcc tgcagcgcca aatgagcttt gcctctgtcc gcatcggcct gtatgattct   180
gtcaaacagt tctacaccaa gggctctgag c                                  211

<210> SEQ ID NO 374
<211> LENGTH: 50
<212> TYPE: DNA
<213> ORGANISM: Homo sapiens

<400> SEQUENCE: 374
gtgagtatgg agcaagggtg taggccactg accccatggc tcgcccacag               50

<210> SEQ ID NO 375
<211> LENGTH: 195
<212> TYPE: DNA
<213> ORGANISM: Homo sapiens
```

```
<400> SEQUENCE: 375
atgccagcat tgggagccgc ctcctagcag gcagcaccac aggtgccctg gctgtggctg      60
tggcccagcc cacggatgtg gtaaaggtcc gattccaagc tcaggcccgg ctggaggtg     120 gtcggagata ccaaagcacc gtcaatgcct acaagaccat tgcccgagag gaagggttcc    180
ggggcctctg gaaag                                                     195

<210> SEQ ID NO 376
<211> LENGTH: 50
<212> TYPE: DNA
<213> ORGANISM: Homo sapiens

<400> SEQUENCE: 376
gtgtgtacca gttgttttcc cttccaccca ggatcttcct cctcctacag                50

<210> SEQ ID NO 377
<211> LENGTH: 102
<212> TYPE: DNA
<213> ORGANISM: Homo sapiens

<400> SEQUENCE: 377
ggacctctcc caatgttgct cgtaatgcca ttgtcaactg tgctgagctg gtgacctatg     60
acctcatcaa ggatgccctc ctgaaagcca acctcatgac ag                      102

<210> SEQ ID NO 378
<211> LENGTH: 50
<212> TYPE: DNA
<213> ORGANISM: Homo sapiens

<400> SEQUENCE: 378
gtgagtcatg aggtagacgg tgctgtgcct tgcctgctcc tccttggcag                50

<210> SEQ ID NO 379
<211> LENGTH: 181
<212> TYPE: DNA
<213> ORGANISM: Homo sapiens

<400> SEQUENCE: 379
atgacctccc ttgccacttc acttctgcct ttggggcagg cttctgcacc actgtcatcg     60
cctcccctgt agacgtggtc aagacgagat acatgaactc tgcccgggc cagtacagta    120 gcgctggcca ctgtgccctt accatgctcc agaaggaggg gccccgagcc ttctacaaag    180
g                                                                   181

<210> SEQ ID NO 380
<211> LENGTH: 50
<212> TYPE: DNA
<213> ORGANISM: Homo sapiens

<400> SEQUENCE: 380
gtgagcctct ggtcctcccc acccaatgac ctgtgatttt tctcctctag                50

<210> SEQ ID NO 381
<211> LENGTH: 455
<212> TYPE: DNA
<213> ORGANISM: Homo sapiens

<400> SEQUENCE: 381
gttcatgccc tcctttctcc gcttgggttc ctggaacgtg gtgatgttcg tcacctatga     60
```

```
gcagctgaaa cgagccctca tgctgcctg cacttcccga gaggctccct tctgagcctc    120
tcctgctgct gacctgatca cctctggctt tgtctctagc cgggccatgc tttccttttc    180
ttccttcttt ctcttccctc cttcccttct ctccttccct ctttccccac ctcttccttc    240
cgctccttta cctaccacct tccctctttc tacattctca tctactcatt gtctcagtgc    300
tggtggagtt gacatttgac agtgtgggag gcctcgtacc agccaggatc ccaagcgtcc    360
cgtcccttgg aaagttcagc cagaatcttc gtcctgcccc cgacagccca gcctagccca    420
cttgtcatcc ataaagcaag ctcaaccttg gcgtc                              455
```

<210> SEQ ID NO 382
<211> LENGTH: 50
<212> TYPE: DNA
<213> ORGANISM: Homo sapiens

<400> SEQUENCE: 382

```
tcctccctct cttgtagctc ttaccagagg tcttggtcca atggccttt                50
```

<210> SEQ ID NO 383
<211> LENGTH: 15174
<212> TYPE: DNA
<213> ORGANISM: Homo sapiens

<400> SEQUENCE: 383

```
tccagcctgg gcaacaagag tgaaactcgg tctcaaaaaa aaaaaaaaga gaagaagaag     60
aaagaaaact aggtggagtg tggtggcttg cacctataat cccagcactt tgggaggccg    120
aggtgggtgg atctattgag gctaggagtt caagatcaac ctgccaacat gacgaaaccc    180
cacctctact aaaaatacaa aaaattagca cggcgtggtg tgtgtgcctg taatcctagc    240
tacttggaag gctgaggcag gaatcgcttg aacctggggg gcagaggttg cagtgagcca    300
agatcttgcc actgcactcc aggctgggcg acacagcaca actctatctc aaaaaaaaaa    360
agaaaaaaca aagaaaaact aatatatcaa ataatttct agttagttgg attcactcac    420
ttattcattc aatgacttat tgaattatca tatattacta gtgctttta atacatacct    480 tctacaattt ttcaactgaa aattacttca ttgatcaggg ctctttaaac tgatctccat    540
ttgcattgtt ttactaacta tagttattat tcatgtatta gcactctgag cctactgtaa    600
tgatgtgtac cttaataaag aactgaatat ttgtaatggc tggcagtgaa tttagtagtt    660
cttgaattta gagctcaaaa tatgggagta atttgctgct ttatttcctt tgagaggtaa    720
tagaggaaaa acagaatcta ataacaatca cagattttcg ggaaagcact gtaaaccat    780 atgatcaatt ctagcttctt atgtaaacat ggaaagattg ccagctgaac acctgtcatg    840
ctctaagaag ttggggagaa tttgcatttt tagaactgtg agcaaaatga aacgactgc    900 tatgttcatg ctttgtgaat ttagctttat ttcattcaca caattcatgg gaaaaaatgc    960
atcttttaac tcggtgtttt tcaattcaac ttttaaaata caggagtggg ccagacccgg   1020
tggctcacac ctgtaatctc atcactttgg gaggccgagg caggtggacc acaaggtcaa   1080
gagatagaca ccatcctggc caacatggtg aaacccccatc tccactaaaa atacaaaaat   1140
tagctgggca tgttggcacg tacctgtaat cccagctact cggagactg aggcaggaga   1200 atcgcttgaa cctgggagat ggaggttaca gtaagccgag atcgcgccac tgcactccag   1260
cctggcgaca gagcaagact ccatctcaaa aaaaaaaaa aaaaaaaaa aaaaaaaaaa   1320 aaaaaccag gatgtgttac caaggaaaat tcatttacaa tggttaatta tgtgacaaac   1380
atgtcaagta attccatctg gctttgtgtc accatttccc caccctttt tcagaaacca   1440
```

-continued

| | |
|---|---|
| aaaccaagaa gaagaacaaa catcaaaatg gacatggaaa ttaacaaata tatgattcaa | 1500 |
| tttaatctcc taagaggttt tttaaaatta ttttattttg agacggagtc ttgctctgtc | 1560 |
| gccaggctgg agtgcagtgg caggatctca gctcactgca acctccatct cccaggttca | 1620 |
| agcgattctc ctgcttcagc ctcccaagta gctggaacta caggcaagca ccaccacacc | 1680 |
| cagctaatgt ttgtattttt ggtagagatg gggtttcacc atgttggcca ggatggtctc | 1740 |
| gatctcttga cctcatgatc cacccgcctt ggcctcccaa agtgctggga ttacaggtat | 1800 |
| tttttatttt ttttgagaca gggtcaccct gtcacccagg ctggagtgta gtggcacaat | 1860 |
| catggctcac tgcagcctca acctcccagg ctcaggtgat cctccatgtc agcctcccaa | 1920 |
| gtagctggaa ctataggcgt gcaacaccat gcccagctaa tttttgtatt ttttgtagag | 1980 |
| acagggattt gccatgttgg ccaggctggt cttcaactcc tggcctcaag tgatccaccc | 2040 |
| gtctcaacct cccaaactgc taggattaca ggtgtgagcc accgtgcccc atctcatctg | 2100 |
| ctaagtgggt ttaaagaaat tcagtttcat gtcaattttt aaaatgtatg gttatcaaat | 2160 |
| tcgacttctt tttaaaaatg caatcagata actgtatgct tgtttgatga ggggaggaaa | 2220 |
| gttaatatag ccaatctact caatatttt agcagaaatt atcagagact aaggaaatgt | 2280 |
| ttaagttttt ctcatgttgg ttttaattac ctaatgtttt cagttttctc tttcattctt | 2340 |
| gtgtctttt ttcattttca gtgtttcaaa tacagtttgt atttaaagat ttagaagttc | 2400 |
| caaaactgta agcacagtgg attgtttcct gggatgatgt taaaattata caacaaaata | 2460 |
| tatgaaactt tgtcaatttg gttattggca catacaaaat atttacaaat aaacgtgtgt | 2520 |
| gtgtgtgcgt gtacacacaa ttcaatgaaa tagatgtgaa acaagttttc tttttttttt | 2580 |
| ttttgagaca gagtcttgct ctgtcgccca ggctggagtg caatgtcgca gtctcagctc | 2640 |
| actgcaacct ctgcctcccg ggttcaagcg attctcctgc ctcagcctcc cgagtagctg | 2700 |
| ggactacagg cacctaccac cactcccagc taatttttgt gttttagta gagacagggt | 2760 |
| ttcaccatgt tagccaggct agtctccaac tcctgacctc aggtgatctg cccgcctcag | 2820 |
| cctcccaaag tgctgggatt gcaggcgtga gccactcac ctggctacaa gttttcaaaa | 2880 |
| tacatttatc tgtacccata cattctccag tttgtccaca ggacatctta tgacttgagc | 2940 |
| aagctgctaa aaatccaagg gtgcagcgtt tgtatgtcta taggattgct cagatctgcc | 3000 |
| cccaccctga aagaatttaa gagaaatttct tgaggccagg cacagtggct cacacctgta | 3060 |
| attccagtac tgtgagagtc cgaggtcaga ggactgcttg aggccaggag ttcaagagca | 3120 |
| gcctggacaa catagggaga cctgtcacta caaagaataa ataaattagc caggcttagt | 3180 |
| ggctcatccc tgtggtccca gctactaggg aggcagaagt aggactgctt gtcccaggag | 3240 |
| gtcaagactg cagtgagctg agacccagcc acctgcattc cagcctgggc aacaaaaaga | 3300 |
| gaccctgtct caaaaaataa gttaaataaa taaataataa aaatagttta aaccctaaac | 3360 |
| acatcttctt tttcaaagag gacttcttaa ggacttcatg ctgcgtcctg ttgatctcca | 3420 |
| cttcccttt tcagcgtcca cacttttaac agtctctttt gccaaggata taagtatat | 3480 |
| agtttctgga atccagattc ttccctgttt ggacagccag ggggacaatt tttggtctgc | 3540 |
| aggcctttgc atctgttctg ctgttgctca gcaatctcac agcaaatttg ccgagcctct | 3600 |
| ccggaatgca cagccagaca gagctcagcg caaaagctag agaacctggc ggagggagac | 3660 |
| tcacagtgcc acaaaaaaac tttatctttt ctttttttttt ttcttttctt tctttctctt | 3720 |
| tctttcttgt ctttctgtct ttcctctctc tctctctgtc tttctttcct ctctttcttt | 3780 |

```
cttttttcct acatggcaag atctcctcat ggcagaaata atctgccttg acttctgttt    3840
ccacgctgct tctgccagga ccatgcgctc ggcgtgtttt tctttccgct ataattatcc    3900
aggcccatcc cagctctggt cccctcagct gttccctggc agtcccttct gctggtgaaa    3960
acacatatgg cgccggcctg accagggtgt aagtgtgtga atatcaggaa gatgactgaa    4020
cgtcttt ggg actccgtttc ctcattgtaa aatggaggtt aataccagcc ttcttctact    4080
ccccaaacgc acgtgtttgt cccggccaga gggcccaatt gttggctgtt cacgcgtcag    4140
ttaccccc ac aggacgggtc agccaattaa aggcgaacca ggcccggtcc atctcctgac    4200
gccttttctc atcccagggc tggacaggca gctggcctgg gcccggctct gccttgtcac    4260
gtgcgggggc cggcccgttt gcttgtctgt gtgtaggagc gtgaggtcac gctgggtgct    4320
cccgccccgc cggggccttt agtgtcctgg tccctaaacg ccaggccgct ccaccggggg    4380
agaaggcgcg aaccccagcc gagcccaacg gctgttgtcg gttgccgggc cacctgttgc    4440
tgcagttctg attggttcct tcccccgaca acgcggcggc tgtaaccaat cgacagcgag    4500
gccggtcgcg aggccccagt cccgccctgc aggagccagc cgcgcgctcg ctcgcaggag    4560
ggtgggtagt ttgcccagcg tagggggggct gggcccataa aagaggaagt gcacttaaga    4620
cacggccccg ctgacgctg ttagaaaccg tcctggctgg gaaggcaaga ggtgtgtgac    4680
tggacaagac ttgttt ctgg cggtcagtct tgccatcctc acagaggttg gcggcccgag    4740
agagtgtgag gcagaggcgg ggagtggcaa gggagtgacc atctcgggga acgaaggagt    4800
aaacgcggtg atgggacgca cggaaacggg agtggagaaa gtcatggaga gaaccctagg    4860
cggggcggtc cccgcggaaa ggcggctgct ccagggtctc cgcacccaag taggagctgg    4920
caggcccggc cccgccccgc aggccccacc ccgggccccg ccccgaggc ttaagccgcg    4980
ccgccgcctg cgcggagccc cactgcgaag cccagctgcg cgcgccttgg gattgactgt    5040
ccacgctcgc ccggctcgtc cgacgcgccc tccgccagcc gacagacaca gccgcacgca    5100
ctgccgtgtt ctccctgcgg ctcggtgagc ctggccccag ccctgcgccc tttgcgcccc    5160
ccacgcttgt tctgcgtgcg ctgcccgctc ttccatttac cttctctccc acccaagttt    5220
gtactctttt ctttctctcg gttttatttt ttgttttt gt ttgtttgttt gagacaggct    5280
ttcgctctgt ctcccaggct ggagtgcagt ggcgcgatct cggctcactg cagcctccac    5340
ctcccaggtt caagcgatcc gcctgccgag tagctgggat tacaggcgcc cgccaccacg    5400
cctggctaat ttttgtgttt tgtagagatg gggtttcgcc atgttggcca ggctggcctc    5460
gaactgctga gctcaagcaa tccgcccgcc tcggcctcac aaagtcctag aatttt aggc    5520
atgagcctcc gggtccggcc tgtgctaatc ctttctgtcc ttggttctt t att tctcttc    5580
tctcttttt c ttagtccctt tgttcttttc cctctcccgt tcagttggct gtcgtttgag    5640
cctccacctt ttcactccct cctttccacc acgatgccga gccctgcctt ggatggggac    5700
catcagcgat gaccacaatg acctctccct taccaggcag ctccaggcag tgttcctgca    5760
ccgcctttcc cagggcttgg gggcttt ttc tagtgggctt tgagctgctc aatctggcct    5820
ctgcagggcc ggctcccagc ccttccaacc tcctcacagc ccgacctggg acctagccaa    5880
ttcccggaga gtctctgtcc catcgtgacc ccctcacaac tctcccactc accaaagtct    5940
gatgactgtg ctagggggtg cttatataga gtactgagtg ttacaaaagc agaagtctgg    6000
atgagaacca atttgtgata ttaagcaggt ggggtggggg tggggagtgt acctaggttc    6060
attttccgc ctgcttttcc cctttccagt gtgtgcactt aaccagtccc tgggccctgt    6120
tccccatccc cctccaaggc atggattggg tgggcttgtg tgtcttgggg caggtggccc    6180
```

```
tttctaaact ctctgccttt gctcacccac aggacacata gtatgaccat taggtgtttc    6240
gtctcccacc cattttctat ggaaaaccaa ggggatcggg ccatgatagc cactggcagc    6300
tttgaagaac gggacacctt tagagaagct tgatcttgga ggcctcaccg tgagacctta    6360
caaagccggg taagagtcca gtccaaggaa gaggtctctt gctgcctcct aaccctgtgg    6420
tctaggggca ggagtcagca gggcattaac aaaaataatt accatcccca ccccgacag    6480 tgaagtggct ctttccagtt cacagagcac tctcacacct ccccgctctc attctggccc    6540
ttcagctgac tcggacaagc caaggatctt ggtccccatt ttataaagga gaaaactgag    6600
gcccacgtgt aacagtgatt ggccccaagt catcccggga gccagcagaa gagctaggac    6660
aggaacctat tgttctaact tcatattgat gctagctttt gactatccct gaaaccgaga    6720
ttggtaatca gcccggctct gaaactggtt atttgctggg gactgtaaaa taggattaac    6780
tatttctagt cctgcatttt aattgctgtt agtagggcca tcttacccac cctctgaagg    6840
acctgacttg gcaagcccaa ggcaacattc agaatatggc agctgaacct ctgtgcactt    6900
gtctttgggc agcagctggg tcttattctt ctctggcctt cacaacatcc tgcaacccag    6960
ctcaaggtca ggaatgtgac agactcatgt catcatatct ctgatgccca gagaagggat    7020
accatttgcc tgagccttct cagtactgtt taatcagcct gtgagaactt tccttgtgaa    7080
aggccctgtc tgtgcctggg gctgataaaa cagcaagaac gaactgagga gctgggcagc    7140
agtgcaaagc aaatactacc agctttggtg cctgtaagtg tggctcttac tcatctcaca    7200
tggaaataag ggcagccacc ttgcagggct gctctgagga ttgagctaat acagtgccct    7260
gggcgttggg gtggggaaag ttgtggagca cctcctgggg gaaggggtg tcagagcagg    7320 gaatctgggg agtccgaggg caccttcatc aacccaatct gtcatttgag caccagtctt    7380
cactgagcct cgtgggcaag ctggagggaa acaggaataa ggtcaggccc tgttctatag    7440
gtcccagtgt agttgctatg gtgagtatct tcatttccct gcttcccca gccacctgga    7500 gtgagaagcc caagaggaag ctgggtgagc tgtttgtttc catgggtctc tgtgttcaca    7560
gctgactccc ttcaccagcc agcccttca cctgagcccc agcaacaaag gcagtcaggc    7620
ggggctcaaa gcagctgctc caatgaagtc aaagaaataa gctcagggga agaagcaggt    7680
caccctcccc cactagggtg ctgggctcac ttcctcctgg ggcagtggag gagggtgtgg    7740
ttccaactca gaacaaaatg gggcttttgg tttactttat cactcttcac agctctgacc    7800
tggacccctc atccctgcct gtcttgtggt gtaagtgcgg atcccctaa gttggaggaa    7860 aggaaactgg cccaaacaaa aaggagagca gttttctctg catcacatgg taggccagga    7920
ggagtctaat gccccagagt ttactctcag cccccaaaat cacctagcta aatgttacct    7980
tatctaagaa gtccttaggt ttttgggggt ttgttttttt ttttttttgag acaaggtctc    8040 actctctcac ccagactgga gcacagtggc acaatcacag ctcactgcag cctcaacctc    8100
ctgggctcaa gcaatcgtcc caagtagctg ggactatagg cctgcaccac catgtccagc    8160
taatttattt ttatttatat ttttagaca gggtctcatt atgttgccct ggctggtctt    8220
gaactcctgg gttcaagcag tcctcccacc tctgcctccc aaagtgctag gttttttttt    8280
gtttgtttgt ctgtttttg aaacagagtc ttgctctgtc gcctaggctg gagtgcagtg    8340
gcacgatctc agctactgca acctccacct cctgggttca agtgattctc ctgcctcagc    8400
ctcctaagta gttgggaata caggcgtgtg ccaacacacc cagctcattt ttgtatttt    8460 agcggagatg gggtttgcc atgttggcca agctggtctc aaactcctga cctcaggtga    8520
```

```
ttcgcccgcc tcagcctccc aaagtgctgg gtttacaggc gtgagccacc acacccagcc    8580
caagaagtct tttctgatca cccactcttc cttctctccc aatggcatta gttgttccct    8640
cctttgcatt ttgagagtat gtcctgtaag ccccaaatgc agcttgaatc atctgcccat    8700
ccaccccctg tgcccaacag taagcctcct ctagagtaga tactatctcc tgcatctcag    8760
tgaaccactg cccagcaaag cagtcttgct aaaacaatga ctctagagat cctaagctgt    8820
gtgagagctg gaggagagaa ttagactgat ggtctgggaa gggattgaat tagtcatctt    8880
gtaccttttc ttcttgactt aagttccaga cctgtagcaa ccattcctgc ttagacatcc    8940
agaacataag cctatgggtc tgtgcctgtt gggtcttagt ctgggtgaaa cttttctcta    9000
cttctgtcag ctctccagat gaaccacaga agcaggaatg tgggcatcat cagtgaaatc    9060
tctgcataca gcagacaaag ggctggtcca gtggctgttt atgaggcagc gctaggagag    9120
ctctgatcca gactctccct gcagtgaaag ggagggagcc cttcatgaag tattgactgc    9180
ttgagcagga attgcttcac cagcacctaa ctgagtgcct ctcgagctca catcggtttt    9240
ccctcatgag gccacttgga gtcttgctga gggacttggt tctattaggg aaggtgagtt    9300
tggggatggt gagcagggag ggcctgggga cattgtggct aatggggctt ttctcctctt    9360
ggcttagatt ccgcagagt tcctctatct cgtcttgttg ctgattaaag gtgccnctgt    9420
```

```
tccaagctca ggcccgggct ggaggtggtc ggagatacca aagcaccgtc aatgcctaca   10980
agaccattgc ccgagaggaa gggttccggg gcctctggaa aggtgtgtac cagttgtttt   11040
cccttcccct tttcctcctc cccgatactc tggtctcacc caggatcttc ctcctcctac   11100
agggacctct cccaatgttg ctcgtaatgc cattgtcaac tgtgctgagc tggtgaccta   11160
tgacctcatc aaggatgccc tcctgaaagc aacctcatg acaggtgagt catgaggtag    11220
acggtgctgg gtctcaccct tcccccatgc caggagcagg tgcggggtc tagctgacac    11280 cagaagacca catcttttca tcctatttgc cctttgcagg gagagtaaga tatctcttac   11340
ttgccatatt gaagccaatt gggatgaagc tcccactttg cacattgagg aactgaggct   11400
agattggcaa aatgactctt tcaggtcctc agaagatgtc tcagctggag tccctgtctg   11460
tttttgtttt tttgtttgtt tgttttttgt ttttttgag atagagtctc actctgttac    11520
ccgtgtaatc tcagctcact gcaaccttct cctcctgggt tcaagcgatt cttgtgcctc   11580
agcctcccga gtagctggga tgacaggtgt gcaccagcac actggctaat ttttgtattt   11640
ttagtagaga tggagtttca ccatgttagc caggctggtc tcgaactcct ggcctcaagt   11700
gatctgccca ccttggcctc ccaatgtgct gggattacag gtgtgagcct ctgcgcccca   11760
tcctcttgtt tgttttttga cagggtct tgctcggttg cccaggctgg agtgcagtgg     11820
ggtgattaat ggctcattgc agcctcgacc tccctgactc aagcaatcct cccacctcag   11880
cctcctgagt agctggggct gactacaggc atgcacactg tgcctggcta attttgtat    11940 tttgtagaga cagggttttt gccatgttac ccagtctggt cttgaactcc tgggctcaag   12000
tgatccaccc acctcggcct ccaaaagaag tcctggatta caggcatgag acattgtgcc   12060
cagcctctct gtctctttaa aatcatgaaa actcgtagct acttaagtaa ttctcctgcc   12120
ttctggaatg atgggtgaag atcttgactg ccttgcctgc tcctccttgg cagatgacct   12180
cccttgccac ttcacttctg cctttggggc aggcttctgc accactgtca tcgcctcccc   12240
tgtagacgtg gtcaagacga gatacatgaa ctctgccctg ggccagtaca gtagcgctgg   12300
ccactgtgcc cttaccatgc tccagaagga gggccccga gccttctaca aagggtgagc    12360
ctctggtcct ccccacccag ttcaggcctc ttggctatgc atgtctattg tgggtgggag   12420
agaaccacct ggaagtgagt agcagccaag tgtgactatt tctgatcctg gtcctggcat   12480
ttcaccagca ttcacctatc cccttaattc cttcctccca gaattgctac catcactgtt   12540
tattaggtgt taaatggaga ctcaaaggga attcatgctt atagccaagc agctgtgagc   12600
tcagttcatt gagtcctccc agcctccttt gggacagagc aactgggttg gattgaatac   12660
caggcccagt gagggaagtg ggaggtggag gtgccccat gacctgtgat ttttctcctc    12720
taggttcatg ccctcctttc tccgcttggg ttcctggaac gtggtgatgt tcgtcaccta   12780
tgagcagctg aaacgagccc tcatggctgc ctgcacttcc cgagaggctc ccttctgagc   12840
ctctcctgct gctgacctga tcacctctgg cttgtctct agccgggcca tgctttcctt    12900
ttcttccttc tttctcttcc ctccttccct tctctccttc cctctttccc cacctcttcc   12960
ttccgctcct ttacctacca ccttccctct ttctacattc tcatctactc attgtctcag   13020
tgctggtgga gttgacattt gacagtgtgg gaggcctcgt accagccagg atcccaagcg   13080
tcccgtccct tggaaagttc agccagaatc ttcgtcctgc ccccgacagc ccagcctagc   13140
ccacttgtca tccataaagc aagctcaacc ttggcgtctc ctccctctct tgtagctctt   13200
accagaggtc ttggtccaat ggccttttg gtacctggtg ggcaggggag gaaccacctg     13260
```

```
actttgaaaa tgggtgtgat ccaccttcca cctccagcat ccaatctgaa gcccgtgtag    13320
gtcatctggt ccatttctct ctagacccag gccctgtact aacatgggga gtgcaggagc    13380
cacctgagag acagcagtgc ctccccttcc tttgccgggc cacttgagct cttactcaga    13440
atctggtact ctagtgcctg ccatcccaac cccccacccc agccgcaggc ctgtttatct    13500
gcacaacaag agtgctcctg tgtgccctgc atctcctgca gttccagagg aacatgagac    13560
tcttagatgc tgttgacttt attttattcc attttacaaa tggaaggaag acccacctcc    13620
cccaaagtcc cagaccttgt gagaacaagt cagtcagcct ccttccaccc tccacagcca    13680
cagccacacc cacagaggaa atgttactga actgggtgga gcaggccctg actccacaga    13740
gggtgggtgg aggctgcagg gcaaacatct ggtctctgcc tgaggatact ttccatttgt    13800 gtttttttgtt gttttgagac agagtctcac ttgctgtcac ccaggctgga gtgcagtggt    13860
gcaatcttgg ctcactgcaa cctctcccag gttcaggcga ttctcctgcc tcagcctccc    13920
aagtagctgg gattacaggc atacaccatc atacctggct aattttttgtg tttttggtag    13980 aaacggggtt ttgccatgtt ggccaggctg gtctcaaact cctgacctca agtgatccac    14040
ctacctcagc ctcccaaagt gctgggatta caggcatgag ccactgtgcc tggccaggat    14100
attttccatt tggagtctca ccaccacaac cccccctccac ctgcccctgc cccagctagg    14160
catccaagga ggccgcaaga agccagggcc ttggctgcac aggggtctcc gcttctctgt    14220
ccctgttctt atcacctgca ctcagaggca ggtgggcagg ggtactacaa tttcaaggag    14280
tggagactgt gaggtcctgg aatcccaagg catctcctgt agggctgggc ccttagaatt    14340
atgtcactca gacccagttt gtaggtgtct gaagaaactg aggcctgaca caggtgatgc    14400
aggcaagaac acccagaaag tccactactg aactgggacc gggacccagt cctccttccc    14460
cttgtggact cccccagaga ccagtgctgg ggtccttggg gaagcctgtt tggcagctgt    14520
ggagctaggc cctgagaaca cgaccaccct ccctcttccc tcagcctcaa gccgctgaag    14580
ccactgctgc ttcgccgcct cgtaagccca atggtcagag ctggaggcta gacccttcag    14640
tgcttgggtt gagggccagg gtgttagatt ggttttttgga gaaggaacga gggcccagga    14700
ttcttcagct tcttagtttt tgacaaattg agctgaggcc ccatagtcct cgggagggac    14760
agggttgagt gccataagtc ggcaaaccag ggtaaaggtg acaggcagct cagccaggct    14820
gcagggggtg gcatatacag aggacctggc cactacttta tgtaccttct tacactaatt    14880
ctgtgaggca ggctgtttgt tagctctgct ctggacggga agaagtaggg gcagtttggt    14940
aggtgtgtgt caaagctaaa caggctgggg gggcatgagc aagtcagctg gttcattcag    15000
cagccttaat agacacgagg ctacccaact tcactgtggt tctgggtgtg gccttaggac    15060
aatgagctgg gaacagtggt aggaaccact ggaaaacata ccagtgggtc tcattcattc    15120
tgatcacagg tagatcactt ctctttggtt cccaacccctt taatgcctat taag          15174
```